US012146152B2

(12) United States Patent
Lu et al.

(10) Patent No.: US 12,146,152 B2
(45) Date of Patent: *Nov. 19, 2024

(54) SYSTEMS, METHODS, AND COMPOSITIONS FOR CORRECTION OF FRAMESHIFT MUTATIONS

(71) Applicant: Massachusetts Institute of Technology, Cambridge, MA (US)

(72) Inventors: Timothy Lu, Cambridge, MA (US); Shota Nakade, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 177 days.

This patent is subject to a terminal disclaimer.

(21) Appl. No.: 18/055,718

(22) Filed: Nov. 15, 2022

(65) Prior Publication Data

US 2023/0183754 A1 Jun. 15, 2023

Related U.S. Application Data

(63) Continuation of application No. 17/067,379, filed on Oct. 9, 2020, now Pat. No. 11,530,425.

(60) Provisional application No. 62/984,422, filed on Mar. 3, 2020, provisional application No. 62/913,048, filed on Oct. 9, 2019.

(51) Int. Cl.

| | |
|---|---|
| ***C12N 15/90*** | (2006.01) |
| ***A61K 48/00*** | (2006.01) |
| ***C12N 9/12*** | (2006.01) |
| ***C12N 9/22*** | (2006.01) |
| ***C12N 15/10*** | (2006.01) |
| ***C12N 15/11*** | (2006.01) |

(52) U.S. Cl.

CPC ............ *C12N 15/907* (2013.01); *A61K 48/00* (2013.01); *C12N 9/22* (2013.01); *C12N 15/11* (2013.01); *C12N 2310/20* (2017.05); *C12N 2800/80* (2013.01)

(58) Field of Classification Search

None

See application file for complete search history.

(56) References Cited

U.S. PATENT DOCUMENTS 4,554,101 A 11/1985 Hopp

FOREIGN PATENT DOCUMENTS

| | | | |
|---|---|---|---|
| WO | WO 2012/118717 A2 | 9/2012 |
| WO | WO 2013/163628 A2 | 10/2013 |
| WO | WO 2017/147056 A1 | 8/2017 |
| WO | WO 2018/165629 A1 | 9/2018 |
| WO | WO 2019/099943 A1 | 5/2019 |
| WO | WO 2019/118949 A1 | 6/2019 |
| WO | WO 2019/123014 A1 | 6/2019 |

OTHER PUBLICATIONS

Anderson, "Human Gene Therapy", *Science* 256:808-813 (1992).

Chakrabarti et al., "Target-Specific Precision of CRISPR-Mediated Genome Editing", Molecular Cell 73(4):699-713 (2018).

Chu et al., "Increasing the efficiency of homology-directed repair for CRISPR-Cas9-induced precise gene editing in mammalian cells", *Nature Biotechnology* 33(5):543-548 (2015).

Dillon, "Regulating gene expression in gene therapy", *Tibtech* 11:167-173 (1993).

Haddada et al., "Gene Therapy Using Adenovirus Vectors", *The Molecular Repertoire of Adenoviruses III, Current Topics in Microbiology and Immunology*, pp. 297-306 (1995).

International Search Report and Written Opinion for International Application No. PCT/US2020/055131 dated Jan. 25, 2021.

Kremer et al., "Adenovirus and adeno-associated virus mediated gene transfer", *British Medical Bulletin* 51(1):31-44 (1995).

Kyte et al., "A Simple Method for Displaying the Hydropathic Character of a Protein", *Journal of Molecular Biology* 157:105-132 (1982).

Lai et al., "Efficient in vivo gene expression by trans-splicing adeno-associated viral vectors", *Nature Biotechnology* 23(11):1435-1439 (2005), doi: 10.1038/nbt1153.

Levy et al., "Cytosine and adenine base editing of the brain, liver, retina, heart and skeletal muscle of mice via adeno-associated viruses", *Nature Biomedical Engineering* 4:97-110 (2020).

Miller, "Human gene therapy comes of age", *Nature* 357:455-460 (1992).

Mitani et al., "Delivering therapeutic genes—matching approach and application", *Tibtech* 11:162-166 (1993).

Nabel et al., "Direct gene transfer for immunotherapy and immunization", *Tibtech* 11:211-217 (1993).

Nakamura et al., "Codon usage tabulated from the international DNA sequence databases: status for the year 2000", *Nucleic Acids Research* 28(1):292 (2000).

Perez-Pinera et al., "Gene targeting to the ROSA26 locus directed by engineered zinc finger nucleases", *Nucleic Acids Research* 40(8):3741-3752 (2012).

Shou et al., Precise and Predictable CRISPR Chromosomal Rearrangements Reveal Principles of Cas9-Mediated Nucleotide Insertion, *Molecular Cell* 71(4):498-509 (2018).

Taher-Ghahfarokhi et al., Decoding non-random mutational signatures at Cas9 targeted sites, *Nucleic Acids Research* 46(16):8417-8434 (2018).

Van Brunt, "Molecular Farming: Transgenic Animals as Bioreactors", *Biotechnology* 6(10):1149-1153 (1988).

Vigne et al., "Third-generation adenovectors for gene therapy", *Restorative Neurology and Neuroscience* 8:35-36 (1995).

Yu et al., "Progress towards gene therapy for HIV infection", *Gene Therapy* 1(1):13-26 (1994).

*Primary Examiner* — Suzanne M Noakes

*Assistant Examiner* — Jae W Lee

(74) *Attorney, Agent, or Firm* — Lathrop GPM LLP; Laura A. Labeots

(57) ABSTRACT

The disclosure provides systems, methods, and compositions for a target specific nuclease and a blunting enzyme to correct frameshift mutations for genome editing and treatment of diseases. In some embodiments, the target specific nuclease and the blunting enzyme are combined with a guide RNA and/or a microhomology-mediated end joining (MMEJ) inhibitor.

19 Claims, 23 Drawing Sheets

Specification includes a Sequence Listing.

[All types of frameshifts]

| Frameshifts | i.e. | In-frame correction |
|---|---|---|
| WT | : AAA GGC GCT | |
| + 1 bp (3n+1(n≧0)) | : AAA CGG CGC T | → -1 frameshift SpCas9 |
| + 2 bp (3n+2(n≧0)) | : AAA CCG GCG CT | → +1 frameshift SpCas9 |
| - 1 bp (-3n+2(n≧1)) | : AAA -GCG CT | → +1 frameshift SpCas9 |
| - 2 bp (-3n+1(n≧1)) | : AAA --CGC T | → -1 frameshift SpCas9 |
| + 3 bp (3n(n≧1)) | : In-frame | |
| - 3 bp (-3n(n≧1)) | : In-frame | |

SEQUENCE LISTING

```
Sequence total quantity: 149
SEQ ID NO: 1             moltype = DNA  length = 1728
FEATURE                  Location/Qualifiers
source                   1..1728
                         mol_type = unassigned DNA
                         organism = Homo sapiens
SEQUENCE: 1
atggatccca ggggtatctt gaaggcattt cccaagcggc agaaaattca tgctgatgca  60
tcatcaaaag tacttgcaaa gattcctagg agggaagagg gagaagaagc agaagagtgg  120
ctgagctccc ttcgggccca tgttgtgcgc actggcattg gacgagcccg ggcagaactc  180
tttgagaagc agattgttca gcatggcggc cagctatgcc ctgcccaggg cccaggtgtc  240
actcacattg tggtggatga aggcatggac tatgagcgag ccctccgcct tctcagacta  300
ccccagctgc cccgggtgc tcagctggtg aagtcagcct ggctgagctt gtgccttcag  360
gagaggaggc tggtggatgt agctggattc agcatcttca tccccagtag gtacttggac  420
catccacagc ccagcaaggc agagcaggat gcttctattc ctcctggcac ccatgaggcc  480
ctgcttcaga cagccctttc tcctcctcct cctcccacca ggcctgtgtc tcctccccaa  540
aaggcaaaag aggcaccaaa cacccaagcc cagcccatct ctgatgatga agccagtgat  600
ggggaagaaa cccaggttag tgcagctgat ctggaagccc tcatcagtgg ccactacccc  660
acctcccttg agggagattg tgagcctagc ccagcccctg ctgtcctgga taagtgggtc  720
tgtgcacagc cctcaagcca gaaggcgacc aatcacaacc tccatatcac agagaagctg  780
gaagttctgg ccaaagccta cagtgttcag ggagacaagt ggagggccct gggctatgcc  840
aaggccatca atgccctcaa gagcttccat aagcctgtca cctcgtacca ggaggcctgc  900
```

-continued

```
agtatccctg ggattgggaa gcggatggct gagaaaatca tagagatcct ggagagcggg  960
catttgcgga agctggacca tatcagtgag agcgtgcctg tcttggagct cttctccaac  1020
atctggggag ctgggaccaa gactgcccag atgtggtacc aacagggctt ccgaagtctg  1080
gaagacatcc gcagccaggc ctccctgaca acccagcagg ccatcggcct gaagcattac  1140
agtgacttcc tggaacgtat gcccagggag gaggctacag agattgagca gacagtccag  1200
aaagcagccc aggcctttaa ctctgggctg ctgtgtgtgg catgtggttc ataccgacgg  1260
ggaaaggcga cctgtggtga tgtcgacgtg ctcatcactc acccagatgg ccggtcccac  1320
cggggtatct tcagccgcct ccttgacagt cttcggcagg aagggttcct cacagatgac  1380
ttggtgagcc aagaggagaa tggtcagcaa cagaagtact tgggggtgtg ccggctccca  1440
gggccagggc ggcggcaccg gcgcctggac atcatcgtgg tgccctatag cgagtttgcc  1500
tgtgccctgc tctacttcac cggctctgca cacttcaacc gctccatgcg agccctggcc  1560
aaaaccaagg gcatgagtct gtcagaacat gccctcagca ctgctgtggt ccggaacacc  1620
catggctgca aggtggggcc tggccgagtg ctgcccactc ccactgagaa ggatgtcttc  1680
aggctcttag gcctccccta ccgagaacct gctgagcggg actggtga              1728

SEQ ID NO: 2            moltype = DNA  length = 1488
FEATURE                 Location/Qualifiers
source                  1..1488
                        mol_type = unassigned DNA
                        organism = Homo sapiens
SEQUENCE: 2
atggctctgc caaagagaag acgcgcacgg gttgggtccc cttcagggga cgcagcctcc  60
tctacacctc catctacgag atttccgggt gttgcaatat acctcgtcga gccccggatg  120
ggacgcagta gacgggcttt ccttacgggt ctcgcccgaa gtaaaggctt tcgggtgttg  180
gacgcatgtt ctagtgaagc gacccatgtc gttatggagg agacgagtgc tgaggaggct  240
gtaagctggc aagagcgccg aatggctgct gcaccacccg gctgcactcc gcctgctttg  300
ttggatatat cttggctgac cgaaagtctt ggggctggac aaccagtacc ggttgagtgc  360
cgacatcgat tggaagtagc tggtccgagg aaaggccccc tctcaccggc ctggatgcct  420
gcatatgcct gccaacggcc cacccctctg acgcaccaca acactgggct ttccgaggca  480
ttggagatat tggcggaagc tgcgggcttt gaagggtccg aagggagatt gctcacgttc  540
tgtagagcag catccgttct taaagcgctg ccgagtcccg taactacact gtctcaactg  600
cagggcctgc cacacttcgg cgaacactca agccgggtcg tacaagaact cctggagcac  660
ggggtctgcg aggaagttga gagggtgagg cgaagcgaac gataccaaac gatgaagctg  720
tttacacaaa tctttggagt tggagtcaag acggcggaca gatggtatcg agaggggctt  780
cgaacgctcg acgatctgcg cgagcaaccg caaaagctga cccaacagca aaaggccgga  840
ctgcagcatc accaggacct ttcaacacct gttcttcggt ctgacgttga tgctctccaa  900
caagtcgtcg aggaggcagt aggccaggcc cttccgggcg ctactgttac gctcacggga  960
ggatttagac gcggcaaact tcaaggtcac gatgtcgatt tcttgataac tcacccaaaa  1020
gaggggcagg aggctggttt gctgccgcgg gtaatgtgcc gattgcaaga ccaaggcttg  1080
atactgtacc accaacacca acattcatgt tgcgagtcac ccacgcgcct cgcacagcag  1140
agccatatgg acgctttcga gagatcattt tgcatattca gacttcctca gcccccaggt  1200
gcggcggtcg gtgggtccac taggccgtgt ccatcttgga aggctgtgcg ggtggatttg  1260
gtcgtagcgc ccgtcagcca gtttcccttt gcactcctgg ggtggaccgg cagtaaactg  1320
ttccaaagag agctgcgaag gttctcacga aaagagaagg gcctctggct taactcccac  1380
ggcctgttcg accccgagca aaaaactttc tttcaggctg cgagcgaaga agatatcttc  1440
cgccacctgg gacttgagta ccttcccccc gagcagcgca acgcctga              1488

SEQ ID NO: 3            moltype = DNA  length = 1488
FEATURE                 Location/Qualifiers
source                  1..1488
                        mol_type = unassigned DNA
                        organism = Homo sapiens
SEQUENCE: 3
atggctctgc caaagagaag acgcgcacgg gttgggtccc cttcagggga cgcagcctcc  60
tctacacctc catctacgag atttccgggt gttgcaatat acctcgtcga gccccggatg  120
ggacgcagta gacgggcttt ccttacgggt ctcgcccgaa gtaaaggctt tcgggtgttg  180
gacgcatgtt ctagtgaagc gacccatgtc gttatggagg agacgagtgc tgaggaggct  240
gtaagctggc aagagcgccg aatggctgct gcaccacccg gctgcactcc gcctgctttg  300
ttggatatat cttggctgac cgaaagtctt ggggctggac aaccagtacc ggttgagtgc  360
cgacatcgat tggaagtagc tggtccgagg aaaggccccc tctcaccggc ctggatgcct  420
gcatatgcct gccaacggcc cacccctctg acgcaccaca acactgggct ttccgaggca  480
ttggagatat tggcggaagc tgcgggcttt gaagggtccg aagggagatt gctcacgttc  540
tgtagagcag catccgttct taaagcgctg ccgagtcccg taactacact gtctcaactg  600
cagggcctgc cacacttcgg cgaacactca agccgggtcg tacaagaact cctggagcac  660
ggggtctgcg aggaagttga gagggtgagg cgaagcgaac gataccaaac gatgaagctg  720
tttacacaaa tctttggagt tggagtcaag acggcggaca gatggtatcg agaggggctt  780
cgaacgctcg acgatctgcg cgagcaaccg caaaagctga cccaacagca aaaggccgga  840
ctgcagcatc accaggacct ttcaacacct gttcttcggt ctgacgttga tgctctccaa  900
caagtcgtcg aggaggcagt aggccaggcc cttccgggcg ctactgttac gctcacggga  960
ggatttagac gcggcaaact tcaaggtggc gatgtcgatt tcttgataac tcacccaaaa  1020
gaggggcagg aggctggttt gctgccgcgg gtaatgtgcc gattgcaaga ccaaggcttg  1080
atactgtacc accaacacca acattcatgt tgcgagtcac ccacgcgcct cgcacagcag  1140
agccatatgg acgctttcga gagatcaaaa tgcatattca gacttcctca gcccccaggt  1200
gcggcggtcg gtgggtccac taggccgtgt ccatcttgga aggctgtgcg ggtggatttg  1260
gtcgtagcgc ccgtcagcca gtttcccttt gcactcctgg ggtggaccgg cagtaaactg  1320
ttccaaagag agctgcgaag gttctcacga aaagagaagg gcctctggct taactcccac  1380
ggcctgttcg accccgagca aaaaactttc tttcaggctg cgagcgaaga agatatcttc  1440
cgccacctgg gacttgagta ccttcccccc gagcagcgca acgcctga              1488
```

-continued

```
SEQ ID NO: 4            moltype = DNA  length = 1488
FEATURE                 Location/Qualifiers
source                  1..1488
                        mol_type = unassigned DNA
                        organism = Homo sapiens
SEQUENCE: 4
atggctctgc caaagagaag acgcgcacgg gttgggtccc cttcagggga cgcagcctcc  60
tctacacctc catctacgag atttccgggt gttgcaatat acctcgtcga gccccggatg  120
ggacgcagta gacgggcttt ccttacgggt ctcgcccgaa gtaaaggctt tcgggtgttg  180
gacgcatgtt ctagtgaagc gacccatgtc gttatggagg agacgagtgc tgaggaggct  240
gtaagctggc aagagcgccg aatggctgct gcaccacccg gctgcactcc gcctgctttg  300
ttggatatat cttggctgac cgaaagtctt ggggctggac aaccagtacc ggttgagtgc  360
cgacatcgat tggaagtagc tggtccgagg aaaggccccc tctcaccggc ctggatgcct  420
gcatatgcct gccaacggcc caccccctctg acgcaccaca acactgggct ttccgaggca  480
ttggagatat tggcggaagc tgcgggcttt gaagggtccg aagggagatt gctcacgttc  540
tgtagagcag catccgttct taaagcgctg ccgagtcccg taactacact gtctcaactg  600
cagggcctgc cacacttcgg cgaacactca agccgggtcg tacaagaact cctggagcac  660
ggggtctgcg aggaagttga gagggtgagg cgaagcgaac gataccaaac gatgaagctg  720
tttacacaaa tctttggagt tggagtcaag acggcggaca gatggtatcg agaggggctt  780
cgaacgctcg acgatctgcg cgagcaaccg caaaagctga cccaacagca aaaggccgga  840
ctgcagcatc accaggacct ttcaacacct gttcttcggt ctgacgttga tgctctccaa  900
caagtcgtcg aggaggcagt aggccaggcc cttccgggcg ctactgttac gctcacggga  960
ggatttagac gcggcaaact tcaaggtggc gatgtcgatt tcttgataac tcacccaaaa  1020
gaggggcagg aggctggttt gctgccgcgg gtaatgtgcc gattgcaaga ccaaggcttg  1080
atactgtacc accaacacca acattcatgt tgcgagtcac ccacgcgcct cgcacagcag  1140
agccatatgg acgctttcga gagatcattt tgcatattca gacttcctca gcccccaggt  1200
gcggcggtcg gtgggtccac taggccgtgt ccatcttgga aggctgtgcg ggtggatttg  1260
gtcgtagcgc ccgtcagcca gtttcccttt gcactcctgg ggtggaccgg cagtaaactg  1320
ttccaaagag agctgcgaag gttctcacga aaagagaagg gcctctggct taactcccac  1380
ggcctgttcg accccgagca aaaaactttc tttcaggctg cgagcgaaga agatatcttc  1440
cgccacctgg gacttgagta ccttcccccc gagcagcgca acgcctga               1488

SEQ ID NO: 5            moltype = DNA  length = 1674
FEATURE                 Location/Qualifiers
source                  1..1674
                        mol_type = unassigned DNA
                        organism = Homo sapiens
SEQUENCE: 5
atggctctgc caaagagaag acgcgcacgg gttgggtccc cttcagggga cgcagcctcc  60
tctacacctc catctacgag atttccgggt gttgcaatat acctcgtcga gccccggatg  120
ggacgcagta gacgggcttt ccttacgggt ctcgcccgaa gtaaaggctt tcgggtgttg  180
gacgcatgtt ctagtgaagc gacccatgtc gttatggagg agacgagtgc tgaggaggct  240
gtaagctggc aagagcgccg aatggctgct gcaccacccg gctgcactcc gcctgctttg  300
ttggatatat cttggctgac cgaaagtctt ggggctggac aaccaatccc cagtaggtac  360
ttggaccatc cacagcccag caaggcagag caggatgctt ctattcctcc tggcacccat  420
gaggccctgc ttcagacagc cctttctcct cctcctcctc ccaccaggcc tgtgtctcct  480
ccccaaaagg caaaagaggc accaaacacc caagcccagc ccatctctga tgatgaagcc  540
agtgatgggg aagaaaccca ggttagtgca gctgatctgg aagccctcat cagtggccac  600
taccccacct cccttgaggg agattgtgag cctagcccag cccctgctgt cctggataag  660
tgggtctgtg cacagccctc aagccagaag gcgaccaatc acaacctcca tatcacagag  720
aagctggaag ttctggccaa agcctacagt gttcagggag acaagtggag ggccctgggc  780
tatgccaagg ccatcaatgc cctcaagagc ttccataagc ctgtcacctc gtaccaggag  840
gcctgcagta tccctgggat tgggaagcgg atggctgaga aaatcataga gatcctggag  900
agcgggcatt tgcggaagct ggaccatatc agtgagagcg tgcctgtctt ggagctcttc  960
tccaacatct ggggagctgg gaccaagact gcccagatgt ggtaccaaca gggcttccga  1020
agtctggaag acatccgcag ccaggcctcc ctgacaaccc agcaggccat cggcctgaag  1080
cattacagtg acttcctgga acgtatgccc agggaggagg ctacagagat tgagcagaca  1140
gtccagaaag cagcccaggc ctttaactct gggctgctgt gtgtggcatg tggttcatac  1200
cgacggggaa aggcgacctg tggtgatgtc gacgtgctca tcactcaccc agatggccgg  1260
tcccaccggg gtatcttcag ccgcctcctt gacagtcttc ggcaggaagg gttcctcaca  1320
gatgacttgg tgagccaaga ggagaatggt cagcaacaga agtacttggg ggtgtgccgg  1380
ctcccagggc cagggcggcg gcaccggcgc ctggacatca tcgtggtgcc ctatagcgag  1440
tttgcctgtg ccctgctcta cttcaccggc tctgcacact tcaaccgctc catgcgagcc  1500
ctggccaaaa ccaagggcat gagtctgtca gaacatgccc tcagcactgc tgtggtccgg  1560
aacacccatg gctgcaaggt ggggcctggc cgagtgctgc ccactcccac tgagaaggat  1620
gtcttcaggc tcttaggcct cccctaccga gaacctgctg agcgggactg gtga        1674

SEQ ID NO: 6            moltype = DNA  length = 1401
FEATURE                 Location/Qualifiers
source                  1..1401
                        mol_type = unassigned DNA
                        organism = Homo sapiens
SEQUENCE: 6
atggctctgc caaagagaag acgcgcacgg gttgggtccc cttcagggga cgcagcctcc  60
tctacacctc catctacgag atttccgggt gttgcaatat acctcgtcga gccccggatg  120
ggacgcagta gacgggcttt ccttacgggt ctcgcccgaa gtaaaggctt tcgggtgttg  180
gacgcatgtt ctagtgaagc gacccatgtc gttatggagg agacgagtgc tgaggaggct  240
gtaagctggc aagagcgccg aatggctgct gcaccacccg gctgcactcc gcctgctttg  300
ttggatatat cttggctgac cgaaagtctt ggggctggac aaccagtacc ggttgagtgc  360
```

-continued

```
cgacatcgat tggaagtagc tggtccgagg aaaggccccc tctcatcaag ccagaaggcg  420
accaatcaca acctccatat cacagagaag ctggaagttc tggccaaagc ctacagtgtt  480
cagggagaca agtggagggc cctgggctat gccaaggcca tcaatgccct caagagcttc  540
cataagcctg tcacctcgta ccaggaggcc tgcagtatcc ctgggattgg gaagcggatg  600
gctgagaaaa tcatagagat cctggagagc gggcatttgc ggaagctgga ccatatcagt  660
gagagcgtgc ctgtcttgga gctcttctcc aacatctggg gagctgggac caagactgcc  720
cagatgtggt accaacaggg cttccgaagt ctggaagaca tccgcagcca ggcctccctg  780
acaacccagc aggccatcgg cctgaagcat tacagtgact tcctggaacg tatgcccagg  840
gaggaggcta cagagattga gcagacagtc cagaaagcag cccaggcctt taactctggg  900
ctgctgtgtg tggcatgtgg ttcataccga cggggaaagg cgacctgtgg tgatgtcgac  960
gtgctcatca ctcacccaga tggccggtcc caccggggta tcttcagccg cctccttgac  1020
agtcttcggc aggaagggtt cctcacagat gacttggtga gccaagagga gaatggtcag  1080
caacagaagt acttgggggt gtgccggctc ccagggccag ggcggcggca ccggcgcctg  1140
gacatcatcg tggtgcccta tagcgagttt gcctgtgccc tgctctactt caccggctct  1200
gcacacttca accgctccat gcgagccctg gccaaaacca agggcatgag tctgtcagaa  1260
catgccctca gcactgctgt ggtccggaac acccatggct gcaaggtggg gcctggccga  1320
gtgctgccca ctcccactga gaaggatgtc ttcaggctct taggcctccc ctaccgagaa  1380
cctgctgagc gggactggtg a                                            1401

SEQ ID NO: 7            moltype = DNA  length = 1224
FEATURE                 Location/Qualifiers
source                  1..1224
                        mol_type = unassigned DNA
                        organism = Homo sapiens
SEQUENCE: 7
atggactata aggaccacga cggagactac aaggatcatg atattgatta caaagacgat  60
gacgataaga tggccccaaa gaagaagcgg aaggtcggta tccacggagt cccagcagcc  120
gctatcaaga gtatcgcttc ccgcctccgg ggttcccgtc gttttctgag cggcttcgtg  180
gctggggctg tagtgggcgc tgcgggagct gggctcgcgg ccctgcagtt cttccggagt  240
cagggcgctg agggagcgtt gacagggaag cagccggatg gatctgcaga aaaggctgtc  300
ttggaacaat ttggattccc tttaactgga acagaggcaa ggtgttacac taatcacgct  360
ttgtcttatg atcaggcaaa gcgggtgcct agatgggttc ttgaacatat ttccaaaagc  420
aagataatgg gtgatgcaga cagaaagcat tgtaaattta agcctgatcc caatatccct  480
ccaaccttca gtgccttcaa tgaagattat gttggaagtg ggtggtcacg aggacacatg  540
gctccagcag gaaataacaa attttcaagt aaagccatgg ctgaaacctt ttacctttct  600
aacattgtgc ctcaggattt tgataataat tctggatatt ggaacagaat agaaatgtac  660
tgtcgagagc tgacagaaag gtttgaagat gtttgggtgg tatctgggcc tttgacctta  720
cctcagacta gaggcgatgg aaagaaaata gttagttacc aggtgattgg cgaggacaac  780
gtggcagtcc cctcacacct ttataaggta atcctggccc gcagaagctc agtatctacc  840
gaaccactgg cgctaggggc ctttgtggta cccaatgaag ccatcggctt ccagccccag  900
ttaactgaat tccaagtgag cctccaggac ctagagaagt tgtcaggact ggtgtttttt  960
cctcatttgg atagaactag tgatatccgg aatatctgct ctgtggacac ctgtaagctc  1020
ctggatttcc aggagttcac cttgtacttg agtacaagaa agattgaagg agcccgatca  1080
gtgctcagac tggaaaagat catggaaaac ttgaagaatg cagagattga accagatgat  1140
tactttatga gtcgctatga gaagaagcta gaagaactca aagctaagga gcagtcagga  1200
acccagataa gaaagccatc ctag                                         1224

SEQ ID NO: 8            moltype = DNA  length = 981
FEATURE                 Location/Qualifiers
source                  1..981
                        mol_type = genomic DNA
                        note = Aspergillus oryzae
                        organism = unidentified
SEQUENCE: 8
atggactata aggaccacga cggagactac aaggatcatg atattgatta caaagacgat  60
gacgataaga tggccccaaa gaagaagcgg aaggtcggta tccacggagt cccagcagcc  120
cccaggctcc tgcctatatc cgccgcaacc ctcgctctgg cccaacttac ttatggctgg  180
ggcaatctgg gccatgaaac tgtcgcttac attgctcaat ctttcgtcgc gtcaagtacc  240
gagagcttct gccaaaacat attgggggac gactctactt catatttggc caacgtggca  300
acatgggcgg atacttacaa atatacggat gcgggcgaat ttagcaaacc ctatcacttt  360
atagacgcac aggataaccc accccaatca tgcggggttg actatgacag ggattgtggg  420
tccgccgggt gctctatctc agcaattcaa aactacacga acatactgct ggaaagtcct  480
aatgggagcg aggctctgaa cgcactgaaa tttgttgtcc atattatagg agatattcat  540
cagccgttgc atgacgaaaa tttggaggca ggaggaaatg gcatcgatgt gacatatgac  600
ggggagacta cgaaccttca tcacatttgg gatactaaca tgccggaaga agccgcggga  660
gggtatagct tgtccgtggc aaagacttat gcagatttgc tcaccgagag gataaaaaca  720
ggtacttact cctcaaaaaa ggatagctgg accgatggaa ttgatataaa agatccagta  780
agcacgtcta tgatttgggc ggcggatgca aacacctacg tctgtagtac ggtacttgat  840
gacggtcttg cttatattaa ttccactgac ctctccggcg aatactacga caagtcacaa  900
ccagtcttcg aagaacttat agccaaagcg ggttatagac ttgcggcttg gctggacctt  960
attgcgtccc agcccagctg a                                            981

SEQ ID NO: 9            moltype = DNA  length = 912
FEATURE                 Location/Qualifiers
source                  1..912
                        mol_type = unassigned DNA
                        note = Penicillium citrinum
                        organism = unidentified
SEQUENCE: 9
```

-continued

```
atggactata aggaccacga cggagactac aaggatcatg atattgatta caaagacgat  60
gacgataaga tggccccaaa gaagaagcgg aaggtcggta tccacggagt cccagcagcc  120
tggggtgccc tcggccatgc gacagtagcc tatgtagctc aacattatgt aagtcccgaa  180
gccgcgtctt gggcgcaagg catttgggt tcctcaagtt catcatattt ggcttcaata  240
gcttcttggg ccgatgaata ccggctgacc tccgccggca agtggagtgc tagtttgcac  300
tttattgatg ccgaagataa tccacccacg aactgcaacg tcgactatga acgggattgt  360
ggatcttccg ggtgctccat atcagctata gctaattata cacagcgagt aagtgactca  420
agtctttctt ccgaaaatca tgcggaagca ctgcgattct tggtacactt catcggggac  480
atgacacagc ctttgcacga tgaagcctac gcggtgggcg gtaataaaat aaacgttaca  540
tttgatggtt atcatgacaa cctgcacagc gattgggaca cgtatatgcc acagaaattg  600
atcggcggtc atgcgctttc agacgcagag tcctgggcaa agacgctggt tcaaaatatc  660
gaatctggaa attacaccgc gcaggccatt ggttggatca aaggcgacaa catctcagaa  720
ccaatcacaa ccgcaacgcg atgggcgtca gacgccaatg ctcttgtatg tacggtggtt  780
atgcctcacg gagctgcggc acttcagaca ggtgaccttt atccgactta ctacgactct  840
gtgatagata ctattgaact tcaaatagct aaaggaggct accggctcgc gaactggata  900
aacgagatat ag                                                      912

SEQ ID NO: 10          moltype = DNA  length = 1197
FEATURE                Location/Qualifiers
source                 1..1197
                       mol_type = unassigned DNA
                       organism = Homo sapiens
SEQUENCE: 10
atggactata aggaccacga cggagactac aaggatcatg atattgatta caaagacgat  60
gacgataaga tggccccaaa gaagaagcgg aaggtcggta tccacggagt cccagcagcc  120
aagatgaagt tatttcagac catttgcagg cagctcagga gttcaaagtt ttctgtggaa  180
tcagctgccc ttgtggcttt ctctacttcc tcttactcat gtggccggaa gaaaaaagtg  240
aacccatatg aagaagtgga ccaagaaaaa tactctaatt tagttcagtc tgtcttgtca  300
tccagaggcg tcgcccagac cccgggatcg gtggaggaag atgctttgct ctgtggaccc  360
gtgagcaagc ataagctgcc aaaccaaggt gaggacagac gagtgccaca aaactggttt  420
cctatcttca atccagagag aagtgataaa ccaaatgcaa gtgatccttc agttcctttg  480
aaaatcccct tgcaaaggaa tgtgatacca agtgtgaccc gagtccttca gcagaccatg  540
acaaaacaac aggttttctt gttggagagg tggaaacagc ggatgattct ggaactggga  600
gaagatggct ttaaagaata cacttcaagt tttcatgttt gtgatcatgt gtatatgaag  660
aacctagcca gggacgtctt tttacaaggg aaacggttcc acgaagcctt ggaaagcata  720
ctttcacccc aggaaacctt aaaagagaga gatgaaaatc tcctcaagtc tggttacatt  780
gaaagtgtcc agcatattct gaaagatgtc agtggagtgc gagctcttga aagtgctgtt  840
caacatgaaa ccttaaacta tataggtctg ctggactgtg tggctgagta tcagggcaag  900
ctctgtgtga ttgattggaa gacatcagag aaaccaaagc cttttattca aagtacattt  960
gacaacccac tgcaagttgt ggcatacatg ggtgccatga accatgatac caactacagc  1020
tttcaggttc aatgtggctt aattgtggtg gcctacaaag atggatcacc tgcccaccca  1080
catttcatgg atgcagagct ctgttcccag tactggacca agtggcttct tcgactagaa  1140
gaatatacgg aaaagaaaaa gaaccagaat attcagaaac cagaatattc agaatag     1197

SEQ ID NO: 11          moltype = DNA  length = 1854
FEATURE                Location/Qualifiers
source                 1..1854
                       mol_type = unassigned DNA
                       organism = Escherichia coli
SEQUENCE: 11
atggactata aggaccacga cggagactac aaggatcatg atattgatta caaagacgat  60
gacgataaga tggccccaaa gaagaagcgg aaggtcggta tccacggagt cccagcagcc  120
gtgaagcagc agatccaact tagacgaagg gaagtcgacg aaacagcgga ccttccggct  180
gagttgcctc cccttcttag acgattgtat gcaagtcgcg gggttcgctc tgcacaggaa  240
cttgagcgct ctgtcaaggg aatgctgccc tggcaacagt tgagtggtgt tgaaaaggcc  300
gttgagattc tctataatgc attcagggaa ggaactcgga tcatagtggt aggtgatttc  360
gacgctgatg gagcaacttc aaccgcgttg agcgtactcg ccatgcgctc tctcgggtgc  420
tcaaacattg actatttggt ccccaatcga tttgaagatg gttatggact cagcccggag  480
gtggttgacc aagcgcatgc ccgggggcgcc cagctcatcg tcactgtcga taacgggata  540
agctctcacg ccggtgtcga acacgctcgc agcctcggga ttcccgtgat tgtgactgac  600
caccaccttc cgggagatac actccccgct gctgaggcaa taatcaatcc taaccttcgg  660
gattgtaact ttccgagcaa atcactcgca ggggtagggg tcgcattcta tctcatgctg  720
gcgctcagaa cgttccttcg agatcagggg tggttcgacg agcggaacat agctatacct  780
aatttggccg aacttttgga tctcgtggcg cttggcacgg ttgcagacgt tgtccctctg  840
gacgcgaaca atcgaatttt gacatggcag ggaatgtcta ggattagagc cgggaaatgt  900
aggcctggta ttaaagctct cttggaggtg gcaaaccgag atgcccagaa gctcgcagct  960
agtgacttgg gttttgcttt gggaccccgc ctgaacgctg cagggcgcct ggatgacatg  1020
agcgtaggcg tagcacttct cttgtgcgac aatataggtg aagcgagagt acttgcaaac  1080
gaactggatg cgcttaacca gacaagaaag gaaattgagc agggcatgca gatagaggcg  1140
cttaccctgt gtgaaaagct cgaacgatct cgagacaccc ttccaggcgg actcgcgatg  1200
tatcaccctg aatggcacca gggtgtcgta ggcatcctcg cgtcccgcat aaaagaaagg  1260
ttccaccggc cagttatagc ttttgctccc gcaggtgatg gaacccttaa aggatctggg  1320
agatctatcc aggggcttca tatgcgggat gctttggagc ggcttgacac tctttaccca  1380
ggtatgatgc tcaagttcgg cggtcatgct atggctgccg gcctctcact ggaggaggat  1440
aaatttaaac tctttcaaca gaggttcggg gagcttgtga cggaatggct ggatccgtcc  1500
ttgcttcaag gcgaagtagt tagcgacgga cctctcagtc ctgcggagat gacgatggag  1560
gtagcgcaac tgctcaggga cgctgggccg tggggccaga tgttcccgga gccgttgttc  1620
gacggccatt tcaggttgct tcaacagcgc ctcgtcggag aacggcatct caaagtaatg  1680
gttgagccag tcggtggcgg ccccctgctt gatggcatcg ctttcaatgt agacactgca  1740
```

```
ctgtggcccg ataatggcgt tcgagaggtt cagcttgcct ataagctgga tattaacgag  1800
tttcgaggga accgatctct gcaaattata atagacaata tctggcccat atag        1854

SEQ ID NO: 12          moltype = DNA  length = 2814
FEATURE                Location/Qualifiers
source                 1..2814
                       mol_type = other DNA
                       note = Bacteriophage T4
                       organism = synthetic construct
SEQUENCE: 12
atggactata aggaccacga cggagactac aaggatcatg atattgatta caaagacgat  60
gacgataaga tggccccaaa gaagaagcgg aaggtcggta tccacggagt cccagcagcc  120
aaggaattct atattagtat cgagacagtg ggaaacaaca ttgtagagcg gtatatcgat  180
gaaaacggca aagaaaggac tcgagaggtc gaataccttc cgaccatgtt tcgccactgt  240
aaagaagaat ctaagtacaa agatatttac gggaagaatt gcgctcccca aaaatttccc  300
tccatgaagg atgctcgaga ctggatgaag cgcatggagg acataggtct cgaagcattg  360
gggatgaacg attttaagtt ggcttacatc tccgacactt acgggtcaga aatagtgtac  420
gataggaagt tcgttcgcgt ggcaaattgc gatatagagg tcactggaga taagttcccg  480
gacccgatga aggcggagta cgaaattgac gctataacac actatgactc aatcgacgac  540
cggttctatg tatttgacct gctcaattcc atgtacgggt ctgtaagcaa gtgggacgct  600
aaactcgcgg ctaaacttga ctgtgaagga ggggatgaag tacctcagga aatcttggac  660
agggtaatct acatgccctt tgacaatgaa cgagatatgc ttatggagta cattaatttg  720
tgggagcaaa agcgccccgc aatatttaca ggctggaaca tagaagggtt cgatgtaccg  780
tatattatga atcgggtaaa gatgatcctc ggagagagaa gcatgaaaag attttcacct  840
attggcagag tgaaatctaa gttgatacaa aacatgtatg gctcaaaaga gatctattca  900
atagatggag ttagcatact cgactacctg gatctgtata aaaagtttgc ttttaccaac  960
ttgcctagct tctcccttga aagtgtcgcc caacacgaga ccaagaaagg taagctgccg  1020
tacgatggcc cgattaataa actgcgcgag accaaccatc aaagatatat tagctacaac  1080
ataattgatg tcgaatctgt gcaagccatt gataagataa ggggctttat cgaccttgtc  1140
ctgtcaatgt cctattacgc caaaatgccg ttctcaggtg taatgtcacc cataaagacg  1200
tgggatgcga tcatcttcaa ttctctcaag ggagagcaca aggtgatccc ccaacagggg  1260
tcccacgtaa agcagtcctt cccgggagct tttgtctttg agccaaagcc gatcgcccga  1320
aggtatatca tgtctttcga ccttacgtca ctttaccctt caattattcg acaagtgaat  1380
atatcacccg agactatccg ggccagtttt aaggtacacc caatccatga gtacatagcc  1440
ggtacagccc caaaacccag tgacgaatac tcttgcagcc ctaatgggtg gatgtacgac  1500
aaacaccagg agggcataat cccaaaggaa atcgcgaaag tatttttcca acggaaagac  1560
tggaagaaaa agatgttcgc ggaggaaatg aacgccgagg ctattaaaaa aatcattatg  1620
aagggagcgg gtagctgttc taccaagcca gaggtagagc gctacgtcaa attcagtgat  1680
gacttcctta atgagctgag taactacaca gagtctgtac tgaactcact gattgaggaa  1740
tgtgaaaaag ccgcaacact tgctaatacc aatcaactga atcggaagat cctgattaat  1800
tcactgtatg gcgccttggg caacattcat ttcagatact acgacctcag gaatgccacg  1860
gccattacaa ttttcggtca ggtcgggatc cagtggatcg cccgaaaaat caacgagtac  1920
ctcaataaag tgtgtggtac caatgacgag gattttatcg cagcaggcga taccgatagc  1980
gtgtatgttt gcgtcgacaa ggtcattgaa aaggtagggc tggatcggtt taaggagcag  2040
aatgatcttg tcgagtttat gaaccagttt ggtaaaaaaa agatggaacc gatgatagat  2100
gtagcgtacc gagaactttg tgactacatg aataatcgcg agcacttgat gcacatggac  2160
agggaagcga tttcatgccc cccactcggt tcaaagggcg tagggggttt ctggaaagct  2220
aagaaacggt acgccctcaa cgtctatgac atggaagaca agaggttcgc ggaacctcat  2280
ttgaagataa tggggatgga gacgcaacag tcctcaactc caaaggctgt gcaagaggct  2340
ctggaagaaa gcatacgacg catactccag gagggggaag agagtgttca ggagtattat  2400
aaaaactttg aaaaggagta ccgccagctt gactacaagg taatcgcgga ggttaagact  2460
gcgaatgata tcgccaaata tgatgataaa ggatggcccg gtttcaaatg ccctttccat  2520
atacgagggg tcctcaccta ccgccgcgcc gtgtctggtc tgggggtcgc accaattctc  2580
gacggaaata aggttatggt actcccactc cgcgagggga atccgtttgg tgacaaatgc  2640
atcgcctggc cgtctggtac ggagctcccc aaggaaatac gcagcgacgt cctcagttgg  2700
atcgaccact ccacactgtt tcagaagtca ttcgttaaac ctctggccgg gatgtgtgaa  2760
tccgcgggta tggactacga ggagaaagct tcattggact ttcttttcgg ttga        2814

SEQ ID NO: 13          moltype = DNA  length = 2814
FEATURE                Location/Qualifiers
source                 1..2814
                       mol_type = other DNA
                       note = Bacteriophage T4
                       organism = synthetic construct
SEQUENCE: 13
atggactata aggaccacga cggagactac aaggatcatg atattgatta caaagacgat  60
gacgataaga tggccccaaa gaagaagcgg aaggtcggta tccacggagt cccagcagcc  120
aaggaattct atattagtat cgagacagtg ggaaacaaca ttgtagagcg gtatatcgat  180
gaaaacggca aagaaaggac tcgagaggtc gaataccttc cgaccatgtt tcgccactgt  240
aaagaagaat ctaagtacaa agatatttac gggaagaatt gcgctcccca aaaatttccc  300
tccatgaagg atgctcgaga ctggatgaag cgcatggagg acataggtct cgaagcattg  360
gggatgaacg attttaagtt ggcttacatc tccgacactt acgggtcaga aatagtgtac  420
gataggaagt tcgttcgcgt ggcaaattgc gatatagagg tcactggaga taagttcccg  480
gacccgatga aggcggagta cgaaattgac gctataacac actatgactc aatcgacgac  540
cggttctatg tatttgacct gctcaattcc atgtacgggt ctgtaagcaa gtgggacgct  600
aaactcgcgg ctaaacttga ctgtgaagga ggggatgaag tacctcagga aatcttggac  660
agggtaatct acatgccctt tgacaatgaa cgagatatgc ttatggagta cattaatttg  720
tgggagcaaa agcgccccgc aatatttaca ggctggaaca tagaagggtt cgatgtaccg  780
tatattatga atcgggtaaa gatgatcctc ggagagagaa gcatgaaaag attttcacct  840
```

-continued

```
attggcagag tgaaatctaa gttgatacaa aacatgtatg gctcaaaaga gatctattca  900
atagatggag ttagcatact cgactacctg gatctgtata aaaagtttgc ttttaccaac  960
ttgcctagct tctcccttga aagtgtcgcc caacacgaga ccaagaaagg taagctgccg  1020
tacgatggcc cgattaataa actgcgcgag accaaccatc aaagatatat tagcgccaac  1080
ataattgatg tcgaatctgt gcaagccatt gataagataa ggggctttat cgaccttgtc  1140
ctgtcaatgt cctattacgc caaaatgccg ttctcaggtg taatgtcacc cataaagacg  1200
tgggatgcga tcatcttcaa ttctctcaag ggagagcaca aggtgatccc ccaacagggg  1260
tcccacgtaa agcagtcctt cccgggagct tttgtctttg agccaaagcc gatcgcccga  1320
aggtatatca tgtctttcga ccttacgtca ctttaccctt caattattcg acaagtgaat  1380
atatcacccg agactatccg gggccagttt aaggtacacc caatccatga gtacatagcc  1440
ggtacagccc caaaacccag tgacgaatac tcttgcagcc ctaatgggtg gatgtacgac  1500
aaacaccagg agggcataat cccaaaggaa atcgcgaaag tatttttcca acggaaagac  1560
tggaagaaaa agatgttcgc ggaggaaatg aacgccgagg ctattaaaaa aatcattatg  1620
aagggagcgg gtagctgttc taccaagcca gaggtagagc gctacgtcaa attcagtgat  1680
gacttcctta atgagctgag taactacaca gagtctgtac tgaactcact gattgaggaa  1740
tgtgaaaaag ccgcaacact tgctaatacc aatcaactga atcggaagat cctgattaat  1800
tcactgtatg gcgccttggg caacattcat ttcagatact acgacctcag gaatgccacg  1860
gccattacaa ttttcggtca ggtcgggatc cagtggatcg cccgaaaaat caacgagtac  1920
ctcaataaag tgtgtggtac caatgacgag gattttatcg cagcaggcga taccgatagc  1980
gtgtatgttt gcgtcgacaa ggtcattgaa aaggtagggc tggatcggtt taaggagcag  2040
aatgatcttg tcgagtttat gaaccagttt ggtaaaaaaa agatggaacc gatgatagat  2100
gtagcgtacc gagaactttg tgactacatg aataatcgcg agcacttgat gcacatggac  2160
agggaagcga tttcatgccc cccactcggt tcaaagggcg tagggggttt ctggaaagct  2220
aagaaacggt acgccctcaa cgtctatgac atggaagaca agaggttcgc ggaacctcat  2280
ttgaagataa tggggatgga gacgcaacag tcctcaactc caaaggctgt gcaagaggct  2340
ctggaagaaa gcatacgacg catactccag gagggggaag agagtgttca ggagtattat  2400
aaaaactttg aaaaggagta ccgccagctt gactacaagg taatcgcgga ggttaagact  2460
gcgaatgata tcgccaaata tgatgataaa ggatggcccg gtttcaaatg ccctttccat  2520
atacgagggg tcctcaccta ccgccgcgcc gtgtctggtc tgggggtcgc accaattctc  2580
gacggaaata aggttatggt actcccactc cgcgagggga atccgtttgg tgacaaatgc  2640
atcgcctggc cgtctggtac ggagctcccc aaggaaatac gcagcgacgt cctcagttgg  2700
atcgaccact ccacactgtt tcagaagtca ttcgttaaac ctctggccgg gatgtgtgaa  2760
tccgcgggta tggactacga ggagaaagct tcattggact ttcttttcgg ttga        2814
```

```
SEQ ID NO: 14          moltype = DNA  length = 2814
FEATURE                Location/Qualifiers
source                 1..2814
                       mol_type = other DNA
                       note = Bacteriophage T4
                       organism = synthetic construct
SEQUENCE: 14
atggactata aggaccacga cggagactac aaggatcatg atattgatta caaagacgat  60
gacgataaga tggccccaaa gaagaagcgg aaggtcggta tccacggagt cccagcagcc  120
aaggaattct atattagtat cgagacagtg ggaaacaaca ttgtagagcg gtatatcgat  180
gaaaacggca aagaaaggac tcgagaggtc gaataccttc cgaccatgtt tcgccactgt  240
aaagaagaat ctaagtacaa agatatttac gggaagaatt gcgctcccca aaaatttccc  300
tccatgaagg atgctcgaga ctggatgaag cgcatggagg acataggtct cgaagcattg  360
gggatgaacg attttaagtt ggcttacatc tccgacactt acgggtcaga aatagtgtac  420
gataggaagt tcgttcgcgt ggcaaattgc gatatagagg tcactggaga taagttcccg  480
gacccgatga aggcggagta cgaaattgac gctataacac actatgactc aatcgacgac  540
cggttctatg tatttgacct gctcaattcc atgtacgggt ctgtaagcaa gtgggacgct  600
aaactcgcgg ctaaacttga ctgtgaagga ggggatgaag tacctcagga aatcttggac  660
agggtaatct acatgccctt tgacaatgaa cgagatatgc ttatggagta cattaatttg  720
tgggagcaaa agcgccccgc aatatttaca ggctggaaca tagaagggtt cgatgtaccg  780
tatattatga atcgggtaaa gatgatcctc ggagagagaa gcatgaaaag attttcacct  840
attggcagag tgaaatctaa gttgatacaa aacatgtatg gctcaaaaga gatctattca  900
atagatggag ttagcatact cgactacctg gatctgtata aaaagtttgc ttttaccaac  960
ttgcctagct tctcccttga aagtgtcgcc caacacgaga ccaagaaagg taagctgccg  1020
tacgatggcc cgattaataa actgcgcgag accaaccatc aaagatatat tagctacaac  1080
ataattgatg tcgaatctgt gcaagccatt gataagataa ggggctttat cgaccttgtc  1140
ctgtcaatgt cctattacgc caaaatgccg ttctcaggtg taatgtcacc cataaagacg  1200
tgggatgcga tcatcttcaa ttctctcaag ggagagcaca aggtgatccc ccaacagggg  1260
tcccacgtaa agcagtcctt cccgggagct tttgtctttg agccaaagcc gatcgcccga  1320
aggtatatca tgtctttcga ccttacgtca ctttaccctt caattattcg acaagtgaat  1380
atatcacccg agactatccg gggccagttt aaggtacacc caatccatga gtacatagcc  1440
ggtacagccc caaaacccag tgacgaatac tcttgcagcc ctaatgggtg gatgtacgac  1500
aaacaccagg agggcataat cccaaaggaa atcgcgaaag tatttttcca acggaaagac  1560
tggaagaaaa agatgttcgc ggaggaaatg aacgccgagg ctattaaaaa aatcattatg  1620
aagggagcgg gtagctgttc taccaagcca gaggtagagc gctacgtcaa attcagtgat  1680
gacttcctta atgagctgag taactacaca gagtctgtac tgaactcact gattgaggaa  1740
tgtgaaaaag ccgcaacact tgctaatacc aatcaactga atcggaagat cctgattaat  1800
tcactgtatg gcgccttggg caacattcat ttcagatact acgacctcag gaatgccacg  1860
gccattacaa ttttcggtca ggtcgggatc cagtggatcg cccgaaaaat caacgagtac  1920
ctcaataaag tgtgtggtac caatgacgag gattttatcg cagcaggcga taccgatagc  1980
gtgtatgttt gcgtcgacaa ggtcattgaa aaggtagggc tggatcggtt taaggagcag  2040
aatgatcttg tcgagtttat gaaccagttt ggtaaaaaaa agatggaacc gatgatagat  2100
gtagcgtacc gagaactttg tgactacatg aataatcgcg agcacttgat gcacatggac  2160
agggaagcga tttcatgccc cccactcggt tcaaagggcg tagggggttt ctggaaagct  2220
aagaaacggt acgccctcaa cgtctatgac atggaagaca agaggttcgc ggaacctcat  2280
```

-continued

```
ttgaagataa tggggatgga gacgcaacag tcctcaactc caaaggtggt gcaagaggct  2340
ctggaagaaa gcatacgacg catactccag gagggggaag agagtgttca ggagtattat  2400
aaaaactttg aaaaggagta ccgccagctt gactacaagg taatcgcgga ggttaagact  2460
gcgaatgata tcgccaaata tgatgataaa ggatggcccg gtttcaaatg ccctttccat  2520
atacgagggg tcctcaccta ccgccgcgcc gtgtctggtc tgggggtcgc accaattctc  2580
gacggaaata aggttatggt actcccactc cgcgagggga atccgtttgg tgacaaatgc  2640
atcgcctggc cgtctggtac ggagctcccc aaggaaatac gcagcgacgt cctcagttgg  2700
atcgaccact ccacactgtt tcagaagtca ttcgttaaac ctctggccgg gatgtgtgaa  2760
tccgcgggta tggactacga ggagaaagct tcattggact ttcttttcgg ttga        2814
```

```
SEQ ID NO: 15          moltype = DNA  length = 960
FEATURE                Location/Qualifiers
source                 1..960
                       mol_type = unassigned DNA
                       organism = Homo sapiens
SEQUENCE: 15
atggctccga agcgtgggaa aaagggagcg gtggcggaag acggggatga gctcaggaca  60
gagccagagg ccaagaagag taagacggcc gcaaagaaaa atgacaaaga ggcagcagga  120
gagggcccag ccctgtatga ggaccccca gatcagaaaa cctcacccag tggcaaacct  180
gccacactca agatctgctc ttggaatgtg gatgggcttc gagcctggat taagaagaaa  240
ggattagatt gggtaaagga agaagcccca gatatactgt gccttcaaga gaccaaatgt  300
tcagagaaca aactaccagc tgaacttcag gagctgcctg gactctctca tcaatactgg  360
tcagctcctt cggacaagga agggtacagt ggcgtgggcc tgctttcccg ccagtgccca  420
ctcaaagttt cttacggcat aggcgatgag gagcatgatc aggaaggccg ggtgattgtg  480
gctgaatttg actcgtttgt gctggtaaca gcatatgtac ctaatgcagg ccgaggtctg  540
gtacgactgg agtaccggca gcgctgggat gaagcctttc gcaagttcct gaagggcctg  600
gcttcccgaa agccccttgt gctgtgtgga gacctcaatg tggcacatga agaaattgac  660
cttcgcaacc ccaaggggaa caaaaagaat gctggcttca cgccacaaga gcgccaaggc  720
ttcgggggaat tactgcaggc tgtgccactg gctgacagct ttaggcacct ctaccccaac  780
acaccctatg cctacacctt ttggacttat atgatgaatg ctcgatccaa gaatgttggt  840
tggcgccttg attacttttt gttgtcccac tctctgttac ctgcattgtg tgacagcaag  900
atccgttcca aggccctcgg cagtgatcac tgtcctatca ccctatacct agcactgtga  960
```

```
SEQ ID NO: 16          moltype = DNA  length = 894
FEATURE                Location/Qualifiers
source                 1..894
                       mol_type = unassigned DNA
                       organism = Homo sapiens
SEQUENCE: 16
atggtgcggg gttctggcaa gcccatcccc aaccccctgc tgggcctgga cagcaccgga  60
aagtcttacc caactgtgag tgctgattac caggacgccg ttgagaaggc gaagaagaag  120
ctcagaggct tcatcgctga gaagagatgc gctcctctaa tgctccgttt ggcattccac  180
tctgctggaa cctttgacaa gggcacgaag accggtggac ccttcggaac catcaagcac  240
cctgccgaac tggctcacag cgctaacaac ggtcttgaca tcgctgttag gcttttggag  300
ccactcaagg cggagttccc tattttgagc tacgccgatt tctaccagtt ggctggcgtt  360
gttgccgttg aggtcacggg tggacctaag gttccattcc accctggaag agaggacaag  420
cctgagccac caccagaggg tcgcttgcct gatcccacta agggttctga ccatttgaga  480
gatgtgtttg gcaaagctat ggggcttact gaccaagata tcgttgctct atctgggggt  540
cacactattg gagctgcaca caaggagcgt tctggatttg agggtccctg gacctctaat  600
cctcttattt tcgacaactc atacttcacg gagttgttga gtggtgagaa ggaaggtctc  660
cttcagctac cttctgacaa ggctcttttg tctgaccctg tattccgccc tctcgttgat  720
aaatatgcag cggacgaaga tgccttcttt gctgattacg ctgaggctca ccaaaagctt  780
tccgagcttg ggtttgctga tgccgaattc agcagggccg accccaagaa gaagaggaag  840
gtggacccca agaagaagag gaaggtggac cccaagaaga agaggaaggt gtga        894
```

```
SEQ ID NO: 17          moltype = DNA  length = 1005
FEATURE                Location/Qualifiers
source                 1..1005
                       mol_type = unassigned DNA
                       organism = Homo sapiens
SEQUENCE: 17
atggagagaa aaataagcag aatccacctt gtttctgaac ccagtataac tcattttcta  60
caagtatctt gggagaaaac actggaatct ggttttgtta ttacacttac tgatggtcat  120
tcagcatgga ctgggacagt ttctgaatca gagatttccc aagaagctga tgacatggca  180
atggaaaaag ggaaatatgt tggtgaactg agaaaagcat tgttgtcagg agcaggacca  240
gctgatgtat acacgtttaa tttttctaaa gagtcttgtt atttcttctt tgagaaaaac  300
ctgaaagatg tctcattcag acttggttcc ttcaacctag agaaagttga aaacccagct  360
gaagtcatta gagaacttat ttgttattgc ttggacacca ttgcagaaaa tcaagccaaa  420
aatgagcacc tgcagaaaga aaatgaaagg cttctgagag attggaatga tgttcaagga  480
cgatttgaaa aatgtgtgag tgctaaggaa gctttggaga ctgatcttta taagcggttt  540
attctggtgt tgaatgagaa gaaaacaaaa atcagaagtt tgcataataa attattaaat  600
gcagctcaag aacgagaaaa ggacatcaaa caagaagggg aaactgcaat ctgttctgaa  660
atgactgctg accgagatcc agtctatgat gagagtactg atgaggaaag tgaaaaccaa  720
actgatctct ctgggttggc ttcagctgct gtaagtaaag atgattccat tatttcaagt  780
cttgatgtca ctgatattgc accaagtaga aaaaggagac agcgaatgca aagaaatctt  840
gggacagaac ctaaaatggc tcctcaggag aatcagcttc aagaaaagga aaagcctgat  900
tcttcactac ctgagacgtc taaaaaggag cacatctcag ctgaaaacat gtctttagaa  960
actctgagaa acagcagccc agaagacctc tttgatgaga tttaa                  1005
```

-continued

```
SEQ ID NO: 18          moltype = DNA  length = 5289
FEATURE                Location/Qualifiers
source                 1..5289
                       mol_type = unassigned DNA
                       organism = Homo sapiens
SEQUENCE: 18
atggacgcac aaacacgacg acgtgagcgt cgcgctgaga aacaagctca atggaaagct  60
gcaaacggtg gatctcctcc acatatggct tacccatacg atgttccaga ttacgctcct  120
ccatctcgag ctcaagcttc gaattctgca gtcgacggta ccgcgggcat gggagtcccc  180
aagttttaca gatggatctc agagcggtat ccctgtctca gcgaagtggt gaaagagcat  240
cagattcctg aatttgacaa cttgtacctg gatatgaatg gaattataca tcagtgctcc  300
catcctaatg atgatgatgt tcactttaga atttcagatg ataaaatctt tactgatatt  360
tttcactacc tggaggtgtt gtttcgcatt attaaaccca ggaaagtgtt ctttatggct  420
gtagatggtg tggctcctcg agcaaaaatg aaccagcagc gtgggaggcg ttttaggtca  480
gcaaaggagg cagaagacaa aattaaaaag gcaatagaga agggagaaac tcttcctaca  540
gaggccagat ttgattccaa ctgtatcaca ccaggaactg aatttatggc caggttacat  600
gaacatctga agtattttgt aaatatgaaa atttccacag acaagtcatg gcaaggagtt  660
accatctact tctcaggcca tgagactcct ggagaaggag agcataaaat catggaattt  720
atcagatccg agaaagcaaa gccagatcat gatccaaaca ccagacactg tctttatggt  780
ttagatgctg acttgattat gcttggatta acaagtcatg aggcacattt ttctctctta  840
agagaagaag ttcgatttgg tggcaaaaaa acacaacggg tatgtgctcc agaagaaact  900
acatttcacc ttctacactt gtctttaatg agagagtata ttgactatga gttttcagta  960
ttaaaagaaa agatcacatt taaatatgat attgaaagga taatagatga ttggattttg  1020
atggggtttc ttgttggtaa tgattttatc cctcatctac ctcatttaca tattaatcat  1080
gatgcactgc ctcttcttta tggaacatat gttaccatcc tgccagaact tgggggttat  1140
attaatgaaa gtgggcacct caacttacct cgatttgaga aatacettgt gaaactatca  1200
gattttgatc gggagcactt cagtgaagtt tttgtggacc taaaatggtt tgaaagcaaa  1260
gttggtaaca agtacctcaa tgaagcagca ggtgtcgcag cagaagaagc caggaactac  1320
aaggaaaaga aaaagttaaa gggccaggaa aattctctgt gttggactgc tttagacaaa  1380
aatgaaggcg aaatgataac ttctaaggat aatttagaag atgagactga agatgatgac  1440
ctatttgaaa ctgagtttag acaatataaa agaacatatt acatgacgaa gatgggggtt  1500
gacgtagtat ctgatgactt tctggctgat caagctgcat gttatgttca ggcaatacag  1560
tggattttgc actattacta tcatggagtt cagtcctgga gctggtatta tccttatcat  1620
tatgcgcctt tcctgtctga tatacacaac atcagtacac tcaaaatcca ttttgaacta  1680
ggaaaacctt ttaagccatt tgaacagctt cttgctgtac ttccagcagc cagcaaaaat  1740
ttacttcctg catgctacca gcatttgatg accaatgaag actcaccaat tatagaatat  1800
tacccacctg attttaaaac tgacctaaat gggaaacaac aggaatggga agctgtggtg  1860
ttaatccctt ttattgatga gaagcgatta ttggaagcca tggagacatg taaccactcc  1920
ctcaaaaagg aagagaggaa aagaaaccaa catagtgagt gcctaatgtg ctggtatgat  1980
agagacacag agtttatcta tccttctcca tggccagaaa agttccctgc catagaacga  2040
tgttgtacaa ggtataaaat aatatcctta gatgcttggc gtgtagacat aaacaaaaac  2100
aaaataacca gaattgacca gaaagcatta tatttctgtg gatttcctac tctgaaacac  2160
atcagacaca aattttttttt gaagaaaagt ggtgttcaag tattccagca aagcagtcgt  2220
ggagaaaaca tgatgttgga aatcttagtg gatgcagaat cagatgaact taccgtagaa  2280
aatgtagctt catcagtgct tggaaaatct gtctttgtta attggcctca ccttgaggaa  2340
gctagagtcg tggctgtatc agatggagaa actaagtttt acttggaaga acctccagga  2400
acacagaagc tttattcagg aagaactgcc ccaccatcta aagtggttca tcttggagat  2460
aaagaacaat ctaactgggc aaaagaagta caaggaattt cagaacacta cctgagaaga  2520
aaaggaataa taataaatga aacatctgca gttgtgtatg ctcagttact cacaggtcgt  2580
aaatatcaaa taaatcaaaa tggtgaagtt cgtctagaga aacagtggtc aaaacaagtt  2640
gttccttttg tttatcaaac tattgtcaag gacatccgag ctttcgactc ccgtttctcc  2700
aatatcaaaa cattggatga tttgtttcct ctgagaagta tggtctttat gctgggaact  2760
ccctattatg gctgcactgg agaagttcag gattcaggtg atgtgattac agaaggtagg  2820
attcgtgtga ttttcagcat tccatgtgaa cccaatcttg atgctttaat acagaaccag  2880
cataaatatt ctataaagta caacccagga tatgtgttgg ccagtcgcct tggagtgagt  2940
ggatacettg tttcaaggtt tacaggaagt atttttattg gaagaggatc taggagaaac  3000
cctcatggag accataaagc aaatgtgggt ttaaatctca aattcaacaa gaaaaatgag  3060
gaggtacctg gatatactaa gaaagttgga agtgaatgga tgtattcatc tgcagcagaa  3120
caacttctgg cagagtactt agagagagct ccagaactat ttagttatat agccaaaaat  3180
agccaagagg atgtgttcta tgaagatgac atttggcctg gagaaaatga gaatggtgct  3240
gaaaaagttc aagaaattat tacttggcta aaaggacatc ctgtcagtac tttatctcgt  3300
tcttcttgtg atttacaaat tctggatgca gctattgttg agaaaattga ggaagaagtc  3360
gaaaagtgca agcaaagaaa gaataataag aaggtgcgag taacagtgaa accccatttg  3420
ctatacagac ctttagaaca gcaacatgga gtcattcctg atcgggatgc agaatttttgt  3480
ctttttgacc gtgttgtaaa tgtgagagaa aacttctcag ttccagttgg ccttcgaggc  3540
accatcatag gaataaaagg agctaataga gaagccgatg tactatttga agtattattt  3600
gatgaagaat ttcctggagg gttaacaata agatgctcac ctggtagagg ttatcgactg  3660
ccaacaagtg ccttggtgaa cctttctcat gggagtcgct ctgaaactgg aaatcagaag  3720
ttgacagcca tcgtaaaacc acaaccagct gtacatcaac atagctcaag ttcatcagtt  3780
tcctctgggc atttgggagc cctcaaccat tcccctcaat cactttttgt tcctactcaa  3840
gtacctacta aagatgatga tgaattctgc aacatttggc agtccttaca gggatctgga  3900
aagatgcaat actttcagcc aactatacaa gagaagggtg cagttctacc tcaagaaata  3960
agccaagtaa atcaacatca taaatctggc tttaatgaca acagtgttaa atatcagcaa  4020
agaaaacatg accctcacag aaaatttaaa gaagagtgta agagtcctaa agctgagtgt  4080
tggtcccaaa aaatgtccaa taagcagcct aactctggaa ttgagaactt tttagcatct  4140
ttgaatatct ccaaagaaaa tgaagtacag tcatctcatc atggggagcc tccaagtgaa  4200
gagcatttgt caccacagtc atttgccatg ggaacacgga tgcttaaaga aattctaaaa  4260
attgatggct ctaacactgt ggaccataag aatgaaatca aacagattgc taatgaaatc  4320
cctgtttcct ctaacagaag agatgaatat ggattaccct ctcagcctaa acaaaataag  4380
```

-continued

```
aaattagcat cttatatgaa caagcctcac agtgctaatg agtaccataa tgttcagtct  4440
atggacaata tgtgttggcc tgcccccagc cagatccctc ctgtatccac accagtaact  4500
gaactttctc gaatttgttc ccttgttgga atgccacaac ctgatttctc ctttcttagg  4560
atgccacaga caatgaccgt ttgccaagta aaattatcta atggcttact ggtacatggg  4620
ccacagtgcc actctgaaaa tgaagccaaa gagaaagctg cacttttgc tttacaacag  4680
ttgggctcct taggcatgaa tttccctttg ccttcacaag tatttgcaaa ttatccttca  4740
gctgtaccac ctggaaccat tcctccagcc tttcccccac ctactggctg ggatcactat  4800
ggaagcaact atgcattggg ggcagctaat ataatgcctt cgtcgtctca tctctttggc  4860
tcaatgccat ggggaccatc ggtgccagtt cctgggaagc ccttccatca tactttatat  4920
tctgggacca tgcccatggc tgggggaata ccagggggtg tgcacaatca gtttatacct  4980
ctgcaggtta ctaaaaaaag ggttgcaaac aaaaagaact ttgagaataa ggaagcccag  5040
agttctcaag ccactccagt tcagactagc cagccagatt cttccaacat tgtcaaagta  5100
agtccacggg agagctcatc agcttctttg aagtcctctc cgattgctca acctgcatct  5160
tcttttcaag ttgaaactgc ctctcaaggc catagtatat ctcaccataa gtcaacacca  5220
atctcttctt caagaagaaa atcaagaaaa ctggctgtta attttggtgt ttctaaacct  5280
tctgagtaa                                                          5289

SEQ ID NO: 19          moltype = DNA  length = 3183
FEATURE                Location/Qualifiers
source                 1..3183
                       mol_type = unassigned DNA
                       organism = Homo sapiens
SEQUENCE: 19
atggagcagc tgaacgaact ggagctgctg atggagaaga gtttttggga ggaggcggag  60
ctgccggcgg agctatttca gaagaaagtg gtagcttcct ttccaagaac agttctgagc  120
acaggaatgg ataaccggta cctggtgttg gcagtcaata ctgtacagaa caaagaggga  180
aactgtgaaa agcgcctggt catcactgct tcacagtcac tagaaaataa agaactatgc  240
atccttagga atgactggtg ttctgttcca gtagagccag gagatatcat tcatttggag  300
ggagactgca catctgacac ttggataata gataaagatt ttggatattt gattctgtat  360
ccagacatgc tgatttctgg caccagcata gccagtagta ttcgatgtat gagaagagct  420
gtcctgagtg aaacttttag gagctctgat ccagccacac gccaaatgct aattggtacg  480
gttctccatg aggtgtttca aaaagccata aataatagct ttgccccaga aaagctacaa  540
gaacttgctt ttcaaacaat tcaagaaata agacatttga aggaaatgta ccgcttaaat  600
ctaagtcaag atgaaataaa acaagaagta gaggactatc ttccttcgtt ttgtaaatgg  660
gcaggagatt tcatgcataa aaacacttcg actgacttcc ctcagatgca gctctctctg  720
ccaagtgata atagtaagga taattcaaca tgtaacattg aagtcgtgaa accaatggat  780
attgaagaaa gcatttggtc ccctaggttt ggattgaaag gcaaaataga tgttacagtt  840
ggtgtgaaaa tacatcgagg gtataaaaca aaatacaaga taatgccgct ggaacttaaa  900
actggcaaag aatcaaattc tattgaacac cgtagtcagg ttgttctgta cactctacta  960
agccaagaga gaagagctga tccagaggct ggcttgcttc tctacctcaa gactggtcag  1020
atgtaccctg tgcctgccaa ccatctagat aaaagagaat tattaaagct aagaaaccag  1080
atggcattct cattgtttca ccgtattagc aaatctgcta ctagacagaa gacacagctt  1140
gcttctttgc cacaaataat tgaggaagag aaaacttgta aatattgttc acaaattggc  1200
aattgtgctc tttatagcag agcagttgaa caacagatgg attgtagttc agtcccaatt  1260
gtgatgctgc ccaaaataga agaagaaacc cagcatctga agcaaacaca cttagaatat  1320
ttcagccttt ggtgtctaat gttaaccctg gagtcacaat cgaaggataa taaaaagaat  1380
caccaaaata tctggctaat gcctgcttcg gaaatggaga agagtggcag ttgcattgga  1440
aacctgatta gaatggaaca tgtaaagata gtttgtgatg ggcaatattt acataatttc  1500
caatgtaaac atggtgccat acctgtcaca aatctaatgg caggtgacag agttattgta  1560
agtggagaag aaaggtcact gtttgctttg tctagaggat atgtgaagga gattaacatg  1620
acaacagtaa cttgtttatt agacagaaac ttgtcggtcc ttccagaatc aactttgttc  1680
agattagacc aagaagaaaa aaattgtgat atagataccc cattaggaaa tctttccaaa  1740
ttgatggaaa acacgtttgt cagcaaaaaa cttcgagatt taattattga ctttcgtgaa  1800
cctcagttta tatcctacct tagttctgtt cttccacatg atgcaaagga tacagttgcc  1860
tgcattctaa agggtttgaa taagcctcag aggcaagcga tgaaaaaggt acttctttca  1920
aaagactaca cactcatcgt gggtatgcct gggacaggaa aaacaactac gatatgtact  1980
ctcgtaagaa ttctctacgc ctgtggtttt agcgttttgt tgaccagcta tacacactct  2040
gctgttgaca atattctttt gaagttagcc aagtttaaaa taggattttt gcgtttgggt  2100
cagattcaga aggttcatcc agctatccag caatttacag agcaagaaat ttgcagatca  2160
aagtccatta aatccttagc tcttctagaa gaactctaca atagtcaact tatagttgca  2220
acaacatgta tgggaataaa ccatccaata ttttcccgta aaatttttga tttttgtatt  2280
gtggatgaag cctctcaaat tagccaacca atttgtctgg gcccccttttt tttttcacgg  2340
agatttgtgt tagtggggga ccatcagcag cttcctcccc tggtgctaaa ccgtgaagca  2400
agagctcttg gcatgagtga aagcttattc aagaggctgg agcagaataa gagtgctgtt  2460
gtacagttaa ccgtgcagta cagaatgaac agtaaaatta tgtccttaag taataagctg  2520
acctatgagg gcaagctgga gtgtggatca gacaaagtgg ccaatgcagt gataaaccta  2580
cgtcacttta aagatgtgaa gctggaactg gaattttatg ctgactattc tgataatcct  2640
tggttgatgg gagtatttga acccaacaat cctgtttgtt tccttaatac agacaaggtt  2700
ccagcgccag aacaagttga aaaaggtggt gtgagcaatg taacagaagc caaactcata  2760
gttttcctaa cctccatttt tgttaaggct ggatgcagtc cctctgatat tggtattatt  2820
gcaccgtaca ggcagcaatt aaagatcatc aatgatttat tggcacgttc tattgggatg  2880
gtcgaagtta atacagtaga caaataccaa ggaagggaca aaagtattgt cctagtatct  2940
tttgttagaa gtaataagga tggaactgtt ggtgaactct tgaaagattg gcgacgtctt  3000
aatgttgcta taaccagagc caaacataaa ctgattcttc tggggtgtgt gccctcacta  3060
aattgctatc ctcctttgga gaagctgctt aatcatttaa actcagaaaa attaatcatt  3120
gatcttccat caagagaaca tgaaagtctt tgccacatat tgggtgactt tcaaagagaa  3180
taa                                                                3183

SEQ ID NO: 20          moltype = DNA  length = 7857
```

```
FEATURE                Location/Qualifiers
source                 1..7857
                       mol_type = unassigned DNA
                       organism = Homo sapiens
SEQUENCE: 20
atggaacaaa agttgatttc tgaagaagat ttgttaagaa agagagggat cctgaatctt  60
ctgcgtcgga gtgggaaacg gcggcgttca gaatcaggct cagattcgtt ctcgggaagc  120
ggcggtgaca gcagtgccag cccccagttc ctctccgggt ccgtgctgag cccgccgccc  180
ggccttggtc gctgcctgaa ggccgcagct gcaggagaat gcaagcctac agttcctgac  240
tacgaaatag acaagctact attggcaaac tggggacttc ctaaagcagt tctggaaaaa  300
taccacagtt ttggtgtaaa aaagatgttt gaatggcagg cagagtgcct tttgcttgga  360
caagtcctgg aaggaaagaa tttagtttat tcagctccta caagtgctgg gaagactctt  420
gtggcagaat tacttatttt gaagcgggtt ttggaaatgc ggaagaaagc tttgtttatt  480
cttccctttg tttctgtggc taaagagaag aaatactacc tccagagtct gtttcaggaa  540
gtaggaataa aagtagacgg ttatatgggc agcacctctc catcaaggca tttctcttca  600
ttggatattg cagtctgcac aattgagaga gccaatggtc tgatcaatcg cctcatagag  660
gaaaataaga tggatctgtt aggaatggtg gttgtggatg aattacatat gctgggagac  720
tctcaccgag ggtatctgct ggaacttttg ctgaccaaga tttgctatat tactcggaaa  780
tcagcatctt gtcaggcaga tctagccagt tctctgtcta atgctgtgca aatcgttggc  840
atgagtgcta cccttcctaa tttggagctt gtggcttcct ggttgaatgc tgaactctac  900
cataccgact ttcgccctgt accgcttttg gagtcagtaa aagttggaaa ttccatatat  960
gactcttcaa tgaaacttgt gagggaattt gagcccatgc ttcaagtgaa gggagatgag  1020
gaccatgttg ttagcttatg ttatgagacg atttgtgata accattcagt attacttttt  1080
tgtccatcaa agaaatggtg tgagaagctg gcagatatca ttgctcgaga gttttataat  1140
ctacatcatc aagctgaggg attggtgaaa ccctctgaat gcccaccagt aattctggaa  1200
caaaaagaac tcctggaagt gatggatcag ttaagacggt tgccttcagg actggactct  1260
gtattacaga aaactgtacc atggggagta gcatttcatc atgcaggtct tacttttgag  1320
gagagggata tcattgaagg agcctttcgt caaggtctca ttcgagtctt ggcggcaact  1380
tctactcttt cttctggggt gaatttacct gcacgtcgtg tgattattcg aacccctatt  1440
tttggtggtc gacctctaga tattcttact tataagcaga tggttggtcg tgctggcagg  1500
aaaggagtgg acacagtagg cgagagtatc ttaatttgta agaactctga gaaatcaaaa  1560
ggcatagctc tccttcaggg ttctctaaag cctgttcgca gctgtctgca aagacgagaa  1620
ggagaagaag taactggcag catgatacga gctattctgg agataatagt tggtggagtg  1680
gcaagtacat cacaagatat gcatacttat gctgcctgca catttttggc tgcaagtatg  1740
aaagaaggga agcaaggaat tcagagaaat caagagtctg ttcagcttgg agcgattgag  1800
gcctgtgtga tgtggctact agaaaatgaa ttcatccaga gtacagaagc cagtgatgga  1860
acagaaggaa aggtgtatca tccaacacat cttggttcgg ccactctttc ttcttcactt  1920
tctccagctg atactttaga tatttttgct gacctgcaaa gagcaatgaa gggctttgtt  1980
ttagagaatg atcttcatat tctctatctg gttacaccta tgtttgagga ttggactact  2040
attgattggt atcgattttt ctgtttatgg gagaagttgc caacttcaat gaaaagggtg  2100
gcagagctag tgggagttga agaggggttc ttggcccgtt gtgtgaaagg aaaagtagta  2160
gccagaactg agagacagca tcgacaaatg gccatccata aaggtttttt caccagtctt  2220
gtgctattag atttaatcag tgaagttccc ttaagggaaa taaatcagaa atatggatgc  2280
aatcgtgggc agattcaatc tttgcaacag tcagctgctg tttatgcagg gatgattaca  2340
gtattttcca accgtctggg ctggcacaac atggaactac tactttccca atttcagaag  2400
cgtcttacgt ttggcatcca gagggagctg tgtgacctgg ttcgggtatc cttactaaat  2460
gctcagagag ccagggttct ctatgcttct ggctttcata ctgtggcaga ccttgctaga  2520
gcaaatattg tggaggtgga ggtgattctg aaaaatgctg tgcctttcaa aagtgcccgg  2580
aaggcagtgg atgaggaaga ggaagcagtt gaagaacgtc gcaatatgcg aactatctgg  2640
gtgactggca gaaaaggttt aactgaaagg gaagcagcag cccttatagt ggaagaagcc  2700
agaatgattc tgcagcagga cttagttgaa atgggagtgc aatggaatcc atgtgccctg  2760
ttacattcta gtacatgctc attgactcat agtgagtccg aagtaaagga acacacattt  2820
atatcccaaa ctaagagttc ttataaaaaa ttaacatcaa agaacaaaag taacacaata  2880
tttagtgatt cttatattaa gcattcacca aatatagtgc aagacttaaa taaaagtaga  2940
gagcatacaa gttcctttaa ttgtaatttc cagaatggga atcaagaaca tcagagatgt  3000
tccattttca gagcaagaaa acgggcctct ttagatataa ataaagagaa gccaggagcc  3060
tctcagaatg aggggaaaac aagtgataag aaagttgttc agacttttc acagaaaaca  3120
aaaaaggcac ctttgaattt caattcagaa aagatgagca gaagttttcg atcttggaaa  3180
cgtagaaagc atctaaagcg atctagggac agcagcccc  tgaaagactc tggagcgtgt  3240
agaatccatt tacaaggaca gactctgtct aatcctagtc tttgtgaaga cccgtttacc  3300
ttagatgaga agaaaacgga atttagaaat tcagggccat ttgctaaaaa tgtatctttg  3360
agtggtaagg aaaaagataa taaaacatca ttcccattac aaataaagca aaattgttca  3420
tggaacataa cactaactaa tgataatttt gtggagcata ttgtcacagg atctcagagt  3480
aaaaatgtga cttgtcaggc cactagtgtg gttagtgaaa agggcagagg agtagctgtt  3540
gaggcagaaa aaataaatga agtgctgata caaaatggtt caaaaaacca gaatgtttat  3600
atgaaacacc atgacatcca tccaattaac cagtacctgc gaaagcaatc tcatgaacag  3660
acaagcacta ttaccaaaca gaaaaatata atagagagac aaatgccctg tgaagcagtc  3720
agtagttaca taaatagaga ctcaaatgtt actatcaatt gtgaaaggat aaagcttaat  3780
acagaggaaa ataaaccaag tcattttcag gcattaggag atgatataag cagaactgtg  3840
atacccagtg aagtacttcc atcagctgga gcatttagca aatcagaagg ccagcatgag  3900
aattttctaa atatttctag actacaagaa aaaacaggta cttatacaac aaacaaaact  3960
aaaaataatc atgtttctga cttaggttta gtcctctgtg attttgaaga tagtttctat  4020
ctggatactc agtcagagaa aataatacaa cagatggcaa ctgaaaatgc caaactagga  4080
gcaaaggaca ccaacctggc agcagggata atgcagaaga gcttagtcca acagaactca  4140
atgaactctt ttcagaagga gtgtcacatt ccttttcctg ctgaacagca ccctctagga  4200
gcgactaaga tagatcattt ggaccttaag actgtaggta ctatgaaaca aagcagtgat  4260
tcacatgggg ttgatatcct gactccagaa agcccgattt tccattctcc aatactattg  4320
gaggaaaatg gtcttttttt aaaaaagaat gaagtttctg ttactgattc acaattaaat  4380
agttttcttc aaggttatca aacacaagaa actgtgaaac cagttatact tctgattcct  4440
```

-continued

```
caaaagagaa ctcccactgg tgtagaagga gaatgtcttc cagttcctga aacaagtttg  4500
aatatgagtg atagtttact atttgatagc ttcagtgatg actatctagt aaaagaacaa  4560
ttacctgata tgcaaatgaa agaacccctt ccttcagaag taacatcaaa ccattttagt  4620
gattctctgt gtctacaaga agacctaatt aaaaaatcaa atgtaaatga gaatcaagat  4680
acccaccagc agttgacttg ttccaatgat gaatctatta tattttcaga aatggattct  4740
gttcagatgg ttgaagcttt ggacaatgtg gatatatttc ctgtccaaga gaagaatcat  4800
actgtagtat ctcctagagc attagaacta agtgatccag tacttgatga gcaccaccaa  4860
ggtgatcaag atggaggaga tcaagatgaa agggctgaaa aatcaaaatt aactgggacc  4920
aggcaaaatc attcattcat ttggtcaggg gcatcatttg atctaagtcc aggactgcaa  4980
aggattttag ataaagtatc cagtcctcta gaaaatgaaa agctaaaatc aatgactata  5040
aacttttcca gtttgaatag aaaaaataca gagttaaatg aagaacaaga agttatttca  5100
aacttggaga caaaacaagt gcagggaatt tcattttctt ctaataatga agtaaaaagc  5160
aagattgaga tgctagaaaa caatgccaat catgatgaaa cctcatccct cttacctcgt  5220
aaagaaagta atatagttga tgataatggt ctcattcctc ctacacccat tccaacatct  5280
gcttctaagc tgacatttcc agggattctt gaaacacctg taaacccttg gaaaactaat  5340
aatgttttac aacctggtga aagttattta tttggctcac cttcagatat taaaaaccac  5400
gatttaagtc cagggagtag aaatgggttc aaagacaaca gccctattag tgacacaagc  5460
ttttcacttc agttatcaca ggatggatta cagttaactc cagcctcaag cagttcagaa  5520
agtttgtcca taattgatgt agcaagtgac caaaatcttt tccaaacatt cattaaggag  5580
tggcggtgca aaaagcgatt ttccatctca ctggcttgtg aaaagattag aagtttgaca  5640
tcttctaaaa ctgctactat tggcagtagg tttaagcaag ctagctcacc tcaggaaatt  5700
cctattagag atgatggatt tcccattaaa ggttgtgatg acaccttggt ggttggactg  5760
gcagtatgct ggggtggaag ggatgcctat tatttttcac tgcagaagga acaaaagcat  5820
tctgaaatta gtgccagttt ggttccacct tctttagatc caagcctgac tttgaaagac  5880
aggatgtggt accttcaatc ttgcttgcga aaggaatctg ataaagaatg ttctgttgtc  5940
atctatgact tcatccagag ctataaaatt cttcttcttt cttgtggcat ctccttggag  6000
caaagttatg aagatcctaa ggtggcatgc tggttactag atccagattc tcaggagccg  6060
actcttcata gcatagttac cagttttctt cctcatgagc ttccactcct agaagggatg  6120
gagaccagcc aagggattca aagcctgggg ctaaatgctg gcagtgagca ttctgggcga  6180
tacagagcat ctgtggagtc cattctcatc ttcaactcta tgaatcagct caactctttg  6240
ttgcagaagg aaaaccttca agatgttttc cgtaaggtgg aaatgccctc tcagtactgc  6300
ttggccttgc tagaactaaa tggaattggc tttagtactg cagaatgtga aagtcagaaa  6360
catataatgc aagccaagct ggatgcaatt gagacccagg cctatcaact agctggccac  6420
agtttttctt tcaccagttc agatgacatc gctgaggttt tatttttgga attgaagttg  6480
cccccaaata gagagatgaa aaaccaaggc agcaagaaaa ctctgggttc taccagaaga  6540
gggattgaca atggacgcaa gctaaggctg ggaagacagt tcagcactag taaggacgtt  6600
ttaaataaat taaaggcatt acatccttta ccaggcttga tattagaatg gagaagaatc  6660
actaatgcta ttaccaaagt ggtctttccc cttcagcggg aaaagtgtct taatcctttt  6720
cttggaatgg aaagaatcta tcctgtatca cagtcgcaca ctgctacagg acgaataacc  6780
tttacagaac caaatattca gaatgtgcca agagatttg aaatcaaaat gccaacacta  6840
gtaggagaaa gcccaccttc tcaagctgta ggcaaaggcc tacttcccat gggcagagga  6900
aaatataaga agggtttcag cgtgaatcct agatgccagg cacagatgga ggagagagct  6960
gcagacagag gaatgccatt ttcaattagc atgcgacatg cctttgtgcc tttcccaggt  7020
ggttcaatac tggctgctga ctactctcag cttgaactga ggatcttggc tcatttatcc  7080
catgatcgtc gtctcattca agtgttaaac actggagctg atgttttcag gagcattgca  7140
gcagagtgga agatgattga gccagagtct gttggggatg atctgaggca gcaggcaaaa  7200
cagatttgct atgggatcat ttatggaatg ggagctaaat ctttgggaga gcagatgggc  7260
attaaagaaa atgatgctgc atgctatatt gactccttca aatccagata cacagggatt  7320
aatcaattca tgacagagac agtgaagaat tgtaaaagag acggatttgt tcagaccatt  7380
ttgggaaggc gtagatattt gccaggaatc aaagacaaca acccttatcg taaagctcac  7440
gctgagcgtc aagctatcaa cacaatagtc caaggatcag cagctgatat tgtcaaaata  7500
gccacagtta acattcagaa gcaattagag accttccact caaccttcaa atcccatggt  7560
catcgagagg gtatgctcca aagtgaccga acaggattgt cacgaaagag aaaactgcaa  7620
gggatgttct gcccaatcag aggaggcttc ttcatccttc aactccatga tgaactccta  7680
tatgaagtgg cagaagaaga tgttgttcag gtagctcaga ttgtcaagaa tgaaatggaa  7740
agtgctgtaa aactgtctgt gaaattgaaa gtgaaagtga aaataggcgc cagctgggga  7800
gagctaaagg actttgatgt gcccgggatg gactacaaag acgatgacga caagtaa     7857
```

```
SEQ ID NO: 21           moltype = DNA  length = 1128
FEATURE                 Location/Qualifiers
source                  1..1128
                        mol_type = unassigned DNA
                        organism = Homo sapiens
SEQUENCE: 21
atggactata aggaccacga cggagactac aaggatcatg atattgatta caaagacgat  60
gacgataaga tggccccaaa gaagaagcgg aaggtcggta tccacggagt cccagcagcc  120
gctagcaaac ggaaggcgcc gcaggagact ctcaacgggg gaatcaccga catgctcaca  180
gaactcgcaa actttgagaa gaacgtgagc caagctatcc acaagtacaa tgcttacaga  240
aaagcagcat ctgttatagc aaaataccca cacaaaataa agagtggagc tgaagctaag  300
aaattgcctg gagtaggaac aaaaattgct gaaaagattg atgagttttt agcaactgga  360
aaattacgta aactggaaaa gattcggcag gatgatacga gttcatccat caatttcctg  420
actcgagtta gtggcattgg tccatctgct gcaaggaagt ttgtagatga aggaattaaa  480
acactagaag atctcagaaa aaatgaagat aaattgaacc atcatcagcg aattgggctg  540
aaatattttg gggactttga aaaaagaatt cctcgtgaag agatgttaca aatgcaagat  600
attgtactaa atgaagttaa aaaagtggat tctgaataca ttgctacagt ctgtggcagt  660
ttcagaagag gtgcagagtc cagtggtgac atggatgttc tcctgaccca tcccagcttc  720
acttcagaat caaccaaaca gccaaaactg ttacatcagg ttgtggagca gttacaaaag  780
gttcatttta tcacagatac cctgtcaaag ggtgagacaa agttcatggg tgtttgccag  840
cttcccagta aaaatgatga aaaagaatat ccacacagaa gaattgatat caggttgata  900
```

-continued

```
cccaaagatc agtattactg tggtgttctc tatttcactg ggagtgatat tttcaataag  960
aatatgaggg ctcatgccct agaaaagggt ttcacaatca atgagtacac catccgtccc  1020
ttgggagtca ctggagttgc aggagaaccc ctgccagtgg atagtgaaaa agacatcttt  1080
gattacatcc agtggaaata ccgggaaccc aaggaccgga gcgaatga               1128

SEQ ID NO: 22          moltype = DNA  length = 2142
FEATURE                Location/Qualifiers
source                 1..2142
                       mol_type = unassigned DNA
                       organism = Homo sapiens
SEQUENCE: 22
atggctactg gacaggatcg agtggttgct ctcgtggaca tggactgttt ttttgttcaa  60
gtggagcagc ggcaaaatcc tcatttgagg aataaacctt gtgcagttgt acagtacaaa  120
tcatggaagg gtggtggaat aattgcagtg agttatgaag ctcgtgcatt tggagtcact  180
agaagtatgt gggcagatga tgctaagaag ttatgtccag atcttctact ggcacaagtt  240
cgtgagtccc gtgggaaagc taacctcacc aagtaccggg aagccagtgt tgaagtgatg  300
gagataatgt ctcgttttgc tgtgattgaa cgtgccagca ttgatgaggc ttacgtagat  360
ctgaccagtg ctgtacaaga gagactacaa aagctacaag gtcagcctat ctcggcagac  420
ttgttgccaa gcacttacat tgaagggttg ccccaaggcc ctacaacggc agaagagact  480
gttcagaaag aggggatgcg aaaacaaggc ttatttcaat ggctcgattc tcttcagatt  540
gataacctca cctctccaga cctgcagctc accgtgggag cagtgattgt ggaggaaatg  600
agagcagcca tagagaggga gactggtttt cagtgttcag ctggaatttc acacaataag  660
gtcctggcaa aactggcctg tggactaaac aagcccaacc gccaaaccct ggtttcacat  720
gggtcagtcc cacagctctt cagccaaatg cccattcgca aaatccgtag tcttggagga  780
aagctagggg cctctgtcat tgagatccta gggatagaat acatgggtga actgacccag  840
ttcactgaat cccagctcca gagtcatttt ggggagaaga atgggtcttg gctatatgcc  900
atgtgccgag ggattgaaca tgatccagtt aaacccaggc aactacccaa aaccattggc  960
tgtagtaaga acttcccagg aaaaacagct cttgctactc gggaacaggt acaatggtgg  1020
ctgttgcaat tagcccagga actagaggag agactgacta aagaccgaaa tgataatgac  1080
agggtagcca cccagctggt tgtgagcatt cgtgtacaag gagacaaacg cctcagcagc  1140
ctgcgccgct gctgtgccct tacccgctat gatgctcaca agatgagcca tgatgcattt  1200
actgtcatca agaactgtaa tacttctgga atccagacag aatggtctcc tcctctcaca  1260
atgcttttcc tctgtgctac aaaattttct gcctctgccc cttcatcttc tacagacatc  1320
accagcttct tgagcagtga cccaagttct ctgccaaagg tgccagttac cagctcagaa  1380
gctaagaccc agggaagtgg cccagcggtg acagccacta agaaagcaac cacgtctctg  1440
gaatcattct tccaaaaagc tgcagaaagg cagaaagtta aagaagcttc gctttcatct  1500
cttactgctc ccactcaggc tcccatgagc aattcaccat ccaagccctc attacctttt  1560
caaaccagtc aaagtacagg aactgagccc ttctttaagc agaaaagtct gcttctaaag  1620
cagaaacagc ttaataattc ttcagtttct tccccccaac aaaacccatg gtccaactgt  1680
aaagcattac caaactcttt accaacagag tatccagggt gtgtccctgt ttgtgaaggg  1740
gtgtcgaagc tagaagaatc ctctaaagca actcctgcag agatggattt ggcccacaac  1800
agccaaagca tgcacgcctc ttcagcttcc aaatctgtgc tggaggtgac tcagaaagca  1860
accccaaatc caagtcttct agctgctgag gaccaagtgc cctgtgagaa gtgtggctcc  1920
ctggtaccgg tatgggatat gccagaacac atggactatc attttgcatt ggagttgcag  1980
aaatcctttt tgcagcccca ctcttcaaac ccccaggttg tttctgccgt atctcatcaa  2040
ggcaaaagaa atcccaagag ccctttggcc tgcactaata aacgccccag gcctgagggc  2100
atgcaaacat tggaatcatt ttttaagcca ttaacacatt ag                     2142

SEQ ID NO: 23          moltype = DNA  length = 3723
FEATURE                Location/Qualifiers
source                 1..3723
                       mol_type = unassigned DNA
                       organism = Homo sapiens
SEQUENCE: 23
atggctagcc gcctgctctg gaggaaggtg gccggcgcca ccgtcgggcc agggccggtt  60
ccagctccgg ggcgctgggt ctccagctcc gtccccgcgt ccgaccccag cgacgggcag  120
cggcggcggc agcagcagca gcagcagcag cagcagcagc aacagcagcc tcagcagccg  180
caagtgctat cctcggaggg cgggcagctg cggcacaacc cattggacat ccagatgctc  240
tcgagagggc tgcacgagca aatcttcggg caaggagggg agatgcctgg cgaggccgcg  300
gtgcgccgca gcgtcgagca cctgcagaag cacgggctct gggggcagcc agccgtgccc  360
ttgcccgacg tggagctgcg cctgccgccc ctctacgggg acaacctgga ccagcacttc  420
cgcctcctgg cccagaagca gagcctgccc tacctggagg cggccaactt gctgttgcag  480
gcccagctgc ccccgaagcc cccggcttgg gcctgggcgg agggctggac ccggtacggc  540
cccgaggggg aggccgtacc cgtggccatc cccgaggagc gggccctggt gttcgacgtg  600
gaggtctgct tggcagaggg aacttgcccc acattggcgg tggccatatc cccctcggcc  660
tggtattcct ggtgcagcca gcggctggtg gaagagcgtt actcttggac cagccagctg  720
tcgccggctg acctcatccc cctggaggtc cctactggtg ccagcagccc cacccagaga  780
gactggcagg agcagttagt ggtggggcac aatgtttcct ttgaccgagc tcatatcagg  840
gagcagtacc tgatccaggg ttcccgcatg cgtttcctgg acaccatgag catgcacatg  900
gccatctcag ggctaagcag cttccagcgc agtctgtgga tagcagccaa gcagggcaaa  960
cacaaggtcc agcccccccac aaagcaaggc cagaagtccc agaggaaagc cagaagaggc  1020
ccagcgatct catcctggga ctggctggac atcagcagtg tcaacagtct ggcagaggtg  1080
cacagacttt atgtaggggg gcctccctta gagaaggagc ctcgagaact gtttgtgaag  1140
ggcaccatga aggacattcg tgagaacttc caggacctga tgcagtactg tgcccaggac  1200
gtgtgggcca cccatgaggt tttccagcag cagctaccgc tcttcttgga gaggtgtccc  1260
cacccagtga ctctggccgg catgctggag atgggtgtct cctacctgcc tgtcaaccag  1320
aactgggagc gttacctggc agaggcacag ggcacttatg aggagctcca gcgggagatg  1380
aagaagtcgt tgatggatct ggccaatgat gcctgccagc tgctctcagg agagaggtac  1440
aaagaagacc cctggctctg ggacctggag tgggacctgc aagaatttaa gcagaagaaa  1500
```

-continued

```
gctaagaagg tgaagaagga accagccaca gccagcaagt tgcccatcga gggggctggg  1560
gcccctggtg atcccatgga tcaggaagac ctcggcccct gcagtgagga ggaggagttt  1620
caacaagatg tcatggcccg cgcctgcttg cagaagctga aggggaccac agagctcctg  1680
cccaagcggc cccagcacct tcctggacac cctggatggt accggaagct ctgcccccgg  1740
ctagacgacc ctgcatggac cccgggcccc agcctcctca gcctgcagat gcgggtcaca  1800
cctaaactca tggcacttac ctgggatggc ttccctctgc actactcaga gcgtcatggc  1860
tggggctact tggtgcctgg gcggcgggac aacctggcca agctgccgac aggtaccacc  1920
ctggagtcag ctggggtggt ctgcccctac agagccatcg agtccctgta caggaagcac  1980
tgtctcgaac aggggaagca gcagctgatg ccccaggagg ccggcctggc ggaggagttc  2040
ctgctcactg acaatagtgc catatggcaa acggtagaag aactggatta cttagaagtg  2100
gaggctgagg ccaagatgga gaacttgcga gctgcagtgc caggtcaacc cctagctctg  2160
actgcccgtg gtggccccaa ggacacccag cccagctatc accatggcaa tggaccttac  2220
aacgacgtgg acatccctgg ctgctggttt ttcaagctgc ctcacaagga tggtaatagc  2280
tgtaatgtgg gaagcccctt tgccaaggac ttcctgccca agatggagga tggcaccctg  2340
caggctggcc caggaggtgc cagtgggccc cgtgctctgg aaatcaacaa aatgatttct  2400
ttctggagga acgcccataa acgtatcagc tcccagatgg tggtgtggct gcccaggtca  2460
gctctgcccc gtgctgtgat caggcacccc gactatgatg aggaaggcct ctatggggcc  2520
atcctgcccc aagtggtgac tgccggcacc atcactcgcc gggctgtgga gcccacatgg  2580
ctcaccgcca gcaatgcccg gcctgaccga gtaggcagtg agttgaaagc catggtgcag  2640
gccccacctg gctacaccct tgtgggtgct gatgtggact cccaagagct gtggattgca  2700
gctgtgcttg gagacgccca ctttgccggc atgcatggct gcacagcctt tgggtggatg  2760
acactgcagg gcaggaagag caggggcact gatctacaca gtaagacagc cactactgtg  2820
ggcatcagcc gtgagcatgc caaaatcttc aactacggcc gcatctatgg tgctgggcag  2880
ccctttgctg agcgcttact aatgcagttt aaccaccggc tcacacagca ggaggcagct  2940
gagaaggccc agcagatgta cgctgccacc aagggcctcc gctggtatcg gctgtcggat  3000
gagggcgagt ggctggtgag ggagttgaac ctcccagtgg acaggactga gggtggctgg  3060
atttccctgc aggatctgcg caaggtccag agagaaactg caaggaagtc acagtggaag  3120
aagtgggagg tggttgctga acgggcatgg aagggggggca cagagtcaga aatgttcaat  3180
aagcttgaga gcattgctac gtctgacata ccacgtaccc cggtgctggg ctgctgcatc  3240
agccgagccc tggagccctc ggctgtccag gaagagttta tgaccagccg tgtgaattgg  3300
gtggtacaga gctctgctgt tgactactta cacctcatgc ttgtggccat gaagtggctg  3360
tttgaagagt ttgccataga tgggcgcttc tgcatcagca tccatgacga ggttcgctac  3420
ctggtgcggg aggaggaccg ctaccgcgct gccctggcct tgcagatcac caacctcttg  3480
accaggtgca tgtttgccta caagctgggt ctgaatgact tgccccagtc agtcgccttt  3540
ttcagtgcag tcgatattga ccggtgcctc aggaaggaag tgaccatgga ttgtaaaacc  3600
ccttccaacc caactgggat ggaaaggaga tacgggattc cccagggtga agcgctggat  3660
atttaccaga taattgaact caccaaaggc tccttggaaa aacgaagcca gcctggacca  3720
tag                                                                3723
```

```
SEQ ID NO: 24           moltype = DNA  length = 2703
FEATURE                 Location/Qualifiers
source                  1..2703
                        mol_type = unassigned DNA
                        organism = Homo sapiens
SEQUENCE: 24
atggaaaatt atgaggcatt ggtaggcttt gatctctgta atacaccgct ctccagtgtt  60
gctcagaaga ttatgtctgc tatgcattca ggtgatttag tggattctaa gacttgggga  120
aagagtacag agactatgga agtgataaac aagtccagtg ttaagtattc agtacaactt  180
gaagacagga agactcaatc accagaaaaa aaggatctta aatctttaag aagtcagaca  240
tcaagaggtt ctgccaagct gtctcctcag tccttcagtg tcaggctcac agatcagctg  300
tctgctgacc aaaaacagaa gagcatcagc tcattgactc tttcaagttg tttaattcca  360
cagtataatc aagaggcttc agttctacag aaaaaggggc ataaaagaaa gcatttccta  420
atggagaata taaataatga aaataaagga agcattaatc ttaaaagaaa acatattaca  480
tataataatt tgtcagagaa aacaagtaaa caaatggcat tggaagaaga tactgatgac  540
gccgaaggct acctaaattc tgggaactca ggagcattga aaaaacattt ttgtgatatt  600
aggcatttgg atgattgggc aaaaagccag ctgattgaaa tgctcaaaca ggcagcagcc  660
ctggtgataa ctgtgatgta tactgatggt tccacccagc taggagctga ccagaccccc  720
gtttcttctg ttagaggaat tgtggtgtta gtaaaacgcc aagcagaggg tggccatggc  780
tgtccagatg ccccggcctg tggtcctgtt ctggagggct ttgtgtcaga tgatccatgc  840
atctacattc aaatagagca ctctgctatc tgggaccaag aacaggaggc acatcaacaa  900
tttgcccgga acgtgctatt tcaaacaatg aaatgtaaat gtcctgttat ttgttttaat  960
gctaaggatt ttgtgagaat agtgctgcag ttttttggca atgatggcag ttggaagcat  1020
gttgctgatt ttatagggct agatcccaga attgctgcat ggcttataga tcctagtgat  1080
gccacaccct cttttgaaga tttagtagaa aaatactgtg aaaaatccat tacagttaaa  1140
gtgaacagca catatggaaa ttcctcaaga aatattgtga atcagaatgt acgtgagaac  1200
ctgaagacac tctacagact tacaatggac ctttgctcta aactgaagga ttatggttta  1260
tggcaactat ttcgtacttt ggagcttcct ctgataccaa ttttggcagt gatggaaagc  1320
catgccattc aggtgaacaa agaggagatg gagaagacgt cagcacttct tggggctcgt  1380
ctcaaggaat tggagcaaga agctcatttt gttgcaggag aacggtttct tataacgagc  1440
aataaccagc ttcgagagat cctctttggc aagttaaagc tgcacctgct gagtcaaagg  1500
aacagtctcc ccagaacggg gttgcagaaa tacccgtcta catcagaagc agtgttaaat  1560
gctctgcgag accttcatcc attacccaag ataattttgg aatacaggca ggttcacaag  1620
atcaagtcaa cctttgtaga tggattacta gcttgcatga aaaagggctc catttcctct  1680
acatggaatc agactggaac tgtgactgga agactttcag ccaagcatcc taatatccaa  1740
ggtatctcca agcacccaat tcagattact acacctaaga attttaaagg taaagaagac  1800
aagattctca cgatctcccc gagggccatg tttgtttcat ccaaaggcca cacctttcta  1860
gcagcagact tttcacagat tgaattgcgc attcttacac atttatctgg agatccggaa  1920
cttctgaagt tattccagga atctgaaaga gatgatgtat tttctactct gacttcacag  1980
tggaaggatg tgcccgtgga acaggtgaca cacgcagaca gagagcaaac caagaaggtg  2040
```

-continued

```
gtgtacgcgg tggtctatgg agcagggaag gagcggctgg ctgcttgcct tggagttcct  2100
attcaggaag ctgcccagtt tttggagagt tttttgcaga agtacaagaa aatcaaggac  2160
ttcgcccgag cagctattgc ccagtgtcac cagacaggct gtgtggtgtc catcatgggc  2220
agaaggagac ccctgccaag gattcacgct catgaccagc aactccgggc acaagcagag  2280
cgacaggcag tgaacttcgt ggtgcaaggc tccgctgctg acctctgcaa gctggccatg  2340
atccatgtct tcactgcagt ggctgcttcc cacaccttga cggccaggct ggtggcccag  2400
atccatgatg agctgctgtt tgaagtggaa gatccgcaga tcccggagtg tgcagctctc  2460
gtcaggagga ccatggagtc cttggaacag gtgcaggcat tggagctgca gcttcaggta  2520
cccctcaagg tgagcctgag tgccggccgc tcatggggac acctggtgcc actgcaggag  2580
gcctggggcc ctccgccagg cccatgtcgc actgagtctc ccagcaacag cctggctgcc  2640
cctgggtccc ctgccagcac ccagcccccca cccctgcatt tttcgccttc attttgtctg  2700
tag                                                                2703
```

```
SEQ ID NO: 25          moltype = DNA  length = 1629
FEATURE                Location/Qualifiers
source                 1..1629
                       mol_type = unassigned DNA
                       organism = Homo sapiens
SEQUENCE: 25
atggcttccc cttgtcctga agaagcagct atgagaagag aggtggtgaa acggatcgaa  60
actgtggtga aagacctttg gccgacggct gatgtacaga tatttggcag ctttagtaca  120
ggtctttatc ttccaactag cgacatagac ctggtggtct tcgggaaatg ggagcgtcct  180
cctttacagc tgctggagca agccctgcgg aagcacaacg tggctgagcc gtgttccatc  240
aaagtccttg acaaggctac ggtaccaata ataaagctca cagatcagga gactgaagtg  300
aaagttgaca tcagctttaa catggagacg ggcgtccggg cagcggagtt catcaagaat  360
tacatgaaga aatattcatt gctgccttac ttgattttag tattgaaaca gttccttctg  420
cagagggacc tgaatgaagt ttttacaggt ggaattagct catacagcct aattttaatg  480
gccattagct ttctacagtt gcatccaaga attgatgccc ggagagctga tgaaaacctt  540
ggaatgcttc ttgtagaatt ttttgaactc tatgggagaa attttaatta cttgaaaacc  600
ggtattagaa tcaaagaagg aggtgcctat atcgccaaag aggagatcat gaaagccatg  660
accagcgggt acagaccgtc gatgctgtgc attgaggacc ccctgctgcc agggaatgac  720
gttggccgga gctcctatgg cgccatgcag gtgaagcagg tcttcgatta tgcctacata  780
gtgctcagcc atgctgtgtc accgctggcc aggtcctatc caaacagaga cgccgaaagt  840
actttaggaa gaatcatcaa agtaactcag gaggtgattg actaccggag gtggatcaaa  900
gagaagtggg gcagcaaagc ccacccgtcg ccaggcatgg acagcaggat caagatcaaa  960
gagcgaatag ccacatgcaa tggggagcag acgcagaacc gagagcccga gtctccctat  1020
ggccagcgct tgactttgtc gctgtccagc cccagctcc tgtcttcagg ctcctcggcc  1080
tcttctgtgt cttcactttc tgggagtgac gttgattcag acacaccgcc ctgcacaacg  1140
cccagtgttt accagttcag tctgcaagcg ccagctcctc tcatggccgg cttacccacc  1200
gccttgccaa tgcccagtgg caaacctcag cccaccactt ccagaacact gatcatgaca  1260
accaacaatc agaccaggtt tactatacct ccaccgaccc taggggttgc tcctgttcct  1320
tgcagacaag ctggtgtaga aggaactgcg tctttgaaag ccgtccacca catgtcttcc  1380
ccggccattc cctcagcgtc cccaacccg ctctcgagcc ctcatctgta tcataagcac  1440
aacggcatga aactgtccat gaagggctct cacggccaca cccaaggcgg cggctacagc  1500
tctgtgggta gcggaggtgt gcggcccccct gtgggcaaca ggggacacca ccagtataac  1560
cgcaccggct ggaggaggaa aaaacacaca cacacacggg acagtctgcc cgtgagcctc  1620
agcagataa                                                          1629
```

```
SEQ ID NO: 26          moltype = DNA  length = 2736
FEATURE                Location/Qualifiers
source                 1..2736
                       mol_type = unassigned DNA
                       organism = Homo sapiens
SEQUENCE: 26
atggctgcct cacaaacttc acaaactgtt gcatctcacg ttccttttgc agatttgtgt  60
tcaactttag aacgaataca gaaaagtaaa ggacgtgcag aaaaaatcag acacttcagg  120
gaatttttag attcttggag aaaatttcat gatgctcttc ataagaacca caaagatgtc  180
acagactctt tttatccagc aatgagacta attcttcctc agctagaaag agagagaatg  240
gcctatggaa ttaaagaaac tatgcttgct aagctttata ttgagttgct taatttacct  300
agagatggaa aagatgccct caaactttta aactacagaa caccccactgg aactcatgga  360
gatgctggag actttgcaat gattgcatat tttgtgttga agccaagatg tttacagaaa  420
ggaagtttaa ccatacagca agtaaacgac cttttagact caattgccag caataattct  480
gctaaaagaa aagacctaat aaaaaagagc cttcttcaac ttataactca gagttcagca  540
cttgagcaaa agtggcttat acggatgatc ataaaggatt taaagcttgg tgttagtcag  600
caaactatct ttctgtttt tcataatgat gctgctgagt tgcataatgt cactacagat  660
ctggaaaaag tctgtaggca actgcatgat ccttctgtag gactcagtga tatttctatc  720
actttatttt ctgcatttaa accaatgcta gctgctattg cagatattga gcacattgag  780
aaggatatga aacatcagag tttctacata gaaaccaagc tagatggtga acgtatgcaa  840
atgcacaaag atggagatgt atataaatac ttctctcgaa atggatataa ctacactgat  900
cagtttggtg cttctcctac tgaaggttct cttaccccat tcattcataa tgcattcaaa  960
gcagatatac aaatctgtat tcttgatggt gagatgatgg cctataatcc taatacacaa  1020
actttcatgc aaaagggaac taagtttgat attaaaagaa tggtagagga ttctgatctg  1080
caaacttgtt attgtgtttt tgatgtattg atggttaata ataaaaagct agggcatgag  1140
actctgagaa agaggtatga gattcttagt agtatttta caccaattcc aggtagaata  1200
gaaatagtgc agaaaacaca agctcatact aagaatgaag taattgatgc attgaatgaa  1260
gcaatagata aaagagaaga gggaattatg gtaaaacaac ctctatccat ctacaagcca  1320
gacaaaagag gtgaagggtg gttaaaaatt aaaccagagt atgtcagtgg actaatggat  1380
gaattggaca ttttaattgt tggaggatat tggggtaaag gatcacgggg tggaatgatg  1440
tctcatttc tgtgtgcagt agcagagaag cccccctcctg gtgagaagcc atctgtgttt  1500
```

-continued

```
catactctct ctcgtgttgg gtctggctgc accatgaaag aactgtatga tctgggtttg  1560
aaattggcca agtattggaa gccttttcat agaaaagctc caccaagcag cattttatgt  1620
ggaacagaga agccagaagt atacattgaa ccttgtaatt ctgtcattgt tcagattaaa  1680
gcagcagaga tcgtacccag tgatatgtat aaaactggct gcaccttgcg ttttccacga  1740
attgaaaaga taagagatga caaggagtgg catgagtgca tgaccctgga cgacctagaa  1800
caacttaggg ggaaggcatc tggtaagctc gcatctaaac acctttatat aggtggtgat  1860
gatgaaccac aagaaaaaaa gcggaaagct gccccaaaga tgaagaaagt tattggaatt  1920
attgagcact taaaagcacc taaccttact aacgttaaca aaatttctaa tatatttgaa  1980
gatgtagagt tttgtgttat gagtggaaca gatagccagc caaagcctga cctggagaac  2040
agaattgcag aatttggtgg ttatatagta caaaatccag gcccagacac gtactgtgta  2100
attgcagggt ctgagaacat cagagtgaaa aacataattt tgtcaaataa acatgatgtt  2160
gtcaagcctg catggctttt agaatgtttt aagaccaaaa gctttgtacc atggcagcct  2220
cgctttatga ttcatatgtg cccatcaacc aaagaacatt ttgcccgtga atatgattgc  2280
tatggtgata gttatttcat tgatacagac ttgaaccaac tgaaggaagt attctcagga  2340
attaaaaatt ctaacgagca gactcctgaa gaaatggctt ctctgattgc tgatttagaa  2400
tatcggtatt cctgggattg ctctcctctc agtatgtttc gacgccacac cgtttatttg  2460
gactcgtatg ctgttattaa tgacctgagt accaaaaatg aggggacaag gttagctatt  2520
aaagccttgg agcttcggtt tcatggagca aaagtagttt cttgtttagc tgagggagtg  2580
tctcatgtaa taattgggga agatcatagt cgtgttgcag attttaaagc ttttagaaga  2640
acttttaaga gaaagtttaa aatcctaaaa gaaagttggg taactgattc aatagacaag  2700
tgtgaattac aagaagaaaa ccagtatttg atttaa                          2736

SEQ ID NO: 27          moltype = DNA  length = 3087
FEATURE                Location/Qualifiers
source                 1..3087
                       mol_type = unassigned DNA
                       organism = Homo sapiens
SEQUENCE: 27
atgggctccg ccgcctgccc ccggggagcc ttgccggagc tcgcgccctg ctgccagcct  60
cgcgagcagt cgcagcccca cacgcgatgg gacgcgggct gtgggattca gcaccccggg  120
ggcgaggaat tcaggaccct cggcggggca agggcctata gggttccgaa ctcgcaggag  180
ggtcgctcct cccctactcg ctttttcccg gcaccggaag gccccgccca ctgctttgtt  240
tcctctccag accgcgcatt ttgggtctcg gaagaggttc agaggctgtt gttgagcaat  300
gcatgccagc caaaagaatg caatggtgta aagattccag ttgatgccag taaacctaat  360
ccaaatgatg tggagtttga taatctgtat ttggatatga atggaatcat ccatccctgt  420
actcatcctg aagacaaacc agcaccaaaa aatgaagatg aaatgatggt tgcaattttt  480
gagtacattg acagactttt cagtattgta agaccaagaa gacttctcta catggcaata  540
gatggagtgg caccacgtgc taaaatgaac cagcagcgtt caaggaggtt cagggcatca  600
aaagaaggaa tggaagcagc agtcgagaag cagcgagtca gggaagaaat attggcaaaa  660
ggtggctttc ttcctccaga agaaataaaa gaaagatttg acagcaactg tattacacca  720
ggaactgaat tcatggacaa tcttgctaaa tgccttcgct attacatagc tgatcgttta  780
aataatgacc ctgggtggaa aaatttgaca gttattttat ctgatgctag tgctcctggt  840
gaaggagaac ataaaatcat ggattacatt agaaggcaaa gagcccagcc taaccatgac  900
ccaaatactc atcattgttt atgtggagca gatgctgatc tcattatgct tggccttgcc  960
acacatgaac cgaactttac cattattaga gaagaattca aaccaaacaa gcccaaacca  1020
tgtggtcttt gtaatcagtt tggacatgag gtcaaagatt gtgaaggttt gccaagagaa  1080
aagaagggaa agcatgatga acttgccgat agtcttcctt gtgcagaagg agagtttatc  1140
ttccttcggc ttaatgttct tcgtgagtat ttggaaagag aactcacaat ggccagccta  1200
ccattcacat ttgatgttga gaggagcatt gatgactggg ttttcatgtg cttctttgtg  1260
ggaaatgact tcctccctca tttgccatcg ttagagatta gggaaaatgc aattgaccgt  1320
ttggttaaca tatacaaaaa tgtggtacac aaaactgggg gttaccttac agaaagtggt  1380
tatgtcaatc tgcaaagagt acagatgatc atgttagcag ttggtgaagt tgaggatagc  1440
atttttaaaa agagaaagga tgatgaggac agttttagaa gacgacagaa agaaaaaaga  1500
aagagaatga agagagatca accagctttc actcctagtg gaatattaac tcctcatgcc  1560
ttgggttcaa gaaattcacc aggttctcaa gtagccagta atccgagaca agcagcctat  1620
gaaatgagga tgcagaataa ctctagtcct tcgatatctc ctaatacgag tttcacatct  1680
gatggctccc cgtctcccatt aggaggaatt aagcgaaaag cagaagacag tgacagtgaa  1740
cctgagccag aggataatgt caggttatgg gaagctggct ggaagcagcg gtactacaag  1800
aacaaatttg atgtggatgc agctgatgag aaattccgtc ggaaagttgt gcagtcgtac  1860
gttgaaggac tttgctgggt tcttagatat tattaccagg gctgtgcttc ctggaagtgg  1920
tattatccat ttcattatgc accatttgct tcagactttg aaggcattgc agacatgcca  1980
tctgattttg agaagggtac gaaaccgttt aaaccactag aacaacttat gggggtattt  2040
ccagctgcaa gtggtaattt tctacctcca tcatggcgga agctcatgag tgatcctgat  2100
tctagtataa ttgacttcta tcctgaagat tttgctattg atttgaatgg gaagaaatat  2160
gcatggcaag gtgttgctct cttgccattc gtggatgagc gaaggctacg agctgcccta  2220
gaagaggtat acccagacct cactccagaa gagaccagaa gaaacagcct tggaggtgat  2280
gtcttatttg tggggaaaca tcacccactc catgacttca ttttagagct gtaccagaca  2340
ggttccacag agccagtgga ggtacccccct gaactatgtc atgggattca aggaaagttt  2400
tctttggatg aagaagccat tcttccagat caaatagtat gttctcctgt tcctatgtta  2460
agggatctga cacagaacac tgtagtcagt attaatttta aagacccaca gtttgctgaa  2520
gattacattt ttaaagctgt aatgcttcca ggagcaagaa agccagcagc agtactgaaa  2580
cctagtgact gggaaaaatc cagcaatgga cggcagtgga agcctcagct tggctttaac  2640
cgtgaccgga ggcctgtgca cctggatcag gcagccttca ggactttggg ccatgtgatg  2700
ccaagaggct caggaactgg catttacagc aatgctgcac caccacctgt gacttaccag  2760
ggaaacttat acaggccgct tttgagagga caagcccaga ttccaaaact tatgtcaaat  2820
atgaggcccc aggattcctg gcgaggtcct cctcccccttt tccagcagca aaggtttgac  2880
agaggcgttg gggctgaacc tctgctccca tggaaccgga tgctgcaaac ccagaatgca  2940
gccttccagc caaaccagta ccagatgcta gctgggcctg gtgggtatcc acccagacga  3000
gatgatcgtg gagggagaca gggatatccc agagaaggaa ggaaataccc tttgccacca  3060
```

-continued

```
ccctcaggaa gatacaattg gaattaa                                      3087

SEQ ID NO: 28          moltype = DNA  length = 1863
FEATURE                Location/Qualifiers
source                 1..1863
                       mol_type = unassigned DNA
                       organism = Escherichia coli
SEQUENCE: 28
atggactata aggaccacga cggagactac aaggatcatg atattgatta caaagacgat  60
gacgataaga tggccccaaa gaagaagcgg aaggtcggta tccacggagt cccagcagcc  120
tcattgaagg gaaaattttt tgcatttctc ccgaacccta acacctcatc caataagttt  180
tttaagtcaa ttcttgagaa gaaaggagct acaattgtat catctattca aaattgcctc  240
cagagttcta ggaaagaggt cattatcctt atagaggaca gtttcgtcga cagtgacatg  300
cacctgacac agaaggacat ttttcaacgc gaggctggct tgaacgacgt agacgagttt  360
ttgggtaaaa ttgaacaatc cggcatccag tgcgttaaga ctagctgcat taccaagtgg  420
gttcaaaacg acaaattcgc ttttcaaaag gacgatttga ttaagttcca accgagtatc  480
atagtcatta gtgacaatgc cgatgatgga cagagtagca ctgacaaaga aagcgaaatc  540
tcaactgacg tagaatcaga gcgaaacgat gactcaaaca acaaagacat gattcaggcc  600
tccaaaccgc tcaaacggtt gcttcaggag gataaaggtc gcgcttccct tgttaccgat  660
aaaaccaagt ataaaaataa tgaacttata ataggcgcgc ttaaacgact taccaagaag  720
tacgagattg agggtgaaaa attccgagct cggtcctacc ggctcgctaa acaatctatg  780
gaaaattgtg atttcaatgt tagaagcgga gaggaagcac atacaaagtt gagaaacatc  840
ggtcctagta ttgctaaaaa aattcaggtc attcttgata cgggagttct cccgggtctc  900
aacgattccg ttggccttga agacaagctg aaatatttta agaactgcta tggaatcggg  960
tcagagatag caaaacggtg gaatctcctt aactttgagt cattttgcgt ggctgctaag  1020
aaagaccccg aggaatttgt gtccgattgg acgatattgt tcgggtggag ttattatgat  1080
gattggcttt gcaaaatgtc caggaatgaa tgcttcgccc atcttaagaa ggtccaaaag  1140
gctttgcgcg gaatcgaccc cgaatgtcag gtcgagcttc aagggtcata caatcggggt  1200
tactcaaaat gcggggatat agatctcctc ttttttaagc cattctgcaa cgataccact  1260
gaactcgcta agatcatgga gacactctgc ataaagcttt ataaagatgg gtatatacat  1320
tgcttcttgc aattgacgcc caacttggag aagctttttc ttaaaagaat tgttgaacgg  1380
ttccggacag ccaagattgt tggctatgga gaacgaaaac gctggtattc atcagaaatt  1440
atcaagaaat tctttatggg agtgaagttg tccccccgcg agctcgaaga attgaaggag  1500
atgaaaaacg acgagggaac cctgttgatc gaggaagaag aagaggaaac gaagctgaag  1560
cccattgacc agtacatgag cctgaacgct aaagacggaa actactgccg aaggttggat  1620
tttttctgtt gtaagtggga cgagctgggg gcggggagga tacactatac gggtagcaaa  1680
gagtataata ggtggataag gatactcgcc gcgcaaaaag ggttcaaact gacccagcat  1740
ggacttttcc ggaacaacat actcctggag tctttcaacg aaaggcgaat cttcgaactc  1800
ctgaacctta agtatgccga gccggagcac cgcaatatag agtgggaaaa aaagacggga  1860
tga                                                                1863

SEQ ID NO: 29          moltype = DNA  length = 1488
FEATURE                Location/Qualifiers
source                 1..1488
                       mol_type = unassigned DNA
                       organism = Escherichia coli
SEQUENCE: 29
atggactata aggaccacga cggagactac aaggatcatg atattgatta caaagacgat  60
gacgataaga tggccccaaa gaagaagcgg aaggtcggta tccacggagt cccagcagcc  120
ctgcctagtc agagccccgc aatatttaca gtgagtcgcc ttaaccaaac cgttcgactg  180
ttgctcgagc acgaaatggg gcaagtctgg atctccgggg aaatatcaaa ttttacgcag  240
ccagcctccg gtcactggta cttcactctt aaagatgaca cggcgcaagt acgctgcgcc  300
atgtttcgga acagcaatag acgagtgacg ttccggccac aacatggaca gcaagtactc  360
gtcagggcca atatcactct ttatgagccg cgcggtgact atcaaataat tgtcgaatct  420
atgcaacccg cgggggaggg tttgctccag caaaagtatg agcaactcaa agcgaagctc  480
caggcagaag gcctgttcga ccagcagtat aaaaaaccgc tcccgtcacc cgctcattgt  540
gttggcgtca taacctctaa gacgggtgct gcgttgcacg acattcttca tgtgcttaag  600
cgccgagacc catctctgcc tgttatcatc tacccagcgg ccgttcaagg cgatgacgct  660
cctgggcaga tagtaagagc aatagaactg gcgaatcagc ggaacgaatg tgatgtgctg  720
atcgttgggc gcggcggagg gagcttggaa gatctttggt ccttcaacga tgagcgcgtc  780
gcacgggcaa tcttcaccag ccggataccg gtagtttcag cggtggggca tgagacggac  840
gtcacaatcg ccgattttgt agccgacctg agagcaccga cgccatcagc ggcagcagaa  900
gtcgtcagcc gcaatcagca ggagctgctc aggcaggtcc agagcacccg gcaacgcctc  960
gagatggcga tggattacta tcttgccaat cgaacacgac gattcaccca gattcaccac  1020
cggttgcagc agcaacatcc ccaacttcgg ctggcccgac agcaaacaat gctggaacgc  1080
ctccagaaac ggatgagttt tgctctggaa aatcagttga agcgaactgg tcaacagcag  1140
caaagactga ctcagcgcct caatcagcaa aatccccaac ctaagatcca tcgggcacaa  1200
acccgcattc aacaactgga gtatagactg gctgagacct tgcgcgccca gctctccgca  1260
actcgcgaga ggttcggaaa tgccgtaacg catttggagg ccgtgagccc actgtcaacc  1320
ctcgctcggg gctactccgt gacgactgcc acggacggca atgtgctcaa aaaggtaaaa  1380
caagtcaaag ctggagaaat gcttactact cggctcgaag acggatggat cgaaagtgaa  1440
gtcaaaaata tacaacctgt caagaagagt cggaaaaagg tgcattga            1488

SEQ ID NO: 30          moltype = DNA  length = 360
FEATURE                Location/Qualifiers
source                 1..360
                       mol_type = unassigned DNA
                       organism = Escherichia coli
SEQUENCE: 30
```

```
atggactata aggaccacga cggagactac aaggatcatg atattgatta caaagacgat  60
gacgataaga tggccccaaa gaagaagcgg aaggtcggta tccacggagt cccagcagcc  120
ccgaaaaaaa acgaagcccc cgcctccttt gagaaagcac ttagcgagct ggagcagatc  180
gtgacgcgct tggaatcagg ggatctccct ttggaagagg cattgaatga gtttgagcga  240
ggagttcagc tcgctagaca aggccaggcc aaacttcaac aggcggaaca gcgagtccag  300
attctcctta gtgataatga ggatgcctct ctgacaccgt tcacgccaga caacgagtga  360
```

```
SEQ ID NO: 31          moltype = DNA  length = 4272
FEATURE                Location/Qualifiers
source                 1..4272
                       mol_type = unassigned DNA
                       organism = Streptococcus pyogenes
SEQUENCE: 31
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtt  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg cccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued ctggccgacg ctaatctgga caaagtgctg tccgcctaca acaagcaccg ggataagccc 4020
atcagagagc aggccgagaa tatcatccac ctgtttaccc tgaccaatct gggagcccct 4080
gccgccttca agtactttga caccaccatc gaccggaaga ggtacaccag caccaaagag 4140
gtgctggacg ccaccctgat ccaccagagc atcaccggcc tgtacgagac acggatcgac 4200
ctgtctcagc tgggaggcga caaaaggccg gcggccacga aaaaggccgg ccaggcaaaa 4260
aagaaaaagt aa 4272

SEQ ID NO: 32 moltype = DNA length = 4269
FEATURE Location/Qualifiers
source 1..4269
mol_type = unassigned DNA
organism = Streptococcus pyogenes SEQUENCE: 32
atggactata aggaccacga cggagactac aaggatcatg atattgatta caaagacgat 60
gacgataaga tggccccaaa gaagaagcgg aaggtcggta tccacggagt cccagcagcc 120
gacaagaagt acagcatcgg cctggacatc ggcaccaact ctgtgggctg ggccgtgatc 180
accgacgagt acaaggtgcc cagcaagaaa ttcaaggtgc tgggcaacac cgaccggcac 240
agcatcaaga agaacctgat cggagccctg ctgttcgaca gcggcgaaac agccgaggcc 300
acccggctga agagaaccgc cagaagaaga tacaccagac ggaagaaccg gatctgctat 360
ctgcaagaga tcttcagcaa cgagatggcc aaggtggacg acagcttctt ccacagactg 420
gaagagtcct tcctggtgga agaggataag aagcacgagc ggcaccccat cttcggcaac 480
atcgtggacg aggtggccta ccacgagaag taccccacca tctaccacct gagaaagaaa 540
ctggtggaca gcaccgacaa ggccgacctg cggctgatct atctggccct ggcccacatg 600
atcaagttcc ggggccactt cctgatcgag ggcgacctga accccgacaa cagcgacgtt 660
gacaagctgt tcatccagct ggtgcagacc tacaaccagc tgttcgagga aaaccccatc 720
aacgccagcg gcgtggacgc caaggccatc ctgtctgcca gactgagcaa gagcagacgg 780
ctggaaaatc tgatcgccca gctgcccggc gagaagaaga atggcctgtt cggaaacctg 840
attgccctga gcctgggcct gacccccaac ttcaagagca acttcgacct ggccgaggat 900
gccaaactgc agctgagcaa ggacacctac gacgacgacc tggacaacct gctggcccag 960
atcggcgacc agtacgccga cctgtttctg gccgccaaga acctgtccga cgccatcctg 1020
ctgagcgaca tcctgagagt gaacaccgag atcaccaagg ccccccctgag cgcctctatg 1080
atcaagagat acgacgagca ccaccaggac ctgaccctgc tgaaagctct cgtgcggcag 1140
cagctgcctg agaagtacaa agagattttc ttcgaccaga gcaagaacgg ctacgccggc 1200
tacattgacg gcggagccag ccaggaagag ttctacaagt tcatcaagcc catcctggaa 1260
aagatggacg gcaccgagga actgctcgtg aagctgaaca gagaggacct gctgcggaag 1320
cagcggacct tcgacaacgg cagcatcccc caccagatcc acctgggaga gctgcacgcc 1380
attctgcggc ggcaggaaga tttttaccca ttcctgaagg acaaccggga aaagatcgag 1440
aagatcctga ccttccgcat cccctactac gtgggccctc tggccagggg aaacagcaga 1500
ttcgcctgga tgaccagaaa gagcgaggaa accatcaccc cctggaactt cgaggaagtg 1560
gtggacaagg gcgcttccgc ccagagcttc atcgagcgga tgaccaactt cgataagaac 1620
ctgcccaacg agaaggtgct gcccaagcac agcctgctgt acgagtactt caccgtgtat 1680
aacgagctga ccaaagtgaa atacgtgacc gagggaatga gaaagcccgc cttcctgagc 1740
ggcgagcaga aaaaggccat cgtggacctg ctgttcaaga ccaaccggaa agtgaccgtg 1800
aagcagctga aagaggacta cttcaagaaa atcgagtgct tcgactccgt ggaaatctcc 1860
ggcgtggaag atcggttcaa cgcctccctg ggcacatacc acgatctgct gaaaattatc 1920
aaggacaagg acttcctgga caatgaggaa aacgaggaca ttctggaaga tatcgtgctg 1980
accctgacac tgtttgagga cagagagatg atcgaggaac ggctgaaaac ctatgcccac 2040
ctgttcgacg acaaagtgat gaagcagctg aagcggcgga gatacaccgg ctggggcagg 2100
ctgagccgga agctgatcaa cggcatccgg gacaagcagt ccggcaagac aatcctggat 2160
ttcctgaagt ccgacggctt cgccaacaga aacttcatgc agctgatcca cgacgacagc 2220
ctgaccttta aagaggacat ccagaaagcc caggtgtccg gccagggcga tagcctgcac 2280
gagcacattg ccaatctggc cggcagcccc gccattaaga agggcatcct gcagacagtg 2340
aaggtggtgg acgagctcgt gaaagtgatg ggccggcaca agcccgagaa catcgtgatc 2400
gaaatggcca gagagaacca gaccacccag aagggacaga agaacagccg cgagagaatg 2460
aagcggatcg aagagggcat caaagagctg ggcagccaga tcctgaaaga acaccccgtg 2520
gaaaacaccc agctgcagaa cgagaagctg tacctgtact acctgcagaa tgggcgggat 2580
atgtacgtgg accaggaact ggacatcaac cggctgtccg actacgatgt ggaccatatc 2640
gtgcctcaga gctttctgaa ggacgactcc atcgacaaca aggtgctgac cagaagcgac 2700
aagaaccggg gcaagagcga caacgtgccc tccgaagagg tcgtgaagaa gatgaagaac 2760
tactggcggc agctgctgaa cgccaagctg attacccaga gaaagttcga caatctgacc 2820
aaggccgaga gaggcggcct gagcgaactg gataaggccg gcatcaagag acagctggtg 2880
gaaacccggc agatcacaaa gcacgtggca cagatcctgg actcccggat gaacactaag 2940
tacgacgaga atgacaagct gatccgggaa gtgaaagtga tcaccctgaa gtccaagctg 3000
gtgtccgatt tccggaagga tttccagttt tacaaagtgc gcgagatcaa caactaccac 3060
cacgcccacg acgcctacct gaacgccgtc gtgggaaccg ccctgatcaa aaagtaccct 3120
aagctggaaa gcgagttcgt gtacggcgac tacaaggtgt acgacgtgcg gaagatgatc 3180
gccaagagcg agcaggaaat cggcaaggct accgccaagt acttcttcta cagcaacatc 3240
atgaactttt tcaagaccga gattaccctg gccaacggcg agatccggaa gcggcctctg 3300
atcgagacaa acggcgaaac cggggagatc gtgtgggata agggccggga ttttgccacc 3360
gtgcggaaag tgctgagcat gccccaagtg aatatcgtga aaaagaccga ggtgcagaca 3420
ggcggcttca gcaaagagtc tatcctgccc aagaggaaca gcgataagct gatcgccaga 3480
aagaaggact gggaccctaa gaagtacggc ggcttcgaca gccccaccgt ggcctattct 3540
gtgctggtgg tggccaaagt ggaaaagggc aagtccaaga aactgaagag tgtgaaagag 3600
ctgctgggga tcaccatcat ggaaagaagc agcttcgaga agaatcccat cgactttctg 3660
gaagccaagg gctacaaaga agtgaaaaag gacctgatca tcaagctgcc taagtactcc 3720
ctgttcgagc tggaaaacgg ccggaagaga atgctggcct ctgccggcga actgcagaag 3780
ggaaacgaac tggccctgcc ctccaaatat gtgaacttcc tgtacctggc cagccactat 3840
gagaagctga agggctcccc cgaggataat gagcagaaac agctgtttgt ggaacagcac 3900
aagcactacc tggacgagat catcgagcag atcagcgagt tctccaagag agtgatcctg 3960

-continued

```
gccgacgcta atctggacaa agtgctgtcc gcctacaaca agcaccggga taagcccatc  4020
agagagcagg ccgagaatat catccacctg tttaccctga ccaatctggg agcccctgcc  4080
gccttcaagt actttgacac caccatcgac cggaagaggt acaccagcac caaagaggtg  4140
ctggacgcca ccctgatcca ccagagcatc accggcctgt acgagacacg gatcgacctg  4200
tctcagctgg gaggcgacaa aaggccggcg gccacgaaaa aggccggcca ggcaaaaaag  4260
aaaaagtaa                                                          4269

SEQ ID NO: 33          moltype = DNA  length = 4272
FEATURE                Location/Qualifiers
source                 1..4272
                       mol_type = unassigned DNA
                       organism = Streptococcus pyogenes
SEQUENCE: 33
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtt  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggcct ttttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                      4272

SEQ ID NO: 34          moltype = DNA  length = 4272
FEATURE                Location/Qualifiers
source                 1..4272
                       mol_type = unassigned DNA
                       organism = Streptococcus pyogenes
SEQUENCE: 34
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtt  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gagacccctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact tttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                 4272

SEQ ID NO: 35          moltype = DNA  length = 4272
FEATURE                Location/Qualifiers
source                 1..4272
                       mol_type = unassigned DNA
                       organism = Streptococcus pyogenes
SEQUENCE: 35
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtg  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg cccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gccccatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                    4272

SEQ ID NO: 36          moltype = DNA  length = 4272
FEATURE                Location/Qualifiers
source                 1..4272
                       mol_type = unassigned DNA
                       organism = Streptococcus pyogenes
SEQUENCE: 36
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtt  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcgc cagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                      4272

SEQ ID NO: 37          moltype = DNA  length = 4272
FEATURE                Location/Qualifiers
source                 1..4272
                       mol_type = unassigned DNA
                       organism = Streptococcus pyogenes
SEQUENCE: 37
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtt  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgccaacaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gaccacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggccg gcttcatcaa gccccagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaactac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

-continued

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                      4272

SEQ ID NO: 38          moltype = DNA  length = 4272
FEATURE                Location/Qualifiers
source                 1..4272
                       mol_type = unassigned DNA
                       organism = Streptococcus pyogenes
SEQUENCE: 38
atggactata aggaccacga cggagactac aaggatcatg atattgatta caaagacgat  60
gacgataaga tggccccaaa gaagaagcgg aaggtcggta tccacggagt cccagcagcc  120
gacaagaagt acagcatcgg cctggacatc ggcaccaact ctgtgggctg ggccgtgatc  180
accgacgagt acaaggtgcc cagcaagaaa ttcaaggtgc tgggcaacac cgaccggcac  240
agcatcaaga agaacctgat cggagccctg ctgttcgaca gcggcgaaac agccgaggcc  300
acccggctga agagaaccgc cagaagaaga tacaccagac ggaagaaccg gatctgctat  360
ctgcaagaga tcttcagcaa cgagatggcc aaggtggacg acagcttctt ccacagactg  420
gaagagtcct tcctggtgga agaggataag aagcacgagc ggcaccccat cttcggcaac  480
atcgtggacg aggtggccta ccacgagaag taccccacca tctaccacct gagaaagaaa  540
ctggtggaca gcaccgacaa ggccgacctg cggctgatct atctggccct ggcccacatg  600
atcaagttcc ggggccactt cctgatcgag ggcgacctga accccgacaa cagcgacgtg  660
gacaagctgt tcatccagct ggtgcagacc tacaaccagc tgttcgagga aaaccccatc  720
aacgccagcg gcgtggacgc caaggccatc ctgtctgcca gactgagcaa gagcagacgg  780
ctggaaaatc tgatcgccca gctgcccggc gagaagaaga atggcctgtt cggaaacctg  840
attgccctga gcctgggcct gacccccaac ttcaagagca acttcgacct ggccgaggat  900
gccaaactgc agctgagcaa ggacacctac gacgacgacc tggacaacct gctggcccag  960
atcggcgacc agtacgccga cctgtttctg gccgccaaga acctgtccga cgccatcctg  1020
ctgagcgaca tcctgagagt gaacaccgag atcaccaagg ccccccctgag cgcctctatg  1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga aagaggacta cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgcctgcaga aacttcatgc agctgatcca cgacgacagc  2220
ctgaccttta aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca agcccgagaa catcgtgatc  2400
gaaatggcca gagagaacca gatcacccag aagggacaga agaacagccg cgagagaatg  2460
aagcggatcg aagagggcat caaagagctg ggcagccaga tcctgaaaga acaccccgtg  2520
gaaaacaccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gaggcggcct gagcgaactg gataaggcca tgttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcaccct gaagtccaag  3000
ctggtgtccg atttccggaa ggatttccag ttttacaaag tgcgcgagat caacaaatac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca agtacttctt ctacagcaac  3240
atcatgaact ttttcaagac cgagattacc ctggccaacg gcgagatccg gaagcggcct  3300
ctgatcgaga caaacggcga aaccggggag atcgtgtggg ataagggccg ggattttgcc  3360
accgtgcgga aagtgctgag catgccccaa gtgaatatcg tgaaaaagac cgaggtgcag  3420
acaggcggct tcagcaaaga gtctatcctg cccaagagga acagcgataa gctgatcgcc  3480
agaaagaagg actgggaccc taagaagtac ggcggcttcg acagccccac cgtggcctat  3540
tctgtgctgg tggtggccaa agtggaaaag ggcaagtcca agaaactgaa gagtgtgaaa  3600
gagctgctgg ggatcaccat catggaaaga agcagcttcg agaagaatcc catcgacttt  3660
ctggaagcca agggctacaa agaagtgaaa aaggacctga tcatcaagct gcctaagtac  3720
tccctgttcg agctggaaaa cggccggaag agaatgctgg cctctgccgg cgaactgcag  3780
aagggaaacg aactggccct gccctccaaa tatgtgaact tcctgtacct ggccagccac  3840
tatgagaagc tgaagggctc ccccgaggat aatgagcaga aacagctgtt tgtggaacag  3900
cacaagcact acctggacga gatcatcgag cagatcagcg agttctccaa gagagtgatc  3960
```

```
ctggccgacg ctaatctgga caaagtgctg tccgcctaca acaagcaccg ggataagccc  4020
atcagagagc aggccgagaa tatcatccac ctgtttaccc tgaccaatct gggagcccct  4080
gccgccttca agtactttga caccaccatc gaccggaaga ggtacaccag caccaaagag  4140
gtgctggacg ccaccctgat ccaccagagc atcaccggcc tgtacgagac acggatcgac  4200
ctgtctcagc tgggaggcga caaaaggccg gcggccacga aaaaggccgg ccaggcaaaa  4260
aagaaaaagt aa                                                      4272

SEQ ID NO: 39          moltype = DNA  length = 4053
FEATURE                Location/Qualifiers
source                 1..4053
                       mol_type = unassigned DNA
                       organism = Staphylococcus aureus
SEQUENCE: 39
atggactata aggaccacga cggagactac aaggatcatg atattgatta caaagacgat  60
gacgataaga tggccccgaa gaaaaagcgc aaggtcgaag cgtccatgaa aaggaactac  120
attctggggc tggacatcgg gattacaagc gtggggtatg ggattattga ctatgaaaca  180
agggacgtga tcgacgcagg cgtcagactg ttcaaggagg ccaacgtgga aaacaatgag  240
ggacggagaa gcaagagggg agccaggcgc ctgaaacgac ggagaaggca cagaatccag  300
agggtgaaga aactgctgtt cgattacaac ctgctgaccg accattctga gctgagtgga  360
attaatcctt atgaagccag ggtgaaaggc ctgagtcaga agctgtcaga ggaagagttt  420
tccgcagctc tgctgcacct ggctaagcgc cgaggagtgc ataacgtcaa tgaggtggaa  480
gaggacaccg gcaacgagct gtctacaaag gaacagatct cacgcaatag caaagctctg  540
gaagagaagt atgtcgcaga gctacagctg gaacggctga agaaagatgg cgaggtgaga  600
gggtcaatta ataggttcaa gacaagcgac tacgtcaaag aagccaagca gctgctgaaa  660
gtgcagaagg cttaccacca gctggatcag agcttcatcg atacttatat cgacctgctg  720
gagactcgga gaacctacta tgagggacca ggagaaggga gccccttcgg atggaaagac  780
atcaaggaat ggtacgagat gctgatggga cattgcacct attttccaga agagctgaga  840
agcgtcaagt acgcttataa cgcagatctg tacaacgccc tgaatgacct gaacaacctg  900
gtcatcacca gggatgaaaa cgagaaactg gaatactatg agaagttcca gatcatcgaa  960
aacgtgttta agcagaagaa aaagcctaca ctgaaacaga ttgctaagga gatcctggtc  1020
aacgaagagg acatcaaggg ctaccgggtg acaagcactg gaaaaccaga gttcaccaat  1080
ctgaaagtgt atcacgatat taaggacatc acagcacgga aagaaatcat tgagaacgcc  1140
gaactgctgg atcagattgc taagatcctg actatctacc agagttccga ggacatccag  1200
gaagagctga ctaacctgaa cagcgagctg acccaggaag agatcgaaca gattagtaat  1260
ctgaagggt acaccggaac acacaacctg tccctgaaag ctatcaatct gattctggat  1320
gagctgtggc atacaaacga caatcagatt gcaatcttta accggctgaa gctggtacca  1380
aaaaaggtgg acctgagtca gcagaaagag atcccaacca cactggtgga cgatttcatt  1440
ctgtcacccg tggtcaagcg gagcttcatc cagagcatca aagtgatcaa cgccatcatc  1500
aagaagtacg gcctgcccaa tgatatcatt atcgagctgg ctagggagaa gaacagcaag  1560
gacgcacaga agatgatcaa tgagatgcag aaacgaaacc ggcagaccaa tgaacgcatt  1620
gaagagatta tccgaactac cgggaaagag aacgcaaagt acctgattga aaaaatcaag  1680
ctgcacgata tgcaggaggg aaagtgtctg tattctctgg aggccatccc cctggaggac  1740
ctgctgaaca atccattcaa ctacgaggtc gatcatatta tccccagaag cgtgtccttc  1800
gacaattcct ttaacaacaa ggtgctggtc aagcaggaag agaactctaa aaagggcaat  1860
aggactcctt tccagtacct gtctagttca gattccaaga tctcttacga aacctttaaa  1920
aagcacattc tgaatctggc caaaggaaag ggccgcatca gcaagaccaa aaaggagtac  1980
ctgctggaag agcgggacat caacagattc tccgtccaga aggattttat taaccggaat  2040
ctggtggaca caagatacgc tactcgcggc ctgatgaatc tgctgcgatc ctatttccgg  2100
gtgaacaatc tggatgtgaa agtcaagtcc atcaacggcg ggttcacatc ttttctgagg  2160
cgcaaatgga agtttaaaaa ggagcgcaac aaagggtaca agcaccatgc cgaagatgct  2220
ctgattatcg caaatgccga cttcatcttt aaggagtgga aaaagctgga caaagccaag  2280
aaagtgatgg agaaccagat gttcgaagag aagcaggccg aatctatgcc cgaaatcgag  2340
acagaacagg agtacaagga gattttcatc actcctcacc agatcaagca tatcaaggat  2400
ttcaaggact acaagtactc tcaccgggtg gataaaaagc ccaacagaga gctgatcaat  2460
gacaccctgt atagtacaag aaaagacgat aaggggaata ccctgattgt gaacaatctg  2520
aacggactgt acgacaaaga taatgacaag ctgaaaaagc tgatcaacaa aagtcccgag  2580
aagctgctga tgtaccacca tgatcctcag acatatcaga aactgaagct gattatggag  2640
cagtacggcg acgagaagaa cccactgtat aagtactatg aagagactgg gaactacctg  2700
accaagtata gcaaaaagga taatggcccc gtgatcaaga agatcaagta ctatgggaac  2760
aagctgaatg cccatctgga catcacagac gattacccta acagtcgcaa caaggtggtc  2820
aagctgtcac tgaagccata cagattcgat gtctatctgg acaacggcgt gtataaattt  2880
gtgactgtca agaatctgga tgtcatcaaa aaggagaact actatgaagt gaatagcaag  2940
tgctacgaag aggctaaaaa gctgaaaaag attagcaacc aggcagagtt catcgcctcc  3000
ttttacaaca acgacctgat taagatcaat ggcgaactgt atagggtcat cggggtgaac  3060
aatgatctgc tgaaccgcat tgaagtgaat atgattgaca tcacttaccg agagtatctg  3120
gaaaacatga atgataagcg cccccctcga attatcaaaa caatcgcctc taagactcag  3180
agtatcaaaa agtactcaac cgacattctg ggaaacctgt atgaggtgaa gagcaaaaag  3240
caccctcaga ttatcaaaaa gggcaggtcc ggcggcggag agggcagagg aagtcttcta  3300
acatgcggtg acgtggagga gaatcccggc ccaatggtga gcaagggcga ggagctgttc  3360
accggggtgg tgcccatcct ggtcgagctg gacggcgacg taaacggcca caagttcagc  3420
gtgtccggcg agggcgaggg cgatgccacc tacggcaagc tgaccctgaa gttcatctgc  3480
accaccggca agctgcccgt gccctggccc accctcgtga ccaccctgac ctacggcgtg  3540
cagtgcttca gccgctaccc cgaccacatg aagcagcacg acttcttcaa gtccgccatg  3600
cccgaaggct acgtccagga gcgcaccatc ttcttcaagg acgacggcaa ctacaagacc  3660
cgcgccgagg tgaagttcga gggcgacacc ctggtgaacc gcatcgagct gaagggcatc  3720
gacttcaagg aggacggcaa catcctgggg cacaagctgg agtacaacta caacagccac  3780
aacgtctata tcatggccga caagcagaag aacggcatca aggtgaactt caagatccgc  3840
cacaacatcg aggacggcag cgtgcagctc gccgaccact accagcagaa cacccccatc  3900
ggcgacggcc ccgtgctgct gcccgacaac cactacctga gcacccagtc cgccctgagc  3960
```

-continued

```
aaagacccca acgagaagcg cgatcacatg gtcctgctgg agttcgtgac cgccgccggg  4020
atcactctcg gcatggacga gctgtacaag taa                               4053

SEQ ID NO: 40          moltype = DNA  length = 4038
FEATURE                Location/Qualifiers
source                 1..4038
                       mol_type = unassigned DNA
                       organism = Francisella sp.
SEQUENCE: 40
atgagcatct accaggagtt cgtcaacaag tattcactga gtaagacact gcggttcgag  60
ctgatcccac agggcaagac actggagaac atcaaggccc gaggcctgat tctggacgat  120
gagaagcggg caaaagacta taagaaagcc aagcagatca ttgataaata ccaccagttc  180
tttatcgagg aaattctgag ctccgtgtgc atcagtgagg atctgctgca gaattactca  240
gacgtgtact tcaagctgaa gaagagcgac gatgacaacc tgcagaagga cttcaagtcc  300
gccaaggaca ccatcaagaa acagattagc gagtacatca aggactccga aaagtttaaa  360
aatctgttca accagaatct gatcgatgct aagaaaggcc aggagtccga cctgatcctg  420
tggctgaaac agtctaagga caatgggatt gaactgttca aggctaactc cgatatcact  480
gatattgacg aggcactgga aatcatcaag agcttcaagg gatggaccac atactttaaa  540
ggcttccacg agaaccgcaa gaacgtgtac tccagcaacg acattcctac ctccatcatc  600
taccgaatcg tcgatgacaa tctgccaaag ttcctggaga acaaggccaa atatgaatct  660
ctgaaggaca aagctcccga ggcaattaat tacgaacaga tcaagaaaga tctggctgag  720
gaactgacat tcgatatcga ctataagact agcgaggtga accagagggt cttttccctg  780
gacgaggtgt ttgaaatcgc caatttcaac aattacctga accagtccgg cattactaaa  840
ttcaatacca tcattggcgg gaagtttgtg aacggggaga ataccaagcg caagggaatt  900
aacgaataca tcaatctgta tagccagcag atcaacgaca aaactctgaa gaaatacaag  960
atgtctgtgc tgttcaaaca gatcctgagt gataccgagt ccaagtcttt tgtcattgat  1020
aaactggaag atgactcaga cgtggtcact accatgcaga gcttttatga gcagatcgcc  1080
gctttcaaga cagtggagga aaaatctatt aaggaaactc tgagtctgct gttcgatgac  1140
ctgaaagccc agaagctgga cctgagtaag atctacttca aaaacgataa gagtctgaca  1200
gacctgtcac agcaggtgtt tgatgactat tccgtgattg ggaccgccgt cctggagtac  1260
attacacagc agatcgctcc aaagaacctg gataatccct ctaagaaaga gcaggaactg  1320
atcgctaaga aaaccgagaa ggcaaaatat ctgagtctgg aaacaattaa gctggcactg  1380
gaggagttca acaagcacag ggatattgac aaacagtgcc gctttgagga aatcctggcc  1440
aacttcgcag ccatccccat gatttttgat gagatcgccc agaacaaaga caatctggct  1500
cagatcagta ttaagtacca gaaccagggc aagaaagacc tgctgcaggc ttcagcagaa  1560
gatgacgtga aagccatcaa ggatctgctg gaccagacca acaatctgct gcacaagctg  1620
aaaatcttcc atattagtca gtcagaggat aaggctaata tcctggataa agacgaacac  1680
ttctacctgg tgttcgagga atgttacttc gagctggcaa acattgtccc cctgtataac  1740
aagattagga actacatcac acagaagcct tactctgacg agaagtttaa actgaacttc  1800
gaaaatagta ccctggccaa cgggtgggat aagaacaagg agcctgacaa cacagctatc  1860
ctgttcatca aggatgacaa gtactatctg ggagtgatga ataagaaaaa caataagatc  1920
ttcgatgaca aagccattaa ggagaacaaa ggggaaggat acaagaaaat cgtgtataag  1980
ctgctgcccg gcgcaaataa gatgctgcct aaggtgttct tcagcgccaa gagtatcaaa  2040
ttctacaacc catccgagga catcctgcgg attagaaatc actcaacaca tactaagaac  2100
gggagccccc agaagggata tgagaaattt gagttcaaca tcgaggattg caggaagttt  2160
attgacttct acaagcagag catctccaaa caccctgaat ggaaggattt tggcttccgg  2220
ttttccgaca cacagagata taactctatc gacgagttct accgcgaggt ggaaaatcag  2280
gggtataagc tgacttttga gaacatttct gaaagttaca tcgacagcgt ggtcaatcag  2340
ggaaagctgt acctgttcca gatctataac aaagattttt cagcatacag caagggcaga  2400
ccaaacctgc atacactgta ctggaaggcc ctgttcgatg agaggaatct gcaggacgtg  2460
gtctataaac tgaacggaga ggccgaactg ttttaccgga agcagtctat tcctaagaaa  2520
atcactcacc cagctaagga ggccatcgct aacaagaaca aggacaatcc taagaaagag  2580
agcgtgttcg aatacgatct gattaaggac aagcggttca ccgaagataa gttctttttc  2640
cattgtccaa tcaccattaa cttcaagtca agcggcgcta acaagttcaa cgacgagatc  2700
aatctgctgc tgaaggaaaa agcaaacgat gtgcacatcc tgagcattga ccgaggagag  2760
cggcatctgg cctactatac cctggtggat ggcaaaggga atatcattaa gcaggataca  2820
ttcaacatca ttggcaatga ccggatgaaa accaactacc acgataaact ggctgcaatc  2880
gagaaggata gagactcagc taggaaggac tggaagaaaa tcaacaacat taaggagatg  2940
aaggaaggct atctgagcca ggtggtccat gagattgcaa agctggtcat cgaatacaat  3000
gccattgtgg tgttcgagga tctgaacttc ggctttaaga gggggcgctt taaggtggaa  3060
aaacaggtct atcagaagct ggagaaaatg ctgatcgaaa agctgaatta cctggtgttt  3120
aaagataacg agttcgacaa gaccggaggc gtcctgagag cctaccagct gacagctccc  3180
tttgaaactt tcaagaaaat gggaaaacag acaggcatca tctactatgt gccagccgga  3240
ttcacttcca agatctgccc cgtgaccggc tttgtcaacc agctgtaccc taaatatgag  3300
tcagtgagca agtcccagga atttttcagc aagttcgata agatctgtta taatctggac  3360
aaggggtact tcgagttttc cttcgattac aagaacttcg gcgacaaggc cgctaagggg  3420
aaatggacca ttgcctcctt cggatctcgc ctgatcaact ttcgaaattc cgataaaaac  3480
cacaattggg acactaggga ggtgtaccca accaaggagc tggaaaagct gctgaaagac  3540
tactctatcg agtatggaca tggcgaatgc atcaaggcag ccatctgtgg cgagagtgat  3600
aagaaatttt tcgccaagct gacctcagtg ctgaatacaa tcctgcagat gcggaactca  3660
aagaccggga cagaactgga ctatctgatt agccccgtgg ctgatgtcaa cggaaacttc  3720
ttcgacagca gacaggcacc caaaaatatg cctcaggatg cagacgccaa cggggcctac  3780
cacatcgggc tgaagggact gatgctgctg ggccggatca agaacaatca ggaggggaag  3840
aagctgaacc tggtcattaa gaacgaggaa tacttcgagt ttgtccagaa tagaaataac  3900
aaaaggccgg cggccacgaa aaaggccggc caggcaaaaa agaaaaaggg atcctaccca  3960
tacgatgttc cagattacgc ttatccctac gacgtgcctg attatgcata cccatatgat  4020
gtccccgact atgcctaa                                                4038

SEQ ID NO: 41          moltype = DNA  length = 4059
```

-continued

```
FEATURE                Location/Qualifiers
source                 1..4059
                       mol_type = unassigned DNA
                       organism = Acidaminococcus sp.
SEQUENCE: 41
atgacacagt tcgagggctt taccaacctg tatcaggtga gcaagacact gcggtttgag  60
ctgatcccac agggcaagac cctgaagcac atccaggagc agggcttcat cgaggaggac  120
aaggcccgca atgatcacta caaggagctg aagcccatca tcgatcggat ctacaagacc  180
tatgccgacc agtgcctgca gctggtgcag ctggattggg agaacctgag cgccgccatc  240
gactcctata gaaaggagaa aaccgaggag acaaggaacg ccctgatcga ggagcaggcc  300
acatatcgca atgccatcca cgactacttc atcggccgga cagacaacct gaccgatgcc  360
atcaataaga gacacgccga gatctacaag ggcctgttca aggccgagct gtttaatggc  420
aaggtgctga agcagctggg caccgtgacc acaaccgagc acgagaacgc cctgctgcgg  480
agcttcgaca agtttacaac ctacttctcc ggcttttatg agaacaggaa gaacgtgttc  540
agcgccgagg atatcagcac agccatccca caccgcatcg tgcaggacaa cttccccaag  600
tttaaggaga attgtcacat cttcacacgc ctgatcaccg ccgtgcccag cctgcgggag  660
cactttgaga acgtgaagaa ggccatcggc atcttcgtga gcacctccat cgaggaggtg  720
ttttccttcc ctttttataa ccagctgctg acacagaccc agatcgacct gtataaccag  780
ctgctgggag gaatctctcg ggaggcaggc accgagaaga tcaagggcct gaacgaggtg  840
ctgaatctgg ccatccagaa gaatgatgag acagcccaca tcatcgcctc cctgccacac  900
agattcatcc ccctgtttaa gcagatcctg tccgatagga acaccctgtc tttcatcctg  960
gaggagttta agagcgacga ggaagtgatc cagtccttct gcaagtacaa gacactgctg  1020
agaaacgaga acgtgctgga gacagccgag gccctgttta acgagctgaa cagcatcgac  1080
ctgacacaca tcttcatcag ccacaagaag ctggagacaa tcagcagcgc cctgtgcgac  1140
cactgggata cactgaggaa tgccctgtat gagcggagaa tctccgagct gacaggcaag  1200
atcaccaagt ctgccaagga gaaggtgcag cgcagcctga agcacgagga tatcaacctg  1260
caggagatca tctctgccgc aggcaaggag ctgagcgagg ccttcaagca gaaaaccagc  1320
gagatcctgt cccacgcaca cgccgccctg gatcagccac tgcctacaac cctgaagaag  1380
caggaggaga aggagatcct gaagtctcag ctggacagcc tgctgggcct gtaccacctg  1440
ctggactggt ttgccgtgga tgagtccaac gaggtggacc ccgagttctc tgcccggctg  1500
accggcatca agctggagat ggagccttct ctgagcttct acaacaaggc cagaaattat  1560
gccaccaaga agccctactc cgtggagaag ttcaagctga actttcagat gcctacactg  1620
gcctctggct gggacgtgaa taaggagaag aacaatggcg ccatcctgtt tgtgaagaac  1680
ggcctgtact atctgggcat catgccaaag cagaagggca ggtataaggc cctgagcttc  1740
gagcccacag agaaaaccag cgagggcttt gataagatgt actatgacta cttccctgat  1800
gccgccaaga tgatcccaaa gtgcagcacc cagctgaagg ccgtgacagc ccactttcag  1860
acccacacaa cccccatcct gctgtccaac aatttcatcg agcctctgga gatcacaaag  1920
gagatctacg acctgaacaa tcctgagaag gagccaaaga agtttcagac agcctacgcc  1980
aagaaaaccg gcgaccagaa gggctacaga gaggccctgt gcaagtggat cgacttcaca  2040
agggatttc tgtccaagta taccaagaca acctctatcg atctgtctag cctgcggcca  2100
tcctctcagt ataaggacct gggcgagtac tatgccgagc tgaatcccct gctgtaccac  2160
atcagcttcc agagaatcgc cgagaaggag atcatggatg ccgtggagac aggcaagctg  2220
tacctgttcc agatctataa caaggacttt gccaagggcc accacggcaa gcctaatctg  2280
cacacactgt attggaccgg cctgttttct ccagagaacc tggccaagac aagcatcaag  2340
ctgaatggcc aggccgagct gttctaccgc cctaagtcca ggatgaagag gatggcacac  2400
cggctgggag agaagatgct gaacaagaag ctgaaggatc agaaaacccc aatccccgac  2460
accctgtacc aggagctgta cgactatgtg aatcacagac tgtcccacga cctgtctgat  2520
gaggccaggg ccctgctgcc caacgtgatc accaaggagg tgtctcacga gatcatcaag  2580
gataggcgct ttaccagcga caagttcttt ttccacgtgc ctatcacact gaactatcag  2640
gccgccaatt ccccatctaa gttcaaccag agggtgaatg cctacctgaa ggagcacccc  2700
gagacaccta tcatcggcat cgatcggggc gagagaaacc tgatctatat cacagtgatc  2760
gactccaccg gcaagatcct ggagcagcgg agcctgaaca ccatccagca gtttgattac  2820
cagaagaagc tggacaacag ggagaaggag agggtggcag caaggcaggc ctggtctgtg  2880
gtgggcacaa tcaaggatct gaagcagggc tatctgagcc aggtcatcca cgagatcgtg  2940
gacctgatga tccactacca ggccgtggtg gtgctggaga acctgaattt cggctttaag  3000
agcaagagga ccggcatcgc cgagaaggcc gtgtaccagc agttcgagaa gatgctgatc  3060
gataagctga attgcctggt gctgaaggac tatccagcag agaaagtggg aggcgtgctg  3120
aacccatacc agctgacaga ccagttcacc tcctttgcca agatgggcac ccagtctggc  3180
ttcctgtttt acgtgcctgc cccatataca tctaagatcg atcccctgac cggcttcgtg  3240
gaccccttcg tgtggaaaac catcaagaat cacgagagcc gcaagcactt cctggagggc  3300
ttcgactttc tgcactacga cgtgaaaacc ggcgacttca tcctgcactt taagatgaac  3360
agaaatctgt ccttccagag gggcctgccc ggctttatgc ctgcatggga tatcgtgttc  3420
gagaagaacg agacacagtt tgacgccaag ggcacccctt tcatcgccgg caagagaatc  3480
gtgccagtga tcgagaatca cagattcacc ggcagatacc gggacctgta tcctgccaac  3540
gagctgatcg ccctgctgga ggagaagggc atcgtgttca gggatggctc caacatcctg  3600
ccaaagctgc tggagaatga cgattctcac gccatcgaca ccatggtggc cctgatccgc  3660
agcgtgctgc agatgcggaa ctccaatgcc gccacaggcg aggactatat caacagcccc  3720
gtgcgcgatc tgaatggcgt gtgcttcgac tcccggtttc agaacccaga gtggcccatg  3780
gacgccgatg ccaatggcgc ctaccacatc gccctgaagg gccagctgct gctgaatcac  3840
ctgaaggaga gcaaggatct gaagctgcag aacggcatct ccaatcagga ctggctggcc  3900
tacatccagg agctgcgcaa caaaaggccg gcggccacga aaaaggccgg ccaggcaaaa  3960
aagaaaaagg gatcctaccc atacgatgtt ccagattacg cttatcccta cgacgtgcct  4020
gattatgcat acccatatga tgtccccgac tatgcctaa                         4059

SEQ ID NO: 42          moltype = DNA  length = 3822
FEATURE                Location/Qualifiers
source                 1..3822
                       mol_type = unassigned DNA
                       note = Lachnospiraceae sp.
```

-continued

```
                        organism = unidentified
SEQUENCE: 42
atgagcaagc tggagaagtt tacaaactgc tactccctgt ctaagaccct gaggttcaag  60
gccatccctg tgggcaagac ccaggagaac atcgacaata agcggctgct ggtggaggac  120
gagaagagag ccgaggatta taagggcgtg aagaagctgc tggatcgcta ctatctgtct  180
tttatcaacg acgtgctgca cagcatcaag ctgaagaatc tgaacaatta catcagcctg  240
ttccggaaga aaaccagaac cgagaaggag aataaggagc tggagaacct ggagatcaat  300
ctgcggaagg agatcgccaa ggccttcaag ggcaacgagg gctacaagtc cctgtttaag  360
aaggatatca tcgagacaat cctgccagag ttcctggacg ataaggacga gatcgccctg  420
gtgaacagct tcaatggctt taccacagcc ttcaccggct tctttgataa cagagagaat  480
atgttttccg aggaggccaa gagcacatcc atcgccttca ggtgtatcaa cgagaatctg  540
acccgctaca tctctaatat ggacatcttc gagaaggtgg acgccatctt tgataagcac  600
gaggtgcagg agatcaagga gaagatcctg aacagcgact atgatgtgga ggatttcttt  660
gagggcgagt tctttaactt tgtgctgaca caggagggca tcgacgtgta taacgccatc  720
atcggcggct tcgtgaccga gagcggcgag aagatcaagg gcctgaacga gtacatcaac  780
ctgtataatc agaaaaccaa gcagaagctg cctaagttta agccactgta taagcaggtg  840
ctgagcgatc gggagtctct gagcttctac ggcgagggct atacatccga tgaggaggtg  900
ctggaggtgt ttagaaacac cctgaacaag aacagcgaga tcttcagctc catcaagaag  960
ctggagaagc tgttcaagaa ttttgacgag tactctagcg ccggcatctt tgtgaagaac  1020
ggccccgcca tcagcacaat ctccaaggat atcttcggcg agtggaacgt gatccgggac  1080
aagtggaatg ccgagtatga cgatatccac ctgaagaaga aggccgtggt gaccgagaag  1140
tacgaggacg atcggagaaa gtccttcaag aagatcggct ccttttctct ggagcagctg  1200
caggagtacg ccgacgccga tctgtctgtg gtggagaagc tgaaggagat catcatccag  1260
aaggtggatg agatctacaa ggtgtatggc tcctctgaga agctgttcga cgccgatttt  1320
gtgctggaga agagcctgaa gaagaacgac gccgtggtgg ccatcatgaa ggacctgctg  1380
gattctgtga agagcttcga gaattacatc aaggccttct ttggcgaggg caaggagaca  1440
aacagggacg agtccttcta tggcgatttt gtgctggcct acgacatcct gctgaaggtg  1500
gaccacatct acgatgccat ccgcaattat gtgacccaga agccctactc taaggataag  1560
ttcaagctgt attttcagaa ccctcagttc atgggcggct gggacaagga taaggagaca  1620
gactatcggg ccaccatcct gagatacggc tccaagtact atctggccat catggataag  1680
aagtacgcca agtgcctgca gaagatcgac aaggacgatg tgaacggcaa ttacgagaag  1740
atcaactata agctgctgcc cggccctaat aagatgctgc caaaggtgtt cttttctaag  1800
aagtggatgg cctactataa ccccagcgag gacatccaga agatctacaa gaatggcaca  1860
ttcaagaagg gcgatatgtt taacctgaat gactgtcaca agctgatcga cttctttaag  1920
gatagcatct cccggtatcc aaagtggtcc aatgcctacg atttcaactt ttctgagaca  1980
gagaagtata aggacatcgc cggcttttac agagaggtgg aggagcaggg ctataaggtg  2040
agcttcgagt ctgccagcaa gaaggaggtg gataagctgg tggaggaggg caagctgtat  2100
atgttccaga tctataacaa ggacttttcc gataagtctc acggcacacc caatctgcac  2160
accatgtact tcaagctgct gtttgacgag aacaatcacg gacagatcag gctgagcgga  2220
ggagcagagc tgttcatgag gcgcgcctcc ctgaagaagg aggagctggt ggtgcaccca  2280
gccaactccc ctatcgccaa caagaatcca gataatccca agaaaaccac aaccctgtcc  2340
tacgacgtgt ataaggataa gaggttttct gaggaccagt acgagctgca catcccaatc  2400
gccatcaata agtgccccaa gaacatcttc aagatcaata cagaggtgcg cgtgctgctg  2460
aagcacgacg ataaccccta tgtgatcggc atcgataggg gcgagcgcaa tctgctgtat  2520
atcgtggtgg tggacggcaa gggcaacatc gtggagcagt attccctgaa cgagatcatc  2580
aacaacttca acggcatcag gatcaagaca gattaccact ctctgctgga caagaaggag  2640
aaggagaggt tcgaggcccg ccagaactgg acctccatcg agaatatcaa ggagctgaag  2700
gccggctata tctctcaggt ggtgcacaag atctgcgagc tggtggagaa gtacgatgcc  2760
gtgatcgccc tggaggacct gaactctggc tttaagaata gccgcgtgaa ggtggagaag  2820
caggtgtatc agaagttcga gaagatgctg atcgataagc tgaactacat ggtggacaag  2880
aagtctaatc cttgtgcaac aggcggcgcc ctgaagggct atcagatcac caataagttc  2940
gagagcttta agtccatgtc tacccagaac ggcttcatct tttacatccc tgcctggctg  3000
acatccaaga tcgatccatc taccggcttt gtgaacctgc tgaaaaccaa gtataccagc  3060
atcgccgatt ccaagaagtt catcagctcc tttgacagga tcatgtacgt gcccgaggag  3120
gatctgttcg agtttgccct ggactataag aacttctctc gcacagacgc cgattacatc  3180
aagaagtgga agctgtactc ctacggcaac cggatcagaa tcttccggaa tcctaagaag  3240
aacaacgtgt tcgactggga ggaggtgtgc ctgaccagcg cctataagga gctgttcaac  3300
aagtacggca tcaattatca gcagggcgat atcagagccc tgctgtgcga gcagtccgac  3360
aaggccttct actctagctt tatggccctg atgagcctga tgctgcagat gcggaacagc  3420
atcacaggcc gcaccgacgt ggattttctg atcagccctg tgaagaactc cgacggcatc  3480
ttctacgata gccggaacta tgaggcccag gagaatgcca tcctgccaaa gaacgccgac  3540
gccaatggcg cctataacat cgccagaaag gtgctgtggg ccatcggcca gttcaagaag  3600
gccgaggacg agaagctgga taaggtgaag atcgccatct ctaacaagga gtggctggag  3660
tacgcccaga ccagcgtgaa gcacaaaagg ccggcggcca cgaaaaaggc cggccaggca  3720
aaaaagaaaa agggatccta cccatacgat gttccagatt acgcttatcc ctacgacgtg  3780
cctgattatg catacccata tgatgtcccc gactatgcct aa  3822

SEQ ID NO: 43           moltype = DNA  length = 36
FEATURE                 Location/Qualifiers
misc_feature            1..36
                        note = 3xGS tag
source                  1..36
                        mol_type = other DNA
                        organism = synthetic construct
SEQUENCE: 43
ggcggcggga gcgggggtgg cagcggcggc gggtcg  36

SEQ ID NO: 44           moltype = DNA  length = 96
FEATURE                 Location/Qualifiers
```

-continued

```
misc_feature          1..96
                      note = Linker
source                1..96
                      mol_type = other DNA
                      organism = synthetic construct
SEQUENCE: 44
tctggaggat ctagcggagg atcctctggc agcgagacac caggaacaag cgagtcagca  60
acaccagaga gcagtggcgg cagcagcggc ggctcg                            96

SEQ ID NO: 45         moltype = DNA  length = 138
FEATURE               Location/Qualifiers
misc_feature          1..138
                      note = Linker
source                1..138
                      mol_type = other DNA
                      organism = synthetic construct
SEQUENCE: 45
gctgaggcgg cggcaaaaga agcagcggca aaagaagctg ccgcaaagga agcagcagca  60
aaagcccttg aagccgaagc tgctgctaag gaggctgccg caaaagaggc tgccgccaaa  120
gaagcagccg ctaaagcg                                                138

SEQ ID NO: 46         moltype = DNA  length = 123
FEATURE               Location/Qualifiers
misc_feature          1..123
                      note = Linker
source                1..123
                      mol_type = other DNA
                      organism = synthetic construct
SEQUENCE: 46
ggatccgact ataaggacca cgacggagac tacaaggatc atgatattga ttacaaagac  60
gatgacgata agatggcccc aaagaagaag cggaaggtcg gtatccacgg agtcccagca  120
gcg                                                                123

SEQ ID NO: 47         moltype = DNA  length = 96
FEATURE               Location/Qualifiers
misc_feature          1..96
                      note = Linker
source                1..96
                      mol_type = other DNA
                      organism = synthetic construct
SEQUENCE: 47
ggatccgact ataaggacca cgacggagac tacaaggatc atgatattga ttacaaagac  60
gatgacgata agggtatcca cggagtccca gcagcg                            96

SEQ ID NO: 48         moltype = DNA  length = 222
FEATURE               Location/Qualifiers
misc_feature          1..222
                      note = Linker
source                1..222
                      mol_type = other DNA
                      organism = synthetic construct
SEQUENCE: 48
ggttctggaa gtgaggcagc tgcgaaggag gctgcggcga aagaagctgc agcaaaggaa  60
gcagcagcaa aggcactgga ggccgctgct gctaaagagg ctgccgccaa agaagctgcg  120
gcaaaggaag ctgcggctaa gggaagtggg agcgcagcgg ccaaagaggc agcggccaag  180
gaagctgctg caaaagaagc agcagctaaa gggagcggat cg                     222

SEQ ID NO: 49         moltype = DNA  length = 222
FEATURE               Location/Qualifiers
misc_feature          1..222
                      note = Artificial sequence
source                1..222
                      mol_type = other DNA
                      organism = synthetic construct
SEQUENCE: 49
gccggaagcg gtggttcagg gggatccgga ggaagtcctg ttccctctac cccaccaact  60
aatagcagct caacccctcc gaccccctct ccgtcaccgg tgccgagtac cccgccaacc  120
aatagctcat caactccgcc tacgccgtcc cctagtccag tacctagcac ccctccaaca  180
aattctagca gtacaccacc cacaccaagc cctagcgcgt cg                     222

SEQ ID NO: 50         moltype = DNA  length = 198
FEATURE               Location/Qualifiers
misc_feature          1..198
                      note = Artificial sequence
source                1..198
                      mol_type = other DNA
                      organism = synthetic construct
SEQUENCE: 50
gctggttctg gtggctcagg gggttccggt ggttccccag taccaagtac tcctcccact  60
```

-continued

```
ccctctccaa gtacgccgcc tacaccctca cccagcggcg gctctggcaa ttccagtggt  120
tcaggcggta gtcccgtgcc aagtacgcca ccaactccaa gtccatcaac accaccgacc  180
ccttctccgt ctgcatcg                                                198

SEQ ID NO: 51          moltype = DNA  length = 786
FEATURE                Location/Qualifiers
misc_feature           1..786
                       note = Artificial sequence
source                 1..786
                       mol_type = other DNA
                       organism = synthetic construct
SEQUENCE: 51
gcgggttctg gaggttcagg cgggagcggt ggcagtccag tgccgagcac accgccaaca  60
ccgagcccaa gtacgccacc gactccaagt cccagcatac agcgaacacc gaagattcag  120
gtctactcac gacacccagc ggaaaacggc aaatctaatt ttctgaattg ctatgtttcc  180
ggttttcacc cctcagacat cgaggtcgac ctgctgaaga acggtgaaag gattgaaaag  240
gttgaacact ccgacttgag ctttagtaag gactggtcat tctatttgct gtattacacc  300
gagttcactc cgaccgaaaa ggatgaatac gcatgtcgag tgaatcatgt cacgctgagc  360
caacccaaga tcgtgaaatg ggacagggac ggggggtctg gggtagcgg aggaagcggc  420
gggtctatcc aacgcactcc aaaaattcaa gtctactcaa gacaccctgc cgagaatgga  480
aaatcaaact ttttgaattg ctacgtctct ggattccatc cgtcagacat cgaagttgat  540
ctgttgaaaa acggtgagcg aattgagaaa gtggagcatt cagatcttag cttcagtaaa  600
gactggtcct ttatctcttt gtattacacg gagttcactc ccacagaaaa agatgaatac  660
gcctgtcgag ttaaccacgt cacgctgtca cagccaaaga tagtgaaatg ggatcgcgac  720
ccagtgccct caacaccccc tactcctagt ccgagcactc ctccaacgcc ttcaccatct  780
gcctcg                                                             786

SEQ ID NO: 52          moltype = DNA  length = 978
FEATURE                Location/Qualifiers
misc_feature           1..978
                       note = Artificial sequence
source                 1..978
                       mol_type = other DNA
                       organism = synthetic construct
SEQUENCE: 52
gctggttccg gcggatctgg tggatctggt ggcagccccg tcccttctac tccacccaca  60
ccgtccccgt caactcctcc caccccgtct ccgtccgatg gaaggtactc tctcacgtac  120
atctacactg ggttgtcaaa gcatgtggaa gacgtgccag ccttccaggc gcttggaagc  180
ctcaatgacc ttcagttttt tcgctacaat agcaaggatc gaaagtcaca acctatgggt  240
ctctggagac aggtcgaagg gatggaggac tggaaacagg atagccaatt gcaaaaagcg  300
agagaggata tctttatgga gacgcttaaa gacattgttg agtattacaa cgactctaac  360
ggtagtcacg tattgcaggg ccgatttggg tgtgagatag agaataaccg gagttccggc  420
gctttttgga aatattatta cgatggcaag gactacatcg agtttaacaa agaaattcca  480
gcctgggtgc cttttgaccc agctgcacaa attacaaaac agaagtggga ggcggagcca  540
gtgtacgttc aaagggcaaa agcatacttg gaggaagagt gtcccgcaac tctccgaaag  600
tacttgaagt attctaaaaa catactggat cgacaggatc ccccttcagt agtcgtaacc  660
tcccaccagg ccccaggtga gaagaagaag ttgaaatgcc ttgcttacga cttctaccca  720
ggcaagattg atgttcactg gacaagggct ggtgaggtcc aagagcccga acttagaggg  780
gatgtgttgc ataacggtaa tgggacgtat cagtcatggg tcgtggtggc agtccctcct  840
caagatacgg caccatactc ttgccatgtg caacacagct cactggcgca gccactcgta  900
gtgccttggg aggccagccc cgtgccatca actcccccaa ctccatcacc tagtaccccc  960
cctactccgt cagcctcg                                                978

SEQ ID NO: 53          moltype = DNA  length = 1818
FEATURE                Location/Qualifiers
misc_feature           1..1818
                       note = Artificial sequence
source                 1..1818
                       mol_type = other DNA
                       organism = synthetic construct
SEQUENCE: 53
gctggttctg gggggtcagg agggagtgga gggtctggag gttctggagg ctcaggaggt  60
agcggtggta gtgacggcag gtacagtctc acctatatct atacaggatt gtctaagcat  120
gttgaagacg tgcccgcctt tcaggcactg ggttctttga acgacctcca gtttttccgc  180
tacaacagta aagaccgaaa atctcagccc atggggctct ggagacaagt tgaaggtatg  240
gaggactgga aacaggacag tcaattgcaa aaggccagag aagatatttt tatggaaacc  300
ttgaaggata ttgtcgagta ctacaacgat tcaaacgggt cccacgtgct gcagggccga  360
ttcggttgcg agatagaaaa taatcgatct agtggtgcct tttggaagta ttactacgac  420
ggaaaagatt atatcgaatt taataaagag attcctgcgt gggtgccgtt tgacccggcg  480
gcacaaatta ctaaacaaaa gtgggaagcg gaaccggtgt atgttcagag ggctaaggcg  540
taccttgaag aagagtgccc cgctacgttg aggaaatacc tcaaatattc caaaaatatc  600
ttggatcgac aagatccacc tagcgtggtt gttacttcac accaagcacc aggtgaaaaa  660
aaaaaattga agtgtcttgc atatgacttc tatcctggga agatcgacgt acactggaca  720
cgagccggag aggtacaaga acctgaactg cgaggggacg tcctccataa cgggaacggt  780
acctatcaaa gttgggtggt ggttgcggtt ccacctcagg acactgcgcc ttactcctgt  840
cacgtgcagc attcctctct cgctcaaccc cttgtcgtgc cgtgggaggc ctccggaggg  900
tctggcggaa gcggaggatc tggtgggtcc gatggtaggt actcacttac ttacatatac  960
acgggtctta gtaaacacgt cgaggatgtc ccggcgttcc aagctctggg tagtttgaat  1020
gatctccaat tttttagata caatagcaaa gatcgaaaaa gccaaccaat gggactctgg  1080
```

-continued

```
agacaggtgg agggaatgga agattggaaa caagattctc aactccagaa ggctagggaa  1140
gacattttca tggaaacgct caaagatatt gtagagtatt ataatgattc taacggcagc  1200
cacgtccttc aggggcgatt tgggtgtgag attgaaaaca atcgatctag cggtgcattt  1260
tggaaatatt actatgatgg caaagactat atcgaattca acaaggaaat tccagcatgg  1320
gtcccattcg accccgcggc tcaaattacc aagcaaaaat gggaagccga acctgtctac  1380
gtacaacggg cgaaggcata tcttgaggag gaatgccccg cgaccctccg aaagtacctt  1440
aagtactcca agaacattct cgatcggcag gaccccctt ctgtggtagt caccagccat  1500
caggcacctg gggagaagaa gaaactcaag tgcctggcct acgatttcta ccctgggaaa  1560
atcgatgtcc actggacgag agcgggtgag gtgcaagagc cagaattgag aggtgatgtc  1620
cttcataacg gcaatggcac ctatcagtca tgggtggtcg tggctgttcc ccctcaagac  1680
acggcaccgt atagctgtca tgtccaacac tcctccctcg ctcaaccact cgtggtccca  1740
tgggaggcta gcccagtgcc cagcacaccc cctactccct ctccttctac tccaccgacc  1800
ccttcaccgt ccgcttcg                                                1818

SEQ ID NO: 54          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 54
gggctgagag agggacaagt gttttagagc tagaaatagc aagttaaaat aaggctagtc  60
cgttatcaac ttgaaaaagt ggcaccgagt cggtgc                            96

SEQ ID NO: 55          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 55
agtgtgcatt gccacctcag gttttagagc tagaaatagc aagttaaaat aaggctagtc  60
cgttatcaac ttgaaaaagt ggcaccgagt cggtgc                            96

SEQ ID NO: 56          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 56
gcaggactcc tttcctccat gttttagagc tagaaatagc aagttaaaat aaggctagtc  60
cgttatcaac ttgaaaaagt ggcaccgagt cggtgc                            96

SEQ ID NO: 57          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 57
ataggagaag atgatgtata gttttagagc tagaaatagc aagttaaaat aaggctagtc  60
cgttatcaac ttgaaaaagt ggcaccgagt cggtgc                            96

SEQ ID NO: 58          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 58
aaaacgtttc caagacatga gttttagagc tagaaatagc aagttaaaat aaggctagtc  60
cgttatcaac ttgaaaaagt ggcaccgagt cggtgc                            96

SEQ ID NO: 59          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 59
ccgccgtcca agacctaccg gttttagagc tagaaatagc aagttaaaat aaggctagtc  60
cgttatcaac ttgaaaaagt ggcaccgagt cggtgc                            96
```

```
SEQ ID NO: 60          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 60
ccaagaagcg caccacctcc gttttagagc tagaaatagc aagttaaaat aaggctagtc  60
cgttatcaac ttgaaaaagt ggcaccgagt cggtgc                            96

SEQ ID NO: 61          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 61
agcctggaag cacgaatggt gttttagagc tagaaatagc aagttaaaat aaggctagtc  60
cgttatcaac ttgaaaaagt ggcaccgagt cggtgc                            96

SEQ ID NO: 62          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 62
acataccaag agaatcaccc gttttagagc tagaaatagc aagttaaaat aaggctagtc  60
cgttatcaac ttgaaaaagt ggcaccgagt cggtgc                            96

SEQ ID NO: 63          moltype = DNA  length = 95
FEATURE                Location/Qualifiers
misc_feature           1..95
                       note = Artificial sequence
source                 1..95
                       mol_type = other DNA
                       organism = synthetic construct
SEQUENCE: 63
gaaggaggag gcctaaggag ttttagagct agaaatagca agttaaaata aggctagtcc  60
gttatcaact tgaaaaagtg gcaccgagtc ggtgc                             95

SEQ ID NO: 64          moltype = DNA  length = 96
FEATURE                Location/Qualifiers
misc_feature           1..96
                       note = Artificial sequence
source                 1..96
                       mol_type = other DNA
                       organism = synthetic construct
SEQUENCE: 64
aagaagacta gctgagctct gttttagagc tagaaatagc aagttaaaat aaggctagtc  60
cgttatcaac ttgaaaaagt ggcaccgagt cggtgc                            96

SEQ ID NO: 65          moltype = AA  length = 575
FEATURE                Location/Qualifiers
source                 1..575
                       mol_type = protein
                       organism = Homo sapiens
SEQUENCE: 65
MDPRGILKAF PKRQKIHADA SSKVLAKIPR REEGEEAEEW LSSLRAHVVR TGIGRARAEL  60
FEKQIVQHGG QLCPAQGPGV THIVVDEGMD YERALRLLRL PQLPPGAQLV KSAWLSLCLQ  120
ERRLVDVAGF SIFIPSRYLD HPQPSKAEQD ASIPPGTHEA LLQTALSPPP PPTRPVSPPQ  180
KAKEAPNTQA QPISDDEASD GEETQVSAAD LEALISGHYP TSLEGDCEPS PAPAVLDKWV  240
CAQPSSQKAT NHNLHITEKL EVLAKAYSVQ GDKWRALGYA KAINALKSFH KPVTSYQEAC  300
SIPGIGKRMA EKIIEILESG HLRKLDHISE SVPVLELFSN IWGAGTKTAQ MWYQQGFRSL  360
EDIRSQASLT TQQAIGLKHY SDFLERMPRE EATEIEQTVQ KAAQAFNSGL LCVACGSYRR  420
GKATCGDVDV LITHPDGRSH RGIFSRLLDS LRQEGFLTDD LVSQEENGQQ QKYLGVCRLP  480
GPGRRHRRLD IIVVPYSEFA CALLYFTGSA HFNRSMRALA KTKGMSLSEH ALSTAVVRNT  540
HGCKVGPGRV LPTPTEKDVF RLLGLPYREP AERDW                             575

SEQ ID NO: 66          moltype = AA  length = 495
FEATURE                Location/Qualifiers
source                 1..495
                       mol_type = protein
                       organism = Homo sapiens
SEQUENCE: 66
```

-continued

```
MALPKRRRAR VGSPSGDAAS STPPSTRFPG VAIYLVEPRM GRSRRAFLTG LARSKGFRVL  60
DACSSEATHV VMEETSAEEA VSWQERRMAA APPGCTPPAL LDISWLTESL GAGQPVPVEC  120
RHRLEVAGPR KGPLSPAWMP AYACQRPTPL THHNTGLSEA LEILAEAAGF EGSEGRLLTF  180
CRAASVLKAL PSPVTTLSQL QGLPHFGEHS SRVVQELLEH GVCEEVERVR RSERYQTMKL  240
FTQIFGVGVK TADRWYREGL RTLDDLREQP QKLTQQQKAG LQHHQDLSTP VLRSDVDALQ  300
QVVEEAVGQA LPGATVTLTG GFRRGKLQGH DVDFLITHPK EGQEAGLLPR VMCRLQDQGL  360
ILYHQHQHSC CESPTRLAQQ SHMDAFERSF CIFRLPQPPG AAVGGSTRPC PSWKAVRVDL  420
VVAPVSQFPF ALLGWTGSKL FQRELRRFSR KEKGLWLNSH GLFDPEQKTF FQAASEEDIF  480
RHLGLEYLPP EQRNA                                                  495

SEQ ID NO: 67          moltype = AA  length = 495
FEATURE                Location/Qualifiers
source                 1..495
                       mol_type = protein
                       organism = Homo sapiens
SEQUENCE: 67
MALPKRRRAR VGSPSGDAAS STPPSTRFPG VAIYLVEPRM GRSRRAFLTG LARSKGFRVL  60
DACSSEATHV VMEETSAEEA VSWQERRMAA APPGCTPPAL LDISWLTESL GAGQPVPVEC  120
RHRLEVAGPR KGPLSPAWMP AYACQRPTPL THHNTGLSEA LEILAEAAGF EGSEGRLLTF  180
CRAASVLKAL PSPVTTLSQL QGLPHFGEHS SRVVQELLEH GVCEEVERVR RSERYQTMKL  240
FTQIFGVGVK TADRWYREGL RTLDDLREQP QKLTQQQKAG LQHHQDLSTP VLRSDVDALQ  300
QVVEEAVGQA LPGATVTLTG GFRRGKLQGG DVDFLITHPK EGQEAGLLPR VMCRLQDQGL  360
ILYHQHQHSC CESPTRLAQQ SHMDAFERSK CIFRLPQPPG AAVGGSTRPC PSWKAVRVDL  420
VVAPVSQFPF ALLGWTGSKL FQRELRRFSR KEKGLWLNSH GLFDPEQKTF FQAASEEDIF  480
RHLGLEYLPP EQRNA                                                  495

SEQ ID NO: 68          moltype = AA  length = 495
FEATURE                Location/Qualifiers
source                 1..495
                       mol_type = protein
                       organism = Homo sapiens
SEQUENCE: 68
MALPKRRRAR VGSPSGDAAS STPPSTRFPG VAIYLVEPRM GRSRRAFLTG LARSKGFRVL  60
DACSSEATHV VMEETSAEEA VSWQERRMAA APPGCTPPAL LDISWLTESL GAGQPVPVEC  120
RHRLEVAGPR KGPLSPAWMP AYACQRPTPL THHNTGLSEA LEILAEAAGF EGSEGRLLTF  180
CRAASVLKAL PSPVTTLSQL QGLPHFGEHS SRVVQELLEH GVCEEVERVR RSERYQTMKL  240
FTQIFGVGVK TADRWYREGL RTLDDLREQP QKLTQQQKAG LQHHQDLSTP VLRSDVDALQ  300
QVVEEAVGQA LPGATVTLTG GFRRGKLQGG DVDFLITHPK EGQEAGLLPR VMCRLQDQGL  360
ILYHQHQHSC CESPTRLAQQ SHMDAFERSF CIFRLPQPPG AAVGGSTRPC PSWKAVRVDL  420
VVAPVSQFPF ALLGWTGSKL FQRELRRFSR KEKGLWLNSH GLFDPEQKTF FQAASEEDIF  480
RHLGLEYLPP EQRNA                                                  495

SEQ ID NO: 69          moltype = AA  length = 557
FEATURE                Location/Qualifiers
source                 1..557
                       mol_type = protein
                       organism = Homo sapiens
SEQUENCE: 69
MALPKRRRAR VGSPSGDAAS STPPSTRFPG VAIYLVEPRM GRSRRAFLTG LARSKGFRVL  60
DACSSEATHV VMEETSAEEA VSWQERRMAA APPGCTPPAL LDISWLTESL GAGQPIPSRY  120
LDHPQPSKAE QDASIPPGTH EALLQTALSP PPPPTRPVSP PQKAKEAPNT QAQPISDDEA  180
SDGEETQVSA ADLEALISGH YPTSLEGDCE PSPAPAVLDK WVCAQPSSQK ATNHNLHITE  240
KLEVLAKAYS VQGDKWRALG YAKAINALKS FHKPVTSYQE ACSIPGIGKR MAEKIIEILE  300
SGHLRKLDHI SESVPVLELF SNIWGAGTKT AQMWYQQGFR SLEDIRSQAS LTTQQAIGLK  360
HYSDFLERMP REEATEIEQT VQKAAQAFNS GLLCVACGSY RRGKATCGDV DVLITHPDGR  420
SHRGIFSRLL DSLRQEGFLT DDLVSQEENG QQQKYLGVCR LPGPGRRHRR LDIIVVPYSE  480
FACALLYFTG SAHFNRSMRA LAKTKGMSLS EHALSTAVVR NTHGCKVGPG RVLPTPTEKD  540
VFRLLGLPYR EPAERDW                                                557

SEQ ID NO: 70          moltype = AA  length = 466
FEATURE                Location/Qualifiers
source                 1..466
                       mol_type = protein
                       organism = Homo sapiens
SEQUENCE: 70
MALPKRRRAR VGSPSGDAAS STPPSTRFPG VAIYLVEPRM GRSRRAFLTG LARSKGFRVL  60
DACSSEATHV VMEETSAEEA VSWQERRMAA APPGCTPPAL LDISWLTESL GAGQPVPVEC  120
RHRLEVAGPR KGPLSSSQKA TNHNLHITEK LEVLAKAYSV QGDKWRALGY AKAINALKSF  180
HKPVTSYQEA CSIPGIGKRM AEKIIEILES GHLRKLDHIS ESVPVLELFS NIWGAGTKTA  240
QMWYQQGFRS LEDIRSQASL TTQQAIGLKH YSDFLERMPR EEATEIEQTV QKAAQAFNSG  300
LLCVACGSYR RGKATCGDVD VLITHPDGRS HRGIFSRLLD SLRQEGFLTD DLVSQEENGQ  360
QQKYLGVCRL PGPGRRHRRL DIIVVPYSEF ACALLYFTGS AHFNRSMRAL AKTKGMSLSE  420
HALSTAVVRN THGCKVGPGR VLPTPTEKDV FRLLGLPYRE PAERDW                466

SEQ ID NO: 71          moltype = AA  length = 407
FEATURE                Location/Qualifiers
source                 1..407
                       mol_type = protein
                       organism = Homo sapiens
```

-continued

```
SEQUENCE: 71
MDYKDHDGDY KDHDIDYKDD DDKMAPKKKR KVGIHGVPAA AIKSIASRLR GSRRFLSGFV  60
AGAVVGAAGA GLAALQFFRS QGAEGALTGK QPDGSAEKAV LEQFGFPLTG TEARCYTNHA  120
LSYDQAKRVP RWVLEHISKS KIMGDADRKH CKFKPDPNIP PTFSAFNEDY VGSGWSRGHM  180
APAGNNKFSS KAMAETFYLS NIVPQDFDNN SGYWNRIEMY CRELTERFED VWVVSGPLTL  240
PQTRGDGKKI VSYQVIGEDN VAVPSHLYKV ILARRSSVST EPLALGAFVV PNEAIGFQPQ  300
LTEFQVSLQD LEKLSGLVFF PHLDRTSDIR NICSVDTCKL LDFQEFTLYL STRKIEGARS  360
VLRLEKIMEN LKNAEIEPDD YFMSRYEKKL EELKAKEQSG TQIRKPS                407

SEQ ID NO: 72          moltype = AA  length = 326
FEATURE                Location/Qualifiers
source                 1..326
                       mol_type = protein
                       note = Aspergillus oryzae
                       organism = unidentified
SEQUENCE: 72
MDYKDHDGDY KDHDIDYKDD DDKMAPKKKR KVGIHGVPAA PRLLPISAAT LALAQLTYGW  60
GNLGHETVAY IAQSFVASST ESFCQNILGD DSTSYLANVA TWADTYKYTD AGEFSKPYHF  120
IDAQDNPPQS CGVDYDRDCG SAGCSISAIQ NYTNILLESP NGSEALNALK FVVHIIGDIH  180
QPLHDENLEA GGNGIDVTYD GETTNLHHIW DTNMPEEAAG GYSLSVAKTY ADLLTERIKT  240
GTYSSKKDSW TDGIDIKDPV STSMIWAADA NTYVCSTVLD DGLAYINSTD LSGEYYDKSQ  300
PVFEELIAKA GYRLAAWLDL IASQPS                                      326

SEQ ID NO: 73          moltype = AA  length = 303
FEATURE                Location/Qualifiers
source                 1..303
                       mol_type = protein
                       note = Penicillium citrinum
                       organism = unidentified
SEQUENCE: 73
MDYKDHDGDY KDHDIDYKDD DDKMAPKKKR KVGIHGVPAA WGALGHATVA YVAQHYVSPE  60
AASWAQGILG SSSSSYLASI ASWADEYRLT SAGKWSASLH FIDAEDNPPT NCNVDYERDC  120
GSSGCSISAI ANYTQRVSDS SLSSENHAEA LRFLVHFIGD MTQPLHDEAY AVGGNKINVT  180
FDGYHDNLHS DWDTYMPQKL IGGHALSDAE SWAKTLVQNI ESGNYTAQAI GWIKGDNISE  240
PITTATRWAS DANALVCTVV MPHGAAALQT GDLYPTYYDS VIDTIELQIA KGGYRLANWI  300
NEI                                                               303

SEQ ID NO: 74          moltype = AA  length = 398
FEATURE                Location/Qualifiers
source                 1..398
                       mol_type = protein
                       organism = Homo sapiens
SEQUENCE: 74
MDYKDHDGDY KDHDIDYKDD DDKMAPKKKR KVGIHGVPAA KMKLFQTICR QLRSSKFSVE  60
SAALVAFSTS SYSCGRKKKV NPYEEVDQEK YSNLVQSVLS SRGVAQTPGS VEEDALLCGP  120
VSKHKLPNQG EDRRVPQNWF PIFNPERSDK PNASDPSVPL KIPLQRNVIP SVTRVLQQTM  180
TKQQVFLLER WKQRMILELG EDGFKEYTSS FHVCDHVYMK NLARDVFLQG KRFHEALESI  240
LSPQETLKER DENLLKSGYI ESVQHILKDV SGVRALESAV QHETLNYIGL LDCVAEYQGK  300
LCVIDWKTSE KPKPFIQSTF DNPLQVVAYM GAMNHDTNYS FQVQCGLIVV AYKDGSPAHP  360
HFMDAELCSQ YWTKWLLRLE EYTEKKKNQN IQKPEYSE                          398

SEQ ID NO: 75          moltype = AA  length = 617
FEATURE                Location/Qualifiers
source                 1..617
                       mol_type = protein
                       organism = Escherichia coli
SEQUENCE: 75
MDYKDHDGDY KDHDIDYKDD DDKMAPKKKR KVGIHGVPAA VKQQIQLRRR EVDETADLPA  60
ELPPLLRRLY ASRGVRSAQE LERSVKGMLP WQQLSGVEKA VEILYNAFRE GTRIIVVGDF  120
DADGATSTAL SVLAMRSLGC SNIDYLVPNR FEDGYGLSPE VVDQAHARGA QLIVTVDNGI  180
SSHAGVEHAR SLGIPVIVTD HHLPGDTLPA AEAIINPNLR DCNFPSKSLA GVGVAFYLML  240
ALRTFLRDQG WFDERNIAIP NLAELLDLVA LGTVADVVPL DANNRILTWQ GMSRIRAGKC  300
RPGIKALLEV ANRDAQKLAA SDLGFALGPR LNAAGRLDDM SVGVALLLCD NIGEARVLAN  360
ELDALNQTRK EIEQGMQIEA LTLCEKLERS RDTLPGGLAM YHPEWHQGVV GILASRIKER  420
FHRPVIAFAP AGDGTLKGSG RSIQGLHMRD ALERLDTLYP GMMLKFGGHA MAAGLSLEED  480
KFKLFQQRFG ELVTEWLDPS LLQGEVVSDG PLSPAEMTME VAQLLRDAGP WGQMFPEPLF  540
DGHFRLLQQR LVGERHLKVM VEPVGGGPLL DGIAFNVDTA LWPDNGVREV QLAYKLDINE  600
FRGNRSLQII IDNIWPI                                                617

SEQ ID NO: 76          moltype = AA  length = 937
FEATURE                Location/Qualifiers
source                 1..937
                       mol_type = protein
                       note = Bacteriophage T4
                       organism = synthetic construct
SEQUENCE: 76
MDYKDHDGDY KDHDIDYKDD DDKMAPKKKR KVGIHGVPAA KEFYISIETV GNNIVERYID  60
ENGKERTREV EYLPTMFRHC KEESKYKDIY GKNCAPQKFP SMKDARDWMK RMEDIGLEAL  120
GMNDFKLAYI SDTYGSEIVY DRKFVRVANC DIEVTGDKFP DPMKAEYEID AITHYDSIDD  180
```

-continued

```
RFYVFDLLNS MYGSVSKWDA KLAAKLDCEG GDEVPQEILD RVIYMPFDNE RDMLMEYINL  240
WEQKRPAIFT GWNIEGFDVP YIMNRVKMIL GERSMKRFSP IGRVKSKLIQ NMYGSKEIYS  300
IDGVSILDYL DLYKKFAFTN LPSFSLESVA QHETKKGKLP YDGPINKLRE TNHQRYISYN  360
IIDVESVQAI DKIRGFIDLV LSMSYYAKMP FSGVMSPIKT WDAIIFNSLK GEHKVIPQQG  420
SHVKQSFPGA FVFEPKPIAR RYIMSFDLTS LYPSIIRQVN ISPETIRGQF KVHPIHEYIA  480
GTAPKPSDEY SCSPNGWMYD KHQEGIIPKE IAKVFFQRKD WKKKMFAEEM NAEAIKKIIM  540
KGAGSCSTKP EVERYVKFSD DFLNELSNYT ESVLNSLIEE CEKAATLANT NQLNRKILIN  600
SLYGALGNIH FRYYDLRNAT AITIFGQVGI QWIARKINEY LNKVCGTNDE DFIAAGDTDS  660
VYVCVDKVIE KVGLDRFKEQ NDLVEFMNQF GKKKMEPMID VAYRELCDYM NNREHLMHMD  720
REAISCPPLG SKGVGGFWKA KKRYALNVYD MEDKRFAEPH LKIMGMETQQ SSTPKAVQEA  780
LEESIRRILQ EGEESVQEYY KNFEKEYRQL DYKVIAEVKT ANDIAKYDDK GWPGFKCPFH  840
IRGVLTYRRA VSGLGVAPIL DGNKVMVLPL REGNPFGDKC IAWPSGTELP KEIRSDVLSW  900
IDHSTLFQKS FVKPLAGMCE SAGMDYEEKA SLDFLFG                          937

SEQ ID NO: 77          moltype = AA  length = 937
FEATURE                Location/Qualifiers
source                 1..937
                       mol_type = protein
                       note = Bacteriophage T4
                       organism = synthetic construct
SEQUENCE: 77
MDYKDHDGDY KDHDIDYKDD DDKMAPKKKR KVGIHGVPAA KEFYISIETV GNNIVERYID  60
ENGKERTREV EYLPTMFRHC KEESKYKDIY GKNCAPQKFP SMKDARDWMK RMEDIGLEAL  120
GMNDFKLAYI SDTYGSEIVY DRKFVRVANC DIEVTGDKFP DPMKAEYEID AITHYDSIDD  180
RFYVFDLLNS MYGSVSKWDA KLAAKLDCEG GDEVPQEILD RVIYMPFDNE RDMLMEYINL  240
WEQKRPAIFT GWNIEGFDVP YIMNRVKMIL GERSMKRFSP IGRVKSKLIQ NMYGSKEIYS  300
IDGVSILDYL DLYKKFAFTN LPSFSLESVA QHETKKGKLP YDGPINKLRE TNHQRYISAN  360
IIDVESVQAI DKIRGFIDLV LSMSYYAKMP FSGVMSPIKT WDAIIFNSLK GEHKVIPQQG  420
SHVKQSFPGA FVFEPKPIAR RYIMSFDLTS LYPSIIRQVN ISPETIRGQF KVHPIHEYIA  480
GTAPKPSDEY SCSPNGWMYD KHQEGIIPKE IAKVFFQRKD WKKKMFAEEM NAEAIKKIIM  540
KGAGSCSTKP EVERYVKFSD DFLNELSNYT ESVLNSLIEE CEKAATLANT NQLNRKILIN  600
SLYGALGNIH FRYYDLRNAT AITIFGQVGI QWIARKINEY LNKVCGTNDE DFIAAGDTDS  660
VYVCVDKVIE KVGLDRFKEQ NDLVEFMNQF GKKKMEPMID VAYRELCDYM NNREHLMHMD  720
REAISCPPLG SKGVGGFWKA KKRYALNVYD MEDKRFAEPH LKIMGMETQQ SSTPKAVQEA  780
LEESIRRILQ EGEESVQEYY KNFEKEYRQL DYKVIAEVKT ANDIAKYDDK GWPGFKCPFH  840
IRGVLTYRRA VSGLGVAPIL DGNKVMVLPL REGNPFGDKC IAWPSGTELP KEIRSDVLSW  900
IDHSTLFQKS FVKPLAGMCE SAGMDYEEKA SLDFLFG                          937

SEQ ID NO: 78          moltype = AA  length = 937
FEATURE                Location/Qualifiers
source                 1..937
                       mol_type = protein
                       note = Bacteriophage T4
                       organism = synthetic construct
SEQUENCE: 78
MDYKDHDGDY KDHDIDYKDD DDKMAPKKKR KVGIHGVPAA KEFYISIETV GNNIVERYID  60
ENGKERTREV EYLPTMFRHC KEESKYKDIY GKNCAPQKFP SMKDARDWMK RMEDIGLEAL  120
GMNDFKLAYI SDTYGSEIVY DRKFVRVANC DIEVTGDKFP DPMKAEYEID AITHYDSIDD  180
RFYVFDLLNS MYGSVSKWDA KLAAKLDCEG GDEVPQEILD RVIYMPFDNE RDMLMEYINL  240
WEQKRPAIFT GWNIEGFDVP YIMNRVKMIL GERSMKRFSP IGRVKSKLIQ NMYGSKEIYS  300
IDGVSILDYL DLYKKFAFTN LPSFSLESVA QHETKKGKLP YDGPINKLRE TNHQRYISYN  360
IIDVESVQAI DKIRGFIDLV LSMSYYAKMP FSGVMSPIKT WDAIIFNSLK GEHKVIPQQG  420
SHVKQSFPGA FVFEPKPIAR RYIMSFDLTS LYPSIIRQVN ISPETIRGQF KVHPIHEYIA  480
GTAPKPSDEY SCSPNGWMYD KHQEGIIPKE IAKVFFQRKD WKKKMFAEEM NAEAIKKIIM  540
KGAGSCSTKP EVERYVKFSD DFLNELSNYT ESVLNSLIEE CEKAATLANT NQLNRKILIN  600
SLYGALGNIH FRYYDLRNAT AITIFGQVGI QWIARKINEY LNKVCGTNDE DFIAAGDTDS  660
VYVCVDKVIE KVGLDRFKEQ NDLVEFMNQF GKKKMEPMID VAYRELCDYM NNREHLMHMD  720
REAISCPPLG SKGVGGFWKA KKRYALNVYD MEDKRFAEPH LKIMGMETQQ SSTPKVVQEA  780
LEESIRRILQ EGEESVQEYY KNFEKEYRQL DYKVIAEVKT ANDIAKYDDK GWPGFKCPFH  840
IRGVLTYRRA VSGLGVAPIL DGNKVMVLPL REGNPFGDKC IAWPSGTELP KEIRSDVLSW  900
IDHSTLFQKS FVKPLAGMCE SAGMDYEEKA SLDFLFG                          937

SEQ ID NO: 79          moltype = AA  length = 319
FEATURE                Location/Qualifiers
source                 1..319
                       mol_type = protein
                       organism = Homo sapiens
SEQUENCE: 79
MAPKRGKKGA VAEDGDELRT EPEAKKSKTA AKKNDKEAAG EGPALYEDPP DQKTSPSGKP  60
ATLKICSWNV DGLRAWIKKK GLDWVKEEAP DILCLQETKC SENKLPAELQ ELPGLSHQYW  120
SAPSDKEGYS GVGLLSRQCP LKVSYGIGDE EHDQEGRVIV AEFDSFVLVT AYVPNAGRGL  180
VRLEYRQRWD EAFRKFLKGL ASRKPLVLCG DLNVAHEEID LRNPKGNKKN AGFTPQERQG  240
FGELLQAVPL ADSFRHLYPN TPYAYTFWTY MMNARSKNVG WRLDYFLLSH SLLPALCDSK  300
IRSKALGSDH CPITLYLAL                                              319

SEQ ID NO: 80          moltype = AA  length = 297
FEATURE                Location/Qualifiers
REGION                 1..297
                       note = Fusion protein
```

```
source                  1..297
                        mol_type = protein
                        organism = synthetic construct
SEQUENCE: 80
MVRGSGKPIP NPLLGLDSTG KSYPTVSADY QDAVEKAKKK LRGFIAEKRC APLMLRLAFH  60
SAGTFDKGTK TGGPFGTIKH PAELAHSANN GLDIAVRLLE PLKAEFPILS YADFYQLAGV  120
VAVEVTGGPK VPFHPGREDK PEPPPEGRLP DPTKGSDHLR DVFGKAMGLT DQDIVALSGG  180
HTIGAAHKER SGFEGPWTSN PLIFDNSYFT ELLSGEKEGL LQLPSDKALL SDPVFRPLVD  240
KYAADEDAFF ADYAEAHQKL SELGFADAEF SRADPKKKRK VDPKKKRKVD PKKKRKV     297

SEQ ID NO: 81           moltype = AA  length = 334
FEATURE                 Location/Qualifiers
source                  1..334
                        mol_type = protein
                        organism = Homo sapiens
SEQUENCE: 81
MERKISRIHL VSEPSITHFL QVSWEKTLES GFVITLTDGH SAWTGTVSES EISQEADDMA  60
MEKGKYVGEL RKALLSGAGP ADVYTFNFSK ESCYFFFEKN LKDVSFRLGS FNLEKVENPA  120
EVIRELICYC LDTIAENQAK NEHLQKENER LLRDWNDVQG RFEKCVSAKE ALETDLYKRF  180
ILVLNEKKTK IRSLHNKLLN AAQEREKDIK QEGETAICSE MTADRDPVYD ESTDEESENQ  240
TDLSGLASAA VSKDDSIISS LDVTDIAPSR KRRQRMQRNL GTEPKMAPQE NQLQEKEKPD  300
SSLPETSKKE HISAENMSLE TLRNSSPEDL FDEI                              334

SEQ ID NO: 82           moltype = AA  length = 1762
FEATURE                 Location/Qualifiers
REGION                  1..1762
                        note = Fusion protein
source                  1..1762
                        mol_type = protein
                        organism = synthetic construct
SEQUENCE: 82
MDAQTRRRER RAEKQAQWKA ANGGSPPHMA YPYDVPDYAP PSRAQASNSA VDGTAGMGVP  60
KFYRWISERY PCLSEVVKEH QIPEFDNLYL DMNGIIHQCS HPNDDDVHFR ISDDKIFTDI  120
FHYLEVLFRI IKPRKVFFMA VDGVAPRAKM NQQRGRRFRS AKEAEDKIKK AIEKGETLPT  180
EARFDSNCIT PGTEFMARLH EHLKYFVNMK ISTDKSWQGV TIYFSGHETP GEGEHKIMEF  240
IRSEKAKPDH DPNTRHCLYG LDADLIMLGL TSHEAHFSLL REEVRFGGKK TQRVCAPEET  300
TFHLLHLSLM REYIDYEFSV LKEKITFKYD IERIIDDWIL MGFLVGNDFI PHLPHLHINH  360
DALPLLYGTY VTILPELGGY INESGHLNLP RFEKYLVKLS DFDREHFSEV FVDLKWFESK  420
VGNKYLNEAA GVAAEEARNY KEKKKLKGQE NSLCWTALDK NEGEMITSKD NLEDETEDDD  480
LFETEFRQYK RTYYMTKMGV DVVSDDFLAD QAACYVQAIQ WILHYYYHGV QSWSWYYPYH  540
YAPFLSDIHN ISTLKIHFEL GKPFKPFEQL LAVLPAASKN LLPACYQHLM TNEDSPIIEY  600
YPPDFKTDLN GKQQEWEAVV LIPFIDEKRL LEAMETCNHS LKKEERKRNQ HSECLMCWYD  660
RDTEFIYPSP WPEKFPAIER CCTRYKIISL DAWRVDINKN KITRIDQKAL YFCGFPTLKH  720
IRHKFFLKKS GVQVFQQSSR GENMMLEILV DAESDELTVE NVASSVLGKS VFVNWPHLEE  780
ARVVAVSDGE TKFYLEEPPG TQKLYSGRTA PPSKVVHLGD KEQSNWAKEV QGISEHYLRR  840
KGIIINETSA VVYAQLLTGR KYQINQNGEV RLEKQWSKQV VPFVYQTIVK DIRAFDSRFS  900
NIKTLDDLFP LRSMVFMLGT PYYGCTGEVQ DSGDVITEGR IRVIFSIPCE PNLDALIQNQ  960
HKYSIKYNPG YVLASRLGVS GYLVSRFTGS IFIGRGSRRN PHGDHKANVG LNLKFNKKNE  1020
EVPGYTKKVG SEWMYSSAAE QLLAEYLERA PELFSYIAKN SQEDVFYEDD IWPGENENGA  1080
EKVQEIITWL KGHPVSTLSR SSCDLQILDA AIVEKIEEEV EKCKQRKNNK KVRVTVKPHL  1140
LYRPLEQQHG VIPDRDAEFC LFDRVVNVRE NFSVPVGLRG TIIGIKGANR EADVLFEVLF  1200
DEEFPGGLTI RCSPGRGYRL PTSALVNLSH GSRSETGNQK LTAIVKPQPA VHQHSSSSSV  1260
SSGHLGALNH SPQSLFVPTQ VPTKDDDEFC NIWQSLQGSG KMQYFQPTIQ EKGAVLPQEI  1320
SQVNQHHKSG FNDNSVKYQQ RKHDPHRKFK EECKSPKAEC WSQKMSNKQP NSGIENFLAS  1380
LNISKENEVQ SSHHGEPPSE EHLSPQSFAM GTRMLKEILK IDGSNTVDHK NEIKQIANEI  1440
PVSSNRRDEY GLPSQPKQNK KLASYMNKPH SANEYHNVQS MDNMCWPAPS QIPPVSTPVT  1500
ELSRICSLVG MPQPDFSFLR MPQTMTVCQV KLSNGLLVHG PQCHSENEAK EKAALFALQQ  1560
LGSLGMNFPL PSQVFANYPS AVPPGTIPPA FPPPTGWDHY GSNYALGAAN IMPSSSHLFG  1620
SMPWGPSVPV PGKPFHHTLY SGTMPMAGGI PGGVHNQFIP LQVTKKRVAN KKNFENKEAQ  1680
SSQATPVQTS QPDSSNIVKV SPRESSSASL KSSPIAQPAS SFQVETASQG HSISHHKSTP  1740
ISSSRRKSRK LAVNFGVSKP SE                                           1762

SEQ ID NO: 83           moltype = AA  length = 1060
FEATURE                 Location/Qualifiers
source                  1..1060
                        mol_type = protein
                        organism = Homo sapiens
SEQUENCE: 83
MEQLNELELL MEKSFWEEAE LPAELFQKKV VASFPRTVLS TGMDNRYLVL AVNTVQNKEG  60
NCEKRLVITA SQSLENKELC ILRNDWCSVP VEPGDIIHLE GDCTSDTWII DKDFGYLILY  120
PDMLISGTSI ASSIRCMRRA VLSETFRSSD PATRQMLIGT VLHEVFQKAI NNSFAPEKLQ  180
ELAFQTIQEI RHLKEMYRLN LSQDEIKQEV EDYLPSFCKW AGDFMHKNTS TDFPQMQLSL  240
PSDNSKDNST CNIEVVKPMD IEESIWSPRF GLKGKIDVTV GVKIHRGYKT KYKIMPLELK  300
TGKESNSIEH RSQVVLYTLL SQERRADPEA GLLLYLKTGQ MYPVPANHLD KRELLKLRNQ  360
MAFSLFHRIS KSATRQKTQL ASLPQIIEEE KTCKYCSQIG NCALYSRAVE QQMDCSSVPI  420
VMLPKIEEET QHLKQTHLEY FSLWCLMLTL ESQSKDNKKN HQNIWLMPAS EMEKSGSCIG  480
NLIRMEHVKI VCDGQYLHNF QCKHGAIPVT NLMAGDRVIV SGEERSLFAL SRGYVKEINM  540
TTVTCLLDRN LSVLPESTLF RLDQEEKNCD IDTPLGNLSK LMENTFVSKK LRDLIIDFRE  600
PQFISYLSSV LPHDAKDTVA CILKGLNKPQ RQAMKKVLLS KDYTLIVGMP GTGKTTTICT  660
```

-continued

```
LVRILYACGF SVLLTSYTHS AVDNILLKLA KFKIGFLRLG QIQKVHPAIQ QFTEQEICRS  720
KSIKSLALLE ELYNSQLIVA TTCMGINHPI FSRKIFDFCI VDEASQISQP ICLGPLFFSR  780
RFVLVGDHQQ LPPLVLNREA RALGMSESLF KRLEQNKSAV VQLTVQYRMN SKIMSLSNKL  840
TYEGKLECGS DKVANAVINL RHFKDVKLEL EFYADYSDNP WLMGVFEPNN PVCFLNTDKV  900
PAPEQVEKGG VSNVTEAKLI VFLTSIFVKA GCSPSDIGII APYRQQLKII NDLLARSIGM  960
VEVNTVDKYQ GRDKSIVLVS FVRSNKDGTV GELLKDWRRL NVAITRAKHK LILLGCVPSL  1020
NCYPPLEKLL NHLNSEKLII DLPSREHESL CHILGDFQRE                       1060

SEQ ID NO: 84          moltype = AA  length = 2618
FEATURE                Location/Qualifiers
REGION                 1..2618
                       note = Fusion protein
source                 1..2618
                       mol_type = protein
                       organism = synthetic construct
SEQUENCE: 84
MEQKLISEED LLRKRGILNL LRRSGKRRRS ESGSDSFSGS GGDSSASPQF LSGSVLSPPP  60
GLGRCLKAAA AGECKPTVPD YEIDKLLLAN WGLPKAVLEK YHSFGVKKMF EWQAECLLLG  120
QVLEGKNLVY SAPTSAGKTL VAELLILKRV LEMRKKALFI LPFVSVAKEK KYYLQSLFQE  180
VGIKVDGYMG STSPSRHFSS LDIAVCTIER ANGLINRLIE ENKMDLLGMV VVDELHMLGD  240
SHRGYLLELL LTKICYITRK SASCQADLAS SLSNAVQIVG MSATLPNLEL VASWLNAELY  300
HTDFRPVPLL ESVKVGNSIY DSSMKLVREF EPMLQVKGDE DHVVSLCYET ICDNHSVLLF  360
CPSKKWCEKL ADIIAREFYN LHHQAEGLVK PSECPPVILE QKELLEVMDQ LRRLPSGLDS  420
VLQKTVPWGV AFHHAGLTFE ERDIIEGAFR QGLIRVLAAT STLSSGVNLP ARRVIIRTPI  480
FGGRPLDILT YKQMVGRAGR KGVDTVGESI LICKNSEKSK GIALLQGSLK PVRSCLQRRE  540
GEEVTGSMIR AILEIIVGGV ASTSQDMHTY AACTFLAASM KEGKQGIQRN QESVQLGAIE  600
ACVMWLLENE FIQSTEASDG TEGKVYHPTH LGSATLSSSL SPADTLDIFA DLQRAMKGFV  660
LENDLHILYL VTPMFEDWTT IDWYRFFCLW EKLPTSMKRV AELVGVEEGF LARCVKGKVV  720
ARTERQHRQM AIHKRFFTSL VLLDLISEVP LREINQKYGC NRGQIQSLQQ SAAVYAGMIT  780
VFSNRLGWHN MELLLSQFQK RLTFGIQREL CDLVRVSLLN AQRARVLYAS GFHTVADLAR  840
ANIVEVEVIL KNAVPFKSAR KAVDEEEEAV EERRNMRTIW VTGRKGLTER EAAALIVEEA  900
RMILQQDLVE MGVQWNPCAL LHSSTCSLTH SESEVKEHTF ISQTKSSYKK LTSKNKSNTI  960
FSDSYIKHSP NIVQDLNKSR EHTSSFNCNF QNGNQEHQRC SIFRARKRAS LDINKEKPGA  1020
SQNEGKTSDK KVVQTFSQKT KKAPLNFNSE KMSRSFRSWK RRKHLKRSRD SSPLKDSGAC  1080
RIHLQGQTLS NPSLCEDPFT LDEKKTEFRN SGPFAKNVSL SGKEKDNKTS FPLQIKQNCS  1140
WNITLTNDNF VEHIVTGSQS KNVTCQATSV VSEKGRGVAV EAEKINEVLI QNGSKNQNVY  1200
MKHHDIHPIN QYLRKQSHEQ TSTITKQKNI IERQMPCEAV SSYINRDSNV TINCERIKLN  1260
TEENKPSHFQ ALGDDISRTV IPSEVLPSAG AFSKSEGQHE NFLNISRLQE KTGTYTTNKT  1320
KNNHVSDLGL VLCDFEDSFY LDTQSEKIIQ QMATENAKLG AKDTNLAAGI MQKSLVQQNS  1380
MNSFQKECHI PFPAEQHPLG ATKIDHLDLK TVGTMKQSSD SHGVDILTPE SPIFHSPILL  1440
EENGLFLKKN EVSVTDSQLN SFLQGYQTQE TVKPVILLIP QKRTPTGVEG ECLPVPETSL  1500
NMSDSLLFDS FSDDYLVKEQ LPDMQMKEPL PSEVTSNHFS DSLCLQEDLI KKSNVNENQD  1560
THQQLTCSND ESIIFSEMDS VQMVEALDNV DIFPVQEKNH TVVSPRALEL SDPVLDEHHQ  1620
GDQDGGDQDE RAEKSKLTGT RQNHSFIWSG ASFDLSPGLQ RILDKVSSPL ENEKLKSMTI  1680
NFSSLNRKNT ELNEEQEVIS NLETKQVQGI SFSSNNEVKS KIEMLENNAN HDETSSLLPR  1740
KESNIVDDNG LIPPTPIPTS ASKLTFPGIL ETPVNPWKTN NVLQPGESYL FGSPSDIKNH  1800
DLSPGSRNGF KDNSPISDTS FSLQLSQDGL QLTPASSSSE SLSIIDVASD QNLFQTFIKE  1860
WRCKKRFSIS LACEKIRSLT SSKTATIGSR FKQASSPQEI PIRDDGFPIK GCDDTLVVGL  1920
AVCWGGRDAY YFSLQKEQKH SEISASLVPP SLDPSLTLKD RMWYLQSCLR KESDKECSVV  1980
IYDFIQSYKI LLLSCGISLE QSYEDPKVAC WLLDPDSQEP TLHSIVTSFL PHELPLLEGM  2040
ETSQGIQSLG LNAGSEHSGR YRASVESILI FNSMNQLNSL LQKENLQDVF RKVEMPSQYC  2100
LALLELNGIG FSTAECESQK HIMQAKLDAI ETQAYQLAGH SFSFTSSDDI AEVLFLELKL  2160
PPNREMKNQG SKKTLGSTRR GIDNGRKLRL GRQFSTSKDV LNKLKALHPL PGLILEWRRI  2220
TNAITKVVFP LQREKCLNPF LGMERIYPVS QSHTATGRIT FTEPNIQNVP RDFEIKMPTL  2280
VGESPPSQAV GKGLLPMGRG KYKKGFSVNP RCQAQMEERA ADRGMPFSIS MRHAFVPFPG  2340
GSILAADYSQ LELRILAHLS HDRRLIQVLN TGADVFRSIA AEWKMIEPES VGDDLRQQAK  2400
QICYGIIYGM GAKSLGEQMG IKENDAACYI DSFKSRYTGI NQFMTETVKN CKRDGFVQTI  2460
LGRRRYLPGI KDNNPYRKAH AERQAINTIV QGSAADIVKI ATVNIQKQLE TFHSTFKSHG  2520
HREGMLQSDR TGLSRKRKLQ GMFCPIRGGF FILQLHDELL YEVAEEDVVQ VAQIVKNEME  2580
SAVKLSVKLK VKVKIGASWG ELKDFDVPGM DYKDDDDK                         2618

SEQ ID NO: 85          moltype = AA  length = 375
FEATURE                Location/Qualifiers
source                 1..375
                       mol_type = protein
                       organism = Homo sapiens
SEQUENCE: 85
MDYKDHDGDY KDHDIDYKDD DDKMAPKKKR KVGIHGVPAA ASKRKAPQET LNGGITDMLT  60
ELANFEKNVS QAIHKYNAYR KAASVIAKYP HKIKSGAEAK KLPGVGTKIA EKIDEFLATG  120
KLRKLEKIRQ DDTSSSINFL TRVSGIGPSA ARKFVDEGIK TLEDLRKNED KLNHHQRIGL  180
KYFGDFEKRI PREEMLQMQD IVLNEVKKVD SEYIATVCGS FRRGAESSGD MDVLLTHPSF  240
TSESTKQPKL LHQVVEQLQK VHFITDTLSK GETKFMGVCQ LPSKNDEKEY PHRRIDIRLI  300
PKDQYYCGVL YFTGSDIFNK NMRAHALEKG FTINEYTIRP LGVTGVAGEP LPVDSEKDIF  360
DYIQWKYREP KDRSE                                                   375

SEQ ID NO: 86          moltype = AA  length = 713
FEATURE                Location/Qualifiers
source                 1..713
                       mol_type = protein
```

```
                         organism = Homo sapiens
SEQUENCE: 86
MATGQDRVVA LVDMDCFFVQ VEQRQNPHLR NKPCAVVQYK SWKGGGIIAV SYEARAFGVT  60
RSMWADDAKK LCPDLLLAQV RESRGKANLT KYREASVEVM EIMSRFAVIE RASIDEAYVD  120
LTSAVQERLQ KLQGQPISAD LLPSTYIEGL PQGPTTAEET VQKEGMRKQG LFQWLDSLQI  180
DNLTSPDLQL TVGAVIVEEM RAAIERETGF QCSAGISHNK VLAKLACGLN KPNRQTLVSH  240
GSVPQLFSQM PIRKIRSLGG KLGASVIEIL GIEYMGELTQ FTESQLQSHF GEKNGSWLYA  300
MCRGIEHDPV KPRQLPKTIG CSKNFPGKTA LATREQVQWW LLQLAQELEE RLTKDRNDND  360
RVATQLVVSI RVQGDKRLSS LRRCCALTRY DAHKMSHDAF TVIKNCNTSG IQTEWSPPLT  420
MLFLCATKFS ASAPSSSTDI TSFLSSDPSS LPKVPVTSSE AKTQGSGPAV TATKKATTSL  480
ESFFQKAAER QKVKEASLSS LTAPTQAPMS NSPSKPSLPF QTSQSTGTEP FFKQKSLLLK  540
QKQLNNSSVS SPQQNPWSNC KALPNSLPTE YPGCVPVCEG VSKLEESSKA TPAEMDLAHN  600
SQSMHASSAS KSVLEVTQKA TPNPSLLAAE DQVPCEKCGS LVPVWDMPEH MDYHFALELQ  660
KSFLQPHSSN PQVVSAVSHQ GKRNPKSPLA CTNKRPRPEG MQTLESFFKP LTH         713

SEQ ID NO: 87            moltype = AA  length = 1240
FEATURE                  Location/Qualifiers
source                   1..1240
                         mol_type = protein
                         organism = Homo sapiens
SEQUENCE: 87
MASRLLWRKV AGATVGPGPV PAPGRWVSSS VPASDPSDGQ RRRQQQQQQQ QQQQQQPQQP  60
QVLSSEGGQL RHNPLDIQML SRGLHEQIFG QGGEMPGEAA VRRSVEHLQK HGLWGQPAVP  120
LPDVELRLPP LYGDNLDQHF RLLAQKQSLP YLEAANLLLQ AQLPPKPPAW AWAEGWTRYG  180
PEGEAVPVAI PEERALVFDV EVCLAEGTCP TLAVAISPSA WYSWCSQRLV EERYSWTSQL  240
SPADLIPLEV PTGASSPTQR DWQEQLVVGH NVSFDRAHIR EQYLIQGSRM RFLDTMSMHM  300
AISGLSSFQR SLWIAAKQGK HKVQPPTKQG QKSQRKARRG PAISSWDWLD ISSVNSLAEV  360
HRLYVGGPPL EKEPRELFVK GTMKDIRENF QDLMQYCAQD VWATHEVFQQ QLPLFLERCP  420
HPVTLAGMLE MGVSYLPVNQ NWERYLAEAQ GTYEELQREM KKSLMDLAND ACQLLSGERY  480
KEDPWLWDLE WDLQEFKQKK AKKVKKEPAT ASKLPIEGAG APGDPMDQED LGPCSEEEEF  540
QQDVMARACL QKLKGTTELL PKRPQHLPGH PGWYRKLCPR LDDPAWTPGP SLLSLQMRVT  600
PKLMALTWDG FPLHYSERHG WGYLVPGRRD NLAKLPTGTT LESAGVVCPY RAIESLYRKH  660
CLEQGKQQLM PQEAGLAEEF LLTDNSAIWQ TVEELDYLEV EAEAKMENLR AAVPGQPLAL  720
TARGGPKDTQ PSYHHGNGPY NDVDIPGCWF FKLPHKDGNS CNVGSPFAKD FLPKMEDGTL  780
QAGPGGASGP RALEINKMIS FWRNAHKRIS SQMVVWLPRS ALPRAVIRHP DYDEEGLYGA  840
ILPQVVTAGT ITRRAVEPTW LTASNARPDR VGSELKAMVQ APPGYTLVGA DVDSQELWIA  900
AVLGDAHFAG MHGCTAFGWM TLQGRKSRGT DLHSKTATTV GISREHAKIF NYGRIYGAGQ  960
PFAERLLMQF NHRLTQQEAA EKAQQMYAAT KGLRWYRLSD EGEWLVRELN LPVDRTEGGW  1020
ISLQDLRKVQ RETARKSQWK KWEVVAERAW KGGTESEMFN KLESIATSDI PRTPVLGCCI  1080
SRALEPSAVQ EEFMTSRVNW VVQSSAVDYL HLMLVAMKWL FEEFAIDGRF CISIHDEVRY  1140
LVREEDRYRA ALALQITNLL TRCMFAYKLG LNDLPQSVAF FSAVDIDRCL RKEVTMDCKT  1200
PSNPTGMERR YGIPQGEALD IYQIIELTKG SLEKRSQPGP                        1240

SEQ ID NO: 88            moltype = AA  length = 900
FEATURE                  Location/Qualifiers
source                   1..900
                         mol_type = protein
                         organism = Homo sapiens
SEQUENCE: 88
MENYEALVGF DLCNTPLSSV AQKIMSAMHS GDLVDSKTWG KSTETMEVIN KSSVKYSVQL  60
EDRKTQSPEK KDLKSLRSQT SRGSAKLSPQ SFSVRLTDQL SADQKQKSIS SLTLSSCLIP  120
QYNQEASVLQ KKGHKRKHFL MENINNENKG SINLKRKHIT YNNLSEKTSK QMALEEDTDD  180
AEGYLNSGNS GALKKHFCDI RHLDDWAKSQ LIEMLKQAAA LVITVMYTDG STQLGADQTP  240
VSSVRGIVVL VKRQAEGGHG CPDAPACGPV LEGFVSDDPC IYIQIEHSAI WDQEQEAHQQ  300
FARNVLFQTM KCKCPVICFN AKDFVRIVLQ FFGNDGSWKH VADFIGLDPR IAAWLIDPSD  360
ATPSFEDLVE KYCEKSITVK VNSTYGNSSR NIVNQNVREN LKTLYRLTMD LCSKLKDYGL  420
WQLFRTLELP LIPILAVMES HAIQVNKEEM EKTSALLGAR LKELEQEAHF VAGERFLITS  480
NNQLREILFG KLKLHLLSQR NSLPRTGLQK YPSTSEAVLN ALRDLHPLPK IILEYRQVHK  540
IKSTFVDGLL ACMKKGSISS TWNQTGTVTG RLSAKHPNIQ GISKHPIQIT TPKNFKGKED  600
KILTISPRAM FVSSKGHTFL AADFSQIELR ILTHLSGDPE LLKLFQESER DDVFSTLTSQ  660
WKDVPVEQVT HADREQTKKV VYAVVYGAGK ERLAACLGVP IQEAAQFLES FLQKYKKIKD  720
FARAAIAQCH QTGCVVSIMG RRRPLPRIHA HDQQLRAQAE RQAVNFVVQG SAADLCKLAM  780
IHVFTAVAAS HTLTARLVAQ IHDELLFEVE DPQIPECAAL VRRTMESLEQ VQALELQLQV  840
PLKVSLSAGR SWGHLVPLQE AWGPPPGPCR TESPSNSLAA PGSPASTQPP PLHFSPSFCL  900

SEQ ID NO: 89            moltype = AA  length = 542
FEATURE                  Location/Qualifiers
source                   1..542
                         mol_type = protein
                         organism = Homo sapiens
SEQUENCE: 89
MASPCPEEAA MRREVVKRIE TVVKDLWPTA DVQIFGSFST GLYLPTSDID LVVFGKWERP  60
PLQLLEQALR KHNVAEPCSI KVLDKATVPI IKLTDQETEV KVDISFNMET GVRAAEFIKN  120
YMKKYSLLPY LILVLKQFLL QRDLNEVFTG GISSYSLILM AISFLQLHPR IDARRADENL  180
GMLLVEFFEL YGRNFNYLKT GIRIKEGGAY IAKEEIMKAM TSGYRPSMLC IEDPLLPGND  240
VGRSSYGAMQ VKQVFDYAYI VLSHAVSPLA RSYPNRDAES TLGRIIKVTQ EVIDYRRWIK  300
EKWGSKAHPS PGMDSRIKIK ERIATCNGEQ TQNREPESPY GQRLTLSLSS PQLLSSGSSA  360
SSVSSLSGSD VDSDTPPCTT PSVYQFSLQA PAPLMAGLPT ALPMPSGKPQ PTTSRTLIMT  420
TNNQTRFTIP PPTLGVAPVP CRQAGVEGTA SLKAVHHMSS PAIPSASPNP LSSPHLYHKH  480
```

-continued

```
NGMKLSMKGS HGHTQGGGYS SVGSGGVRPP VGNRGHHQYN RTGWRRKKHT HTRDSLPVSL  540
SR                                                                 542

SEQ ID NO: 90           moltype = AA  length = 911
FEATURE                 Location/Qualifiers
source                  1..911
                        mol_type = protein
                        organism = Homo sapiens
SEQUENCE: 90
MAASQTSQTV ASHVPFADLC STLERIQKSK GRAEKIRHFR EFLDSWRKFH DALHKNHKDV  60
TDSFYPAMRL ILPQLERERM AYGIKETMLA KLYIELLNLP RDGKDALKLL NYRTPTGTHG  120
DAGDFAMIAY FVLKPRCLQK GSLTIQQVND LLDSIASNNS AKRKDLIKKS LLQLITQSSA  180
LEQKWLIRMI IKDLKLGVSQ QTIFSVFHND AAELHNVTTD LEKVCRQLHD PSVGLSDISI  240
TLFSAFKPML AAIADIEHIE KDMKHQSFYI ETKLDGERMQ MHKDGDVYKY FSRNGYNYTD  300
QFGASPTEGS LTPFIHNAFK ADIQICILDG EMMAYNPNTQ TFMQKGTKFD IKRMVEDSDL  360
QTCYCVFDVL MVNNKKLGHE TLRKRYEILS SIFTPIPGRI EIVQKTQAHT KNEVIDALNE  420
AIDKREEGIM VKQPLSIYKP DKRGEGWLKI KPEYVSGLMD ELDILIVGGY WGKGSRGGMM  480
SHFLCAVAEK PPPGEKPSVF HTLSRVGSGC TMKELYDLGL KLAKYWKPFH RKAPPSSILC  540
GTEKPEVYIE PCNSVIVQIK AAEIVPSDMY KTGCTLRFPR IEKIRDDKEW HECMTLDDLE  600
QLRGKASGKL ASKHLYIGGD DEPQEKKRKA APKMKKVIGI IEHLKAPNLT NVNKISNIFE  660
DVEFCVMSGT DSQPKPDLEN RIAEFGGYIV QNPGPDTYCV IAGSENIRVK NIILSNKHDV  720
VKPAWLLECF KTKSFVPWQP RFMIHMCPST KEHFAREYDC YGDSYFIDTD LNQLKEVFSG  780
IKNSNEQTPE EMASLIADLE YRYSWDCSPL SMFRRHTVYL DSYAVINDLS TKNEGTRLAI  840
KALELRFHGA KVVSCLAEGV SHVIIGEDHS RVADFKAFRR TFKRKFKILK ESWVTDSIDK  900
CELQEENQYL I                                                       911

SEQ ID NO: 91           moltype = AA  length = 1028
FEATURE                 Location/Qualifiers
source                  1..1028
                        mol_type = protein
                        organism = Homo sapiens
SEQUENCE: 91
MGSAACPRGA LPELAPCCQP REQSQPHTRW DAGCGIQHPG GEEFRTLGGA RAYRVPNSQE  60
GRSSPTRFFP APEGPAHCFV SSPDRAFWVS EEVQRLLLSN ACQPKECNGV KIPVDASKPN  120
PNDVEFDNLY LDMNGIIHPC THPEDKPAPK NEDEMMVAIF EYIDRLFSIV RPRRLLYMAI  180
DGVAPRAKMN QQRSRRFRAS KEGMEAAVEK QRVREEILAK GGFLPPEEIK ERFDSNCITP  240
GTEFMDNLAK CLRYYIADRL NNDPGWKNLT VILSDASAPG EGEHKIMDYI RRQRAQPNHD  300
PNTHHCLCGA DADLIMLGLA THEPNFTIIR EEFKPNKPKP CGLCNQFGHE VKDCEGLPRE  360
KKGKHDELAD SLPCAEGEFI FLRLNVLREY LERELTMASL PFTFDVERSI DDWVFMCFFV  420
GNDFLPHLPS LEIRENAIDR LVNIYKNVVH KTGGYLTESG YVNLQRVQMI MLAVGEVEDS  480
IFKKRKDDED SFRRRQKEKR KRMKRDQPAF TPSGILTPHA LGSRNSPGSQ VASNPRQAAY  540
EMRMQNNSSP SISPNTSFTS DGSPSPLGGI KRKAEDSDSE PEPEDNVRLW EAGWKQRYYK  600
NKFDVDAADE KFRRKVVQSY VEGLCWVLRY YYQGCASWKW YYPFHYAPFA SDFEGIADMP  660
SDFEKGTKPF KPLEQLMGVF PAASGNFLPP SWRKLMSDPD SSIIDFYPED FAIDLNGKKY  720
AWQGVALLPF VDERRLRAAL EEVYPDLTPE ETRRNSLGGD VLFVGKHHPL HDFILELYQT  780
GSTEPVEVPP ELCHGIQGKF SLDEEAILPD QIVCSPVPML RDLTQNTVVS INFKDPQFAE  840
DYIFKAVMLP GARKPAAVLK PSDWEKSSNG RQWKPQLGFN RDRRPVHLDQ AAFRTLGHVM  900
PRGSGTGIYS NAAPPPVTYQ GNLYRPLLRG QAQIPKLMSN MRPQDSWRGP PPLFQQQRFD  960
RGVGAEPLLP WNRMLQTQNA AFQPNQYQML AGPGGYPPRR DDRGGRQGYP REGRKYPLPP  1020
PSGRYNWN                                                           1028

SEQ ID NO: 92           moltype = AA  length = 620
FEATURE                 Location/Qualifiers
REGION                  1..620
                        note = Fusion protein
source                  1..620
                        mol_type = protein
                        organism = synthetic construct
SEQUENCE: 92
MDYKDHDGDY KDHDIDYKDD DDKMAPKKKR KVGIHGVPAA SLKGKFFAFL PNPNTSSNKF  60
FKSILEKKGA TIVSSIQNCL QSSRKEVIIL IEDSFVDSDM HLTQKDIFQR EAGLNDVDEF  120
LGKIEQSGIQ CVKTSCITKW VQNDKFAFQK DDLIKFQPSI IVISDNADDG QSSTDKESEI  180
STDVESERND DSNNKDMIQA SKPLKRLLQE DKGRASLVTD KTKYKNNELI IGALKRLTKK  240
YEIEGEKFRA RSYRLAKQSM ENCDFNVRSG EEAHTKLRNI GPSIAKKIQV ILDTGVLPGL  300
NDSVGLEDKL KYFKNCYGIG SEIAKRWNLL NFESFCVAAK KDPEEFVSDW TILFGWSYYD  360
DWLCKMSRNE CFAHLKKVQK ALRGIDPECQ VELQGSYNRG YSKCGDIDLL FFKPFCNDTT  420
ELAKIMETLC IKLYKDGYIH CFLQLTPNLE KLFLKRIVER FRTAKIVGYG ERKRWYSSEI  480
IKKFFMGVKL SPRELEELKE MKNDEGTLLI EEEEEETKLK PIDQYMSLNA KDGNYCRRLD  540
FFCCKWDELG AGRIHYTGSK EYNRWIRILA AQKGFKLTQH GLFRNNILLE SFNERRIFEL  600
LNLKYAEPEH RNIEWEKKTG                                              620

SEQ ID NO: 93           moltype = AA  length = 495
FEATURE                 Location/Qualifiers
REGION                  1..495
                        note = Fusion protein
source                  1..495
                        mol_type = protein
                        organism = synthetic construct
SEQUENCE: 93
```

-continued

MDYKDHDGDY KDHDIDYKDD DDKMAPKKKR KVGIHGVPAA LPSQSPAIFT VSRLNQTVRL 60
LLEHEMGQVW ISGEISNFTQ PASGHWYFTL KDDTAQVRCA MFRNSNRRVT FRPQHGQQVL 120
VRANITLYEP RGDYQIIVES MQPAGEGLLQ QKYEQLKAKL QAEGLFDQQY KKPLPSPAHC 180
VGVITSKTGA ALHDILHVLK RRDPSLPVII YPAAVQGDDA PGQIVRAIEL ANQRNECDVL 240
IVGRGGGSLE DLWSFNDERV ARAIFTSRIP VVSAVGHETD VTIADFVADL RAPTPSAAAE 300
VVSRNQQELL RQVQSTRQRL EMAMDYYLAN RTRRFTQIHH RLQQQHPQLR LARQQTMLER 360
LQKRMSFALE NQLKRTGQQQ QRLTQRLNQQ NPQPKIHRAQ TRIQQLEYRL AETLRAQLSA 420
TRERFGNAVT HLEAVSPLST LARGYSVTTA TDGNVLKKVK QVKAGEMLTT RLEDGWIESE 480
VKNIQPVKKS RKKVH 495

SEQ ID NO: 94 moltype = AA length = 119
FEATURE Location/Qualifiers
REGION 1..119
note = Fusion protein
source 1..119
mol_type = protein
organism = synthetic construct
SEQUENCE: 94
MDYKDHDGDY KDHDIDYKDD DDKMAPKKKR KVGIHGVPAA PKKNEAPASF EKALSELEQI 60
VTRLESGDLP LEEALNEFER GVQLARQGQA KLQQAEQRVQ ILLSDNEDAS LTPFTPDNE 119

SEQ ID NO: 95 moltype = AA length = 1423
FEATURE Location/Qualifiers
REGION 1..1423
note = Fusion protein
source 1..1423
mol_type = protein
organism = synthetic construct
SEQUENCE: 95
MDYKDHDGDY KDHDIDYKDD DDKMAPKKKR KVGIHGVPAA DKKYSIGLDI GTNSVGWAVI 60
TDEYKVPSKK FKVLGNTDRH SIKKNLIGAL LFDSGETAEA TRLKRTARRR YTRRKNRICY 120
LQEIFSNEMA KVDDSFFHRL EESFLVEEDK KHERHPIFGN IVDEVAYHEK YPTIYHLRKK 180
LVDSTDKADL RLIYLALAHM IKFRGHFLIE GDLNPDNSDV DKLFIQLVQT YNQLFEENPI 240
NASGVDAKAI LSARLSKSRR LENLIAQLPG EKKNGLFGNL IALSLGLTPN FKSNFDLAED 300
AKLQLSKDTY DDDLDNLLAQ IGDQYADLFL AAKNLSDAIL LSDILRVNTE ITKAPLSASM 360
IKRYDEHHQD LTLLKALVRQ QLPEKYKEIF FDQSKNGYAG YIDGGASQEE FYKFIKPILE 420
KMDGTEELLV KLNREDLLRK QRTFDNGSIP HQIHLGELHA ILRRQEDFYP FLKDNREKIE 480
KILTFRIPYY VGPLARGNSR FAWMTRKSEE TITPWNFEEV VDKGASAQSF IERMTNFDKN 540
LPNEKVLPKH SLLYEYFTVY NELTKVKYVT EGMRKPAFLS GEQKKAIVDL LFKTNRKVTV 600
KQLKEDYFKK IECFDSVEIS GVEDRFNASL GTYHDLLKII KDKDFLDNEE NEDILEDIVL 660
TLTLFEDREM IEERLKTYAH LFDDKVMKQL KRRRYTGWGR LSRKLINGIR DKQSGKTILD 720
FLKSDGFANR NFMQLIHDDS LTFKEDIQKA QVSGQGDSLH EHIANLAGSP AIKKGILQTV 780
KVVDELVKVM GRHKPENIVI EMARENQTTQ KGQKNSRERM KRIEEGIKEL GSQILKEHPV 840
ENTQLQNEKL YLYYLQNGRD MYVDQELDIN RLSDYDVDHI VPQSFLKDDS IDNKVLTRSD 900
KNRGKSDNVP SEEVVKKMKN YWRQLLNAKL ITQRKFDNLT KAERGGLSEL DKAGFIKRQL 960
VETRQITKHV AQILDSRMNT KYDENDKLIR EVKVITLKSK LVSDFRKDFQ FYKVREINNY 1020
HHAHDAYLNA VVGTALIKKY PKLESEFVYG DYKVYDVRKM IAKSEQEIGK ATAKYFFYSN 1080
IMNFFKTEIT LANGEIRKRP LIETNGETGE IVWDKGRDFA TVRKVLSMPQ VNIVKKTEVQ 1140
TGGFSKESIL PKRNSDKLIA RKKDWDPKKY GGFDSPTVAY SVLVVAKVEK GKSKKLKSVK 1200
ELLGITIMER SSFEKNPIDF LEAKGYKEVK KDLIIKLPKY SLFELENGRK RMLASAGELQ 1260
KGNELALPSK YVNFLYLASH YEKLKGSPED NEQKQLFVEQ HKHYLDEIIE QISEFSKRVI 1320
LADANLDKVL SAYNKHRDKP IREQAENIIH LFTLTNLGAP AAFKYFDTTI DRKRYTSTKE 1380
VLDATLIHQS ITGLYETRID LSQLGGDKRP AATKKAGQAK KKK 1423

SEQ ID NO: 96 moltype = AA length = 1422
FEATURE Location/Qualifiers
REGION 1..1422
note = Fusion protein
source 1..1422
mol_type = protein
organism = synthetic construct
SEQUENCE: 96
MDYKDHDGDY KDHDIDYKDD DDKMAPKKKR KVGIHGVPAA DKKYSIGLDI GTNSVGWAVI 60
TDEYKVPSKK FKVLGNTDRH SIKKNLIGAL LFDSGETAEA TRLKRTARRR YTRRKNRICY 120
LQEIFSNEMA KVDDSFFHRL EESFLVEEDK KHERHPIFGN IVDEVAYHEK YPTIYHLRKK 180
LVDSTDKADL RLIYLALAHM IKFRGHFLIE GDLNPDNSDV DKLFIQLVQT YNQLFEENPI 240
NASGVDAKAI LSARLSKSRR LENLIAQLPG EKKNGLFGNL IALSLGLTPN FKSNFDLAED 300
AKLQLSKDTY DDDLDNLLAQ IGDQYADLFL AAKNLSDAIL LSDILRVNTE ITKAPLSASM 360
IKRYDEHHQD LTLLKALVRQ QLPEKYKEIF FDQSKNGYAG YIDGGASQEE FYKFIKPILE 420
KMDGTEELLV KLNREDLLRK QRTFDNGSIP HQIHLGELHA ILRRQEDFYP FLKDNREKIE 480
KILTFRIPYY VGPLARGNSR FAWMTRKSEE TITPWNFEEV VDKGASAQSF IERMTNFDKN 540
LPNEKVLPKH SLLYEYFTVY NELTKVKYVT EGMRKPAFLS GEQKKAIVDL LFKTNRKVTV 600
KQLKEDYFKK IECFDSVEIS GVEDRFNASL GTYHDLLKII KDKDFLDNEE NEDILEDIVL 660
TLTLFEDREM IEERLKTYAH LFDDKVMKQL KRRRYTGWGR LSRKLINGIR DKQSGKTILD 720
FLKSDGFANR NFMQLIHDDS LTFKEDIQKA QVSGQGDSLH EHIANLAGSP AIKKGILQTV 780
KVVDELVKVM GRHKPENIVI EMARENQTTQ KGQKNSRERM KRIEEGIKEL GSQILKEHPV 840
ENTQLQNEKL YLYYLQNGRD MYVDQELDIN RLSDYDVDHI VPQSFLKDDS IDNKVLTRSD 900
KNRGKSDNVP SEEVVKKMKN YWRQLLNAKL ITQRKFDNLT KAERGGLSEL DKAGIKRQLV 960
ETRQITKHVA QILDSRMNTK YDENDKLIRE VKVITLKSKL VSDFRKDFQF YKVREINNYH 1020

```
HAHDAYLNAV VGTALIKKYP KLESEFVYGD YKVYDVRKMI AKSEQEIGKA TAKYFFYSNI  1080
MNFFKTEITL ANGEIRKRPL IETNGETGEI VWDKGRDFAT VRKVLSMPQV NIVKKTEVQT  1140
GGFSKESILP KRNSDKLIAR KKDWDPKKYG GFDSPTVAYS VLVVAKVEKG KSKKLKSVKE  1200
LLGITIMERS SFEKNPIDFL EAKGYKEVKK DLIIKLPKYS LFELENGRKR MLASAGELQK  1260
GNELALPSKY VNFLYLASHY EKLKGSPEDN EQKQLFVEQH KHYLDEIIEQ ISEFSKRVIL  1320
ADANLDKVLS AYNKHRDKPI REQAENIIHL FTLTNLGAPA AFKYFDTTID RKRYTSTKEV  1380
LDATLIHQSI TGLYETRIDL SQLGGDKRPA ATKKAGQAKK KK                    1422

SEQ ID NO: 97           moltype = AA  length = 1423
FEATURE                 Location/Qualifiers
REGION                  1..1423
                        note = Fusion protein
source                  1..1423
                        mol_type = protein
                        organism = synthetic construct
SEQUENCE: 97
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFANR NFMQLIHDDS LTFKEDIQKA QVSGQGDSLH EHIANLAGSP AIKKGILQTV  780
KVVDELVKVM GRHKPENIVI EMARENQTTQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAFFIKRQL  960
VETRQITKHV AQILDSRMNT KYDENDKLIR EVKVITLKSK LVSDFRKDFQ FYKVREINNY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                   1423

SEQ ID NO: 98           moltype = AA  length = 1423
FEATURE                 Location/Qualifiers
REGION                  1..1423
                        note = Fusion protein
source                  1..1423
                        mol_type = protein
                        organism = synthetic construct
SEQUENCE: 98
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFANR NFMQLIHDDS LTFKEDIQKA QVSGQGDSLH EHIANLAGSP AIKKGILQTV  780
KVVDELVKVM GRHKPENIVI EMARENQTTQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAGFIKRPL  960
VETRQITKHV AQILDSRMNT KYDENDKLIR EVKVITLKSK LVSDFRKDFQ FYKVREINNY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                   1423

SEQ ID NO: 99           moltype = AA  length = 1423
FEATURE                 Location/Qualifiers
REGION                  1..1423
                        note = Fusion protein
source                  1..1423
```

```
                        mol_type = protein
                        organism = synthetic construct
SEQUENCE: 99
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFANR NFMQLIHDDS LTFKEDIQKA QVSGQGDSLH EHIANLAGSP AIKKGILQTV  780
KVVDELVKVM GRHKPENIVI EMARENQTTQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAGPIKRQL  960
VETRQITKHV AQILDSRMNT KYDENDKLIR EVKVITLKSK LVSDFRKDFQ FYKVREINNY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                    1423

SEQ ID NO: 100          moltype = AA  length = 1423
FEATURE                 Location/Qualifiers
REGION                  1..1423
                        note = Fusion protein
source                  1..1423
                        mol_type = protein
                        organism = synthetic construct
SEQUENCE: 100
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFANR NFMQLIHDDS LTFKEDIQKA QVSGQGDSLH EHIANLAGSP AIKKGILQTV  780
KVVDELVKVM GRHKPENIVI EMARENQTTQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAGFIARQL  960
VETRQITKHV AQILDSRMNT KYDENDKLIR EVKVITLKSK LVSDFRKDFQ FYKVREINNY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                    1423

SEQ ID NO: 101          moltype = AA  length = 1423
FEATURE                 Location/Qualifiers
REGION                  1..1423
                        note = Fusion protein
source                  1..1423
                        mol_type = protein
                        organism = synthetic construct
SEQUENCE: 101
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
```

-continued

```
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFANR NFMQLIHDDS LTFKEDIQKA QVSGQGDSLH EHIANLAGSP AIKKGILQTV  780
KVVDELVKVM GRHKPENIVI EMARENQTTQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAGFIKPQL  960
VETRQITKHV AQILDSRMNT KYDENDKLIR EVKVITLKSK LVSDFRKDFQ FYKVREINNY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                   1423

SEQ ID NO: 102          moltype = AA  length = 1423
FEATURE                 Location/Qualifiers
REGION                  1..1423
                        note = Fusion protein
source                  1..1423
                        mol_type = protein
                        organism = synthetic construct
SEQUENCE: 102
MDYKDHDGDY KDHDIDYKDD DDKMAPKKKR KVGIHGVPAA DKKYSIGLDI GTNSVGWAVI  60
TDEYKVPSKK FKVLGNTDRH SIKKNLIGAL LFDSGETAEA TRLKRTARRR YTRRKNRICY  120
LQEIFSNEMA KVDDSFFHRL EESFLVEEDK KHERHPIFGN IVDEVAYHEK YPTIYHLRKK  180
LVDSTDKADL RLIYLALAHM IKFRGHFLIE GDLNPDNSDV DKLFIQLVQT YNQLFEENPI  240
NASGVDAKAI LSARLSKSRR LENLIAQLPG EKKNGLFGNL IALSLGLTPN FKSNFDLAED  300
AKLQLSKDTY DDDLDNLLAQ IGDQYADLFL AAKNLSDAIL LSDILRVNTE ITKAPLSASM  360
IKRYDEHHQD LTLLKALVRQ QLPEKYKEIF FDQSKNGYAG YIDGGASQEE FYKFIKPILE  420
KMDGTEELLV KLNREDLLRK QRTFDNGSIP HQIHLGELHA ILRRQEDFYP FLKDNREKIE  480
KILTFRIPYY VGPLARGNSR FAWMTRKSEE TITPWNFEEV VDKGASAQSF IERMTNFDKN  540
LPNEKVLPKH SLLYEYFTVY NELTKVKYVT EGMRKPAFLS GEQKKAIVDL LFKTNRKVTV  600
KQLKEDYFKK IECFDSVEIS GVEDRFNASL GTYHDLLKII KDKDFLDNEE NEDILEDIVL  660
TLTLFEDREM IEERLKTYAH LFDDKVMKQL KRRRYTGWGR LSRKLINGIR DKQSGKTILD  720
FLKSDGFACR NFMQLIHDDS LTFKEDIQKA QVSGQGDSLH EHIANLAGSP AIKKGILQTV  780
KVVDELVKVM GRHKPENIVI EMARENQITQ KGQKNSRERM KRIEEGIKEL GSQILKEHPV  840
ENTQLQNEKL YLYYLQNGRD MYVDQELDIN RLSDYDVDHI VPQSFLKDDS IDNKVLTRSD  900
KNRGKSDNVP SEEVVKKMKN YWRQLLNAKL ITQRKFDNLT KAERGGLSEL DKAMFIKRQL  960
VETRQITKHV AQILDSRMNT KYDENDKLIR EVKVITLKSK LVSDFRKDFQ FYKVREINKY  1020
HHAHDAYLNA VVGTALIKKY PKLESEFVYG DYKVYDVRKM IAKSEQEIGK ATAKYFFYSN  1080
IMNFFKTEIT LANGEIRKRP LIETNGETGE IVWDKGRDFA TVRKVLSMPQ VNIVKKTEVQ  1140
TGGFSKESIL PKRNSDKLIA RKKDWDPKKY GGFDSPTVAY SVLVVAKVEK GKSKKLKSVK  1200
ELLGITIMER SSFEKNPIDF LEAKGYKEVK KDLIIKLPKY SLFELENGRK RMLASAGELQ  1260
KGNELALPSK YVNFLYLASH YEKLKGSPED NEQKQLFVEQ HKHYLDEIIE QISEFSKRVI  1320
LADANLDKVL SAYNKHRDKP IREQAENIIH LFTLTNLGAP AAFKYFDTTI DRKRYTSTKE  1380
VLDATLIHQS ITGLYETRID LSQLGGDKRP AATKKAGQAK KKK                   1423

SEQ ID NO: 103          moltype = AA  length = 1350
FEATURE                 Location/Qualifiers
REGION                  1..1350
                        note = Fusion protein
source                  1..1350
                        mol_type = protein
                        organism = synthetic construct
SEQUENCE: 103
MDYKDHDGDY KDHDIDYKDD DDKMAPKKKR KVEASMKRNY ILGLDIGITS VGYGIIDYET  60
RDVIDAGVRL FKEANVENNE GRRSKRGARR LKRRRRHRIQ RVKKLLFDYN LLTDHSELSG  120
INPYEARVKG LSQKLSEEEF SAALLHLAKR RGVHNVNEVE EDTGNELSTK EQISRNSKAL  180
EEKYVAELQL ERLKKDGEVR GSINRFKTSD YVKEAKQLLK VQKAYHQLDQ SFIDTYIDLL  240
ETRRTYYEGP GEGSPFGWKD IKEWYEMLMG HCTYFPEELR SVKYAYNADL YNALNDLNNL  300
VITRDENEKL EYYEKFQIIE NVFKQKKKPT LKQIAKEILV NEEDIKGYRV TSTGKPEFTN  360
LKVYHDIKDI TARKEIIENA ELLDQIAKIL TIYQSSEDIQ EELTNLNSEL TQEEIEQISN  420
LKGYTGTHNL SLKAINLILD ELWHTNDNQI AIFNRLKLVP KKVDLSQQKE IPTTLVDDFI  480
LSPVVKRSFI QSIKVINAII KKYGLPNDII IELAREKNSK DAQKMINEMQ KRNRQTNERI  540
EEIIRTTGKE NAKYLIEKIK LHDMQEGKCL YSLEAIPLED LLNNPFNYEV DHIIPRSVSF  600
DNSFNNKVLV KQEENSKKGN RTPFQYLSSS DSKISYETFK KHILNLAKGK GRISKTKKEY  660
LLEERDINRF SVQKDFINRN LVDTRYATRG LMNLLRSYFR VNNLDVKVKS INGGFTSFLR  720
RKWKFKKERN KGYKHHAEDA LIIANADFIF KEWKKLDKAK KVMENQMFEE KQAESMPEIE  780
TEQEYKEIFI TPHQIKHIKD FKDYKYSHRV DKKPNRELIN DTLYSTRKDD KGNTLIVNNL  840
NGLYDKDNDK LKKLINKSPE KLLMYHHDPQ TYQKLKLIME QYGDEKNPLY KYYEETGNYL  900
TKYSKKDNGP VIKKIKYYGN KLNAHLDITD DYPNSRNKVV KLSLKPYRFD VYLDNGVYKF  960
VTVKNLDVIK KENYYEVNSK CYEEAKKLKK ISNQAEFIAS FYNNDLIKIN GELYRVIGVN  1020
NDLLNRIEVN MIDITYREYL ENMNDKRPPR IIKTIASKTQ SIKKYSTDIL GNLYEVKSKK  1080
HPQIIKKGRS GGGEGRGSLL TCGDVEENPG PMVSKGEELF TGVVPILVEL DGDVNGHKFS  1140
VSGEGEGDAT YGKLTLKFIC TTGKLPVPWP TLVTTLTYGV QCFSRYPDHM KQHDFFKSAM  1200
PEGYVQERTI FFKDDGNYKT RAEVKFEGDT LVNRIELKGI DFKEDGNILG HKLEYNYNSH  1260
NVYIMADKQK NGIKVNFKIR HNIEDGSVQL ADHYQQNTPI GDGPVLLPDN HYLSTQSALS  1320
KDPNEKRDHM VLLEFVTAAG ITLGMDELYK                                  1350
```

```
SEQ ID NO: 104          moltype = AA  length = 1345
FEATURE                 Location/Qualifiers
REGION                  1..1345
                        note = Fusion protein
source                  1..1345
                        mol_type = protein
                        organism = synthetic construct
SEQUENCE: 104
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN KRPAATKKAG QAKKKKGSYP  1320
YDVPDYAYPY DVPDYAYPYD VPDYA                                      1345

SEQ ID NO: 105          moltype = AA  length = 1352
FEATURE                 Location/Qualifiers
REGION                  1..1352
                        note = Fusion protein
source                  1..1352
                        mol_type = protein
                        organism = synthetic construct
SEQUENCE: 105
MTQFEGFTNL YQVSKTLRFE LIPQGKTLKH IQEQGFIEED KARNDHYKEL KPIIDRIYKT  60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DKMYYDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI  1020
DKLNCLVLKD YPAEKVGGVL NPYQLTDQFT SFAKMGTQSG FLFYVPAPYT SKIDPLTGFV  1080
DPFVWKTIKN HESRKHFLEG FDFLHYDVKT GDFILHFKMN RNLSFQRGLP GFMPAWDIVF  1140
EKNETQFDAK GTPFIAGKRI VPVIENHRFT GRYRDLYPAN ELIALLEEKG IVFRDGSNIL  1200
PKLLENDDSH AIDTMVALIR SVLQMRNSNA ATGEDYINSP VRDLNGVCFD SRFQNPEWPM  1260
DADANGAYHI ALKGQLLLNH LKESKDLKLQ NGISNQDWLA YIQELRNKRP AATKKAGQAK  1320
KKKGSYPYDV PDYAYPYDVP DYAYPYDVPD YA                             1352

SEQ ID NO: 106          moltype = AA  length = 1273
FEATURE                 Location/Qualifiers
REGION                  1..1273
                        note = Fusion protein
source                  1..1273
                        mol_type = protein
                        organism = synthetic construct
SEQUENCE: 106
MSKLEKFTNC YSLSKTLRFK AIPVGKTQEN IDNKRLLVED EKRAEDYKGV KKLLDRYYLS  60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
```

-continued

```
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKHKR PAATKKAGQA KKKKGSYPYD VPDYAYPYDV  1260
PDYAYPYDVP DYA                                                    1273

SEQ ID NO: 107          moltype = AA  length = 12
FEATURE                 Location/Qualifiers
REGION                  1..12
                        note = Linker
source                  1..12
                        mol_type = protein
                        organism = synthetic construct
SEQUENCE: 107
GGGSGGGSGG GS                                                     12

SEQ ID NO: 108          moltype = AA  length = 32
FEATURE                 Location/Qualifiers
REGION                  1..32
                        note = Linker
source                  1..32
                        mol_type = protein
                        organism = synthetic construct
SEQUENCE: 108
SGGSSGGSSG SETPGTSESA TPESSGGSSG GS                               32

SEQ ID NO: 109          moltype = AA  length = 46
FEATURE                 Location/Qualifiers
REGION                  1..46
                        note = Linker
source                  1..46
                        mol_type = protein
                        organism = synthetic construct
SEQUENCE: 109
AEAAAKEAAA KEAAAKEAAA KALEAEAAAK EAAAKEAAAK EAAAKA                46

SEQ ID NO: 110          moltype = AA  length = 41
FEATURE                 Location/Qualifiers
REGION                  1..41
                        note = Linker
source                  1..41
                        mol_type = protein
                        organism = synthetic construct
SEQUENCE: 110
GSDYKDHDGD YKDHDIDYKD DDDKMAPKKK RKVGIHGVPA A                     41

SEQ ID NO: 111          moltype = AA  length = 32
FEATURE                 Location/Qualifiers
REGION                  1..32
                        note = Linker
source                  1..32
                        mol_type = protein
                        organism = synthetic construct
SEQUENCE: 111
GSDYKDHDGD YKDHDIDYKD DDDKGIHGVP AA                               32

SEQ ID NO: 112          moltype = AA  length = 74
FEATURE                 Location/Qualifiers
REGION                  1..74
                        note = Linker
source                  1..74
                        mol_type = protein
                        organism = synthetic construct
SEQUENCE: 112
GSGSEAAAKE AAAKEAAAKE AAAKALEAAA AKEAAAKEAA AKEAAAKGSG SAAAKEAAAK  60
EAAAKEAAAK GSGS                                                   74

SEQ ID NO: 113          moltype = AA  length = 74
```

```
FEATURE              Location/Qualifiers
REGION               1..74
                     note = Linker
source               1..74
                     mol_type = protein
                     organism = synthetic construct
SEQUENCE: 113
AGSGGSGGSG GSPVPSTPPT NSSSTPPTPS PSPVPSTPPT NSSSTPPTPS PSPVPSTPPT  60
NSSSTPPTPS PSAS                                                    74

SEQ ID NO: 114       moltype = AA  length = 66
FEATURE              Location/Qualifiers
REGION               1..66
                     note = Linker
source               1..66
                     mol_type = protein
                     organism = synthetic construct
SEQUENCE: 114
AGSGGSGGSG GSPVPSTPPT PSPSTPPTPS PSGGSGNSSG SGGSPVPSTP PTPSPSTPPT  60
PSPSAS                                                             66

SEQ ID NO: 115       moltype = AA  length = 262
FEATURE              Location/Qualifiers
REGION               1..262
                     note = Artificial sequence
source               1..262
                     mol_type = protein
                     organism = synthetic construct
SEQUENCE: 115
AGSGGSGGSG GSPVPSTPPT PSPSTPPTPS PSIQRTPKIQ VYSRHPAENG KSNFLNCYVS  60
GFHPSDIEVD LLKNGERIEK VEHSDLSFSK DWSFYLLYYT EFTPTEKDEY ACRVNHVTLS  120
QPKIVKWDRD GGSGGSGGSG GSIQRTPKIQ VYSRHPAENG KSNFLNCYVS GFHPSDIEVD  180
LLKNGERIEK VEHSDLSFSK DWSFYLLYYT EFTPTEKDEY ACRVNHVTLS QPKIVKWDRD  240
PVPSTPPTPS PSTPPTPSPS AS                                           262

SEQ ID NO: 116       moltype = AA  length = 326
FEATURE              Location/Qualifiers
REGION               1..326
                     note = Artificial sequence
source               1..326
                     mol_type = protein
                     organism = synthetic construct
SEQUENCE: 116
AGSGGSGGSG GSPVPSTPPT PSPSTPPTPS PSDGRYSLTY IYTGLSKHVE DVPAFQALGS  60
LNDLQFFRYN SKDRKSQPMG LWRQVEGMED WKQDSQLQKA REDIFMETLK DIVEYYNDSN  120
GSHVLQGRFG CEIENNRSSG AFWKYYYDGK DYIEFNKEIP AWVPFDPAAQ ITKQKWEAEP  180
VYVQRAKAYL EEECPATLRK YLKYSKNILD RQDPPSVVVT SHQAPGEKKK LKCLAYDFYP  240
GKIDVHWTRA GEVQEPELRG DVLHNGNGTY QSWVVVAVPP QDTAPYSCHV QHSSLAQPLV  300
VPWEASPVPS TPPTPSPSTP PTPSAS                                       326

SEQ ID NO: 117       moltype = AA  length = 606
FEATURE              Location/Qualifiers
REGION               1..606
                     note = Artificial sequence
source               1..606
                     mol_type = protein
                     organism = synthetic construct
SEQUENCE: 117
AGSGGSGGSG GSGGSGGSGG SGGSDGRYSL TYIYTGLSKH VEDVPAFQAL GSLNDLQFFR  60
YNSKDRKSQP MGLWRQVEGM EDWKQDSQLQ KAREDIFMET LKDIVEYYND SNGSHVLQGR  120
FGCEIENNRS SGAFWKYYYD GKDYIEFNKE IPAWVPFDPA AQITKQKWEA EPVYVQRAKA  180
YLEEECPATL RKYLKYSKNI LDRQDPPSVV VTSHQAPGEK KKLKCLAYDF YPGKIDVHWT  240
RAGEVQEPEL RGDVLHNGNG TYQSWVVVAV PPQDTAPYSC HVQHSSLAQP LVVPWEASGG  300
SGGSGGSGGS DGRYSLTYIY TGLSKHVEDV PAFQALGSLN DLQFFRYNSK DRKSQPMGLW  360
RQVEGMEDWK QDSQLQKARE DIFMETLKDI VEYYNDSNGS HVLQGRFGCE IENNRSSGAF  420
WKYYYDGKDY IEFNKEIPAW VPFDPAAQIT KQKWEAEPVY VQRAKAYLEE ECPATLRKYL  480
KYSKNILDRQ DPPSVVVTSH QAPGEKKKLK CLAYDFYPGK IDVHWTRAGE VQEPELRGDV  540
LHNGNGTYQS WVVVAVPPQD TAPYSCHVQH SSLAQPLVVP WEASPVPSTP PTPSPSTPPT  600
PSPSAS                                                             606

SEQ ID NO: 118       moltype = DNA  length = 31
FEATURE              Location/Qualifiers
misc_feature         1..31
                     note = Artificial Sequence
source               1..31
                     mol_type = other DNA
                     organism = synthetic construct
SEQUENCE: 118
acattgtagc cctctgtgtg ctcaaggggg g                                 31
```

```
SEQ ID NO: 119         moltype = DNA  length = 31
FEATURE                Location/Qualifiers
misc_feature           1..31
                       note = Artificial Sequence
source                 1..31
                       mol_type = other DNA
                       organism = synthetic construct
SEQUENCE: 119
ccccccttga gcacacagag ggctacaatg t                                   31

SEQ ID NO: 120         moltype = DNA  length = 22
FEATURE                Location/Qualifiers
misc_feature           1..22
                       note = Artificial Sequence
source                 1..22
                       mol_type = other DNA
                       organism = synthetic construct
SEQUENCE: 120
acattgtagc cctctgtgtg ct                                             22

SEQ ID NO: 121         moltype = DNA  length = 23
FEATURE                Location/Qualifiers
misc_feature           1..23
                       note = Artificial Sequence
source                 1..23
                       mol_type = other DNA
                       organism = synthetic construct
SEQUENCE: 121
gagcacacag agggctacaa tgt                                            23

SEQ ID NO: 122         moltype =     length =
SEQUENCE: 122
000

SEQ ID NO: 123         moltype =     length =
SEQUENCE: 123
000

SEQ ID NO: 124         moltype = DNA  length = 22
FEATURE                Location/Qualifiers
misc_feature           1..22
                       note = Artificial Sequence
source                 1..22
                       mol_type = other DNA
                       organism = synthetic construct
SEQUENCE: 124
acattgtagc cctctgtgtg ct                                             22

SEQ ID NO: 125         moltype = DNA  length = 22
FEATURE                Location/Qualifiers
misc_feature           1..22
                       note = Artificial Sequence
source                 1..22
                       mol_type = other DNA
                       organism = synthetic construct
SEQUENCE: 125
agcacacaga gggctacaat gt                                             22

SEQ ID NO: 126         moltype =     length =
SEQUENCE: 126
000

SEQ ID NO: 127         moltype =     length =
SEQUENCE: 127
000

SEQ ID NO: 128         moltype = DNA  length = 23
FEATURE                Location/Qualifiers
misc_feature           1..23
                       note = Artificial Sequence
source                 1..23
                       mol_type = other DNA
                       organism = synthetic construct
SEQUENCE: 128
acattgtagc cctctgtgtg ctc                                            23

SEQ ID NO: 129         moltype = DNA  length = 23
FEATURE                Location/Qualifiers
```

-continued

```
misc_feature            1..23
                        note = Artificial Sequence
source                  1..23
                        mol_type = other DNA
                        organism = synthetic construct
SEQUENCE: 129
gagcacacag agggctacaa tgt                                            23

SEQ ID NO: 130          moltype =   length =
SEQUENCE: 130
000

SEQ ID NO: 131          moltype =   length =
SEQUENCE: 131
000

SEQ ID NO: 132          moltype = DNA  length = 22
FEATURE                 Location/Qualifiers
misc_feature            1..22
                        note = Artificial Sequence
source                  1..22
                        mol_type = other DNA
                        organism = synthetic construct
SEQUENCE: 132
acattgtagc cctctgtgtg ct                                             22

SEQ ID NO: 133          moltype = DNA  length = 22
FEATURE                 Location/Qualifiers
misc_feature            1..22
                        note = Artificial Sequence
source                  1..22
                        mol_type = other DNA
                        organism = synthetic construct
SEQUENCE: 133
agcacacaga gggctacaat gt                                             22

SEQ ID NO: 134          moltype =   length =
SEQUENCE: 134
000

SEQ ID NO: 135          moltype =   length =
SEQUENCE: 135
000

SEQ ID NO: 136          moltype = DNA  length = 32
FEATURE                 Location/Qualifiers
misc_feature            1..32
                        note = Artificial Sequence
source                  1..32
                        mol_type = other DNA
                        organism = synthetic construct
SEQUENCE: 136
acattgtagc cctctgtgtg ctccaagggg gg                                  32

SEQ ID NO: 137          moltype = DNA  length = 30
FEATURE                 Location/Qualifiers
misc_feature            1..30
                        note = Artificial Sequence
source                  1..30
                        mol_type = other DNA
                        organism = synthetic construct
SEQUENCE: 137
acattgtagc cctctgtgtg ctaagggggg                                     30

SEQ ID NO: 138          moltype = DNA  length = 27
FEATURE                 Location/Qualifiers
misc_feature            1..27
                        note = Artificial Sequence
source                  1..27
                        mol_type = other DNA
                        organism = synthetic construct
SEQUENCE: 138
aatccttatg cagaatcaga gctcaaa                                        27

SEQ ID NO: 139          moltype = DNA  length = 27
FEATURE                 Location/Qualifiers
misc_feature            1..27
                        note = Artificial Sequence
source                  1..27
```

```
                         mol_type = other DNA
                         organism = synthetic construct
SEQUENCE: 139
aatccttatg cagacagaat cagagct                                          27

SEQ ID NO: 140           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 140
agatcggcta taaaaaagat aatggaa                                          27

SEQ ID NO: 141           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 141
agatcggcta taaaaaaaga taatgga                                          27

SEQ ID NO: 142           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 142
agatcggcta taaaaaaagt aatggaa                                          27

SEQ ID NO: 143           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 143
ggaacccccc cgatttgccg acaagcc                                          27

SEQ ID NO: 144           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 144
ggaacccccc gatttgccga caagccc                                          27

SEQ ID NO: 145           moltype = DNA  length = 27
FEATURE                  Location/Qualifiers
misc_feature             1..27
                         note = Artificial Sequence
source                   1..27
                         mol_type = other DNA
                         organism = synthetic construct
SEQUENCE: 145
ggaacccccc cgatttgccg acaagcc                                          27

SEQ ID NO: 146           moltype = DNA  length = 24
FEATURE                  Location/Qualifiers
misc_feature             1..24
                         note = Artificial Sequence
source                   1..24
                         mol_type = other DNA
                         organism = synthetic construct
SEQUENCE: 146
ccgactttgt ccctctctca gccc                                             24

SEQ ID NO: 147           moltype = DNA  length = 24
FEATURE                  Location/Qualifiers
misc_feature             1..24
                         note = Artificial Sequence
```

-continued

```
source                  1..24
                        mol_type = other DNA
                        organism = synthetic construct
SEQUENCE: 147
gggctgagag agggacaaag tcgg                                  24

SEQ ID NO: 148          moltype = DNA  length = 24
FEATURE                 Location/Qualifiers
misc_feature            1..24
                        note = Artificial Sequence
source                  1..24
                        mol_type = other DNA
                        organism = synthetic construct
SEQUENCE: 148
ccgactttgt ccctctctca gccc                                  24

SEQ ID NO: 149          moltype = DNA  length = 24
FEATURE                 Location/Qualifiers
misc_feature            1..24
                        note = Artificial Sequence
source                  1..24
                        mol_type = other DNA
                        organism = synthetic construct
SEQUENCE: 149
gggctgagag agggacaaag tcgg                                  24
```

SYSTEMS, METHODS, AND COMPOSITIONS FOR CORRECTION OF FRAMESHIFT MUTATIONS

RELATED APPLICATIONS

This application is a continuation of U.S. application Ser. No. 17/067,379, filed on Oct. 9, 2020, which claims the benefit of U.S. Provisional Application No. 62/913,048 filed on Oct. 9, 2019 and U.S. Provisional Application No. 62/984,422, filed on Mar. 3, 2020, the entire disclosures of which are hereby incorporated herein by reference.

STATEMENT REGARDING FEDERALLY SPONSORED RESEARCH

The invention was made with government support under Grant No. U01CA250554 awarded by the U.S. National Institute of Health (NIT)/National Cancer Institute (NCI) Next Generation of Cancer Model (NGCM) program. The government has certain rights in the invention.

SEQUENCE LISTING

The instant application contains a Sequence Listing which has been submitted electronically in XML format and is hereby incorporated by reference in its entirety. The XML file, created on Jan. 24, 2023, is named 735898_083474-011USCON.xml and is 307,000 bytes in size.

FIELD

The subject matter disclosed herein is generally related to systems, methods, and compositions for correction frameshift mutations, accurate genome editing and treatment of diseases.

BACKGROUND

Frameshift mutations are genetic mutations that are caused by insertion or deletion (indels) of nucleotides in a coding region of a nucleic acid sequence that is not divisible by three. The indel results in mutated sequences that, due to the triplet nature of gene expression by codons, changes the reading frame of the codon and therefore change the translation of the nucleic acid sequence.

Frameshift mutations are present in number of diseases, but genetic treatments for these diseases are limited. They often involve removing large section from a genome sequence and lead to undesired side effects.

Therefore, there is need for more efficient tools to correct frameshift mutations.

SUMMARY

The present disclosure provides systems, methods, and compositions for correction frameshift mutations, accurate genome editing and treatment of diseases.

The present disclosure provides a composition, which comprises a target specific nuclease, wherein the target comprises a double stranded DNA (dsDNA), and a double strand break (DSB)-end blunting enzyme. The target specificity of the nuclease can be provided by a guide RNA (gRNA). The gRNA can be a single guide RNA (sgRNA). The sgRNA can comprise a nucleic acid sequence at least 75% identical to the nucleic acid sequence of SEQ ID NOs: 54-64. If desired, the composition can further comprise a MS2-binding protein, wherein the sgRNA can comprise one or more MS2 stem loops, and wherein the MS2-binding protein can be linked to the sgRNA by the one or more MS2 stem loops and can bind to the DSB-end blunting enzyme. If desired, the nuclease predominantly can induce staggered ends on the cleaved dsDNA. If desired, the nuclease can be an altered scissile variant. If desired, the altered scissile variant can be AF916, LZ3Cas9 (N690C, T769I, G915M, N980K), G915F, F916P, R918A, R919P or Q920P. If desired, the nuclease can be selected from the group consisting of SpCas9, LbCas12a, AsCas12a and FnCas12a.

In some embodiments, the nuclease can comprise an amino acid sequence at least 85% identical to an amino acid sequence selected from the group consisting of SEQ ID NOs: 95-106.

In some embodiments, the nuclease can comprise an amino acid sequence at least 90% identical to an amino acid sequence selected from the group consisting of SEQ ID NOs: 95-106.

In some embodiments, the nuclease can comprise an amino acid sequence at least 95% identical to an amino acid sequence selected from the group consisting of SEQ ID NOs: 95-106.

In some embodiments, the nuclease can comprise an amino acid sequence at least 99% identical to an amino acid sequence selected from the group consisting of SEQ ID NOs: 95-106.

In some embodiments, the nuclease can comprise an amino acid sequence selected from the group consisting of SEQ ID NOs: 95-106.

In some embodiments, the amino acid sequence can specifically bind to a protospacer-adjacent motif (PAM). The PAM can be selected from the group consisting of NNNN-GATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

In some embodiments, the DSB-end blunting enzyme can be a polymerase. The polymerase can be selected from the group consisting of DNA polymerase λ (POLL), DNA polymerase μ (POLM), DNA polymerase β (POLB), DNA polymerase γ (POLG), DNA polymerase ι (POLI), DNA polymerase η (POLH), TENT4A, DNA polymerase ν (POLN), DNA Ligase 4, DNTT, XRCC4, DNA Polymerase IV, fungi pol IV-like DNA polymerase, DNA polymerase/3'-5' exonuclease Pol X, and T4 DNA polymerase (T4pol).

In some embodiments, the DSB-end blunting enzyme can be a single-strand DNA specific nuclease. The single-strand DNA specific nuclease can be selected from the group consisting of MGME1, FEN1, DNA2, XRN2, EXOG, EXO5, AP endonuclease, RecJ exonuclease (RecJ), XseA, XseB, S1 nuclease (nucS), P1 nuclease, Artemis, T4 DNA polymerase (T4pol), and Csm1.

In some embodiments, the DSB-end blunting enzyme can be covalently bound to the nuclease by a linker. The linker can be a peptide.

In some embodiments, the dsDNA can be in a cell. The cell can be a eukaryotic cell.

The eukaryotic cell can be a mammalian cell. The mammalian cell can be a human cell.

In some embodiments, the composition can further comprise an inhibitor of the microhomology-mediated end joining (MMEJ) pathway. The MMEJ pathway inhibitor can be a CtIP or MRN inhibitor. The CtIP inhibitor can be selected from KLHL15 and PIN1. The MRN inhibitor can be selected from E1b55K and E40rf6.

In some embodiments, a first nucleic acid molecule encoding the nuclease is disclosed.

In some embodiments, a second nucleic acid molecule encoding the DSB-end blunting enzyme is disclosed.

In some embodiments, a third nucleic acid molecule encoding the sgRNA is disclosed.

In some embodiments, one or more vectors comprising the nucleic acid molecule are disclosed.

In some embodiments, a cell comprising the composition, the nucleic acid molecule or the one or more vectors is disclosed. If desirable, the cell can be a prokaryotic cell. If desirable, the cell can be a eukaryotic cell. If desired, the eukaryotic cell can be a mammalian cell. If desired, the mammalian cell can be a human cell.

In some embodiments, a method of inserting or deleting one or more single base pairs in a double-stranded DNA (dsDNA) is disclosed, the method comprises cleaving the dsDNA at a target site with a target specific nuclease, wherein the cleavage results in overhangs on both dsDNA ends, inserting a nucleotide complementary to the overhanging nucleotide on both of the dsDNA ends using a double strand break (DSB)-end blunting enzyme, or removing the overhanging nucleotide on both of the dsDNA ends using the DSB-end blunting enzyme, and ligating the dsDNA ends together, thereby inserting or deleting a single base pair in the dsDNA. The target specificity of the nuclease can be provided by a guide RNA (gRNA). The gRNA can be a single guide RNA (sgRNA). The sgRNA can comprise a nucleic acid sequence at least 75% identical to the nucleic acid sequence of SEQ ID NOs: 54-64. The sgRNA can comprise one or more MS2 stem loops that link a MS2-binding protein to the sgRNA, and wherein the MS2-binding protein can bind to the DSB-blunting enzyme. The DSB-end blunting enzyme can be overexpressed. The nuclease can induce staggered ends on the cleaved dsDNA. The nuclease can be an altered scissile variant. The altered scissile variant can be AF916, G915F, F916P, R918A, R919P or Q920P. The nuclease can be selected from the group consisting of SpCas9, LZ3Cas9 (N690C, T769I, G915M, N980K), LbCas12a, AsCas12a and FnCas12a.

In some embodiments, the nuclease of the method can comprise an amino acid sequence at least 85% identical to an amino acid sequence selected from the group consisting of SEQ ID NOs: 95-106.

In some embodiments, the nuclease of the method can comprise an amino acid sequence at least 90% identical to an amino acid sequence selected from the group consisting of SEQ ID NOs: 95-106.

In some embodiments, the nuclease of the method can comprise an amino acid sequence at least 95% identical to an amino acid sequence selected from the group consisting of SEQ ID NOs: 95-106.

In some embodiments, the nuclease of the method can comprise an amino acid sequence at least 99% identical to an amino acid sequence selected from the group consisting of SEQ ID NOs: 95-106.

In some embodiments, the nuclease of the method can comprise an amino acid sequence selected from the group consisting of SEQ ID NOs: 95-106.

In some embodiments, the amino acid sequence of the method can specifically bind to a protospacer-adjacent motif (PAM). The PAM can be selected from the group consisting of NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

In some embodiments, the DSB-end blunting enzyme of the method can be a polymerase. The polymerase can be selected from the group consisting of DNA polymerase λ (POLL), DNA polymerase μ (POLM), DNA polymerase 3, DNA polymerase γ (POLG), DNA polymerase ι (POLI), DNA polymerase η (POLH), TENT4A, DNA polymerase ν (POLN), DNA Ligase 4, DNTT, XRCC4, DNA Polymerase IV, fungi pol IV-like DNA polymerase, DNA polymerase/3'-5' exonuclease Pol X, and T4 DNA polymerase (T4pol).

In some embodiments, the DSB-end blunting enzyme of the method can be a single-strand DNA specific nuclease. The single-strand DNA specific nuclease can be selected from the group consisting of MGME1, FEN1, DNA2, XRN2, EXOG, EXO5, AP endonuclease, RecJ exonuclease, XseA, XseB, S1 nuclease (nucS), P1 nuclease, Artemis, T4 DNA polymerase (T4pol), and Csm1. The DSB-end blunting enzyme can be covalently bound to the nuclease by a linker. The linker can be a peptide.

In some embodiments, the dsDNA of the method can be a cell. The cell can be a eukaryotic cell. The eukaryotic cell can be a mammalian cell. The mammalian cell can be a human cell.

In some embodiments, the method can further comprise an inhibitor of the microhomology-mediated end joining (MMEJ) pathway. The MMEJ pathway inhibitor can be a CtIP or MRN inhibitor. The CtIP inhibitor can be selected from KLHL15 and PIN1. The MRN inhibitor can be selected from E1b55K and E40rf6.

In some embodiments, a method of treating a disease caused by a frameshift mutation in the dsDNA in a subject in need thereof comprising administering to the subject a therapeutically effective amount of the composition, the nucleic acid molecule, the vector or the cell is disclosed.

In some embodiments, a method of treating a disease caused by a frameshift mutation in the dsDNA in a subject in need thereof comprising inserting or deleting a single base pair in the dsDNA with the frameshift mutation according is disclosed.

In some embodiments, a method of enhancing out-frame mutation in the dsDNA in a subject in need thereof comprising administering to the subject a therapeutically effective amount of the composition, the nucleic acid molecule, the vector, or the cell is disclosed.

BRIEF DESCRIPTION OF THE DRAWINGS

Aspects, features, benefits, and advantages of the embodiments described herein will be apparent with regard to the following description, appended claims, and accompanying drawings where:

DETAILED DESCRIPTION

Figures 1, 2:
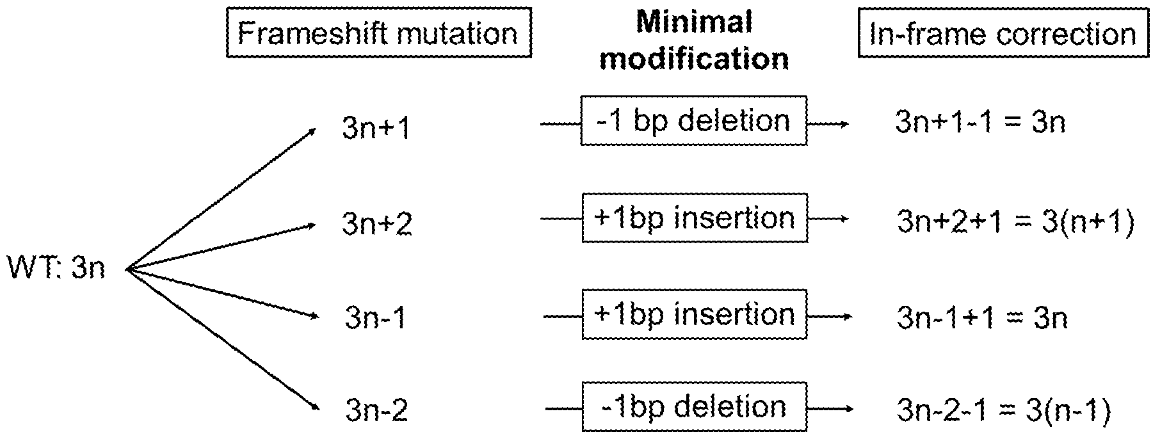
FIG. 1 is a schematic illustration of a variety of different frameshift mutations according to embodiments of the present teachings.
FIG. 2 is a schematic illustration of how frameshift mutations can be corrected according to embodiments of the present teachings.
Figure 3A:
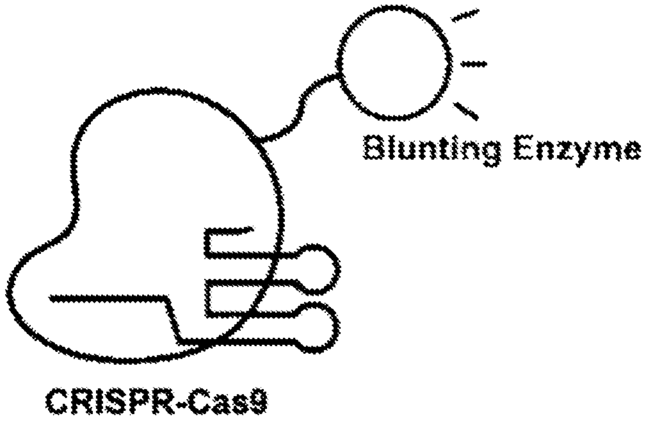
FIG. 3A is a schematic representation of a CRISPR-Cas9 and a blunting enzyme connected to the CRISPR-Cas9 by a linker, without the use of a donor template according to embodiments of the present teachings.
Figure 3B:
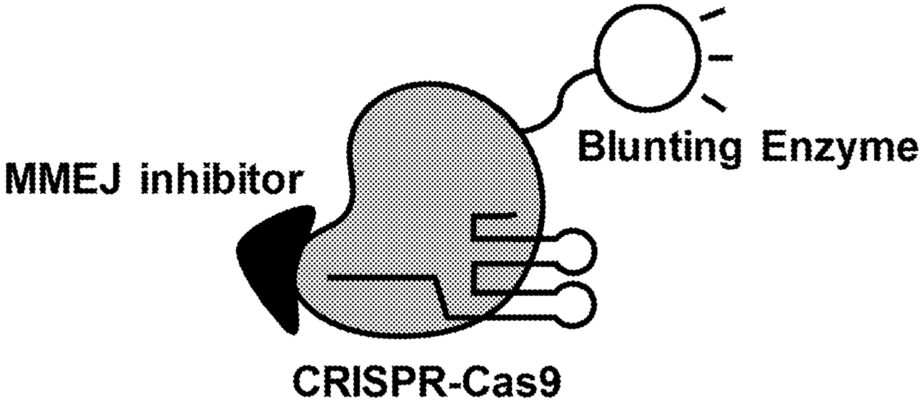
FIG. 3B is a schematic representation of a CRISPR-Cas9, a blunting enzyme and a microhomology-mediated end joining (MMEJ) inhibitor without the use of a donor template according to embodiments of the present teachings.
Figure 3C:
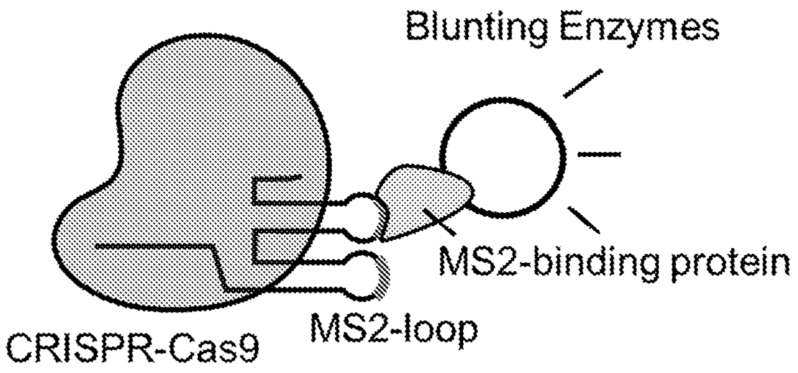
FIG. 3C is a schematic representation of a CRISPR-Cas9, a MS2-loop, MS2-binding protein, and a blunting enzyme according to embodiments of the present teachings.
Figure 3D:
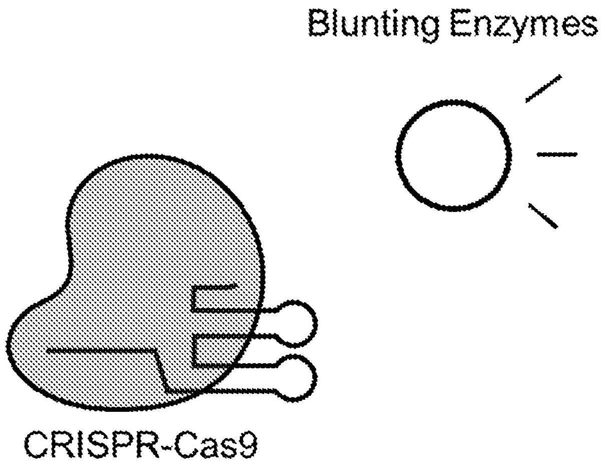
FIG. 3D is a schematic representation of a CRISPR-Cas9 and a blunting enzyme, without the use of a donor template according to embodiments of the present teachings.

It will be appreciated that for clarity, the following disclosure will describe various aspects of embodiments. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

The term "staggered end" when it refers to a double stranded DNA (dsDNA) molecule refers to the 5' and or 3' ends of that molecule having at least one nucleotide that is not hybridized to the opposite strand of the dsDNA.

The term "blunt end" when it refers to a dsDNA molecule refers to the 5' and or 3' ends of that molecule having nucleotides that hybridize to the opposite strand of the dsDNA.

The term "variant" as used herein means a polypeptide or nucleotide sequence that differs from a given polypeptide or nucleotide sequence in amino acid or nucleic acid sequence by the addition (e.g., insertion), deletion, or conservative substitution of amino acids or nucleotides, but that retains the biological activity of the given polypeptide (e.g., a variant nucleic acid could still encode the same or a similar amino acid sequence). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. The present disclosure provides amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. The present disclosure provides substitutions are performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity. Use of "variant" herein is intended to encompass fragments of a variant unless otherwise contradicted by context. The term "protospacer-adjacent motif" as used herein refers to a DNA sequence immediately following a DNA sequence targeted by a nuclease. Examples of protospacer-adjacent motif include, without limitation, NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

The term "MS2 stem loop" as used herein refers to a pattern in a single stranded nucleotide strand originated from a bacterial virus when two regions of the same strand base-pair to form a double helix that ends in an unpaired loop.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also, mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively, or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 70% sequence identity to its parent polynucleotide. The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80) available e.g. on www.ebi.ac.uk/Tools/clustalw/ or on www.ebi.ac.uk/Tools/clustalw2/index.html or on npsa-pbil-.ibcp.fr/cgi-bin/npsa_automat.pl?page=/NPSA/npsa_clustalw.html. Preferred parameters used are the default parameters as they are set on www.ebi.ac.uk/Tools/clustalw/ or www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLAS TN and BLASTP programs of Altschul et al. (1990) J. Mol. Biol. 215:403-410. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

Overview

Some embodiments disclosed herein provide non-naturally occurring or engineered systems, methods, and compositions for target specific nucleases combined with blunting enzymes to correct frameshift mutations for genome editing and treatment of diseases. Frameshift mutations are genetic mutations that are caused by insertion and deletion (indels) of nucleotides in a DNA nucleic acid sequence that is not divisible by three. Due to the triplet nature of gene expression by codons, the indel can change the reading frame of the codon and therefore change the translation of the gene. Different types of frameshift mutations and examples of in-frame corrections of them are shown in FIGS. 1 and 2.

In some embodiments, the systems disclosed herein comprise a target specific nuclease, wherein the target comprises a double-stranded DNA (dsDNA) as well as a blunting enzyme. The systems disclosed herein can also comprise targeting moiety and/or a microhomology-mediated end joining (MMEJ) inhibitor.

In some embodiments, the target specific nuclease can be a CRISPR associated protein (Cas). In some embodiments, the targeted nuclease is a Cas9 protein as illustrated in FIGS. 3A-3D. In some embodiments, the blunting enzyme is joined to the targeted nuclease by a linker. In some embodiments, the blunting enzyme is separate from the targeted nuclease. In some embodiments, the composition further comprises a MMEJ inhibitor. In some embodiments, the composition further comprises a single guide RNA (sgRNA). In some embodiments, the composition further comprises a sgRNA and a MS2-binding protein, wherein the sgRNA comprises one or more MS2 stem loops. The MS2-binding protein is linked to the sgRNA by the one or more MS2 stem loops and binds to the blunting enzyme to form a blunting enzyme fused-MS2 binding protein.

Figure 4:
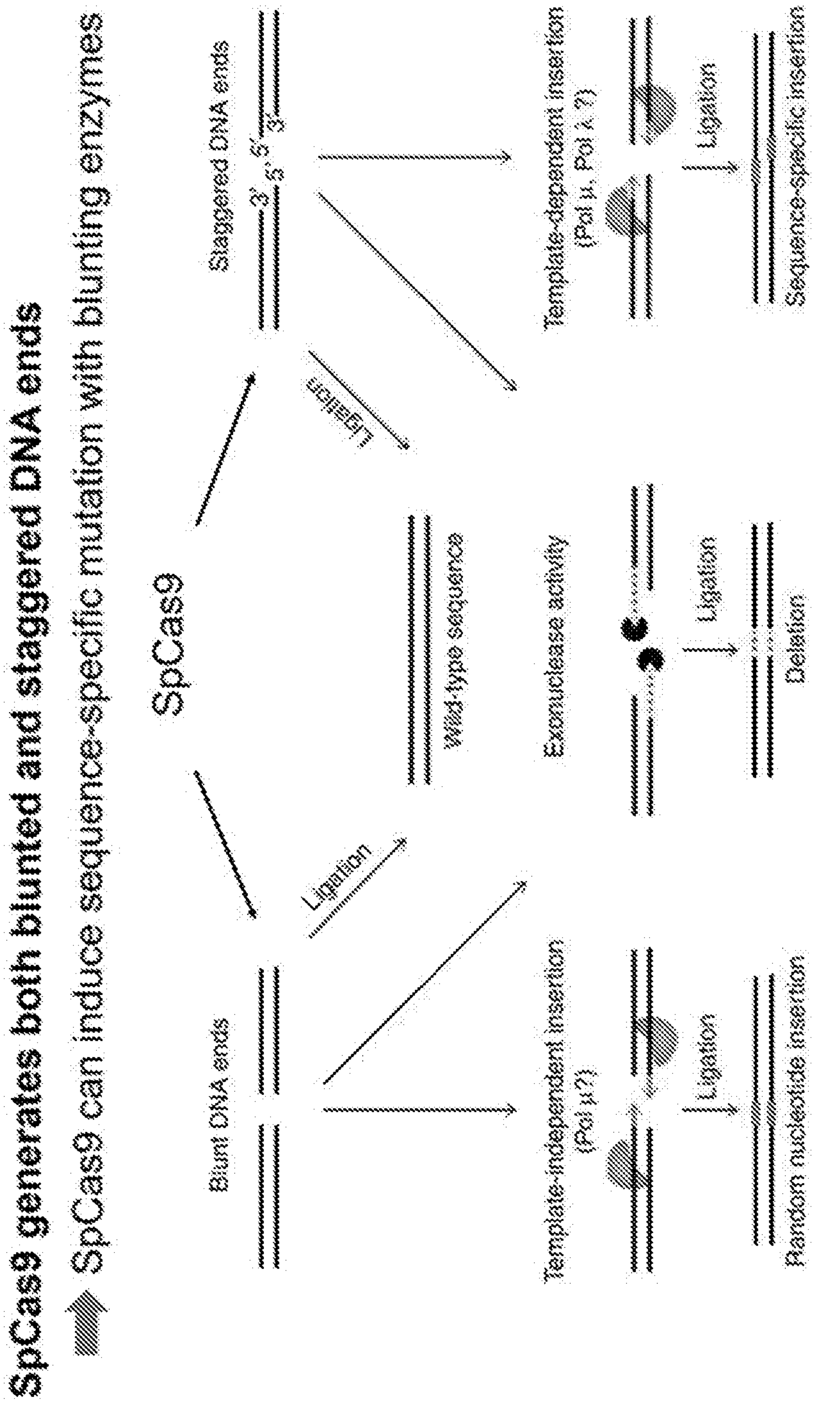
FIG. 4 is a schematic illustration of the process of using SpCas9 to generate both blunted and staggered DNA ends according to embodiments of the present teachings.
Figure 5:
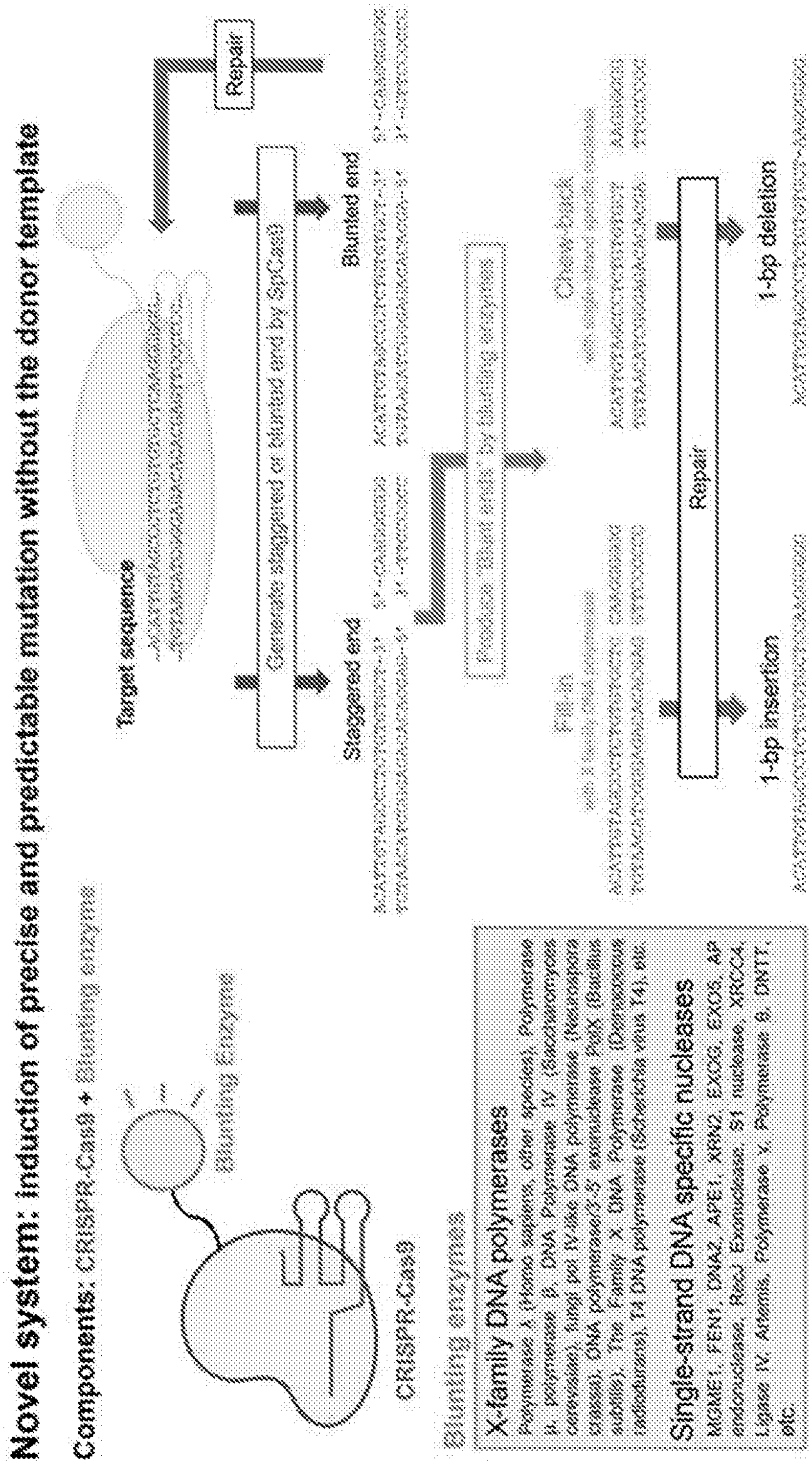
FIG. 5 is a schematic illustration of a Cas9 gene editing system resulting in an induction of a precise and predictable mutations without the use of a donor template according to embodiments of the present teachings. The Cas9 gene editing system comprises: a target sequence of the sequences of SEQ ID NO: 118 (acattgtagccctctgtgtgctcaagggggg) and SEQ ID NO: 119 (ccccccttgagcacacagagggctacaatgt); staggered end sequences of the sequences of SEQ ID NO: 120 (acattgtagccctctgtgtgct) and SEQ ID NO: 121 (gagcacacagagggctacaatgt), and SEQ ID NO: 122 (caagggggg) and SEQ ID NO: 123 (cccccctt); blunted end sequences of the sequences of SEQ ID NO: 124 (acattgtagccctctgtgtgct) and SEQ ID NO: 125 (agcacacagagggctacaatgt), and SEQ ID NO: 126 (caagggggg) and SEQ ID NO: 127 (cccccctt g); produce "blunt ends" fill-in sequences of the sequences of SEQ ID NO: 128 (acattgtagccctctgtgtgctc) and SEQ ID NO: 129 (gagcacacagagggctacaatgt), and SEQ ID NO: 130 (caagggggg) and SEQ ID NO: 131 (ccccccttg); produce "blunt ends" chew-back sequences of the sequences of SEQ ID NO: 132 (acattgtagc cctctgtgtgct) and SEQ ID NO: 133 (agcacacagagggctacaatgt), and SEQ ID NO: 134 (aaggggggg) and SEQ ID NO: 135 (cccccctt); a repair insertion sequence of the sequence of SEQ ID NO: 136 (acattgtagccctctgtgtgctccaagggggg); and a deletion sequence of the sequence of SEQ ID NO: 137 (acattgtagccctctgtgtgctaagggggg)

The target specific nuclease combined with a blunting enzyme can correct frameshift mutations in genes in cells and tissues. In some embodiments, cells include eukaryotic cells, mammalian cells, and human cells. The target specific nuclease combined with a blunting enzyme can induce one or more single-base insertions and deletions (indels). In some embodiments, the targeted nuclease creates staggered ends when it cleaves the target dsDNA. When the staggered ends are created by the target specific nuclease, a blunting enzyme can be used to ether "fill in" the staggered end with a polymerase or "chew back" the staggered end with a nuclease. Filling in followed by ligation creates a one or more bp insertion and chewing back followed by ligation creates one or more bp deletion. (See FIGS. 4-5). In some embodiments, the target specific nuclease and a blunting enzyme induce a precise and predictable mutation in a dsDNA without the use of a donor template.

Microhomology-mediated end joining (MMEJ) is one of the pathways for repairing double-strand breaks in DNA. In MMEJ, microhomologous sequences are used to align broken ends often resulting in deletions flanking the original break. In some embodiments, if a target specific nuclease were used to cleave dsDNA, MMEJ could create an unintended deletion.

Figure 6:
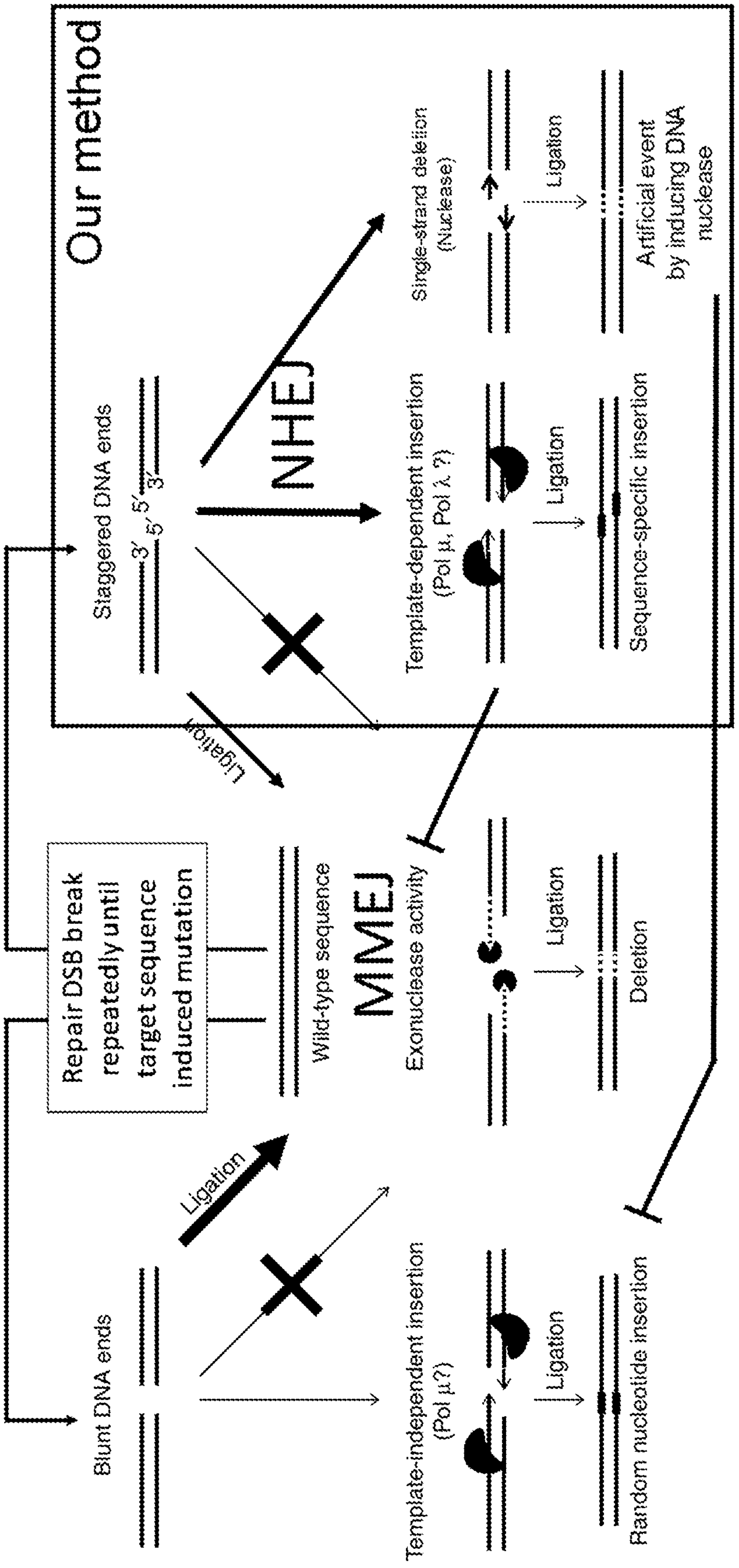
FIG. 6 is a schematic illustration of a variety of different frameshift mutations and how the composition in the instant disclosure corrects them according to embodiments of the present teachings.
Figure 7:
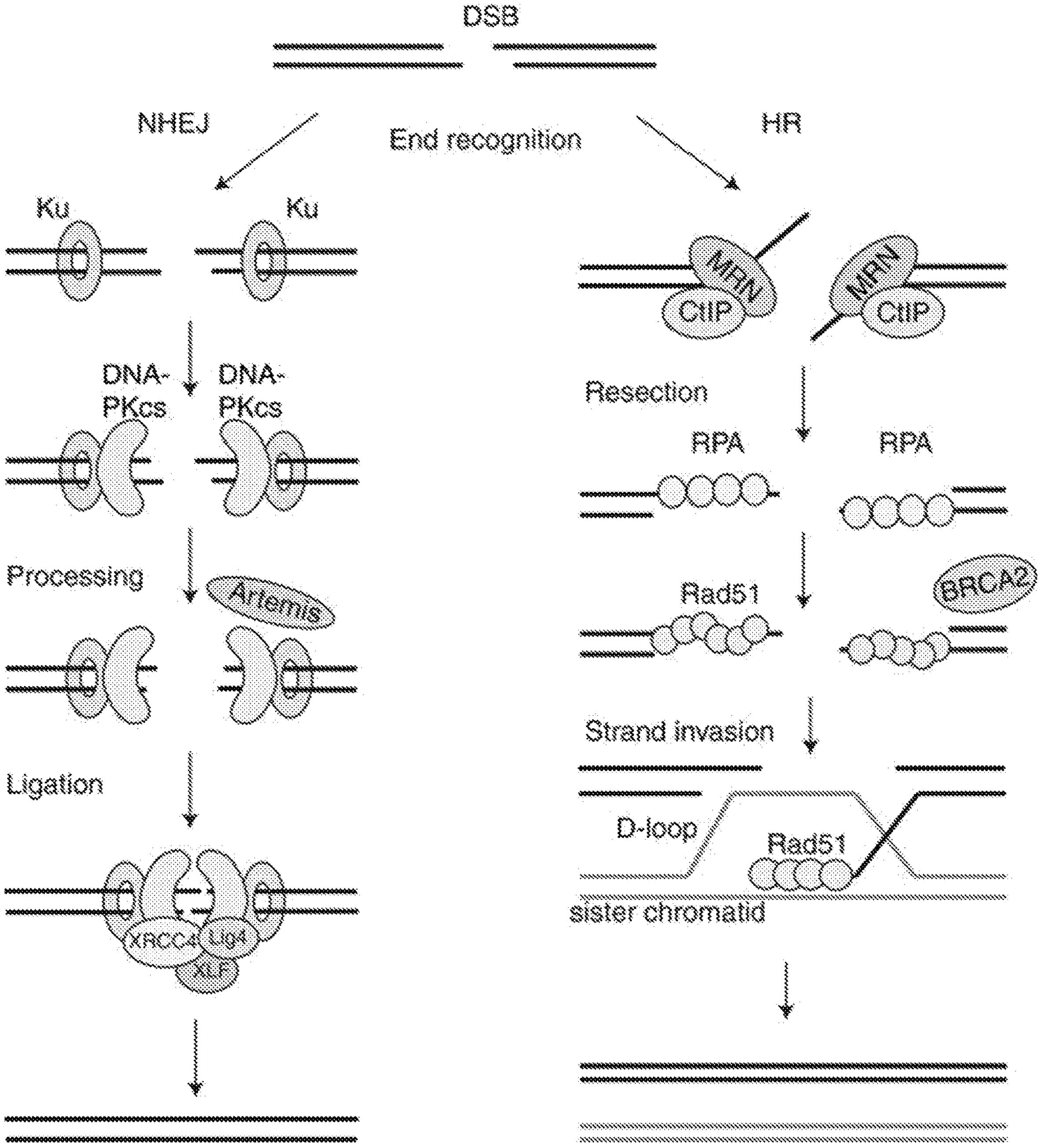
FIG. 7 is a schematic representation of two double-strand break repair pathways according to embodiments of the present teachings.

Non-homologous end joining (NHEJ) is another pathway for repairing double-strand breaks in DNA. In NHEJ, the broken ends are directly ligated together without use of a homologous template. In some embodiments, if a target specific nuclease were used to cleave dsDNA, NHEJ would directly ligate the cleaved dsDNA without deletions and therefore accurately edit the target sequence. (See FIGS. 6 and 7).

In some embodiments, an inhibitor of MMEJ is used to keep cleaved DNA from undergoing MMEJ and being subject to unintended deletion of the sequence of the dsDNA flanking the cleavage.

Target Specific Nucleases

In some embodiments, a target specific nuclease is a nuclease that cleaves a dsDNA and, at least in some cases, leaves a staggered end at the cleavage site. The target specific nuclease disclosed herein can be for example, without limitation, Cas12a, LbCas12a, FnCas12a, AsCas12a, Cas9, SpCas9, SaCas9, LZ3Cas9, Casφ, and the double combinations of Cas9 nickase, zinc finger nuclease (ZFN), and TAL Effector Nuclease (TALEN). The LZ3Cas9 disclosed here can be N690C, T7691, G915M, or N980K. In some embodiments, the target specific nuclease cleaves dsDNA in the genome of a cell providing staggered ends. In some embodiments, the target specific nuclease provides a dsDNA cleavage resulting in staggered ends more than 10% of the time. In some embodiments, the target specific nuclease provides a dsDNA cleavage resulting in staggered ends more than 20% of the time. In other embodiments, the target specific nuclease provides a dsDNA cleavage resulting in staggered ends more than 3, 40, 50, 60, 70, 80, 90, 95, or 99% of the time.

In some embodiments, the target specific nuclease is a CRISPR associated protein (Cas). In these embodiments, the Cas uses a guide RNA (gRNA) to provide specificity. In some embodiments, the gRNA is a single guide RNA (sgRNA) i.e., a fusion of two noncoding RNAs: a synthetic CRISPR RNA (crRNA) and a trans-activating CRISPR RNA (tracrRNA).

In general, a guide sequence is any polynucleotide sequence having sufficient complementarity with a target polynucleotide sequence to hybridize with the target sequence and direct sequence-specific binding of a Cas protein to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more, Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, ClustaIX, BLAT, Novoalign (Novocraft Technologies, ELAND (Illumina, San Diego, Calif), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay.

In some embodiments, the sgRNA comprises a nucleic acid sequence selected from the group consisting of SEQ ID NOs: 54-64. For example, the sgRNA can comprise a nucleic acid sequence at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleic acid sequence selected from the group consisting of SEQ ID NOs: 54-64.

In some embodiments, the target specific nuclease is Cas9. In some embodiments, the target nuclease is a scissile variant. In some embodiments, the Cas9 is a scissile variant of Cas9. In some embodiments, the scissile is for example, without limitation, AF916, LZ3Cas9, G915F, F916P, R918A, R919P, Q920P, N690C, T7691, G915M and N980K. In some embodiments, the LZ3Cas9 is N690C, T7691, G915M, or N980K.

The target specific nuclease can comprise an amino acid sequence selected from the group consisting of SEQ ID NOs: 95-106. For example, the target specific nuclease comprises an amino acid sequence at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 95-106.

In some embodiments, the target specific nuclease is a zinc finger nuclease (ZFN). A single zinc finger contains approximately 30 amino acids and the domain functions by binding 3 consecutive base pairs of DNA via interactions of a single amino acid side chain per base pair. The modular structure of the zinc finger motif permits the conjunction of several domains in series, allowing for the recognition and targeting of extended sequences in multiples of 3 nucleotides. These targeted DNA-binding domains can be combined with a nuclease domain, such as FokI, to generate a site-specific nuclease, called a “zinc finger nuclease” (ZFNs) that can be used to introduce site-specific double strand breaks at targeted genomic loci. This DNA cleavage stimulates the natural DNA-repair machinery, leading to one of two possible repair pathways, NHEJ and HDR. For example, the ZFN can target the Rosa26 locus (Perez-Pinera et al. Nucleic Acids Research (2012) 40:3741-3752) or a dystrophin gene.

In some embodiments, the target specific nuclease is a TAL effector nuclease (TALEN). The TALEN can be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage can stimulate the natural DNA-repair machinery, leading to one of two possible repair pathways: homology-directed repair (HDR) or the non-homologous end joining (NHEJ) pathway. The TALENs can be designed to target any gene involved in a genetic disease.

The TALENs can include a nuclease and a TALE DNA-binding domain that binds to the target gene in a TALEN target region. The target gene can have a mutation such as a frameshift mutation or a nonsense mutation. If the target gene has a mutation that causes a premature stop codon, the TALEN can be designed to recognize and bind a nucleotide sequence upstream or downstream from the premature stop codon. A “TALEN target region” includes the binding regions for two TALENs and the spacer region, which occurs between the binding regions. The two TALENs bind to different binding regions within the TALEN target region, after which the TALEN target region is cleaved. Examples of TALENs are described in International Patent Application No. PCT/US2013/038536, which is incorporated by reference in its entirety.

In some embodiments, the target specific nucleases include tags including for example, without limitation, 3×Flag, nuclear localization sequence (NLS), and the combination of 3×Flag and NLS.

Blunting Enzymes

In some embodiments, the blunting enzyme or double strand break-end blunting enzyme (both terms are used interchangeably herein), is an enzyme that is able either to remove or add nucleotides to a staggered end of a double stranded DNA molecule to produce a blunt end. In some embodiments, the blunting enzyme disclosed herein is a polymerase or a nuclease. In some embodiments, the DSB-blunting enzyme is a single-strand DNA specific nuclease.

In some embodiments, the blunting enzyme is a polymerase selected from polymerase κ (POLL), polymerase μ (POLM), polymerase ν (POLN), polymerase η (POLH), polymerase β (POLB), DNA polymerase θ (POLQ), DNA polymerase κ (POLK), DNA polymerase IV (*Saccharomyces cerevisiae*), DNA polymerase γ (POLG), DNA polymerase ι (POLI), DNA polymerase ξ, DNA polymerase ν (POLN), DNA nucleotidylexotransferase (DNTT), TENT4A, DNA ligase 4, fungi pol IV-like DNA polymerase (*Neurospora crassa*), DNA polymerase/3'-5' exonuclease PolX (*Bacillus subtilis*), Family X DNA Polymerase (Deinococcus radiodurans), and T4 DNA polymerase (Scherichia virus T4). In some embodiments, the blunting enzyme is a nuclease. In some embodiments, the nuclease is a single-strand DNA specific nuclease. In some embodiments, the nuclease is selected from MGME1, EXOG, APEX1, APEX2, FEN1, DNA2, APE1, XRN1, XRN2, EXOG, EXO5, AP endonuclease, RecJ Exonuclease (RecJ), XseA, XseB, S1 nuclease (nucS), P1 nuclease, XRCC4, Ligase IV, Artemis, and Csm1.

Except as specified above, the blunting enzymes can be from any organism. In some embodiments, the organism is a mammal. In other embodiments, the mammal is a human.

Figure 8:
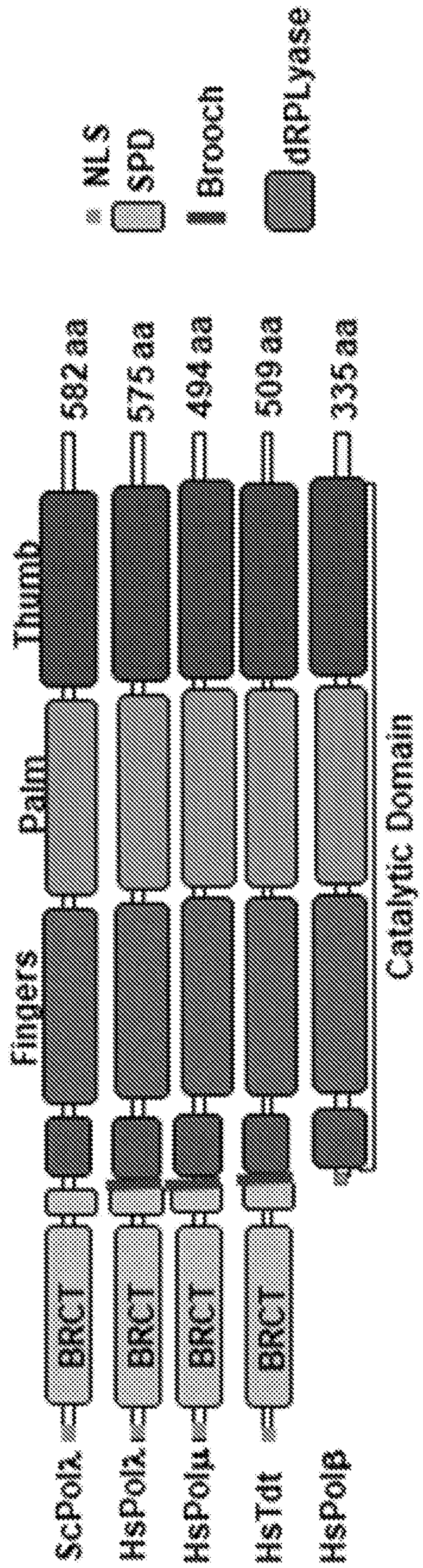
FIG. 8 is a schematic representation of the primary structures of family X polymerases according to embodiments of the present teachings.

Optimal enzymes can be selected that will enable the precision indel alleles to be stably increased in various cells and target sequences. In some embodiments, the blunting enzymes can be selected from variants such as mutants, truncations or chimeric variants of DNA polymerases and single-base specific DNA nucleases. Representative variants of DNA polymerases and single-base specific DNA nucleases, including but not limited to human POLM (H329G), human POLM (H329G, R389K), human BRCT(POLM)_POLL1, human BRCT(POLM) POLL2, T4 DNA polymerase(Y320A), T4 DNA polymerase(A737V). Other variants include the family X polymerases ScPolk, HsPolk, HsPolp, HsTdt and HsPolp, shown schematically in FIG. 8. In some embodiments, the blunting enzymes or the variants thereof can be modified with protein tags such as Myc, Flag, VStag, nuclease localization sequence. For example, the blunting enzymes or the variants thereof can include but not limited to 3×Flag-NLS-EXOG, 3×Flag-NLS-T4 DNA polymerase, 3×Flag-NLS-T4 DNA polymerase(Y320A), VStag-APEX2-NLS-NLS, 3×Flag-NLS-XseA.

In some embodiments, the blunting enzyme is covalently bound to the target specific nuclease by a linker. In some embodiments, the linker is an amino acid, a peptide, or a polypeptide.

Microhomology-Mediated End Joining (MMEJ) Inhibitor

The target specific nuclease and blunting enzyme disclosed herein can be combined with a microhomology-mediated end joining (MMEJ) inhibitor. In some embodiments, the MMEJ inhibitor is a CtIP inhibitor (e.g., KLHL15, PIN1). In some embodiments, the MMEJ inhibitor is an MRN inhibitor (e.g., E1b55K+E40rf6).

Pathogenic Frameshift Mutations

Figure 9:
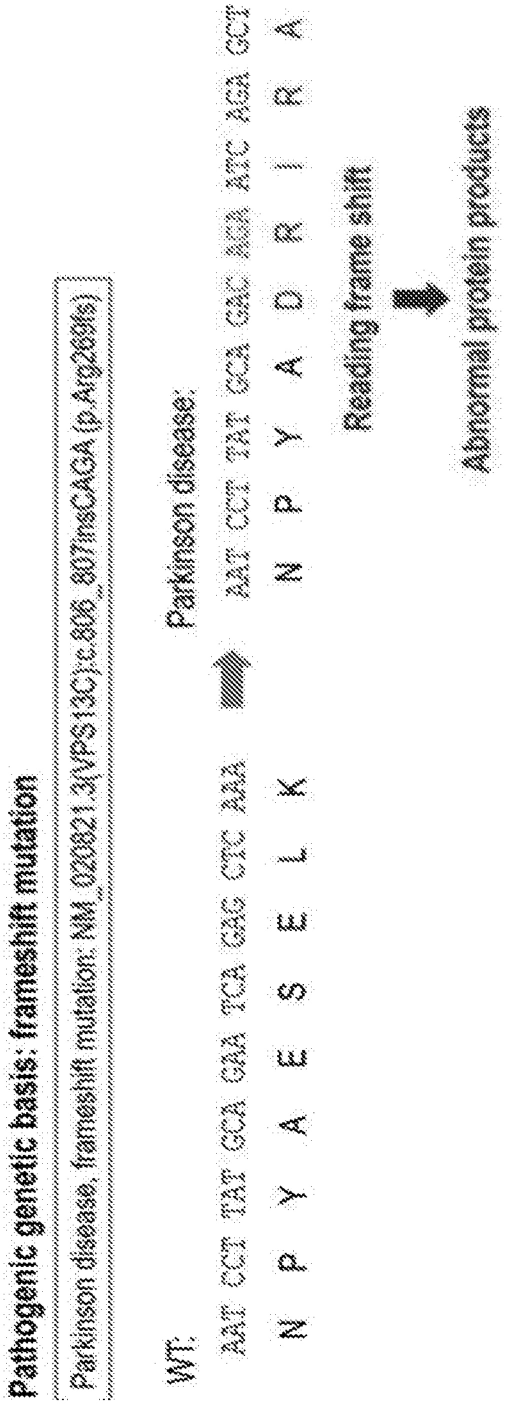
FIG. 9 is a schematic illustration of a frameshift mutation which is present in Parkinson's disease according to embodiments of the present teachings. The frameshift mutation comprises a WT sequence of the sequence of SEQ ID NO: 138 (aatccttatgcagaatcagagctcaaa) and a Parkinson disease sequence of the sequence of SEQ ID NO: 139 (aatccttatgcagacagaatcagagct)

The non-naturally occurring or engineered systems, methods, and compositions disclosed herein can be used to repair pathogenic genes in human cells and tissues, and can be used to correct the underlying genetic basis of many diseases, especially those conditions caused by a frameshift mutation. Pathogenic frameshifts can cause a wide variety of illnesses. One particular condition caused by a frameshift mutation is Parkinson's disease, caused by the frameshift mutation depicted in FIG. 9.

Figure 10:
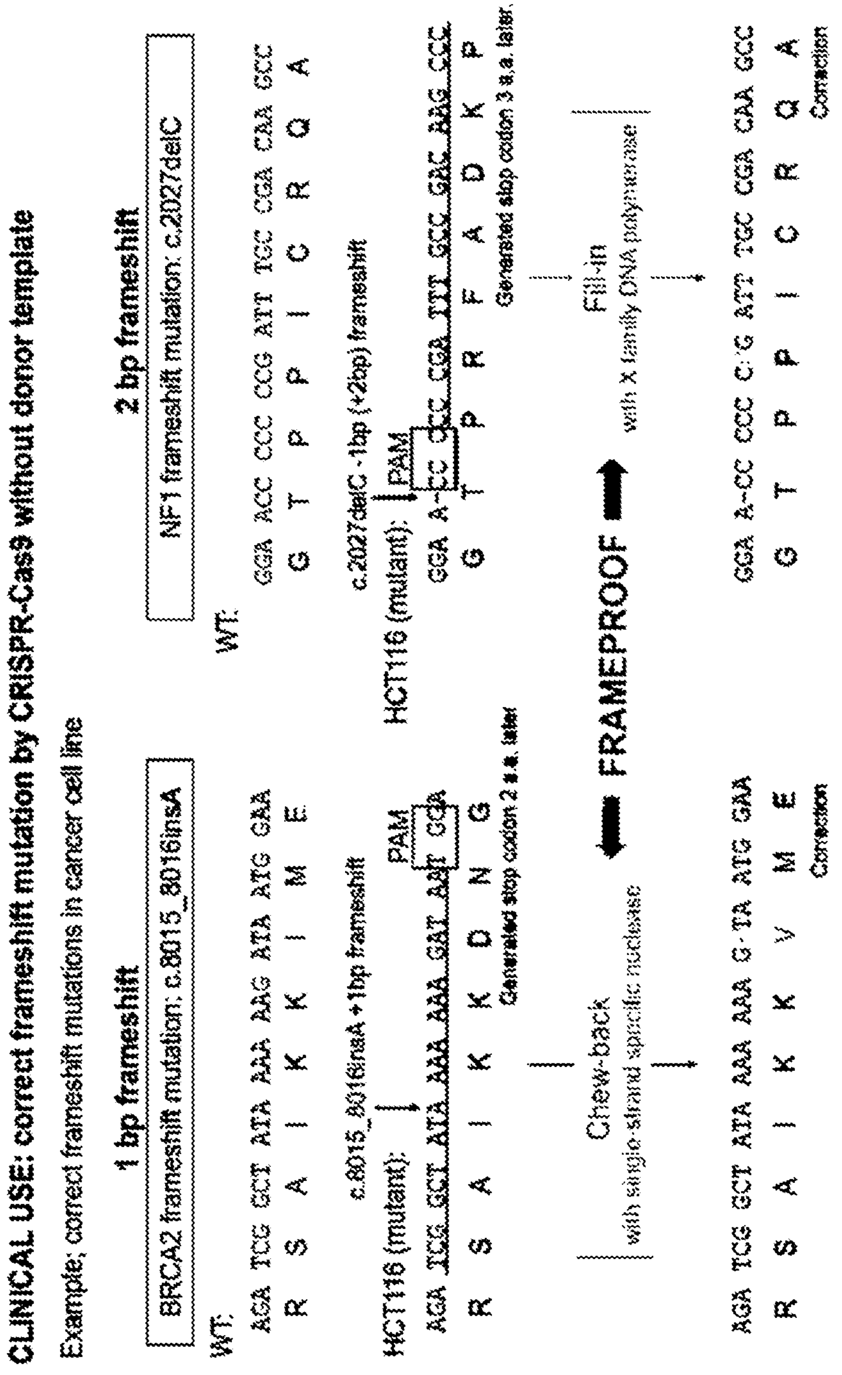
FIG. 10 is a schematic illustration of the use of the Cas9 gene editing system to correct a 1 bp BRCA2 frameshift mutation (c.8015_8016insA) and a 2 bp NF1 frameshift mutation (c.2027delC) according to embodiments of the present teachings. The 1 bp frameshift editing system comprises a WT sequence of the sequence of SEQ ID NO: 140 (agatcggctataaaaaagataatggaa), a HCT116 (mutant) sequence of the sequence of SEQ ID NO: 141 (agatcggctataaaaaaagataatgga), and a chew-back sequence of the sequence of SEQ ID NO: 142 (agatcggctataaaaaaagtaatggaa). The 2 bp frameshift editing system comprises a WT sequence of the sequence of SEQ ID NO: 143 (ggaacccccccgatttgccgacaagcc), a HCT116 (mutant) sequence of the sequence of SEQ ID NO: 144 (ggaacccccgatttgccgacaagccc), and a fill-in sequence of the sequence of SEQ ID NO: 145 (ggaacccccccgatttgccgacaagcc)
Figure 11A:
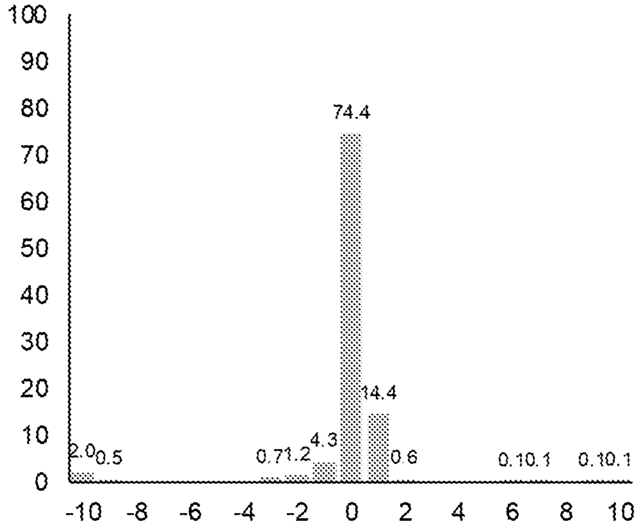
FIG. 11A is a diagram showing the probability distribution of indel mutations in PCSK9 exon 12 when induced by Cas9 only according to embodiments of the present teachings.
Figure 11B:
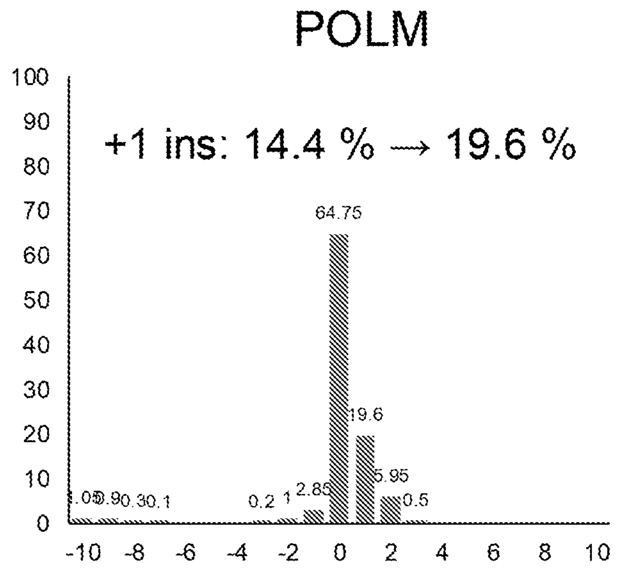
FIG. 11B is a diagram showing the probability distribution of indel mutations in PCSK9 exon 12 when induced by Cas9 and DNA polymerase μ (POLM) according to embodiments of the present teachings.
Figure 11C:
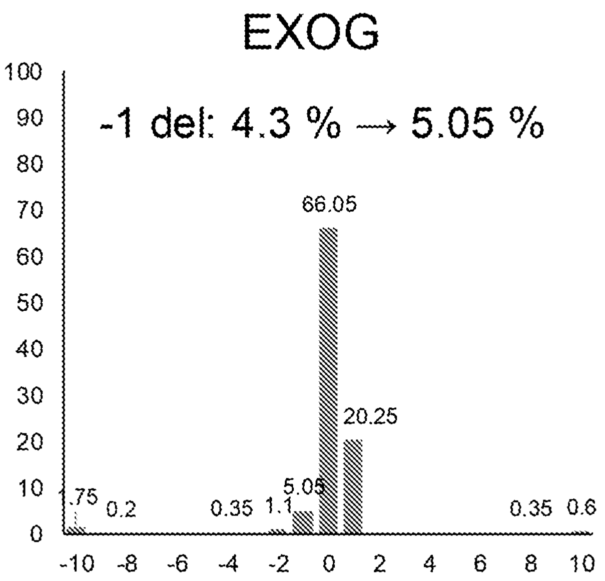
FIG. 11C is a diagram showing the probability distribution of indel mutations in PCSK9 exon 12 when induced by Cas9 and EXOG according to embodiments of the present teachings.
Figure 11D:
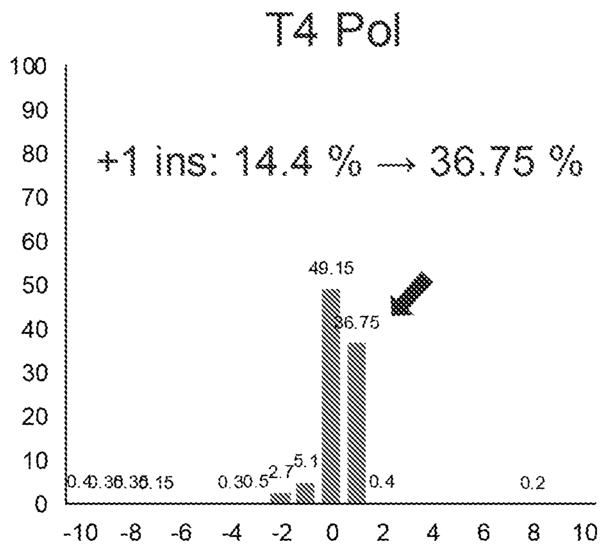
FIG. 11D is a diagram showing the probability distribution of indel mutations in PCSK9 exon 12 when induced by Cas9 and T4 DNA polymerase (T4pol) according to embodiments of the present teachings.
Figure 11E:
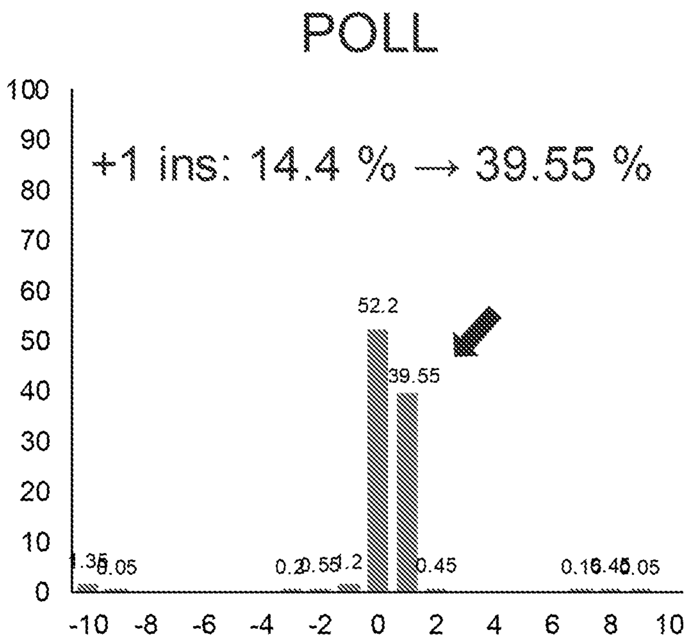
FIG. 11E is a diagram showing the probability distribution of indel mutations in PCSK9 exon 12 when induced by Cas9 and DNA polymerase κ (POLL) according to embodiments of the present teachings.
Figure 11F:
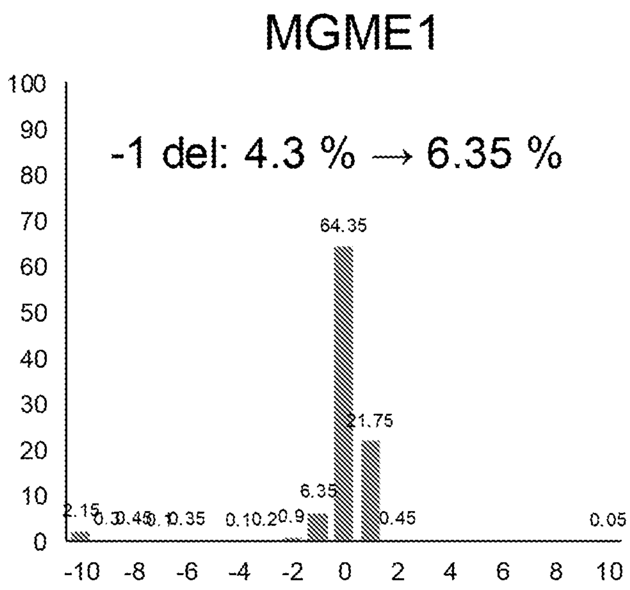
FIG. 11F is a diagram showing the probability distribution of indel mutations in PCSK9 exon 12 when induced by Cas9 and MGME1 according to embodiments of the present teachings.
Figure 11G:
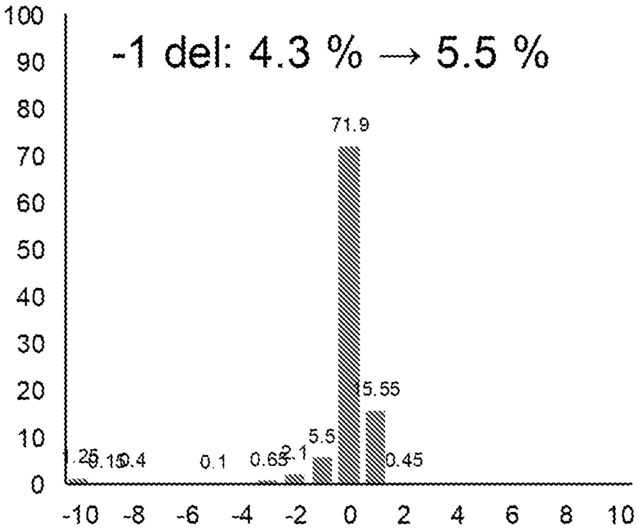
FIG. 11G is a diagram showing the probability distribution of indel mutations in PCSK9 exon 12 when induced by Cas9 and RecJ exonuclease (RecJ) according to embodiments of the present teachings.
Figure 11H:
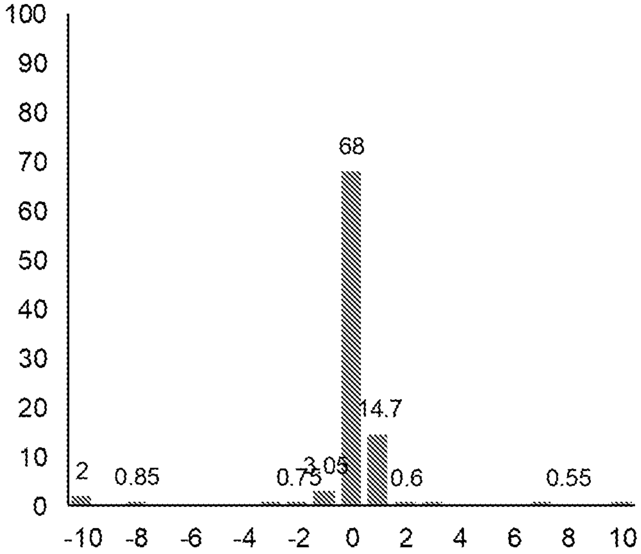
FIG. 11H is a diagram showing the probability distribution of indel mutations in PCSK9 exon 12 when induced by Cas9 and S1 Nuclease (nucS) according to embodiments of the present teachings.

FIG. 10 illustrates the editing of a gene using CRISPR-Cas9 and a blunting enzyme without the use of a donor template. The Cas9 gene editing system corrects a 1 bp BRCA2 frameshift mutation (c.8015_8016insA) and a 2 bp NF1 frameshift mutation (c.2027delC). As the schematic in FIG. 10 demonstrates, a stop codon is prematurely generated due to the frameshift mutation. By using this technique, combining Cas9 and a blunting enzyme without the use of a donor template results in repair of the frameshift mutations.

Other conditions caused by frameshift mutations include, inter alia, the following: various cancers, Parkinson's disease, muscular dystrophy, cardiomyopathy, anemia, Crohn's disease, cystic fibrosis, tuberous sclerosis, Xia-Gibbs syndrome, dermatitis, atopic, ichthyosis vulgaris, Usher syndrome, hypothyroidism, ventricular tachycardia, hemochromatosis, retinitis pigmentosa, arthrogryposis, Robinow syndrome, peroxisome biogenesis disorders, Zellweger syndrome spectrum, cortisone reductase deficiency, deficiency of pyrroline-5-carboxylate reductase, Van der Woude syndrome, Neonatal hypotonia, MYH-associated polyposis, neutropenia, methylmalonic acidemia with homocystinuria, hypobetalipoproteinemia, medium-chain acyl-coenzyme A dehydrogenase deficiency, Sezary syndrome, Stargardt disease, glycogen storage disease, maple syrup urine disease, fibrochondrogenesis, Chudley-McCullough syndrome, spastic paraplegia, frontonasal dysplasia, monocarboxylate transporter 1 deficiency, urofacial syndrome, Hajdu-Cheney syndrome, radial aplasia-thrombocytopenia syndrome, Nager syndrome, White-Sutton syndrome, ichthyosis vulgaris, FLG-Related Disorders, Grange syndrome, Charcot-Marie-Tooth disease, achromatopsia, amelogenesis imperfecta, adult junctional epidermolysis bullosa, fumarase deficiency, and Senior-Loken syndrome.

The systems, methods, and compositions described herein can also be used to enhance out-frame mutations by avoiding indel in multiples of three by a predictable mutation. Out-frame mutation occurs when the reading frame of the target dsDNA is completely disrupted. Therefore, the systems, methods, and compositions described herein can produce knockout cell lines and organisms.

Delivery

In some embodiments, the target specific nuclease and blunting enzyme are introduced into a cell as a nucleic acid encoding each protein. The nucleic acid introduced into the eukaryotic cell is a plasmid DNA or viral vector. In some embodiments, the target specific nuclease and blunting enzyme are introduced into a cell via a ribonucleoprotein (RNP).

Preferably, delivery is in the form of a vector which may be a viral vector, such as a *lenti*- or baculo- or adeno-viral/adeno-associated viral vectors, but other means of delivery are known (such as yeast systems, microvesicles, gene guns/means of attaching vectors to gold nanoparticles) and are provided. The viral vector may be selected from a variety of families/genera of viruses, including, but not limited to Myoviridae, Siphoviridae, Podoviridae, Corticoviridae, Lipothrixviridae, Poxviridae, Iridoviridae, Adenoviridae, Polyomaviridae, Papiliomaviridae, Mimiviridae, Pandoravirusa, Salterprovirusa, Inoviridae, Microviridae, Parvoviridae, Circoviridae, Hepadnaviridae, Caulimoviridae, Retroviridae, Cystoviridae, Reoviridae, Birnaviridae, Totiviridae, Parlitiviridae, Filoviridae, Orthomyxoviridae, Deltavirusa, Leviviridae, Picornaviridae, Marnaviridae, Secoviridae, Potyviridae, Caliciviridae, Hepeviridae, Astroviridae, Nodaviridae, Tetraviridae, Luteoviridae, Tombusviridae, Coronaviridae, Arteriviridae, Flaviviridae, Togaviridae, Virgaviridae, Bromoviridae, Tymoviridae, Alphaflexiviridae, Sobemovirusa, or Idaeovirusa.

A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. For example, baculoviruses may be used for expression in insect cells. These insect cells may, in turn be useful for producing large quantities of further vectors, such as AAV or lentivirus adapted for delivery of the present invention. Also envisaged is a method of delivering the target specific nuclease and blunting enzyme comprising delivering to a cell mRNAs encoding each.

In some embodiments, expression of a nucleic acid sequence encoding the target specific nuclease and/or the blunting enzyme may be driven by a promoter. In some embodiments, the target specific nuclease is a Cas. In some embodiments, a single promoter drives expression of a nucleic acid sequence encoding a Cas and one or more of the guide sequences. In some embodiments, the Cas and guide sequence(s) are operably linked to and expressed from the same promoter. In some embodiments, the CRISPR enzyme and guide sequence(s) are expressed from different promoters. For example, the promoter(s) can be, but are not limited to, a UBC promoter, a PGK promoter, an EFIA promoter, a CMV promoter, an EFS promoter, a SV40 promoter, and a TRE promoter. The promoter may be a weak or a strong promoter. The promoter may be a constitutive promoter or an inducible promoter. In some embodiments, the promoter can also be an AAV ITR, and can be advantageous for eliminating the need for an additional promoter element, which can take up space in the vector. The additional space freed up by use of an AAV ITR can be used to drive the expression of additional elements, such as guide sequences. In some embodiments, the promoter may be a tissue specific promoter.

In some embodiments, an enzyme coding sequence encoding a target specific nuclease and/or a blunting enzyme is codon-optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a Cas protein correspond to the most frequently used codon for a particular amino acid.

In some embodiments, a vector encodes a target specific nuclease and/or a blunting enzyme comprising one or more nuclear localization sequences (NLSs), such as about or more than about 1, 2, 3, 4, 5, 6, 7, 8, 9, 10, or more NLSs. In some embodiments, the Cas protein comprises about or more than 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 1, 15, 20, 25, 30, 40, 50, or more amino acids along the polypeptide chain from the N- or C-terminus. Typically, an NLS consists of one or more short sequences of positively charged lysines or arginines exposed on the protein surface, bur other types of NLS are known. In some embodiments, the NLS is between two domains, for example between the Cas13 protein and the viral protein. The NLS may also be between two functional domains separated or flanked by a glycine-serine linker.

In general, the one or more NLSs are of sufficient strength to drive accumulation of the target specific nuclease and/or the blunting enzyme in a detectable amount in the nucleus of a eukaryotic cell. In general, strength of nuclear localization activity may derive from the number of NLSs in the target specific nuclease and/or blunting enzyme, the particular NLS used, or a combination of these factors. Detection of accumulation in the nucleus may be performed by any suitable technique. For example, a detectable marker may be fused to the target specific nuclease and/or the blunting enzyme, such that location within a cell may be visualized, such as in combination with a means for detecting the location of the nucleus (e.g., a stain specific for the nucleus such as DAPI). Examples of detectable markers include fluorescent proteins (such as green fluorescent proteins, or GFP; RFP; CFP), and epitope tags (HA tag, FLAG tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some aspects, the invention provides methods comprising delivering one or more polynucleotides, such as one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a Cas protein in combination with (and optionally complexed) with a guide sequence is delivered to a cell. Conventional viral and non-viral based gene transfer methods can be used to introduce nucleic acids in mammalian cells or target tissues. Such methods can be used to administer nucleic acids encoding a target specific nuclease and/or a blunting enzyme to cells in culture, or in a host organism. Non-viral vector delivery systems include DNA plasmids, RNA (e.g., a transcript of a vector described herein), naked nucleic acid, nucleic acid complexed with a delivery vehicle, such as a liposome, and ribonucleoprotein. Viral vector delivery systems include DNA and RNA viruses, which have either episomal or integrated genomes after delivery to the cell. For a review of gene therapy procedures, see Anderson, Science 256:808-8313 (1992); Navel and Felgner, TIBTECH 11:211-217 (1993): Mitani and Caskey, TIBTECH 11:162-166 (1993); Dillon, TIBTECH 11:167-175 (1993); Miller, Nature 357:455-460 (1992); Van Brunt, Biotechnology 6(10).1149-1154 (1988); Vigne, Restorative Neurology and Neuroscience 8:35-36 (1995); Kremer and Perricaudet, British Medical Bulletin 51(1):31-44 (1995); Haddada et al., in Current Topics in Microbiology and immunology. Doerfler and Bohm (eds) (1995); and Yu et al., Gene Therapy 1:13-26 (1994).

The target specific nuclease and/or the blunting enzyme can be delivered using adeno-associated virus (AAV), lentivirus, adenovirus, or other viral vector types, or combinations thereof. In some embodiments, Cas protein(s) and one or more guide RNAs can be packaged into one or more viral vectors. In some embodiments, the targeted trans-splicing system is delivered via AAV as a split intein system, similar to Levy et al. (Nature Biomedical Engineering, 2020, DOT: doi.org/10.1038/s41551-019-0501-5) in other embodiments, the target specific nuclease and/or the blunting enzyme can be delivered via AAV as a trans-splicing system, similar to Lai et al. (Nature Biotechnology, 2005, DOI: 10.1038/nbt1153). In some embodiments, the viral vector is delivered to the tissue of interest by, for example, an intramuscular injection, while other times the viral delivery is via intravenous, transdermal, intranasal, oral, mucosal, intrathecal, intracranial or other delivery methods. Such delivery may be either via a single dose, or multiple doses. One skilled in the art understands that the actual dosage to be delivered herein may vary greatly depending upon a variety of factors, such as the vector chosen, the target cell organism, or tissue, the general condition of the subject to be treated, the degree of transformation/modification sought, the administration route, the administration mode, the type of transformation/modification sought, etc.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. Viral-mediated in vivo delivery of Cas13 and guide RNA provides a rapid and powerful technology for achieving precise mRNA perturbations within cells, especially in post-mitotic cells and tissues.

In certain embodiments, delivery of the target specific nuclease and/or the blunting enzyme to a cell is non-viral. In certain embodiments, the non-viral delivery system is selected from a ribonucleoprotein, cationic lipid vehicle, electroporation, nucleofection, calcium phosphate transfection, transfection through membrane disruption using mechanical shear forces, mechanical transfection, and nanoparticle delivery.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. Cell lines are available from a variety of sources known to those with skill in the art (see, e.g. the American Type Culture Collection (ATCC) (Manassas, VA)). In some embodiments, a cell transfected with one or more vectors described herein is used to establish a new cell line comprising one or more vector-derived sequences.

Kits

The present disclosure provides kits for carrying out a method. The present disclosure provides the invention provides kits containing any one or more of the elements disclosed in the above methods and compositions. In some embodiments, the kit comprises a vector system and instructions for using the kit. In some embodiments, the kit comprises a vector system comprising regulatory elements and polynucleotides encoding the target specific nuclease and/or the blunting enzyme. In some embodiments, the kit comprises a viral delivery system of the target specific nuclease and/or the blunting enzyme. In some embodiments, the kit comprises a non-viral delivery system of the target specific nuclease and/or the blunting enzyme. Elements may be provided individually or in combinations, and may be provided in any suitable container, such as a vial, a bottle, or a tube. In some embodiments, the kit includes instruction in one or more languages, for examples, in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element.

Sequences

Sequences of nucleases, enzymes, guides, and linkers can be found in Table 1 below.

TABLE 1

| SEQ ID NO | SEQUENCE |
|---|---|
| SEQ ID NO 1<br>POLL<br>*Homo sapiens* | atggatcccaggggtatcttgaaggcatttcccaagcggcagaaaattcatgctgatgcatcatcaaaagtacttgcaaagattcctaggagg<br>gaagagggagaagaagcagaagagtggctgagctcccttcgggcccatgttgtgcgcactggcattggacgagcccgggcagaactctt<br>tgagaagcagattgttcagcatggcggccagctatgccctgcccagggcccaggtgtcactcacattgtggtggatgaaggcatggactat<br>gagcgagccctccgccttctcagactaccccagctgcccccgggtgctcagctggtgaagtcagcctggctgagcttgtgccttcaggaga<br>ggaggctggtggatgtagctggattcagcatcttcatccccagtaggtacttggaccatccacagcccagcaaggcagagcaggatgcttc<br>tattcctcctggcacccatgaggccctgcttcagacagccctttctcctcctcctcccaccaggcctgtgtctcctccccaaaaggcaaaa<br>gaggcaccaaacacccaagcccagcccatctctgatgatgaagccagtgatggggaagaaacccaggttagtgcagctgatctggaagc<br>cctcatcagtggccactaccccacctcccttgagggagattgtgagcctagcccagcccctgctgtcctggataagtgggtctgtgcacagc<br>cctcaagccagaaggcgaccaatcacaacctccatatcacagagaagctggaagttctggccaaagcctacagtgttcagggagacaagt<br>ggagggccctgggctatgccaaggccatcaatgccctcaagagcttccataagcctgtcacctcgtaccaggaggcctgcagtatccctg<br>ggattgggaagcggatggctgagaaaatcatagagatcctggagagcgggcatttgcggaagctggaccatatcagtgagagcgtgcct<br>gtcttggagctcttctccaacatctggggagctgggaccaagactgcccagatgtggtaccaacagggcttccgaagtctggaagacatcc<br>gcagccaggcctccctgacaacccagcaggccatcggcctgaagcattacagtgacttcctggaacgtatgcccagggaggaggctaca<br>gagattgagcagacagtccagaaagcagcccaggcctttaactctgggctgctgtgtgtggcatgtggttcataccgacggggaaaggcg<br>acctgtggtgatgtcgacgtgctcatcactcacccagatggccggtcccaccggggtatcttcagccgcctccttgacagtcttcggcagga<br>agggttcctcacagatgacttggtgagccaagaggagaatggtcagcaacagaagtacttgggggtgtgccggctcccagggccagggc<br>ggcggcaccggcgcctggacatcatcgtggtgccctatagcgagtttgcctgtgccctgctctacttcaccggctctgcacacttcaaccgc<br>tccatgcgagccctggccaaaaccaagggcatgagtctgtcagaacatgccctcagcactgctgtggtccggaacacccatggctgcaag<br>gtggggcctggccgagtgctgcccactcccactgagaaggatgtcttcaggctcttaggcctcccctaccgagaacctgctgagcgggac<br>tggtga |
| SEQ ID NO 2<br>POLM<br>*Homo sapiens* | atggctctgccaaagagaagacgcgcacgggttgggtccccttcaggggacgcagcctcctctacacctccatctacgagatttccgggtgtt<br>gcaatatacctcgtcgagccccggatgggacgcagtagacgggctttccttacgggtctcgcccgaagtaaaggctttcgggtgttggacgca<br>tgttctagtgaagcgacccatgtcgttatggaggagacgagtgctgaggaggctgtaagctggcaagagcgccgaatggctgctgcaccacc<br>cggctgcactccgcctgctttgttggatatatcttggctgaccgaaagtcttggggctggacaaccagtaccggttgagtgccgacatcgattgg<br>aagtagctggtccgaggaaaggccccctctcaccggcctggatgcctgcatatgcctgccaacggcccacccctctgacgcaccacaacact<br>gggctttccgaggcattggagatattggcggaagctgcgggctttgaagggtccgaagggagattgctcacgttctgtagagcagcatccgttc<br>ttaaagcgctgccgagtcccgtaactacactgtctcaactgcagggcctgccacacttcggcgaacactcaagccgggtcgtacaagaactcc<br>tggagcacggggtctgcgaggaagttgagagggtgaggcgaagcgaacgataccaaacgatgaagctgtttacacaaatctttggagttgga<br>gtcaagacggcggacagatggtatcgagaggggcttcgaacgctcgacgatctgcgcgagcaaccgcaaaagctgacccaacagcaaaa<br>ggccggactgcagcatcaccaggacctttcaacacctgttcttcggtctgacgttgatgctctccaacaagtcgtcgaggaggcagtaggccag<br>gcccttccgggcgctactgttacgctcacgggaggatttagacgcggcaaacttcaaggtcacgatgtcgatttcttgataactcacccaaaaga<br>ggggcaggaggctggtttgctgccgcgggtaatgtgccgattgcaagaccaaggcttgatactgtaccaccaacaccaacattcatgttgcga<br>gtcacccacgcgcctcgcacagcagagccatatggacgctttcgagagatcattttgcatattcagacttcctcagcccccaggtgcggcggtc<br>ggtgggtccactaggccgtgtccatcttggaaggctgtgcgggtggatttggtcgtagcgcccgtcagccagtttccctttgcactcctggggtg<br>gaccggcagtaaactgttccaaagagagctgcgaaggttctcacgaaaagagaagggcctctggcttaactcccacggcctgttcgaccccg<br>agcaaaaaactttctttcaggctgcgagcgaagaagatatcttccgccacctgggacttgagtaccttcccccgagcagcgcaacgcctga |
| SEQ ID NO 3<br>POLM<br>(H329G)<br>*Homo sapiens* | atggctctgccaaagagaagacgcgcacgggttgggtccccttcaggggacgcagcctcctctacacctccatctacgagatttccgggtgtt<br>gcaatatacctcgtcgagccccggatgggacgcagtagacgggctttccttacgggtctcgcccgaagtaaaggctttcgggtgttggacgca<br>tgttctagtgaagcgacccatgtcgttatggaggagacgagtgctgaggaggctgtaagctggcaagagcgccgaatggctgctgcaccacc<br>cggctgcactccgcctgctttgttggatatatcttggctgaccgaaagtcttggggctggacaaccagtaccggttgagtgccgacatcgattgg<br>aagtagctggtccgaggaaaggccccctctcaccggcctggatgcctgcatatgcctgccaacggcccacccctctgacgcaccacaacact<br>gggctttccgaggcattggagatattggcggaagctgcgggctttgaagggtccgaagggagattgctcacgttctgtagagcagcatccgttc<br>ttaaagcgctgccgagtcccgtaactacactgtctcaactgcagggcctgccacacttcggcgaacactcaagccgggtcgtacaagaactcc<br>tggagcacggggtctgcgaggaagttgagagggtgaggcgaagcgaacgataccaaacgatgaagctgtttacacaaatctttggagttgga<br>gtcaagacggcggacagatggtatcgagaggggcttcgaacgctcgacgatctgcgcgagcaaccgcaaaagctgacccaacagcaaaa<br>ggccggactgcagcatcaccaggacctttcaacacctgttcttcggtctgacgttgatgctctccaacaagtcgtcgaggaggcagtaggccag<br>gcccttccgggcgctactgttacgctcacgggaggatttagacgcggcaaacttcaaggtggcgatgtcgatttcttgataactcacccaaaag |

TABLE 1-continued

| SEQ ID NO | SEQUENCE |
|---|---|
| | aggggcaggaggctggtttgctgccgcgggtaatgtgccgattgcaagaccaaggcttgatactgtaccaccaacaccaacattcatgttgcg<br>agtcacccacgcgcctcgcacagcagagccatatggacgctttcgagagatcaaaatgcatattcagacttcctcagcccccaggtgcggcg<br>gtcggtgggtccactaggccgtgtccatcttggaaggctgtgcgggtggatttggtcgtagcgcccgtcagccagtttccctttgcactcctggg<br>gtggaccggcagtaaactgttccaaagagagctgcgaaggttctcacgaaaagagaagggcctctggcttaactcccacggcctgttcgacc<br>ccgagcaaaaaactttctttcaggctgcgagcgaagaagatatcttccgccacctgggacttgagtaccttcccccgagcagcgcaacgcct<br>ga |
| SEQ ID NO 4<br>POLM<br>(H329G, R389K)<br>*Homo sapiens* | atggctctgccaaagagaagacgcgcacgggttgggtccccttcaggggacgcagcctcctctacacctccatctacgagatttccgggtgtt<br>gcaatatacctcgtcgagccccggatgggacgcagtagacgggctttccttacgggtctcgcccgaagtaaaggctttcgggtgttggacgca<br>tgttctagtgaagcgacccatgtcgttatggaggagacgagtgctgaggaggctgtaagctggcaagagcgccgaatggctgctgcaccacc<br>cggctgcactccgcctgctttgttggatatatcttggctgaccgaaagtcttggggctggacaaccagtaccggttgagtgccgacatcgattgg<br>aagtagctggtccgaggaaaggcccctctcaccggcctggatgcctgcatatgcctgccaacggcccacccctctgacgcaccacaacact<br>gggctttccgaggcattggagatattggcggaagctgcgggctttgaagggtccgaagggagattgctcacgttctgtagagcagcatccgttc<br>ttaaagcgctgccgagtcccgtaactacactgtctcaactgcagggcctgccacacttcggcgaacactcaagccgggtcgtacaagaactcc<br>tggagcacggggtctgcgaggaagttgagagggtgaggcgaagcgaacgataccaaacgatgaagctgtttacacaaatctttggagttgga<br>gtcaagacggcggacagatggtatcgagaggggcttcgaacgctcgacgatctgcgcgagcaaccgcaaaagctgacccaacagcaaaa<br>ggccggactgcagcatcaccaggacctttcaacacctgttcttcggtctgacgttgatgctctccaacaagtcgtcgaggaggcagtaggccag<br>gcccttccgggcgctactgttacgctcacgggaggatttagacgcggcaaacttcaaggtggcgatgtcgatttcttgataactcacccaaaag<br>aggggcaggaggctggtttgctgccgcgggtaatgtgccgattgcaagaccaaggcttgatactgtaccaccaacaccaacattcatgttgcg<br>agtcacccacgcgcctcgcacagcagagccatatggacgctttcgagagatcattttgcatattcagacttcctcagcccccaggtgcggcggt<br>cggtgggtccactaggccgtgtccatcttggaaggctgtgcgggtggatttggtcgtagcgcccgtcagccagtttccctttgcactcctggggt<br>ggaccggcagtaaactgttccaaagagagctgcgaaggttctcacgaaaagagaagggcctctggcttaactcccacggcctgttcgacccc<br>gagcaaaaaactttctttcaggctgcgagcgaagaagatatcttccgccacctgggacttgagtaccttcccccgagcagcgcaacgcctga |
| SEQ ID NO 5<br>BRCT<br>(POLM)<br>POLL 1<br>*Homo sapiens* | atggctctgccaaagagaagacgcgcacgggttgggtccccttcaggggacgcagcctcctctacacctccatctacgagatttccgggtgtt<br>gcaatatacctcgtcgagccccggatgggacgcagtagacgggctttccttacgggtctcgcccgaagtaaaggctttcgggtgttggacgca<br>tgttctagtgaagcgacccatgtcgttatggaggagacgagtgctgaggaggctgtaagctggcaagagcgccgaatggctgctgcaccacc<br>cggctgcactccgcctgctttgttggatatatcttggctgaccgaaagtcttggggctggacaaccaatccccagtaggtacttggaccatccac<br>agcccagcaaggcagagcaggatgcttctattcctcctggcacccatgaggccctgcttcagacagccctttctcctcctcctcctcccaccag<br>gcctgtgtctcctccccaaaaggcaaaagaggcaccaaacacccaagcccagcccatctctgatgatgaagccagtgatggggaagaaacc<br>caggttagtgcagctgatctggaagccctcatcagtggccactaccccacctcccttgagggagattgtgagcctagcccagcccctgctgtcc<br>tggataagtgggtctgtgcacagccctcaagccagaaggcgaccaatcacaacctccatatcacagagaagctggaagttctggccaaagcc<br>tacagtgttcagggagacaagtggagggccctgggctatgccaaggccatcaatgccctcaagagcttccataagcctgtcacctcgtaccag<br>gaggcctgcagtatccctgggattgggaagcggatggctgagaaaatcatagagatcctggagagcgggcatttgcggaagctggaccatat<br>cagtgagagcgtgcctgtcttggagctcttctccaacatctggggagctgggaccaagactgcccagatgtggtaccaacagggcttccgaag<br>tctggaagacatccgcagccaggcctccctgacaacccagcaggccatcggcctgaagcattacagtgacttcctggaacgtatgcccaggg<br>aggaggctacagagattgagcagacagtccagaaagcagcccaggcctttaactctgggctgctgtgtgtggcatgtggttcataccgacggg<br>gaaaggcgacctgtggtgatgtcgacgtgctcatcactcacccagatggccggtcccaccggggtatcttcagccgcctccttgacagtcttcg<br>gcaggaagggttcctcacagatgacttggtgagccaagaggagaatggtcagcaacagaagtacttgggggtgtgccggctcccagggcca<br>gggcggcggcaccggcgcctggacatcatcgtggtgccctatagcgagtttgcctgtgccctgctctacttcaccggctctgcacacttcaacc<br>gctccatgcgagccctggccaaaaccaagggcatgagtctgtcagaacatgccctcagcactgctgtggtccggaacacccatggctgcaag<br>gtggggcctggccgagtgctgcccactcccactgagaaggatgtcttcaggctcttaggcctcccctaccgagaacctgctgagcgggactg<br>gtga |
| SEQ ID NO 6<br>BRCT<br>(POLM)<br>POLL2<br>*Homo sapiens* | atggctctgccaaagagaagacgcgcacgggttgggtccccttcaggggacgcagcctcctctacacctccatctacgagatttccgggtgtt<br>gcaatatacctcgtcgagccccggatgggacgcagtagacgggctttccttacgggtctcgcccgaagtaaaggctttcgggtgttggacgca<br>tgttctagtgaagcgacccatgtcgttatggaggagacgagtgctgaggaggctgtaagctggcaagagcgccgaatggctgctgcaccacc<br>cggctgcactccgcctgctttgttggatatatcttggctgaccgaaagtcttggggctggacaaccagtaccggttgagtgccgacatcgattgg<br>aagtagctggtccgaggaaaggcccctctcatcaagccagaaggcgaccaatcacaacctccatatcacagagaagctggaagttctggcc<br>aaagcctacagtgttcagggagacaagtggagggccctgggctatgccaaggccatcaatgccctcaagagcttccataagcctgtcacctcg<br>taccaggaggcctgcagtatccctgggattgggaagcggatggctgagaaaatcatagagatcctggagagcgggcatttgcggaagctgg |

TABLE 1-continued

| SEQ ID NO | SEQUENCE |
|---|---|
| | accatatcagtgagagcgtgcctgtcttggagctcttctccaacatctggggagctgggaccaagactgcccagatgtggtaccaacagggctt<br>ccgaagtctggaagacatccgcagccaggcctccctgacaacccagcaggccatcggcctgaagcattacagtgacttcctggaacgtatgc<br>ccagggaggaggctacagagattgagcagacagtccagaaagcagcccaggcctttaactctgggctgctgtgtgtggcatgtggttcatacc<br>gacggggaaaggcgacctgtggtgatgtcgacgtgctcatcactcacccagatggccggtcccaccggggtatcttcagccgcctccttgaca<br>gtcttcggcaggaagggttcctcacagatgacttggtgagccaagaggagaatggtcagcaacagaagtacttgggggtgtgccggctccca<br>gggccagggcggcggcaccggcgcctggacatcatcgtggtgccctatagcgagtttgcctgtgccctgctctacttcaccggctctgcacac<br>ttcaaccgctccatgcgagccctggccaaaaccaagggcatgagtctgtcagaacatgccctcagcactgctgtggtccggaacacccatgg<br>ctgcaaggtggggcctggccgagtgctgcccactcccactgagaaggatgtcttcaggctcttaggcctcccctaccgagaacctgctgagcg<br>ggactggtga |
| SEQ ID NO 7<br>3xFlag-NLS-<br>EXOG<br>*Homo sapiens* | atggactataaggaccacgacggagactacaaggatcatgatattgattacaaagacgatgacgataagatggccccaaagaagaagcggaa<br>ggtcggtatccacggagtcccagcagccgctatcaagagtatcgcttcccgcctccggggttcccgtcgttttctgagcggcttcgtggctggg<br>gctgtagtgggcgctgcgggagctgggctcgcggccctgcagttcttccggagtcagggcgctgagggagcgttgacagggaagcagccg<br>gatggatctgcagaaaaggctgtcttggaacaatttggattccctttaactggaacagaggcaaggtgttacactaatcacgctttgtcttatgatc<br>aggcaaagcgggtgcctagatgggttcttgaacatatttccaaaagcaagataatgggtgatgcagacagaaagcattgtaaatttaagcctgat<br>cccaatatccctccaaccttcagtgccttcaatgaagattatgttggaagtgggtggtcacgaggacacatggctccagcaggaaataacaaatt<br>ttcaagtaaagccatggctgaaaccttttacctttctaacattgtgcctcaggattttgataataattctggatattggaacagaatagaaatgtactgt<br>cgagagctgacagaaaggtttgaagatgtttgggtggtatctgggcctttgaccttacctcagactagaggcgatggaaagaaaatagttagtta<br>ccaggtgattggcgaggacaacgtggcagtcccctcacacctttataaggtaatcctggcccgcagaagctcagtatctaccgaaccactggc<br>gctaggggcctttgtggtacccaatgaagccatcggcttccagccccagttaactgaattccaagtgagcctccaggacctagagaagttgtca<br>ggactggtgtttttcctcatttggatagaactagtgatatccggaatatctgctctgtggacacctgtaagctcctggatttccaggagttcaccttgt<br>acttgagtacaagaaagattgaaggagcccgatcagtgctcagactggaaaagatcatggaaaacttgaagaatgcagagattgaaccagatg<br>attactttatgagtcgctatgagaagaagctagaagaactcaaagctaaggagcagtcaggaacccagataagaaagccatcctag |
| SEQ ID NO 8<br>3xFlag-NLS-<br>nucS<br>Aspergillus<br>*oryzae* | atggactataaggaccacgacggagactacaaggatcatgatattgattacaaagacgatgacgataagatggccccaaagaagaagcggaa<br>ggtcggtatccacggagtcccagcagcccccaggctcctgcctatatccgccgcaaccctcgctctggcccaacttacttatggctggggcaat<br>ctgggccatgaaactgtcgcttacattgctcaatctttcgtcgcgtcaagtaccgagagcttctgccaaaacatattgggggacgactctacttcat<br>atttggccaacgtggcaacatgggcggatacttacaaatatacggatgcgggcgaatttagcaaaccctatcactttatagacgcacaggataa<br>cccaccccaatcatgcggggttgactatgacagggattgtgggtccgccgggtgctctatctcagcaattcaaaactacacgaacatactgctg<br>gaaagtcctaatgggagcgaggctctgaacgcactgaaatttgttgtccatattataggagatattcatcagccgttgcatgacgaaaatttggag<br>gcaggaggaaatggcatcgatgtgacatatgacggggagactacgaaccttcatcacatttgggatactaacatgccggaagaagccgcggg<br>agggtatagcttgtccgtggcaaagacttatgcagatttgctcaccgagaggataaaaacaggtacttactcctcaaaaaaggatagctggacc<br>gatggaattgatataaaagatccagtaagcacgtctatgatttgggcggcggatgcaaacacctacgtctgtagtacggtacttgatgacggtctt<br>gcttatattaattccactgacctctccggcgaatactacgacaagtcacaaccagtcttcgaagaacttatagccaaagcgggttatagacttgcg<br>gcttggctggaccttattgcgtcccagcccagctga |
| SEQ ID NO 9<br>3xFlag-NLS-<br>NucP1<br>*Penicillium*<br>*citrinum* | atggactataaggaccacgacggagactacaaggatcatgatattgattacaaagacgatgacgataagatggccccaaagaagaagcggaa<br>ggtcggtatccacggagtcccagcagcctggggtgccctcggccatgcgacagtagcctatgtagctcaacattatgtaagtcccgaagccgc<br>gtcttgggcgcaaggcattttgggttcctcaagttcatcatatttggcttcaatagcttcttgggccgatgaataccggctgacctccgccggcaag<br>tggagtgctagtttgcactttattgatgccgaagataatccacccacgaactgcaacgtcgactatgaacgggattgtggatcttccgggtgctcc<br>atatcagctatagctaattatacacagcgagtaagtgactcaagtctttcttccgaaaatcatgcggaagcactgcgattcttggtacacttcatcgg<br>ggacatgacacagcctttgcacgatgaagcctacgcggtgggcggtaataaaataaacgttacatttgatggttatcatgacaacctgcacagc<br>gattgggacacgtatatgccacagaaattgatcggcggtcatgcgctttcagacgcagagtcctgggcaaagacgctggttcaaaatatcgaat<br>ctggaaattacaccgcgcaggccattggttggatcaaaggcgacaacatctcagaaccaatcacaaccgcaacgcgatgggcgtcagacgc<br>caatgctcttgtatgtacggtggttatgcctcacggagctgcggcacttcagacaggtgacctttatccgacttactacgactctgtgatagatact<br>attgaacttcaaatagctaaaggaggctaccggctcgcgaactggataaacgagatatag |
| SEQ ID NO<br>10<br>3xFlag-NLS-<br>MGME1 | atggactataaggaccacgacggagactacaaggatcatgatattgattacaaagacgatgacgataagatggccccaaagaagaagcggaa<br>ggtcggtatccacggagtcccagcagccaagatgaagttatttcagaccatttgcaggcagctcaggagttcaaagttttctgtggaatcagctg<br>cccttgtggctttctctacttcctcttactcatgtggccggaagaaaaaagtgaacccatatgaagaagtggaccaagaaaaatactctaatttagtt<br>cagtctgtcttgtcatccagaggcgtcgcccagaccccgggatcggtggaggaagatgctttgctctgtggacccgtgagcaagcataagctg |

TABLE 1-continued

| SEQ ID NO | SEQUENCE |
|---|---|
| *Homo sapiens* | ccaaaccaaggtgaggacagacgagtgccacaaaactggtttcctatcttcaatccagagagaagtgataaaccaaatgcaagtgatccttcag<br>ttcctttgaaaatccccttgcaaaggaatgtgataccaagtgtgacccgagtccttcagcagaccatgacaaaacaacaggttttcttgttggaga<br>ggtggaaacagcggatgattctggaactgggagaagatggctttaaagaatacacttcaagttttcatgtttgtgatcatgtgtatatgaagaacct<br>agccagggacgtctttttacaagggaaacggttccacgaagccttggaaagcatactttcaccccaggaaaccttaaaagagagagatgaaaa<br>tctcctcaagtctggttacattgaaagtgtccagcatattctgaaagatgtcagtggagtgcgagctcttgaaagtgctgttcaacatgaaaccttaa<br>actatataggtctgctggactgtgtggctgagtatcagggcaagctctgtgtgattgattggaagacatcagagaaaccaaagccttttattcaaa<br>gtacatttgacaacccactgcaagttgtggcatacatgggtgccatgaaccatgataccaactacagctttcaggttcaatgtggcttaattgtggt<br>ggcctacaaagatggatcacctgcccacccacatttcatggatgcagagctctgttcccagtactggaccaagtggcttcttcgactagaagaat<br>atacggaaaagaaaaagaaccagaatattcagaaaccagaatattcagaatag |
| SEQ ID NO<br>11<br>3xFlag-NLS-<br>RecJ<br>*Escherichia*<br>*coli* | atggactataaggaccacgacggagactacaaggatcatgatattgattacaaagacgatgacgataagatggccccaaagaagaagcggaa<br>ggtcggtatccacggagtcccagcagccgtgaagcagcagatccaacttagacgaagggaagtcgacgaaacagcggaccttccggctga<br>gttgcctccccttcttagacgattgtatgcaagtcgcggggttcgctctgcacaggaacttgagcgctctgtcaagggaatgctgccctggcaac<br>agttgagtggtgttgaaaaggccgttgagattctctataatgcattcagggaaggaactcggatcatagtggtaggtgatttcgacgctgatgga<br>gcaacttcaaccgcgttgagcgtactcgccatgcgctctctcgggtgctcaaacattgactatttggtccccaatcgatttgaagatggttatggac<br>tcagcccggaggtggttgaccaagcgcatgcccggggcgcccagctcatcgtcactgtcgataacgggataagctctcacgccggtgtcgaa<br>cacgctcgcagcctcgggattcccgtgattgtgactgaccaccaccttccgggagatacactccccgctgctgaggcaataatcaatcctaacc<br>ttcgggattgtaactttccgagcaaatcactcgcaggggtaggggtcgcattctatctcatgctggcgctcagaacgttccttcgagatcaggggt<br>ggttcgacgagcggaacatagctatacctaatttggccgaacttttggatctcgtggcgcttggcacggttgcagacgttgtccctctggacgcg<br>aacaatcgaattttgacatggcagggaatgtctaggattagagccgggaaatgtaggcctggtattaaagctctcttggaggtggcaaaccgag<br>atgcccagaagctcgcagctagtgacttgggttttgctttgggaccccgcctgaacgctgcagggcgcctggatgacatgagcgtaggcgtag<br>cacttctcttgtgcgacaatataggtgaagcgagagtacttgcaaacgaactggatgcgcttaaccagacaagaaaggaaattgagcagggca<br>tgcagatagaggcgcttaccctgtgtgaaaagctcgaacgatctcgagacacccttccaggcggactcgcgatgtatcaccctgaatggcacc<br>agggtgtcgtaggcatcctcgcgtcccgcataaaagaaaggttccaccggccagttatagcttttgctcccgcaggtgatggaacccttaaagg<br>atctgggagatctatccaggggcttcatatgcgggatgctttggagcggcttgacactctttacccaggtatgatgctcaagttcggcggtcatgc<br>tatggctgccggcctctcactggaggaggataaatttaaactctttcaacagaggttcggggagcttgtgacggaatggctggatccgtccttgc<br>ttcaaggcgaagtagttagcgacggacctctcagtcctgcggagatgacgatggaggtagcgcaactgctcagggacgctgggccgtgggg<br>ccagatgttcccggagccgttgttcgacggccatttcaggttgcttcaacagcgcctcgtcggagaacggcatctcaaagtaatggttgagcca<br>gtcggtggcggcccccctgcttgatggcatcgctttcaatgtagacactgcactgtggcccgataatggcgttcgagaggttcagcttgcctataa<br>gctggatattaacgagtttcgagggaaccgatctctgcaaattataatagacaatatctggcccatatag |
| SEQ ID NO<br>12<br>3xFlag-NLS-<br>T4 DNA<br>polymerase<br>Bacteriophage<br>t4 | atggactataaggaccacgacggagactacaaggatcatgatattgattacaaagacgatgacgataagatggccccaaagaagaagcggaa<br>ggtcggtatccacggagtcccagcagccaaggaattctatattagtatcgagacagtgggaaacaacattgtagagcggtatatcgatgaaaac<br>ggcaaagaaaggactcgagaggtcgaataccttccgaccatgtttcgccactgtaaagaagaatctaagtacaaagatatttacgggaagaatt<br>gcgctccccaaaaatttccctccatgaaggatgctcgagactggatgaagcgcatggaggacataggtctcgaagcattggggatgaacgatt<br>ttaagttggcttacatctccgacacttacgggtcagaaatagtgtacgataggaagttcgttcgcgtggcaaattgcgatatagaggtcactggag<br>ataagttcccggacccgatgaaggcggagtacgaaattgacgctataacacactatgactcaatcgacgaccggttctatgtatttgacctgctc<br>aattccatgtacgggtctgtaagcaagtgggacgctaaactcgcggctaaacttgactgtgaaggaggggatgaagtacctcaggaaatcttgg<br>acagggtaatctacatgccctttgacaatgaacgagatatgcttatggagtacattaatttgtgggagcaaaagcgccccgcaatatttacaggct<br>ggaacatagaagggttcgatgtaccgtatattatgaatcgggtaaagatgatcctcggagagagaagcatgaaaagattttcacctattggcaga<br>gtgaaatctaagttgatacaaaacatgtatggctcaaaagagatctattcaatagatggagttagcatactcgactacctggatctgtataaaaagtt<br>tgcttttaccaacttgcctagcttctcccttgaaagtgtcgcccaacacgagaccaagaaaggtaagctgccgtacgatggcccgattaataaact<br>gcgcgagaccaaccatcaaagatatattagctacaacataattgatgtcgaatctgtgcaagccattgataagataaggggctttatcgaccttgt<br>cctgtcaatgtcctattacgccaaaatgccgttctcaggtgtaatgtcacccataaagacgtgggatgcgatcatcttcaattctctcaagggaga<br>gcacaaggtgatcccccaacaggggtcccacgtaaagcagtccttcccgggagcttttgtctttgagccaaagccgatcgcccgaaggtatat<br>catgtattcgaccttacgtcactttacccttcaattattcgacaagtgaatatatcacccgagactatccggggccagtttaaggtacacccaatcc<br>atgagtacatagccggtacagccccaaaacccagtgacgaatactcttgcagccctaatgggtggatgtacgacaaacaccaggagggcata<br>atcccaaaggaaatcgcgaaagtatttttccaacggaaagactggaagaaaaagatgttcgcggaggaaatgaacgccgaggctattaaaaa<br>aatcattatgaagggagcgggtagctgttctaccaagccagaggtagagcgctacgtcaaattcagtgatgacttccttaatgagctgagtaact<br>acacagagtctgtactgaactcactgattgaggaatgtgaaaaagccgcaacacttgctaataccaatcaactgaatcggaagatcctgattaatt<br>cactgtatggcgccttgggcaacattcatttcagatactacgacctcaggaatgccacggccattacaattttcggtcaggtcgggatccagtgg |

TABLE 1-continued

| SEQ ID NO | SEQUENCE |
|---|---|
| | atcgcccgaaaaatcaacgagtacctcaataaagtgtgtggtaccaatgacgaggattttatcgcagcaggcgataccgatagcgtgtatgtttg |
| | cgtcgacaaggtcattgaaaaggtagggctggatcggtttaaggagcagaatgatcttgtcgagtttatgaaccagtttggtaaaaaaaagatgg |
| | aaccgatgatagatgtagcgtaccgagaactttgtgactacatgaataatcgcgagcacttgatgcacatggacagggaagcgatttcatgccc |
| | cccactcggttcaaagggcgtaggggggtttctggaaagctaagaaacggtacgccctcaacgtctatgacatggaagacaagaggttcgcgg |
| | aacctcatttgaagataatggggatggagacgcaacagtcctcaactccaaaggctgtgcaagaggctctggaagaaagcatacgacgcata |
| | ctccaggagggggaagagagtgttcaggagtattataaaaactttgaaaaggagtaccgccagcttgactacaaggtaatcgcggaggttaag |
| | actgcgaatgatatcgccaaatatgatgataaaggatggcccggtttcaaatgccattccatatacgaggggtcctcacctaccgccgcgccgt |
| | gtctggtctgggggtcgcaccaattctcgacggaaataaggttatggtactcccactccgcgaggggaatccgtttggtgacaaatgcatcgcc |
| | tggccgtctggtacggagctccccaaggaaatacgcagcgacgtcctcagttggatcgaccactccacactgtttcagaagtcattcgttaaac |
| | ctctggccgggatgtgtgaatccgcgggtatggactacgaggagaaagcttcattggactttcttttcggttga |
| | |
| SEQ ID NO | atggactataaggaccacgacggagactacaaggatcatgatattgattacaaagacgatgacgataagatggccccaaagaagaagcggaa |
| 13 | ggtcggtatccacggagtcccagcagccaaggaattctatattagtatcgagacagtgggaaacaacattgtagagcggtatatcgatgaaaac |
| 3xFlag-NLS- | ggcaaagaaaggactcgagaggtcgaataccttccgaccatgtttcgccactgtaaagaagaatctaagtacaaagatatttacgggaagaatt |
| T4 DNA | gcgctccccaaaaatttccctccatgaaggatgctcgagactggatgaagcgcatggaggacataggtctcgaagcattggggatgaacgatt |
| polymerase | ttaagttggcttacatctccgacacttacgggtcagaaatagtgtacgataggaagttcgttcgcgtggcaaattgcgatatagaggtcactggag |
| (Y320A) | ataagttcccggacccgatgaaggcggagtacgaaattgacgctataacacactatgactcaatcgacgaccggttctatgtatttgacctgctc |
| Bacteriophage | aattccatgtacgggtctgtaagcaagtgggacgctaaactcgcggctaaacttgactgtgaaggaggggatgaagtacctcaggaaatcttgg |
| t4 | acagggtaatctacatgccctttgacaatgaacgagatatgcttatggagtacattaatttgtgggagcaaaagcgccccgcaatatttacaggct |
| | ggaacatagaagggttcgatgtaccgtatattatgaatcgggtaaagatgatcctcggagagagaagcatgaaaagattttcacctattggcaga |
| | gtgaaatctaagttgatacaaaacatgtatggctcaaaagagatctattcaatagatggagttagcatactcgactacctggatctgtataaaaagtt |
| | tgcttttaccaacttgcctagcttctcccttgaaagtgtcgcccaacacgagaccaagaaaggtaagctgccgtacgatggcccgattaataaact |
| | gcgcgagaccaaccatcaaagatatattagcgccaacataattgatgtcgaatctgtgcaagccattgataagataaggggctttatcgaccttgt |
| | cctgtcaatgtcctattacgccaaaatgccgttctcaggtgtaatgtcacccataaagacgtgggatgcgatcatcttcaattctctcaagggaga |
| | gcacaaggtgatcccccaacaggggtcccacgtaaagcagtccttcccgggagcttttgtctttgagccaaagccgatcgcccgaaggtatat |
| | catgtattcgaccttacgtcactttacccttcaattattcgacaagtgaatatatcacccgagactatccggggccagtttaaggtacacccaatcc |
| | atgagtacatagccggtacagccccaaaacccagtgacgaatactcttgcagccctaatgggtggatgtacgacaaacaccaggagggcata |
| | atcccaaaggaaatcgcgaaagtatttttccaacggaaagactggaagaaaaagatgttcgcggaggaaatgaacgccgaggctattaaaaa |
| | aatcattatgaagggagcgggtagctgttctaccaagccagaggtagagcgctacgtcaaattcagtgatgacttccttaatgagctgagtaact |
| | acacagagtctgtactgaactcactgattgaggaatgtgaaaaagccgcaacacttgctaataccaatcaactgaatcggaagatcctgattaatt |
| | cactgtatggcgccttgggcaacattcatttcagatactacgacctcaggaatgccacggccattacaattttcggtcaggtcgggatccagtgg |
| | atcgcccgaaaaatcaacgagtacctcaataaagtgtgtggtaccaatgacgaggattttatcgcagcaggcgataccgatagcgtgtatgtttg |
| | cgtcgacaaggtcattgaaaaggtagggctggatcggtttaaggagcagaatgatcttgtcgagtttatgaaccagtttggtaaaaaaaagatgg |
| | aaccgatgatagatgtagcgtaccgagaactttgtgactacatgaataatcgcgagcacttgatgcacatggacagggaagcgatttcatgccc |
| | cccactcggttcaaagggcgtaggggggtttctggaaagctaagaaacggtacgccctcaacgtctatgacatggaagacaagaggttcgcgg |
| | aacctcatttgaagataatggggatggagacgcaacagtcctcaactccaaaggctgtgcaagaggctctggaagaaagcatacgacgcata |
| | ctccaggagggggaagagagtgttcaggagtattataaaaactttgaaaaggagtaccgccagcttgactacaaggtaatcgcggaggttaag |
| | actgcgaatgatatcgccaaatatgatgataaaggatggcccggtttcaaatgccattccatatacgaggggtcctcacctaccgccgcgccgt |
| | gtctggtctgggggtcgcaccaattctcgacggaaataaggttatggtactcccactccgcgaggggaatccgtttggtgacaaatgcatcgcc |
| | tggccgtctggtacggagctccccaaggaaatacgcagcgacgtcctcagttggatcgaccactccacactgtttcagaagtcattcgttaaac |
| | ctctggccgggatgtgtgaatccgcgggtatggactacgaggagaaagcttcattggactttcttttcggttga |
| | |
| SEQ ID NO | atggactataaggaccacgacggagactacaaggatcatgatattgattacaaagacgatgacgataagatggccccaaagaagaagcggaa |
| 14 | ggtcggtatccacggagtcccagcagccaaggaattctatattagtatcgagacagtgggaaacaacattgtagagcggtatatcgatgaaaac |
| 3xFlag-NLS- | ggcaaagaaaggactcgagaggtcgaataccttccgaccatgtttcgccactgtaaagaagaatctaagtacaaagatatttacgggaagaatt |
| T4 DNA | gcgctccccaaaaatttccctccatgaaggatgctcgagactggatgaagcgcatggaggacataggtctcgaagcattggggatgaacgatt |
| polymerase | ttaagttggcttacatctccgacacttacgggtcagaaatagtgtacgataggaagttcgttcgcgtggcaaattgcgatatagaggtcactggag |
| (A737V) | ataagttcccggacccgatgaaggcggagtacgaaattgacgctataacacactatgactcaatcgacgaccggttctatgtatttgacctgctc |
| Bacteriophage | aattccatgtacgggtctgtaagcaagtgggacgctaaactcgcggctaaacttgactgtgaaggaggggatgaagtacctcaggaaatcttgg |
| t4 | acagggtaatctacatgccctttgacaatgaacgagatatgcttatggagtacattaatttgtgggagcaaaagcgccccgcaatatttacaggct |
| | ggaacatagaagggttcgatgtaccgtatattatgaatcgggtaaagatgatcctcggagagagaagcatgaaaagattttcacctattggcaga |

TABLE 1-continued

| SEQ ID NO | SEQUENCE |
|---|---|
| | gtgaaatctaagttgatacaaaacatgtatggctcaaaagagatctattcaatagatggagttagcatactcgactacctggatctgtataaaaagtt<br>tgcttttaccaacttgcctagcttctcccttgaaagtgtcgcccaacacgagaccaagaaaggtaagctgccgtacgatggcccgattaataaact<br>gcgcgagaccaaccatcaaagatatattagctacaacataattgatgtcgaatctgtgcaagccattgataagataaggggctttatcgaccttgt<br>cctgtcaatgtcctattacgccaaaatgccgttctcaggtgtaatgtcacccataaagacgtgggatgcgatcatcttcaattctctcaagggaga<br>gcacaaggtgatcccccaacaggggtcccacgtaaagcagtccttcccgggagcttttgtctttgagccaaagccgatcgcccgaaggtatat<br>catgtctttcgaccttacgtcactttacccttcaattattcgacaagtgaatatatcacccgagactatccggggccagtttaaggtacacccaatcc<br>atgagtacatagccggtacagccccaaaacccagtgacgaatactcttgcagccctaatgggtggatgtacgacaaacaccaggagggcata<br>atcccaaaggaaatcgcgaaagtatttttccaacggaaagactggaagaaaaagatgttcgcggaggaaatgaacgccgaggctattaaaaa<br>aatcattatgaagggagcgggtagctgttctaccaagccagaggtagagcgctacgtcaaattcagtgatgacttccttaatgagctgagtaact<br>acacagagtctgtactgaactcactgattgaggaatgtgaaaaagccgcaacacttgctaataccaatcaactgaatcggaagatcctgattaatt<br>cactgtatggcgccttgggcaacattcatttcagatactacgacctcaggaatgccacggccattacaattttcggtcaggtcgggatccagtgg<br>atcgcccgaaaaatcaacgagtacctcaataaagtgtgtggtaccaatgacgaggattttatcgcagcaggcgataccgatagcgtgtatgtttg<br>cgtcgacaaggtcattgaaaaggtagggctggatcggtttaaggagcagaatgatcttgtcgagtttatgaaccagtttggtaaaaaaaagatgg<br>aaccgatgatagatgtagcgtaccgagaactttgtgactacatgaataatcgcgagcacttgatgcacatggacagggaagcgatttcatgccc<br>cccactcggttcaaagggcgtaggggggtttctggaaagctaagaaacggtacgccctcaacgtctatgacatggaagacaagaggttcgcgg<br>aacctcatttgaagataatggggatggagacgcaacagtcctcaactccaaaggtggtgcaagaggctctggaagaaagcatacgacgcata<br>ctccaggagggggaagagagtgttcaggagtattataaaaactttgaaaaggagtaccgccagcttgactacaaggtaatcgcggaggttaag<br>actgcgaatgatatcgccaaatatgatgataaaggatggcccggtttcaaatgccctttccatatacgaggggtcctcacctaccgccgcgccgt<br>gtctggtctgggggtcgcaccaattctcgacggaaataaggttatggtactcccactccgcgaggggaatccgtttggtgacaaatgcatcgcc<br>tggccgtctggtacggagctccccaaggaaatacgcagcgacgtcctcagttggatcgaccactccacactgtttcagaagtcattcgttaaac<br>ctctggccgggatgtgtgaatccgcgggtatggactacgaggagaaagcttcattggactttcttttcggttga |
| SEQ ID NO<br>15<br>APEX1<br>*Homo sapiens* | atggctccgaagcgtgggaaaaagggagcggtggcggaagacggggatgagctcaggacagagccagaggccaagaagagtaagacg<br>gccgcaaagaaaaatgacaaagaggcagcaggagagggcccagccctgtatgaggacccccagatcagaaaacctcacccagtggcaa<br>acctgccacactcaagatctgctcttggaatgtggatgggcttcgagcctggattaagaagaaaggattagattgggtaaaggaagaagcccc<br>agatatactgtgccttcaagagaccaaatgttcagagaacaaactaccagctgaacttcaggagctgcctggactctctcatcaatactggtcag<br>ctccttcggacaaggaagggtacagtggcgtgggcctgctttcccgccagtgcccactcaaagtttcttacggcataggcgatgaggagcatg<br>atcaggaaggccgggtgattgtggctgaatttgactcgtttgtgctggtaacagcatatgtacctaatgcaggccgaggtctggtacgactggag<br>taccggcagcgctgggatgaagcctttcgcaagttcctgaagggcctggcttcccgaaagccccttgtgctgtgtggagacctcaatgtggcac<br>atgaagaaattgaccttcgcaaccccaaggggaacaaaaagaatgctggcttcacgccacaagagcgccaaggcttcggggaattactgcag<br>gctgtgccactggctgacagctttaggcacctctaccccaacacaccctatgcctacaccttttggacttatatgatgaatgctcgatccaagaatg<br>ttggttggcgccttgattactttttgttgtcccactctctgttacctgcattgtgtgacagcaagatccgttccaaggccctcggcagtgatcactgtc<br>ctatcaccctatacctagcactgtga |
| SEQ ID NO<br>16<br>VStag-<br>APEX2-NLS-<br>NLS<br>*Homo sapiens* | atggtgcggggttctggcaagcccatccccaacccccctgctgggcctggacagcaccggaaagtcttacccaactgtgagtgctgattaccag<br>gacgccgttgagaaggcgaagaagaagctcagaggcttcatcgctgagaagagatgcgctcctctaatgctccgtttggcattccactctgctg<br>gaacctttgacaagggcacgaagaccggtggacccttcggaaccatcaagcaccctgccgaactggctcacagcgctaacaacggtcttgac<br>atcgctgttaggcttttggagccactcaaggcggagttccctattttgagctacgccgatttctaccagttggctggcgttgttgccgttgaggtcac<br>gggtggacctaaggttccattccaccctggaagagaggacaagcctgagccaccaccagagggtcgcttgcctgatcccactaagggttctg<br>accatttgagagatgtgtttggcaaagctatggggcttactgaccaagatatcgttgctctatctgggggtcacactattggagctgcacacaagg<br>agcgttctggatttgagggtccctggacctctaatcctcttattttcgacaactcatacttcacggagttgttgagtggtgagaaggaaggtctcctt<br>cagctaccttctgacaaggctcttttgtctgaccctgtattccgccctctcgttgataaatatgcagcggacgaagatgccttctttgctgattacgct<br>gaggctcaccaaaagctttccgagcttgggtttgctgatgccgaattcagcagggccgaccccaagaagaagaggaaggtggaccccaaga<br>agaagaggaaggtggaccccaagaagaagaggaaggtgtga |
| SEQ ID NO<br>17<br>XRCC4<br>*Homo sapiens* | atggagagaaaaataagcagaatccaccttgtttctgaacccagtataactcattttctacaagtatcttgggagaaaacactggaatctggttttgt<br>tattacacttactgatggtcattcagcatggactgggacagtttctgaatcagagatttcccaagaagctgatgacatggcaatggaaaaaggga<br>aatatgttggtgaactgagaaaagcattgttgtcaggagcaggaccagctgatgtatacacgtttaatttttctaaagagtcttgttatttcttctttga<br>gaaaaacctgaaagatgtctcattcagacttggttccttcaacctagagaaagttgaaaacccagctgaagtcattagagaacttatttgttattgct<br>tggacaccattgcagaaaatcaagccaaaaatgagcacctgcagaaagaaaatgaaaggcttctgagagattggaatgatgttcaaggacgat<br>ttgaaaaatgtgtgagtgctaaggaagctttggagactgatctttataagcggtttattctggtgttgaatgagaagaaaacaaaaatcagaagttt |

TABLE 1-continued

| SEQ ID NO | SEQUENCE |
|---|---|
| | gcataataaattattaaatgcagctcaagaacgagaaaaggacatcaaacaagaaggggaaactgcaatctgttctgaaatgactgctgaccga |
| | gatccagtctatgatgagagtactgatgaggaaagtgaaaaccaaactgatctctctgggttggcttcagctgctgtaagtaaagatgattccatt |
| | atttcaagtcttgatgtcactgatattgcaccaagtagaaaaaggagacagcgaatgcaaagaaatcttgggacagaacctaaaatggctcctca |
| | ggagaatcagcttcaagaaaaggaaaagcctgattcttcactacctgagacgtctaaaaaggagcacatctcagctgaaaacatgtctttagaa |
| | actctgagaaacagcagcccagaagacctctttgatgagatttaa |
| SEQ ID NO | atggacgcacaaacacgacgacgtgagcgtcgcgctgagaaacaagctcaatggaaagctgcaaacggtggatctcctccacatatggctta |
| 18 | cccatacgatgttccagattacgctcctccatctcgagctcaagcttcgaattctgcagtcgacggtaccgcgggcatgggagtccccaagtttta |
| V5tag-XRN1 | cagatggatctcagagcggtatccctgtctcagcgaagtggtgaaagagcatcagattcctgaatttgacaacttgtacctggatatgaatggaat |
| *Homo sapiens* | tatacatcagtgctcccatcctaatgatgatgatgttcactttagaatttcagatgataaaatctttactgatatttttcactacctggaggtgttgtttcg |
| | cattattaaacccaggaaagtgttctttatggctgtagatggtgtggctcctcgagcaaaaatgaaccagcagcgtgggaggcgttttaggtcag |
| | caaaggaggcagaagacaaaattaaaaaggcaatagagaagggagaaactcttcctacagaggccagatttgattccaactgtatcacacca |
| | ggaactgaatttatggccaggttacatgaacatctgaagtattttgtaaatatgaaaatttccacagacaagtcatggcaaggagttaccatctactt |
| | ctcaggccatgagactcctggagaaggagagcataaaatcatggaatttatcagatccgagaaagcaaagccagatcatgatccaaacacca |
| | gacactgtctttatggtttagatgctgacttgattatgcttggattaacaagtcatgaggcacatttttctctcttaagagaagaagttcgatttggtgg |
| | caaaaaaacacaacgggtatgtgctccagaagaaactacatttcaccttctacacttgtctttaatgagagagtatattgactatgagttttcagtatt |
| | aaaagaaaagatcacatttaaatatgatattgaaaggataatagatgattggattttgatggggtttcttgttggtaatgattttatccctcatctacctc |
| | atttacatattaatcatgatgcactgcctcttctttatggaacatatgttaccatcctgccagaacttggggttatattaatgaaagtgggcacctcaa |
| | cttacctcgatttgagaaataccttgtgaaactatcagattttgatcgggagcacttcagtgaagtttttgtggacctaaaatggtttgaaagcaaagt |
| | tggtaacaagtacctcaatgaagcagcaggtgtcgcagcagaagaagccaggaactacaaggaaaagaaaaagttaaagggccaggaaaa |
| | ttctctgtgttggactgctttagacaaaaatgaaggcgaaatgataacttctaaggataatttagaagatgagactgaagatgatgacctatttgaaa |
| | ctgagtttagacaatataaaagaacatattacatgacgaagatgggggttgacgtagtatctgatgactttctggctgatcaagctgcatgttatgtt |
| | caggcaatacagtggattttgcactattactatcatggagttcagtcctggagctggtattatccttatcattatgcgcctttcctgtctgatatacaca |
| | acatcagtacactcaaaatccatttgaactaggaaaaccttttaagccatttgaacagcttcttgctgtacttccagcagccagcaaaaatttacttc |
| | ctgcatgctaccagcatttgatgaccaatgaagactcaccaattatagaatattacccacctgattttaaaactgacctaaatgggaaacaacagg |
| | aatgggaagctgtggtgttaatcccattattgatgagaagcgattattggaagccatggagacatgtaaccactccctcaaaaaggaagagagg |
| | aaaagaaaccaacatagtgagtgcctaatgtgctggtatgatagagacacagagtttatctatccttctccatggccagaaaagttccctgccata |
| | gaacgatgttgtacaaggtataaaataatatccttagatgcttggcgtgtagacataaacaaaaacaaaataaccagaattgaccagaaagcatt |
| | atatttctgtggatttcctactctgaaacacatcagacacaaatttttttgaagaaaagtggtgttcaagtattccagcaaagcagtcgtggagaaa |
| | acatgatgttggaaatcttagtggatgcagaatcagatgaacttaccgtagaaaatgtagcttcatcagtgcttggaaaatctgtctttgttaattggc |
| | ctcaccttgaggaagctagagtcgtggctgtatcagatggagaaactaagttttacttggaagaacctccaggaacacagaagctttattcagga |
| | agaactgccccaccatctaaagtggttcatcttggagataaagaacaatctaactgggcaaaagaagtacaaggaatttcagaacactacctga |
| | gaagaaaaggaataataataaatgaaacatctgcagttgtgtatgctcagttactcacaggtcgtaaatatcaaataaatcaaaatggtgaagttc |
| | gtctagagaaacagtggtcaaaacaagttgttccttttgtttatcaaactattgtcaaggacatccgagctttcgactcccgtttctccaatatcaaaa |
| | cattggatgatttgtttcctctgagaagtatggtctttatgctgggaactccctattatggctgcactggagaagttcaggattcaggtgatgtgatta |
| | cagaaggtaggattcgtgtgattttcagcattccatgtgaacccaatcttgatgctttaatacagaaccagcataaatattctataaagtacaaccca |
| | ggatatgtgttggccagtcgccttggagtgagtggataccttgtttcaaggtttacaggaagtattttttattggaagaggatctaggagaaaccctc |
| | atggagaccataaagcaaatgtgggtttaaatctcaaattcaacaagaaaaatgaggaggtacctggatatactaagaaagttggaagtgaatg |
| | gatgtattcatctgcagcagaacaacttctggcagagtacttagagagagctccagaactatttagttatatagccaaaaatagccaagaggatgt |
| | gttctatgaagatgacatttggcctggagaaaatgagaatggtgctgaaaaagttcaagaaattattacttggctaaaaggacatcctgtcagtact |
| | ttatctcgttcttcttgtgatttacaaattctggatgcagctattgttgagaaaattgaggaagaagtcgaaaagtgcaagcaaagaaagaataataa |
| | gaaggtgcgagtaacagtgaaaccccatttgctatacagacctttagaacagcaacatggagtcattcctgatcgggatgcagaattttgtcttttt |
| | gaccgtgttgtaaatgtgagagaaaacttctcagttccagttggccttcgaggcaccatcataggaataaaaggagctaatagagaagccgatg |
| | tactatttgaagtattatttgatgaagaatttcctggagggttaacaataagatgctcacctggtagaggttatcgactgccaacaagtgccttggtg |
| | aacctttctcatgggagtcgctctgaaactggaaatcagaagttgacagccatcgtaaaaccacaaccagctgtacatcaacatagctcaagttc |
| | atcagtttcctctgggcatttgggagccctcaaccattcccctcaatcactttttgttcctactcaagtacctactaaagatgatgatgaattctgcaac |
| | atttggcagtccttacagggatctggaaagatgcaatactttcagccaactatacaagagaagggtgcagttctacctcaagaaataagccaagt |
| | aaatcaacatcataaatctggctttaatgacaacagtgttaaatatcagcaaagaaaacatgaccctcacagaaaatttaaagaagagtgtaaga |
| | gtcctaaagctgagtgttggtcccaaaaaatgtccaataagcagcctaactctggaattgagaactttttagcatctttgaatatctccaaagaaaat |
| | gaagtacagtcatctcatcatggggagcctccaagtgaagagcatttgtcaccacagtcatttgccatgggaacacggatgcttaaagaaattct |
| | aaaaattgatggctctaacactgtggaccataagaatgaaatcaaacagattgctaatgaaatccctgtttcctctaacagaagagatgaatatgg |

TABLE 1-continued

| SEQ ID NO | SEQUENCE |
|---|---|
| | attaccctctcagcctaaacaaaataagaaattagcatcttatatgaacaagcctcacagtgctaatgagtaccataatgttcagtctatggacaata<br>tgtgttggcctgcccccagccagatccctcctgtatccacaccagtaactgaactttctcgaatttgttcccttgttggaatgccacaacctgatttct<br>cctttcttaggatgccacagacaatgaccgtttgccaagtaaaattatctaatggcttactggtacatgggccacagtgccactctgaaaatgaag<br>ccaaagagaaagctgcacttttttgctttacaacagttgggctccttaggcatgaatttccctttgccttcacaagtatttgcaaattatccttcagctgt<br>accacctggaaccattcctccagcctttcccccacctactggctgggatcactatggaagcaactatgcattgggggcagctaatataatgccttc<br>gtcgtctcatctctttggctcaatgccatggggaccatcggtgccagttcctgggaagcccttccatcatactttatattctgggaccatgcccatg<br>gctgggggaataccagggggtgtgcacaatcagtttatacctctgcaggttactaaaaaaagggttgcaaacaaaaagaactttgagaataagg<br>aagcccagagttctcaagccactccagttcagactagccagccagattcttccaacattgtcaaagtaagtccacgggagagctcatcagcttct<br>ttgaagtcctctccgattgctcaacctgcatcttcattcaagttgaaactgcctctcaaggccatagtatatctcaccataagtcaacaccaatctctt<br>cttcaagaagaaaatcaagaaaactggctgttaattttggtgtttctaaaccttctgagtaa |
| SEQ ID NO<br>19<br>DNA2<br>*Homo sapiens* | atggagcagctgaacgaactggagctgctgatggagaagagttttgggaggaggcggagctgccggcggagctatttcagaagaaagtgg<br>tagcttcctttccaagaacagttctgagcacaggaatggataaccggtacctggtgttggcagtcaatactgtacagaacaaagagggaaactgt<br>gaaaagcgcctggtcatcactgcttcacagtcactagaaaataaagaactatgcatccttaggaatgactggtgttctgttccagtagagccagg<br>agatatcattcatttggagggagactgcacatctgacacttggataatagataaagattttggatatttgattctgtatccagacatgctgatttctgg<br>caccagcatagccagtagtattcgatgtatgagaagagctgtcctgagtgaaacttttaggagctctgatccagccacacgccaaatgctaattg<br>gtacggttctccatgaggtgtttcaaaaagccataaataatagctttgccccagaaaagctacaagaacttgcttttcaaacaattcaagaaataag<br>acatttgaaggaaatgtaccgcttaaatctaagtcaagatgaaataaaacaagaagtagaggactatcttccttcgttttgtaaatgggcaggaga<br>tttcatgcataaaaacacttcgactgacttccctcagatgcagctctctctgccaagtgataatagtaaggataattcaacatgtaacattgaagtcg<br>tgaaaccaatggatattgaagaaagcatttggtcccctaggtttggattgaaaggcaaaatagatgttacagttggtgtgaaaatacatcgagggt<br>ataaaacaaaatacaagataatgccgctggaacttaaaactggcaaagaatcaaattctattgaacaccgtagtcaggttgttctgtacactctact<br>aagccaagagagaagagctgatccagaggctggcttgcttctctacctcaagactggtcagatgtaccctgtgcctgccaaccatctagataaa<br>agagaattattaaagctaagaaaccagatggcattctcattgtttcaccgtattagcaaatctgctactagacagaagacacagcttgcttctttgcc<br>acaaataattgaggaagagaaaacttgtaaatattgttcacaaattggcaattgtgctctttatagcagagcagttgaacaacagatggattgtagtt<br>cagtcccaattgtgatgctgcccaaaatagaagaagaaacccagcatctgaagcaaacacacttagaatatttcagcctttggtgtctaatgttaa<br>ccctggagtcacaatcgaaggataataaaaagaatcaccaaaatatctggctaatgcctgcttcggaaatggagaagagtggcagttgcattgg<br>aaacctgattagaatggaacatgtaaagatagtttgtgatgggcaatatttacataatttccaatgtaaacatggtgccatacctgtcacaaatctaat<br>ggcaggtgacagagttattgtaagtggagaagaaaggtcactgtttgctttgctagaggatatgtgaaggagattaacatgacaacagtaactt<br>gtttattagacagaaacttgtcggtccttccagaatcaactttgttcagattagaccaagaagaaaaaaattgtgatatagataccccattaggaaat<br>ctttccaaattgatggaaaacacgtttgtcagcaaaaaacttcgagatttaattattgactttcgtgaacctcagtttatatcctaccttagttctgttctt<br>ccacatgatgcaaaggatacagttgcctgcattctaaagggtttgaataagcctcagaggcaagcgatgaaaaaggtacttctttcaaaagacta<br>cacactcatcgtgggtatgcctgggacaggaaaaacaactacgatatgtactctcgtaagaattctctacgcctgtggttttagcgttttgttgacca<br>gctatacacactctgctgttgacaatattcttttgaagttagccaagtttaaaataggattttttgcgtttgggtcagattcagaaggttcatccagctat<br>ccagcaatttacagagcaagaaatttgcagatcaaagtccattaaatccttagctcttctagaagaactctacaatagtcaacttatagttgcaacaa<br>catgtatgggaataaaccatccaatattttcccgtaaaatttttgatttttgtattgtggatgaagcctctcaaattagccaaccaatttgtctgggccc<br>cctttttttttcacggagatttgtgttagtgggggaccatcagcagcttcctcccctggtgctaaaccgtgaagcaagagctcttggcatgagtgaa<br>agcttattcaagaggctggagcagaataagagtgctgttgtacagttaaccgtgcagtacagaatgaacagtaaaattatgtccttaagtaataag<br>ctgacctatgagggcaagctggagtgtggatcagacaaagtggccaatgcagtgataaacctacgtcactttaaagatgtgaagctggaactg<br>gaattttatgctgactattctgataatccttggttgatgggagtatttgaacccaacaatcctgtttgtttccttaatacagacaaggttccagcgccag<br>aacaagttgaaaaaggtggtgtgagcaatgtaacagaagccaaactcatagttttcctaacctccatttttgttaaggctggatgcagtccctctga<br>tattggtattattgcaccgtacaggcagcaattaaagatcatcaatgatttattggcacgttctattgggatggtcgaagttaatacagtagacaaat<br>accaaggaagggacaaaagtattgtcctagtatcttttgttagaagtaataaggatggaactgttggtgaactcttgaaagattggcgacgtcttaa<br>tgttgctataaccagagccaaacataaactgattettctggggtgtgtgccctcactaaattgctatcctccttggagaagctgcttaatcatttaaa<br>ctcagaaaaattaatcattgatcttccatcaagagaacatgaaagtctttgccacatattgggtgactttcaaagagaataa |
| SEQ ID NO<br>20<br>Myc-POLQ-<br>Flag<br>*Homo sapiens* | atggaacaaaagttgatttctgaagaagatttgtaagaaagagagggatcctgaatcttctgcgtcggagtgggaaacggcggcgttcagaat<br>caggctcagattcgttctcgggaagcggcggtgacagcagtgccagcccccagttcctctccgggtccgtgctgagcccgccgcccggcctt<br>ggtcgctgcctgaaggccgcagctgcaggagaatgcaagcctacagttcctgactacgaaatagacaagctactattggcaaactggggactt<br>cctaaagcagttctggaaaaataccacagttttggtgtaaaaaagatgtttgaatggcaggcagagtgccttttgcttggacaagtcctggaagg<br>aaagaatttagtttattcagctcctacaagtgctgggaagactcttgtggcagaattacttattttgaagcgggttttggaaatgcggaagaaagctt<br>tgtttattcttccctttgtttctgtggctaaagagaagaaatactacctccagagtctgtttcaggaagtaggaataaaagtagacggttatatgggca |

TABLE 1-continued

| SEQ ID NO | SEQUENCE |
|---|---|
| | gcacctctccatcaaggcatttctcttcattggatattgcagtctgcacaattgagagagccaatggtctgatcaatcgcctcatagaggaaaataa |
| | gatggatctgttaggaatggtggttgtggatgaattacatatgctgggagactctcaccgagggtatctgctggaacttttgctgaccaagatttgc |
| | tatattactcggaaatcagcatcttgtcaggcagatctagccagttctctgtctaatgctgtgcaaatcgttggcatgagtgctacccttcctaatttg |
| | gagcttgtggcttcctggttgaatgctgaactctaccataccgactttcgccctgtaccgcttttggagtcagtaaaagttggaaattccatatatga |
| | ctcttcaatgaaacttgtgagggaatttgagcccatgcttcaagtgaagggagatgaggaccatgttgttagcttatgttatgagacgatttgtgata |
| | accattcagtattactttttttgtccatcaaagaaatggtgtgagaagctggcagatatcattgctcgagagttttataatctacatcatcaagctgagg |
| | gattggtgaaaccctctgaatgcccaccagtaattctggaacaaaaagaactcctggaagtgatggatcagttaagacggttgccttcaggactg |
| | gactctgtattacagaaaactgtaccatggggagtagcatttcatcatgcaggtcttacttttgaggagagggatatcattgaaggagcctttcgtc |
| | aaggtctcattcgagtcttggcggcaacttctactctttcttctggggtgaatttacctgcacgtcgtgtgattattcgaacccctattttggtggtcg |
| | acctctagatattcttacttataagcagatggttggtcgtgctggcaggaaaggagtggacacagtaggcgagagtatcttaatttgtaagaactct |
| | gagaaatcaaaaggcatagctctccttcagggttctctaaagcctgttcgcagctgtctgcaaagacgagaaggagaagaagtaactggcagc |
| | atgatacgagctattctggagataatagttggtggagtggcaagtacatcacaagatatgcatacttatgctgcctgcacattttggctgcaagtat |
| | gaaagaagggaagcaaggaattcagagaaatcaagagtctgttcagcttggagcgattgaggcctgtgtgatgtggctactagaaaatgaattc |
| | atccagagtacagaagccagtgatggaacagaaggaaaggtgtatcatccaacacatcttggttcggccactctttcttcttcactttctccagctg |
| | atactttagatattttgctgacctgcaaagagcaatgaagggctttgtttagagaatgatcttcatattctctatctggttacacctatgtttgaggatt |
| | ggactactattgattggtatcgatttttctgtttatgggagaagttgccaacttcaatgaaaagggtggcagagctagtgggagttgaagaggggtt |
| | cttggcccgttgtgtgaaaggaaaagtagtagccagaactgagagacagcatcgacaaatggccatccataaaaggtttttcaccagtcttgtgc |
| | tattagatttaatcagtgaagttcccttaagggaaataaatcagaaatatggatgcaatcgtgggcagattcaatctttgcaacagtcagctgctgtt |
| | tatgcagggatgattacagtattttccaaccgtctgggctggcacaacatggaactactactttcccaatttcagaagcgtcttacgtttggcatcca |
| | gagggagctgtgtgacctggttcgggtatccttactaaatgctcagagagccagggttctctatgcttctggctttcatactgtggcagaccttgct |
| | agagcaaatattgtggaggtggaggtgattctgaaaaatgctgtgcctttcaaaagtgcccggaaggcagtggatgaggaagaggaagcagtt |
| | gaagaacgtcgcaatatgcgaactatctgggtgactggcagaaaaggtttaactgaaagggaagcagcagcccttatagtggaagaagccag |
| | aatgattctgcagcaggacttagttgaaatgggagtgcaatggaatccatgtgccctgttacattctagtacatgctcattgactcatagtgagtcc |
| | gaagtaaaggaacacacatttatatcccaaactaagagttcttataaaaaattaacatcaaagaacaaaagtaacacaatatttagtgattcttatatt |
| | aagcattcaccaaatatagtgcaagacttaaataaaagtagagagcatacaagttcctttaattgtaatttccagaatgggaatcaagaacatcag |
| | agatgttccattttcagagcaagaaaacgggcctctttagatataaataaagagaagccaggagcctctcagaatgaggggaaaacaagtgata |
| | agaaagttgttcagactttttcacagaaaacaaaaaaggcacctttgaatttcaattcagaaaagatgagcagaagttttcgatcttggaaacgtag |
| | aaagcatctaaagcgatctagggacagcagcccccctgaaagactctggagcgtgtagaatccatttacaaggacagactctgtctaatcctagt |
| | ctttgtgaagacccgtttaccttagatgagaagaaaacggaatttagaaattcagggccatttgctaaaaatgtatctttgagtggtaaggaaaaag |
| | ataataaaacatcattcccattacaaataaagcaaaattgttcatggaacataacactaactaatgataattttgtggagcatattgtcacaggatctc |
| | agagtaaaaatgtgacttgtcaggccactagtgtggttagtgaaaagggcagaggagtagctgttgaggcagaaaaaataaatgaagtgctga |
| | tacaaaatggttcaaaaaaccagaatgtttatatgaaacaccatgacatccatccaattaaccagtacctgcgaaagcaatctcatgaacagaca |
| | agcactattaccaaacagaaaaatataatagagagacaaatgccctgtgaagcagtcagtagttacataaatagagactcaaatgtactatcaat |
| | tgtgaaaggataaagcttaatacagaggaaaataaaccaagtcattttcaggcattaggagatgatataagcagaactgtgatacccagtgaagt |
| | acttccatcagctggagcatttagcaaatcagaaggccagcatgagaattttctaaatatttctagactacaagaaaaaacaggtacttatacaaca |
| | aacaaaactaaaaataatcatgtttctgacttaggtttagtcctctgtgattttgaagatagtttctatctggatactcagtcagagaaaataatacaac |
| | agatggcaactgaaaatgccaaactaggagcaaaggacaccaacctggcagcagggataatgcagaagagcttagtccaacagaactcaat |
| | gaactcttttcagaaggagtgtcacattccattcctgctgaacagcaccctctaggagcgactaagatagatcatttggaccttaagactgtaggt |
| | actatgaaacaaagcagtgattcacatggggttgatatcctgactccagaaagcccgattttccattctccaatactattggaggaaaatggtcatt |
| | tttaaaaaagaatgaagtttctgttactgattcacaattaaatagttttcttcaaggttatcaaacacaagaaactgtgaaaccagttatacttctgattc |
| | ctcaaaagagaactcccactggtgtagaaggagaatgtcttccagttcctgaaacaagtttgaatatgagtgatagtttactatttgatagcttcagt |
| | gatgactatctagtaaaagaacaattacctgatatgcaaatgaaagaacccccttccttcagaagtaacatcaaaccatttagtgattctctgtgtcta |
| | caagaagacctaattaaaaaatcaaatgtaaatgagaatcaagatacccaccagcagttgacttgttccaatgatgaatctattatattttcagaaat |
| | ggattctgttcagatggttgaagctttggacaatgtggatatatttcctgtccaagagaagaatcatactgtagtatctcctagagcattagaactaa |
| | gtgatccagtacttgatgagcaccaccaaggtgatcaagatggaggagatcaagatgaaagggctgaaaaatcaaaattaactgggaccagg |
| | caaaatcattcattcatttggtcaggggcatcatttgatctaagtccaggactgcaaaggattttagataaagtatccagtcctctagaaaatgaaaa |
| | gctaaaatcaatgactataaacttttccagtttgaatagaaaaaatacagagttaaatgaagaacaagaagttatttcaaacttggagacaaaacaa |
| | gtgcagggaatttcatttcttctaataatgaagtaaaaagcaagattgagatgctagaaaacaatgccaatcatgatgaaacctcatccctcttacc |
| | tcgtaaagaaagtaatatagttgatgataatggtctcattcctcctacacccattccaacatctgcttctaagctgacatttccagggattcttgaaac |
| | acctgtaaacccttggaaaactaataatgttttacaacctggtgaaagttatttatttggctcaccttcagatattaaaaaccacgatttaagtccagg |
| | gagtagaaatgggttcaaagacaacagccctattagtgacacaagcttttcacttcagttatcacaggatggattacagttaactccagcctcaag |

TABLE 1-continued

| SEQ ID NO | SEQUENCE |
|---|---|
| | cagttcagaaagtttgtccataattgatgtagcaagtgaccaaaatcattccaaacattcattaaggagtggcggtgcaaaaagcgattttccatct<br>cactggcttgtgaaaagattagaagtttgacatcttctaaaactgctactattggcagtaggtttaagcaagctagctcacctcaggaaattcctatt<br>agagatgatggatttcccattaaaggttgtgatgacaccttggtggttggactggcagtatgctggggtggaagggatgcctattattttttcactgc<br>agaaggaacaaaagcattctgaaattagtgccagtttggttccaccttctttagatccaagcctgactttgaaagacaggatgtggtaccttcaatc<br>ttgcttgcgaaaggaatctgataaagaatgttctgttgtcatctatgacttcatccagagctataaaattcttcttctttcttgtggcatctccttggagc<br>aaagttatgaagatcctaaggtggcatgctggttactagatccagattctcaggagccgactcttcatagcatagttaccagttttcttcctcatgag<br>cttccactcctagaagggatggagaccagccaagggattcaaagcctggggctaaatgctggcagtgagcattctgggcgatacagagcatct<br>gtggagtccattctcatcttcaactctatgaatcagctcaactctttgttgcagaaggaaaaccttcaagatgttttccgtaaggtggaaatgccctct<br>cagtactgcttggccttgctagaactaaatggaattggctttagtactgcagaatgtgaaagtcagaaacatataatgcaagccaagctggatgc<br>aattgagacccaggcctatcaactagctggccacagtttttctttcaccagttcagatgacatcgctgaggttttatttttggaattgaagttgccccc<br>aaatagagagatgaaaaaccaaggcagcaagaaaactctgggttctaccagaagagggattgacaatggacgcaagctaaggctgggaag<br>acagttcagcactagtaaggacgttttaaataaattaaaggcattacatcctttaccaggcttgatattagaatggagaagaatcactaatgctatta<br>ccaaagtggtctttccccttcagcgggaaaagtgtcttaatccttttcttggaatggaaagaatctatcctgtatcacagtcgcacactgctacagg<br>acgaataacctttacagaaccaaatattcagaatgtgccaagagattttgaaatcaaaatgccaacactagtaggagaaagcccaccttctcaag<br>ctgtaggcaaaggcctacttcccatgggcagaggaaaatataagaagggtttcagcgtgaatcctagatgccaggcacagatggaggagaga<br>gctgcagacagaggaatgccattttcaattagcatgcgacatgcctttgtgcctttcccaggtggttcaatactggctgctgactactctcagcttg<br>aactgaggatcttggctcatttatcccatgatcgtcgtctcattcaagtgttaaacactggagctgatgttttcaggagcattgcagcagagtggaa<br>gatgattgagccagagtctgttggggatgatctgaggcagcaggcaaaacagatttgctatgggatcatttatggaatgggagctaaatctttgg<br>gagagcagatgggcattaaagaaaatgatgctgcatgctatattgactccttcaaatccagatacacagggattaatcaattcatgacagagaca<br>gtgaagaattgtaaaagagacggatttgttcagaccattttgggaaggcgtagatatttgccaggaatcaaagacaacaacccttatcgtaaagc<br>tcacgctgagcgtcaagctatcaacacaatagtccaaggatcagcagctgatattgtcaaaatagccacagttaacattcagaagcaattagaga<br>ccttccactcaaccttcaaatcccatggtcatcgagagggtatgctccaaagtgaccgaacaggattgtcacgaaagagaaaactgcaaggga<br>tgttctgcccaatcagaggaggcttcttcatccttcaactccatgatgaactcctatatgaagtggcagaagaagatgttgttcaggtagctcagatt<br>gtcaagaatgaaatggaaagtgctgtaaaactgtctgtgaaattgaaagtgaaagtgaaaataggcgccagctggggagagctaaaggacttt<br>gatgtgcccgggatggactacaaagacgatgacgacaagtaa |
| SEQ ID NO<br>21<br>POLB<br>*Homo sapiens* | atggactataaggaccacgacggagactacaaggatcatgatattgattacaaagacgatgacgataagatggccccaaagaagaagcggaa<br>ggtcggtatccacggagtcccagcagccgctagcaaacggaaggcgccgcaggagactctcaacgggggaatcaccgacatgctcacag<br>aactcgcaaactttgagaagaacgtgagccaagctatccacaagtacaatgcttacagaaaagcagcatctgttatagcaaaatacccacacaa<br>aataaagagtggagctgaagctaagaaattgcctggagtaggaacaaaaattgctgaaaagattgatgagtttttagcaactggaaaattacgta<br>aactggaaaagattcggcaggatgatacgagttcatccatcaatttcctgactcgagttagtggcattggtccatctgctgcaaggaagtttgtag<br>atgaaggaattaaaacactagaagatctcagaaaaaatgaagataaattgaaccatcatcagcgaattgggctgaaatattttggggactttgaa<br>aaaagaattcctcgtgaagagatgtacaaatgcaagatattgtactaaatgaagttaaaaaagtggattctgaatacattgctacagtctgtggca<br>gtttcagaagaggtgcagagtccagtggtgacatggatgttctcctgacccatcccagcttcacttcagaatcaaccaaacagccaaaactgtta<br>catcaggttgtggagcagttacaaaaggttcattttatcacagataccctgtcaaagggtgagacaaagttcatgggtgtttgccagcttcccagt<br>aaaaatgatgaaaaagaatatccacacagaagaattgatatcaggttgatacccaaagatcagtattactgtggtgttctctatttcactgggagtg<br>atattttcaataagaatatgagggctcatgccctagaaaagggtttcacaatcaatgagtacaccatccgtcccttgggagtcactggagttgcag<br>gagaacccctgccagtggatagtgaaaaagacatctttgattacatccagtggaaataccgggaacccaaggaccggagcgaatga |
| SEQ ID NO<br>22<br>POLH<br>*Homo sapiens* | atggctactggacaggatcgagtggttgctctcgtggacatggactgtttattgttcaagtggagcagcggcaaaatcctcatttgaggaataaa<br>ccttgtgcagttgtacagtacaaatcatggaagggtggtggaataattgcagtgagttatgaagctcgtgcatttggagtcactagaagtatgtgg<br>gcagatgatgctaagaagttatgtccagatcttctactggcacaagttcgtgagtcccgtgggaaagctaacctcaccaagtaccgggaagcca<br>gtgttgaagtgatggagataatgtctcgttttgctgtgattgaacgtgccagcattgatgaggcttacgtagatctgaccagtgctgtacaagaga<br>gactacaaaagctacaaggtcagcctatctcggcagacttgttgccaagcacttacattgaagggttgccccaaggccctacaacggcagaag<br>agactgttcagaaagaggggatgcgaaaacaaggcttatttcaatggctcgattctcttcagattgataacctcacctctccagacctgcagctca<br>ccgtgggagcagtgattgtggaggaaatgagagcagccatagagagggagactggttttcagtgttcagctggaatttcacacaataaggcct<br>ggcaaaactggcctgtggactaaacaagcccaaccgccaaaccctggtttcacatgggtcagtcccacagctcttcagccaaatgcccattcg<br>caaaatccgtagtcttggaggaaagctaggggcctctgtcattgagatcctagggatagaatacatgggtgaactgacccagttcactgaatcc<br>cagctccagagtcattttggggagaagaatgggtcttggctatatgccatgtgccgagggattgaacatgatccagttaaacccaggcaactac<br>ccaaaaccattggctgtagtaagaacttcccaggaaaaacagctcttgctactcgggaacaggtacaatggtggctgttgcaattagcccagga<br>actagaggagagactgactaaagaccgaaatgataatgacagggtagccacccagctggttgtgagcattcgtgtacaaggagacaaacgcc |

TABLE 1-continued

| SEQ ID NO | SEQUENCE |
|---|---|
| | tcagcagcctgcgccgctgctgtgccdtacccgctatgatgctcacaagatgagccatgatgcatttactgtcatcaagaactgtaatacttctg<br>gaatccagacagaatggtctcctcctctcacaatgcttttcctctgtgctacaaaattttctgcctctgccccttcatcttctacagacatcaccagctt<br>cttgagcagtgacccaagttctctgccaaaggtgccagttaccagctcagaagctaagacccagggaagtggcccagcggtgacagccacta<br>agaaagcaaccacgtctctggaatcattcttccaaaaagctgcagaaaggcagaaagttaaagaagcttcgctttcatctcttactgctcccactc<br>aggctcccatgagcaattcaccatccaagccctcattaccattcaaaccagtcaaagtacaggaactgagcccttetttaagcagaaaagtctgc<br>ttctaaagcagaaacagcttaataattcttcagtttcttcccccaacaaaacccatggtccaactgtaaagcattaccaaactctttaccaacagag<br>tatccagggtgtgtccctgtttgtgaaggggtgtcgaagctagaagaatcctctaaagcaactcctgcagagatggatttggcccacaacagcc<br>aaagcatgcacgcctcttcagcttccaaatctgtgctggaggtgactcagaaagcaaccccaaatccaagtcttctagctgctgaggaccaagt<br>gccctgtgagaagtgtggctccctggtaccggtatgggatatgccagaacacatggactatcattttgcattggagttgcagaaatcdttttgca<br>gccccactcttcaaaccccccaggttgtttctgccgtatctcatcaaggcaaaagaaatcccaagagccctttggcctgcactaataaacgcccca<br>ggcctgagggcatgcaaacattggaatcatttttttaagccattaacacattag |
| SEQ ID NO<br>23<br>POLG<br>*Homo sapiens* | atggctagccgcctgctctggaggaaggtggccggcgccaccgtcgggccagggccggttccagctccggggcgctgggtctccagctcc<br>gtccccgcgtccgaccccagcgacgggcagcggcggcggcagcagcagcagcagcagcagcagcagcagcaacagcagcctcagcag<br>ccgcaagtgctatcctcggagggcgggcagctgcggcacaacccattggacatccagatgctctcgagagggctgcacgagcaaatcttcg<br>ggcaaggaggggagatgcctggcgaggccgcggtgcgccgcagcgtcgagcacctgcagaagcacgggctctgggggcagccagccg<br>tgcccttgcccgacgtggagctgcgcctgccgcccctctacggggacaacctggaccagcacttccgcctcctggcccagaagcagagcct<br>gccctacctggaggcggccaacttgctgttgcaggcccagctgcccccgaagcccccggcttgggcctgggcggagggctggacccggta<br>cggcccccgaggggggaggccgtacccgtggccatccccgaggagcgggccctggtgttcgacgtggaggtctgcttggcagagggaacttg<br>ccccacattggcggtggccatatccccctcggcctggtattcctggtgcagccagcggctggtggaagagcgttactcttggaccagccagct<br>gtcgccggctgacctcatccccctggaggtccctactggtgccagcagccccacccagagagactggcaggagcagttagtggtggggcac<br>aatgtttcctttgaccgagctcatatcagggagcagtacctgatccagggttcccgcatgcgtttcctggacaccatgagcatgcacatggccat<br>ctcagggctaagcagcttccagcgcagtctgtggatagcagccaagcagggcaaacacaaggtccagcccccccacaaagcaaggccagaa<br>gtcccagaggaaagccagaagaggcccagcgatctcatcctgggactggctggacatcagcagtgtcaacagtctggcagaggtgcacag<br>actttatgtagggggcctcccttagagaaggagcctcgagaactgtttgtgaagggcaccatgaaggacattcgtgagaacttccaggacctg<br>atgcagtactgtgcccaggacgtgtgggccacccatgaggttttccagcagcagctaccgctettcttggagaggtgtccccacccagtgactc<br>tggccggcatgctggagatgggtgtctcctacctgcctgtcaaccagaactgggagcgttacctggcagaggcacagggcacttatgaggag<br>ctccagcgggagatgaagaagtcgttgatggatctggccaatgatgcctgccagctgctctcaggagagaggtacaaagaagacccctggct<br>ctgggacctggagtgggacctgcaagaatttaagcagaagaaagctaagaaggtgaagaaggaaccagccacagccagcaagttgcccat<br>cgagggggctggggcccctggtgatcccatggatcaggaagacctcggcccctgcagtgaggaggaggagtttcaacaagatgtcatggcc<br>cgcgcctgcttgcagaagctgaaggggaccacagagctcctgcccaagcggccccagcaccttcctggacaccctggatggtaccggaag<br>ctctgcccccggctagacgaccctgcatggaccccgggccccagcctcctcagcctgcagatgcgggtcacacctaaactcatggcacttac<br>ctgggatggcttccctctgcactactcagagcgtcatggctggggctacttggtgcctgggcggcgggacaacctggccaagctgccgacag<br>gtaccaccctggagtcagctggggtggctgcccctacagagccatcgagtccctgtacaggaagcactgtctcgaacaggggaagcagca<br>gctgatgccccaggaggccggcctggcggaggagttcctgctcactgacaatagtgccatatggcaaacggtagaagaactggattacttag<br>aagtggaggctgaggccaagatggagaacttgcgagctgcagtgccaggtcaacccctagctctgactgcccgtggtggccccaaggacac<br>ccagcccagctatcaccatggcaatggaccttacaacgacgtggacatccctggctgctggtttttcaagctgcctcacaaggatggtaatagct<br>gtaatgtgggaagcccctttgccaaggacttcctgcccaagatggaggatggcaccctgcaggctggcccaggaggtgccagtgggccccg<br>tgctctggaaatcaacaaaatgatttctttctggaggaacgcccataaacgtatcagctcccagatggtggtgtggctgcccaggtcagctctgc<br>cccgtgctgtgatcaggcaccccgactatgatgaggaaggcctctatggggccatcctgccccaagtggtgactgccggcaccatcactcgc<br>cgggctgtggagcccacatggctcaccgccagcaatgcccggcctgaccgagtaggcagtgagttgaaagccatggtgcaggccccacct<br>ggctacacccttgtgggtgctgatgtggactcccaagagctgtggattgcagctgtgcttggagacgcccactttgccggcatgcatggctgca<br>cagcctttgggtggatgacactgcagggcaggaagagcaggggcactgatctacacagtaagacagccactactgtgggcatcagccgtga<br>gcatgccaaaatcttcaactacggccgcatctatggtgctgggcagccdttgctgagcgcttactaatgcagtttaaccaccggctcacacagc<br>aggaggcagctgagaaggcccagcagatgtacgctgccaccaagggcctccgctggtatcggctgtcggatgagggcgagtggctggtga<br>gggagttgaacctcccagtggacaggactgagggtggctggatttccctgcaggatctgcgcaaggccagagagaaactgcaaggaagtc<br>acagtggaagaagtgggaggtggttgctgaacgggcatggaagggggcacagagtcagaaatgttcaataagcttgagagcattgctacgt<br>ctgacataccacgtaccccggtgctgggctgctgcatcagccgagccctggagccctcggctgtccaggaagagtttatgaccagccgtgtga<br>attgggtggtacagagctctgctgttgactacttacacctcatgcttgtggccatgaagtggctgtttgaagagtttgccatagatgggcgcttctg<br>catcagcatccatgacgaggttcgctacctggtgcgggaggaggaccgctaccgcgctgccctggccttgcagatcaccaacctcttgacca<br>ggtgcatgtttgcctacaagctgggtctgaatgacttgccccagtcagtcgcctttttcagtgcagtcgatattgaccggtgcctcaggaaggaag |

TABLE 1-continued

| SEQ ID NO | SEQUENCE |
|---|---|
| | tgaccatggattgtaaaaccccttccaacccaactgggatggaaaggagatacgggattccccagggtgaagcgctggatatttaccagataat<br>tgaactcaccaaaggctccttggaaaaacgaagccagcctggaccatag |
| SEQ ID NO<br>24<br>POLN<br>*Homo sapiens* | atggaaaattatgaggcattggtaggctttgatctctgtaatacaccgctctccagtgttgctcagaagattatgtctgctatgcattcaggtgattta<br>gtggattctaagacttggggaaagagtacagagactatggaagtgataaacaagtccagtgttaagtattcagtacaacttgaagacaggaaga<br>ctcaatcaccagaaaaaaaggatcttaaatctttaagaagtcagacatcaagaggttctgccaagctgtctcctcagtccttcagtgtcaggctca<br>cagatcagctgctgctgaccaaaaacagaagagcatcagctcattgactctttcaagttgtttaattccacagtataatcaagaggcttcagttcta<br>cagaaaaaggggcataaaagaaagcatttcctaatggagaatataaataatgaaaataaaggaagcattaatcttaaaagaaaacatattacata<br>taataatttgtcagagaaaacaagtaaacaaatggcattggaagaagatactgatgacgccgaaggctacctaaattctgggaactcaggagca<br>ttgaaaaaacatttttgtgatattaggcatttggatgattgggcaaaaagccagctgattgaaatgctcaaacaggcagcagccctggtgataact<br>gtgatgtatactgatggttccacccagctaggagctgaccagacccccgtttcttctgttagaggaattgtggtgttagtaaaacgccaagcaga<br>gggtggccatggctgtccagatgccccggcctgtggtcctgttctggagggctttgtgtcagatgatccatgcatctacattcaaatagagcactc<br>tgctatctgggaccaagaacaggaggcacatcaacaatttgcccggaacgtgctatttcaaacaatgaaatgtaaatgtcctgttatttgttttaatg<br>ctaaggatttttgtgagaatagtgctgcagtttttggcaatgatggcagttggaagcatgttgctgattttatagggctagatcccagaattgctgcat<br>ggcttatagatcctagtgatgccacaccctcttttgaagatttagtagaaaaatactgtgaaaaatccattacagttaaagtgaacagcacatatgg<br>aaattcctcaagaaatattgtgaatcagaatgtacgtgagaacctgaagacactctacagacttacaatggacctttgctctaaactgaaggattat<br>ggtttatggcaactatttcgtactttggagcttcctctgataccaattttggcagtgatggaaagccatgccattcaggtgaacaaagaggagatgg<br>agaagacgtcagcacttcttggggctcgtctcaaggaattggagcaagaagctcattttgttgcaggagaacggtttcttataacgagcaataac<br>cagcttcgagagatcctctttggcaagttaaagctgcacctgctgagtcaaaggaacagtctccccagaacggggttgcagaaatacccgtcta<br>catcagaagcagtgttaaatgctctgcgagaccttcatccattacccaagataattttggaatacaggcaggttcacaagatcaagtcaacctttgt<br>agatggattactagcttgcatgaaaaagggctccatttcctctacatggaatcagactggaactgtgactggaagactttcagccaagcatcctaa<br>tatccaaggtatctccaagcacccaattcagattactacacctaagaattttaaaggtaaagaagacaagattctcacgatctccccgagggccat<br>gtttgtttcatccaaaggccacacctttctagcagcagacttttcacagattgaattgcgcattcttacacatttatctggagatccggaacttctgaa<br>gttattccaggaatctgaaagagatgatgtattttctactctgacttcacagtggaaggatgtgcccgtggaacaggtgacacacgcagacagag<br>agcaaaccaagaaggtggtgtacgcggtggctatggagcagggaaggagcggctggctgcttgccttggagttcctattcaggaagctgcc<br>cagtttttggagagtttttttgcagaagtacaagaaaatcaaggacttcgcccgagcagctattgcccagtgtcaccagacaggctgtgtggtgtc<br>catcatgggcagaaggagacccctgccaaggattcacgctcatgaccagcaactccgggcacaagcagagcgacaggcagtgaacttcgt<br>ggtgcaaggctccgctgctgacctctgcaagctggccatgatccatgtcttcactgcagtggctgcttcccacaccttgacggccaggctggtg<br>gcccagatccatgatgagctgctgtttgaagtggaagatccgcagatcccggagtgtgcagctctcgtcaggaggaccatggagtccttggaa<br>caggtgcaggcattggagctgcagcttcaggtacccctcaaggtgagcctgagtgccggccgctcatggggacacctggtgccactgcagg<br>aggcctggggccctccgccaggcccatgtcgcactgagtctcccagcaacagcctggctgcccctgggtcccctgccagcacccagccccc<br>acccctgcatttttcgccttcattttgtctgtag |
| SEQ ID NO<br>25<br>TENT4A<br>*Homo sapiens* | atggcttccccttgtcctgaagaagcagctatgagaagagaggtggtgaaacggatcgaaactgtggtgaaagacctttggccgacggctgat<br>gtacagatatttggcagctttagtacaggtctttatcttccaactagcgacatagacctggtggtcttcgggaaatgggagcgtcctcctttacagct<br>gctggagcaagccctgcggaagcacaacgtggctgagccgtgttccatcaaagtccttgacaaggctacggtaccaataataaagctcacag<br>atcaggagactgaagtgaaagttgacatcagctttaacatggagacgggcgtccgggcagcggagttcatcaagaattacatgaagaaatattc<br>attgctgccttacttgattttagtattgaaacagttccttctgcagagggacctgaatgaagtttttacaggtggaattagctcatacagcctaattta<br>atggccattagctttctacagttgcatccaagaattgatgcccggagagctgatgaaaaccttggaatgcttcttgtagaatttttgaactctatggg<br>agaaattttaattacttgaaaaccggtattagaatcaaagaaggaggtgcctatatcgccaaagaggagatcatgaaagccatgaccagcgggt<br>acagaccgtcgatgctgtgcattgaggacccccctgctgccagggaatgacgttggccggagctcctatggcgccatgcaggtgaagcaggtc<br>ttcgattatgcctacatagtgctcagccatgctgtgtcaccgctggccaggcctatccaaacagagacgccgaaagtactttaggaagaatcat<br>caaagtaactcaggaggtgattgactaccggaggtggatcaaagagaagtggggcagcaaagcccacccgtcgccaggcatggacagcag<br>gatcaagatcaaagagcgaatagccacatgcaatggggagcagacgcagaaccgagagcccgagtctccctatggccagcgcttgactttgt<br>cgctgtccagcccccagctcctgtcttcaggctcctcggcctcttctgtgtcttcactttctgggagtgacgttgattcagacacaccgccctgcac<br>aacgcccagtgtttaccagttcagtctgcaagcgccagctcctctcatggccggcttacccaccgccttgccaatgcccagtggcaaacctcag<br>cccaccacttccagaacactgatcatgacaaccaacaatcagaccaggtttactatacctccaccgaccctaggggttgctcctgttccttgcag<br>acaagctggtgtagaaggaactgcgtctttgaaagccgtccaccacatgtcttccccggccattccctcagcgtcccccaacccgctctcgagc<br>cctcatctgtatcataagcacaacggcatgaaactgtccatgaagggctctcacggccacacccaaggcggcggctacagctctgtgggtagc<br>ggaggtgtgcggccccctgtgggcaacaggggacaccaccagtataaccgcaccggctggaggaggaaaaaacacacacacacacggg<br>acagtctgcccgtgagcctcagcagataa |

TABLE 1-continued

| SEQ ID NO | SEQUENCE |
|---|---|
| SEQ ID NO | atggctgcctcacaaacttcacaaactgttgcatctcacgttccttttgcagatttgtgttcaactttagaacgaatacagaaaagtaaaggacgtgc |
| 26 | agaaaaaatcagacacttcagggaatttttagattcttggagaaaatttcatgatgctcttcataagaaccacaaagatgtcacagactctttttatcc |
| DNA Ligase | agcaatgagactaattcttcctcagctagaaagagagagaatggcctatggaattaaagaaactatgcttgctaagctttatattgagttgcttaattt |
| 4 | acctagagatggaaaagatgccctcaaacttttaaactacagaacacccactggaactcatggagatgctggagactttgcaatgattgcatattt |
| *Homo sapiens* | tgtgttgaagccaagatgtttacagaaaggaagtttaaccatacagcaagtaaacgaccttttagactcaattgccagcaataattctgctaaaaga |
| | aaagacctaataaaaaagagccttcttcaacttataactcagagttcagcacttgagcaaaagtggcttatacggatgatcataaaggatttaaag |
| | cttggtgttagtcagcaaactatcttttctgtttttcataatgatgctgctgagttgcataatgtcactacagatctggaaaaagtctgtaggcaactgc |
| | atgatccttctgtaggactcagtgatatttctatcactttattttctgcatttaaaccaatgctagctgctattgcagatattgagcacattgagaaggat |
| | atgaaacatcagagtttctacatagaaaccaagctagatggtgaacgtatgcaaatgcacaaagatggagatgtatataaatacttctctcgaaat |
| | ggatataactacactgatcagtttggtgcttctcctactgaaggttctcttaccccattcattcataatgcattcaaagcagatatacaaatctgtattct |
| | tgatggtgagatgatggcctataatcctaatacacaaactttcatgcaaaagggaactaagtttgatattaaaagaatggtagaggattctgatctg |
| | caaacttgttattgtgtttttgatgtattgatggttaataataaaaagctagggcatgagactctgagaaagaggtatgagattcttagtagtatttttac |
| | accaattccaggtagaatagaaatagtgcagaaaacacaagctcatactaagaatgaagtaattgatgcattgaatgaagcaatagataaaaga |
| | gaagagggaattatggtaaaacaacctctatccatctacaagccagacaaaagaggtgaagggtggttaaaaattaaaccagagtatgtcagtg |
| | gactaatggatgaattggacattttaattgttggaggatattggggtaaaggatcacggggtggaatgatgtctcattttctgtgtgcagtagcaga |
| | gaagccccctcctggtgagaagccatctgtgtttcatactctctctcgtgttgggtctggctgcaccatgaaagaactgtatgatctgggtttgaaat |
| | tggccaagtattggaagccttttcatagaaaagctccaccaagcagcattttatgtggaacagagaagccagaagtatacattgaaccttgtaatt |
| | ctgtcattgttcagattaaagcagcagagatcgtacccagtgatatgtataaaactggctgcaccttgcgttttccacgaattgaaaagataagag |
| | atgacaaggagtggcatgagtgcatgaccctggacgacctagaacaacttaggggaaggcatctggtaagctcgcatctaaacacctttatat |
| | aggtggtgatgatgaaccacaagaaaaaaagcggaaagctgccccaaagatgaagaaagttattggaattattgagcacttaaaagcacctaa |
| | ccttactaacgttaacaaaatttctaatatatttgaagatgtagagttttgtgttatgagtggaacagatagccagccaaagcctgacctggagaac |
| | agaattgcagaatttggtggttatatagtacaaaatccaggcccagacacgtactgtgtaattgcagggtctgagaacatcagagtgaaaaacat |
| | aattttgtcaaataaacatgatgttgtcaagcctgcatggcttttagaatgttttaagaccaaaagctttgtaccatggcagcctcgctttatgattcat |
| | atgtgcccatcaaccaaagaacattttgcccgtgaatatgattgctatggtgatagttatttcattgatacagacttgaaccaactgaaggaagtatt |
| | ctcaggaattaaaaattctaacgagcagactcctgaagaaatggcttctctgattgctgatttagaatatcggtattcctgggattgctctcctdcag |
| | tatgtttcgacgccacaccgtttatttggactcgtatgctgttattaatgacctgagtaccaaaaatgaggggacaaggttagctattaaagccttgg |
| | agcttcggtttcatggagcaaaagtagtttcttgtttagctgagggagtgtdcatgtaataattggggaagatcatagtcgtgttgcagattttaaag |
| | cttttagaagaacttttaagagaaagtttaaaatcctaaaagaaagttgggtaactgattcaatagacaagtgtgaattacaagaagaaaaccagta |
| | tttgatttaa |
| SEQ ID NO | atgggctccgccgcctgcccccggggagccttgccggagctcgcgccctgctgccagcctcgcgagcagtcgcagccccacacgcgatgg |
| 27 | gacgcgggctgtgggattcagcaccccgggggcgaggaattcaggaccctcggcggggcaagggcctatagggttccgaactcgcagga |
| XRN | gggtcgctcctcccctactcgctttttcccggcaccggaaggccccgcccactgctttgtttcctctccagaccgcgcattttgggtctcggaaga |
| *Homo sapiens* | ggttcagaggctgttgttgagcaatgcatgccagccaaaagaatgcaatggtgtaaagattccagttgatgccagtaaacctaatccaaatgatg |
| | tggagtttgataatctgtatttggatatgaatggaatcatccatccctgtactcatcctgaagacaaaccagcaccaaaaaatgaagatgaaatgat |
| | ggttgcaatttttgagtacattgacagacttttcagtattgtaagaccaagaagacttctctacatggcaatagatggagtggcaccacgtgctaaa |
| | atgaaccagcagcgttcaaggaggttcagggcatcaaaagaaggaatggaagcagcagtcgagaagcagcgagtcagggaagaaatattg |
| | gcaaaaggtggctttcttcctccagaagaaataaaagaaagatttgacagcaactgtattacaccaggaactgaattcatggacaatcttgctaaa |
| | tgccttcgctattacatagctgatcgtttaaataatgaccctgggtggaaaaatttgacagttattttatctgatgctagtgctcctggtgaaggagaa |
| | cataaaatcatggattacattagaaggcaaagagcccagcctaaccatgacccaaatactcatcattgtttatgtggagcagatgctgatctcatta |
| | tgcttggccttgccacacatgaaccgaactttaccattattagagaagaattcaaaccaaacaagcccaaaccatgtggtctttgtaatcagtttgg |
| | acatgaggtcaaagattgtgaaggtttgccaagagaaaagaagggaaagcatgatgaacttgccgatagtcttccttgtgcagaaggagagttt |
| | atcttccttcggcttaatgttcttcgtgagtatttggaaagagaactcacaatggccagcctaccattcacatttgatgttgagaggagcattgatga |
| | ctgggttttcatgtgcttctttgtgggaaatgacttcctccctcatttgccatcgttagagattagggaaaatgcaattgaccgtttggttaacatatac |
| | aaaaatgtggtacacaaaactgggggttaccttacagaaagtggttatgtcaatctgcaaagagtacagatgatcatgttagcagttggtgaagtt |
| | gaggatagcatttttaaaaagagaaaggatgatgaggacagttttagaagacgacagaaagaaaaaagaaagagaatgaagagagatcaac |
| | cagctttcactcctagtggaatattaactcctcatgccttgggttcaagaaattcaccaggttctcaagtagccagtaatccgagacaagcagccta |
| | tgaaatgaggatgcagaataactctagtccttcgatatctcctaatacgagtttcacatctgatggctccccgtctccattaggaggaattaagcga |
| | aaagcagaagacagtgacagtgaacctgagccagaggataatgtcaggttatgggaagctggctggaagcagcggtactacaagaacaaat |
| | ttgatgtggatgcagctgatgagaaattccgtcggaaagttgtgcagtcgtacgttgaaggactttgctgggttcttagatattattaccaggctgt |

TABLE 1-continued

| SEQ ID NO | SEQUENCE |
|---|---|
| | gcttcctggaagtggtattatccatttcattatgcaccatttgcttcagactttgaaggcattgcagacatgccatctgattttgagaagggtacgaaa<br>ccgtttaaaccactagaacaacttatgggggtatttccagctgcaagtggtaattttctacctccatcatggcggaagctcatgagtgatcctgattc<br>tagtataattgacttctatcctgaagattttgctattgatttgaatgggaagaaatatgcatggcaaggtgttgctctcttgccattcgtggatgagcg<br>aaggctacgagctgccctagaagaggtatacccagacctcactccagaagagaccagaagaaacagccttggaggtgatgtcttatttgtggg<br>gaaacatcacccactccatgacttcattttagagctgtaccagacaggttccacagagccagtggaggtacccccctgaactatgtcatgggattc<br>aaggaaagttttctttggatgaagaagccattcttccagatcaaatagtatgttctcctgttcctatgttaagggatctgacacagaacactgtagtca<br>gtattaattttaaagacccacagtttgctgaagattacattttttaaagctgtaatgcttccaggagcaagaaagccagcagcagtactgaaacctag<br>tgactgggaaaaatccagcaatggacggcagtggaagcctcagcttggctttaaccgtgaccggaggcctgtgcacctggatcaggcagcct<br>tcaggactttgggccatgtgatgccaagaggctcaggaactggcatttacagcaatgctgcaccaccacctgtgacttaccagggaaacttata<br>caggccgcttttgagaggacaagcccagattccaaaacttatgtcaaatatgaggccccaggattcctggcgaggtcctcctccccttttccagc<br>agcaaaggtttgacagaggcgttggggctgaacctctgctcccatggaaccggatgctgcaaacccagaatgcagccttccagccaaaccag<br>taccagatgctagctgggcctggtgggtatccacccagacgagatgatcgtggagggagacagggatatcccagagaaggaaggaaatacc<br>ctttgccaccaccctcaggaagatacaattggaattaa |
| SEQ ID NO 28 3xFlag_NLS_ PolIV *Escherichia coli* | atggactataaggaccacgacggagactacaaggatcatgatattgattacaaagacgatgacgataagatggccccaaagaagaagcggaa<br>ggtcggtatccacggagtcccagcagcctcattgaagggaaaatttttttgcatttctcccgaaccctaacacctcatccaataagtttttttaagtcaa<br>ttcttgagaagaaaggagctacaattgtatcatctattcaaaattgcctccagagttctaggaaagaggtcattatccttatagaggacagtttcgtc<br>gacagtgacatgcacctgacacagaaggacatttttcaacgcgaggctggcttgaacgacgtagacgagtttttgggtaaaattgaacaatccg<br>gcatccagtgcgttaagactagctgcattaccaagtgggttcaaaacgacaaattcgcttttcaaaaggacgatttgattaagttccaaccgagtat<br>catagtcattagtgacaatgccgatgatggacagagtagcactgacaaagaaagcgaaatctcaactgacgtagaatcagagcgaaacgatg<br>actcaaacaacaaagacatgattcaggcctccaaaccgctcaaacggttgcttcaggaggataaaggtcgcgcttcccttgttaccgataaaac<br>caagtataaaaataatgaacttataataggcgcgcttaaacgacttaccaagaagtacgagattgagggtgaaaaattccgagctcggtcctacc<br>ggctcgctaaacaatctatggaaaattgtgatttcaatgttagaagcggagaggaagcacatacaaagttgagaaacatcggtcctagtattgct<br>aaaaaaattcaggtcattcttgatacgggagttctcccgggtctcaacgattccgttggccttgaagacaagctgaaatattttaagaactgctatg<br>gaatcgggtcagagatagcaaaacggtggaatctccttaactttgagtcattttgcgtggctgctaagaaagaccccgaggaatttgtgtccgatt<br>ggacgatattgttcgggtggagttattatgatgattggctttgcaaaatgtccaggaatgaatgcttcgcccatcttaagaaggtccaaaaggcttt<br>gcgcggaatcgaccccgaatgtcaggtcgagcttcaagggtcatacaatcggggttactcaaaatgcggggatatagatctcctctttttttaagc<br>cattctgcaacgataccactgaactcgctaagatcatggagacactctgcataaagctttataaagatgggtatatacattgcttcttgcaattgacg<br>cccaacttggagaagcttttttcttaaaagaattgttgaacggttccggacagccaagattgttggctatggagaacgaaaacgctggtattcatca<br>gaaattatcaagaaattctttatgggagtgaagttgtcccccccgcgagctcgaagaattgaaggagatgaaaaacgacgagggaaccctgttga<br>tcgaggaagaagaagaggaaacgaagctgaagcccattgaccagtacatgagcctgaacgctaaagacggaaactactgccgaaggttgg<br>atttttttctgttgtaagtgggacgagctgggggcggggaggatacactatacgggtagcaaagagtataataggtggataaggatactcgccgc<br>gcaaaaagggttcaaactgacccagcatggacttttccggaacaacatactcctggagtctttcaacgaaaggcgaatcttcgaactcctgaac<br>cttaagtatgccgagccggagcaccgcaatatagagtgggaaaaaaagacgggatga |
| SEQ ID NO 29 3xFlag_NLS_ XseA *Escherichia coli* | atggactataaggaccacgacggagactacaaggatcatgatattgattacaaagacgatgacgataagatggccccaaagaagaagcggaa<br>ggtcggtatccacggagtcccagcagccctgcctagtcagagccccgcaatatttacagtgagtcgccttaaccaaaccgttcgactgttgctc<br>gagcacgaaatggggcaagtctggatctccggggaaatatcaaattttacgcagccagcctccggtcactggtacttcactcttaaagatgaca<br>cggcgcaagtacgctgcgccatgtttcggaacagcaatagacgagtgacgttccggccacaacatggacagcaagtactcgtcagggccaat<br>atcactctttatgagccgcgcggtgactatcaaataattgtcgaatctatgcaacccgcgggggagggtttgctccagcaaaagtatgagcaact<br>caaagcgaagctccaggcagaaggcctgttcgaccagcagtataaaaaaccgctcccgtcacccgctcattgtgttggcgtcataacctctaa<br>gacgggtgctgcgttgcacgacattcttcatgtgcttaagcgccgagacccatctctgcctgttatcatctacccagcggccgttcaaggcgatg<br>acgctcctgggcagatagtaagagcaatagaactggcgaatcagcggaacgaatgtgatgtgctgatcgttgggcgcggcggagggagctt<br>ggaagatctttggtccttcaacgatgagcgcgtcgcacgggcaatcttcaccagccggataccggtagtttcagcggtggggcatgagacgga<br>cgtcacaatcgccgattttgtagccgacctgagagcaccgacgccatcagcggcagcagaagtcgtcagccgcaatcagcaggagctgctc<br>aggcaggtccagagcacccggcaacgcctcgagatggcgatggattactatcttgccaatcgaacacgacgattcacccagattcaccaccg<br>gttgcagcagcaacatccccaacttcggctggcccgacagcaaacaatgctggaacgcctccagaaacggatgagttttgctctggaaaatca<br>gttgaagcgaactggtcaacagcagcaaagactgactcagcgcctcaatcagcaaaatccccaacctaagatccatcgggcacaaacccgca<br>ttcaacaactggagtatagactggctgagaccttgcgcgcccagctctccgcaactcgcgagaggttcggaaatgccgtaacgcatttggagg<br>ccgtgagcccactgtcaaccctcgctcggggctactccgtgacgactgccacggacggcaatgtgctcaaaaaggtaaaacaagtcaaagct |

TABLE 1-continued

| SEQ ID NO | SEQUENCE |
|---|---|
| | ggagaaatgcttactactcggctcgaagacggatggatcgaaagtgaagtcaaaaatatacaacctgtcaagaagagtcggaaaaaggtgcat |
| | tga |
| SEQ ID NO | atggactataaggaccacgacggagactacaaggatcatgatattgattacaaagacgatgacgataagatggccccaaagaagaagcggaa |
| 30 | ggtcggtatccacggagtcccagcagccccgaaaaaaaacgaagcccccgcctcctttgagaaagcacttagcgagctggagcagatcgtg |
| 3xFlag_NLS_ | acgcgcttggaatcaggggatctccctttggaagaggcattgaatgagtttgagcgaggagttcagctcgctagacaaggccaggccaaactt |
| XseB | caacaggcggaacagcgagtccagattctccttagtgataatgaggatgcctctctgacaccgttcacgccagacaacgagtga |
| *Escherichia* | |
| *coli* | |
| SEQ ID NO | atggactataaggaccacgacggagactacaaggatcatgatattgattacaaagacgatgacgataagatggccccaaagaagaagcggaa |
| 31 | ggtcggtatccacggagtcccagcagccgacaagaagtacagcatcggcctggacatcggcaccaactctgtgggctgggccgtgatcacc |
| 3xFlag-NLS- | gacgagtacaaggtgcccagcaagaaattcaaggtgctgggcaacaccgaccggcacagcatcaagaagaacctgatcggagccctgctg |
| *SpCas9*-NLS | ttcgacagcggcgaaacagccgaggccacccggctgaagagaaccgccagaagaagatacaccagacggaagaaccggatctgctatct |
| (Addgene | gcaagagatcttcagcaacgagatggccaaggtggacgacagcttcttccacagactggaagagtccttcctggtggaagaggataagaagc |
| #1000000055) | acgagcggcaccccatcttcggcaacatcgtggacgaggtggcctaccacgagaagtaccccaccatctaccacctgagaaagaaactggt |
| *Streptococcus* | ggacagcaccgacaaggccgacctgcggctgatctatctggccctggcccacatgatcaagttccggggccacttcctgatcgagggcgacc |
| *pyogenes* | tgaaccccgacaacagcgacgttgacaagctgttcatccagctggtgcagacctacaaccagctgttcgaggaaaaccccatcaacgccagc |
| | ggcgtggacgccaaggccatcctgtctgccagactgagcaagagcagacggctggaaaatctgatcgcccagctgcccggcgagaagaag |
| | aatggcctgttcggaaacctgattgccctgagcctgggcctgacccccaacttcaagagcaacttcgacctggccgaggatgccaaactgcag |
| | ctgagcaaggacacctacgacgacgacctggacaacctgctggcccagatcggcgaccagtacgccgacctgtttctggccgccaagaacc |
| | tgtccgacgccatcctgctgagcgacatcctgagagtgaacaccgagatcaccaaggcccccctgagcgcctctatgatcaagagatacgac |
| | gagcaccaccaggacctgaccctgctgaaagctctcgtgcggcagcagctgcctgagaagtacaaagagattttcttcgaccagagcaagaa |
| | cggctacgccggctacattgacggcggagccagccaggaagagttctacaagttcatcaagcccatcctggaaaagatggacggcaccgag |
| | gaactgctcgtgaagctgaacagagaggacctgctgcggaagcagcggaccttcgacaacggcagcatcccccaccagatccacctggga |
| | gagctgcacgccattctgcggcggcaggaagatttttacccattcctgaaggacaaccgggaaaagatcgagaagatcctgaccttccgcatc |
| | ccctactacgtgggccctctggccaggggaaacagcagattcgcctggatgaccagaaagagcgaggaaaccatcaccccctggaacttcg |
| | aggaagtggtggacaagggcgcttccgcccagagcttcatcgagcggatgaccaacttcgataagaacctgcccaacgagaaggtgctgcc |
| | caagcacagcctgctgtacgagtacttcaccgtgtataacgagctgaccaaagtgaaatacgtgaccgagggaatgagaaagcccgccttcct |
| | gagcggcgagcagaaaaaggccatcgtggacctgctgttcaagaccaaccggaaagtgaccgtgaagcagctgaaagaggactacttcaa |
| | gaaaatcgagtgcttcgactccgtggaaatctccggcgtggaagatcggttcaacgcctccctgggcacataccacgatctgctgaaaattatc |
| | aaggacaaggacttcctggacaatgaggaaaacgaggacattctggaagatatcgtgctgaccctgacactgtttgaggacagagagatgatc |
| | gaggaacggctgaaaacctatgcccacctgttcgacgacaaagtgatgaagcagctgaagcggcggagatacaccggctggggcaggctg |
| | agccggaagctgatcaacggcatccgggacaagcagtccggcaagacaatcctggatttcctgaagtccgacggcttcgccaacagaaactt |
| | catgcagctgatccacgacgacagcctgacctttaaagaggacatccagaaagcccaggtgtccggccagggcgatagcctgcacgagcac |
| | attgccaatctggccggcagccccgccattaagaagggcatcctgcagacagtgaaggtggtggacgagctcgtgaaagtgatgggccggc |
| | acaagcccgagaacatcgtgatcgaaatggccagagagaaccagaccacccagaagggacagaagaacagccgcgagagaatgaagcg |
| | gatcgaagagggcatcaaagagctgggcagccagatcctgaaagaacaccccgtggaaaacacccagctgcagaacgagaagctgtacct |
| | gtactacctgcagaatgggcgggatatgtacgtggaccaggaactggacatcaaccggctgtccgactacgatgtggaccatatcgtgcctca |
| | gagctttctgaaggacgactccatcgacaacaaggtgctgaccagaagcgacaagaaccggggcaagagcgacaacgtgccctccgaaga |
| | ggtcgtgaagaagatgaagaactactggcggcagctgctgaacgccaagctgattacccagagaaagttcgacaatctgaccaaggccgag |
| | agaggcggcctgagcgaactggataaggccggcttcatcaagagacagctggtggaaacccggcagatcacaaagcacgtggcacagatc |
| | ctggactcccggatgaacactaagtacgacgagaatgacaagctgatccgggaagtgaaagtgatcaccctgaagtccaagctggtgtccga |
| | tttccggaaggatttccagttttacaaagtgcgcgagatcaacaactaccaccacgcccacgacgcctacctgaacgccgtcgtgggaaccgc |
| | cctgatcaaaaagtaccctaagctggaaagcgagttcgtgtacggcgactacaaggtgtacgacgtgcggaagatgatcgccaagagcgag |
| | caggaaatcggcaaggctaccgccaagtacttcttctacagcaacatcatgaactttttcaagaccgagattaccctggccaacggcgagatcc |
| | ggaagcggcctctgatcgagacaaacggcgaaaccggggagatcgtgtgggataagggccgggattttgccaccgtgcggaaagtgctga |
| | gcatgccccaagtgaatatcgtgaaaaagaccgaggtgcagacaggcggcttcagcaaagagtctatcctgcccaagaggaacagcgataa |
| | gctgatcgccagaaagaaggactgggaccctaagaagtacggcggcttcgacagccccaccgtggcctattctgtgctggtggtggccaaag |
| | tggaaaagggcaagtccaagaaactgaagagtgtgaaagagctgctggggatcaccatcatggaaagaagcagcttcgagaagaatcccat |
| | cgactttctggaagccaagggctacaaagaagtgaaaaaggacctgatcatcaagctgcctaagtactccctgttcgagctggaaaacggccg |

TABLE 1-continued

| SEQ ID NO | SEQUENCE |
|---|---|
| | gaagagaatgctggcctctgccggcgaactgcagaagggaaacgaactggccctgccctccaaatatgtgaacttcctgtacctggccagcc<br>actatgagaagctgaagggctcccccgaggataatgagcagaaacagctgtttgtggaacagcacaagcactacctggacgagatcatcgag<br>cagatcagcgagttctccaagagagtgatcctggccgacgctaatctggacaaagtgctgtccgcctacaacaagcaccgggataagcccat<br>cagagagcaggccgagaatatcatccacctgtttaccctgaccaatctgggagcccctgccgccttcaagtactttgacaccaccatcgaccgg<br>aagaggtacaccagcaccaaagaggtgctggacgccaccctgatccaccagagcatcaccggcctgtacgagacacggatcgacctgtctc<br>agctgggaggcgacaaaaggccggcggccacgaaaaaggccggccaggcaaaaaagaaaaagtaa |
| SEQ ID NO 32<br>3xFlag-NLS-SpCas9(ΔF916)-NLS<br>*Streptococcus pyogenes* | atggactataaggaccacgacggagactacaaggatcatgatattgattacaaagacgatgacgataagatggccccaaagaagaagcggaa<br>ggtcggtatccacggagtcccagcagccgacaagaagtacagcatcggcctggacatcggcaccaactctgtgggctgggccgtgatcacc<br>gacgagtacaaggtgcccagcaagaaattcaaggtgctgggcaacaccgaccggcacagcatcaagaagaacctgatcggagccctgctg<br>ttcgacagcggcgaaacagccgaggccacccggctgaagagaaccgccagaagaagatacaccagacggaagaaccggatctgctatct<br>gcaagagatcttcagcaacgagatggccaaggtggacgacagcttcttccacagactggaagagtccttcctggtggaagaggataagaagc<br>acgagcggcaccccatcttcggcaacatcgtggacgaggtggcctaccacgagaagtaccccaccatctaccacctgagaaagaaactggt<br>ggacagcaccgacaaggccgacctgcggctgatctatctggccctggcccacatgatcaagttccggggccacttcctgatcgagggcgacc<br>tgaaccccgacaacagcgacgttgacaagctgttcatccagctggtgcagacctacaaccagctgttcgaggaaaaccccatcaacgccagc<br>ggcgtggacgccaaggccatcctgtctgccagactgagcaagagcagacggctggaaaatctgatcgcccagctgcccggcgagaagaag<br>aatggcctgttcggaaacctgattgccctgagcctgggcctgacccccaacttcaagagcaacttcgacctggccgaggatgccaaactgcag<br>ctgagcaaggacacctacgacgacgacctggacaacctgctggcccagatcggcgaccagtacgccgacctgtttctggccgccaagaacc<br>tgtccgacgccatcctgctgagcgacatcctgagagtgaacaccgagatcaccaaggcccccctgagcgcctctatgatcaagagatacgac<br>gagcaccaccaggacctgaccctgctgaaagctctcgtgcggcagcagctgcctgagaagtacaaagagattttcttcgaccagagcaagaa<br>cggctacgccggctacattgacggcggagccagccaggaagagttctacaagttcatcaagcccatcctggaaaagatggacggcaccgag<br>gaactgctcgtgaagctgaacagagaggacctgctgcggaagcagcggaccttcgacaacggcagcatcccccaccagatccacctggga<br>gagctgcacgccattctgcggcggcaggaagatttttacccattcctgaaggacaaccgggaaaagatcgagaagatcctgaccttccgcatc<br>ccctactacgtgggccctctggccaggggaaacagcagattcgcctggatgaccagaaagagcgaggaaaccatcaccccctggaacttcg<br>aggaagtggtggacaagggcgcttccgcccagagcttcatcgagcggatgaccaacttcgataagaacctgcccaacgagaaggtgctgcc<br>caagcacagcctgctgtacgagtacttcaccgtgtataacgagctgaccaaagtgaaatacgtgaccgagggaatgagaaagcccgccttcct<br>gagcggcgagcagaaaaaggccatcgtggacctgctgttcaagaccaaccggaaagtgaccgtgaagcagctgaaagaggactacttcaa<br>gaaaatcgagtgcttcgactccgtggaaatctccggcgtggaagatcggttcaacgcctccctgggcacataccacgatctgctgaaaattatc<br>aaggacaaggacttcctggacaatgaggaaaacgaggacattctggaagatatcgtgctgaccctgacactgtttgaggacagagagatgatc<br>gaggaacggctgaaaacctatgcccacctgttcgacgacaaagtgatgaagcagctgaagcggcggagatacaccggctggggcaggctg<br>agccggaagctgatcaacggcatccgggacaagcagtccggcaagacaatcctggatttcctgaagtccgacggcttcgccaacagaaactt<br>catgcagctgatccacgacgacagcctgacctttaaagaggacatccagaaagcccaggtgtccggccagggcgatagcctgcacgagcac<br>attgccaatctggccggcagccccgccattaagaagggcatcctgcagacagtgaaggtggtggacgagctcgtgaaagtgatgggccggc<br>acaagcccgagaacatcgtgatcgaaatggccagagagaaccagaccacccagaagggacagaagaacagccgcgagagaatgaagcg<br>gatcgaagagggcatcaaagagctgggcagccagatcctgaaagaacaccccgtggaaaacacccagctgcagaacgagaagctgtacct<br>gtactacctgcagaatgggcgggatatgtacgtggaccaggaactggacatcaaccggctgtccgactacgatgtggaccatatcgtgcctca<br>gagctttctgaaggacgactccatcgacaacaaggtgctgaccagaagcgacaagaaccggggcaagagcgacaacgtgccctccgaaga<br>ggtcgtgaagaagatgaagaactactggcggcagctgctgaacgccaagctgattacccagagaaagttcgacaatctgaccaaggccgag<br>agaggcggcctgagcgaactggataaggccggcatcaagagacagctggtggaaacccggcagatcacaaagcacgtggcacagatcct<br>ggactcccggatgaacactaagtacgacgagaatgacaagctgatccgggaagtgaaagtgatcaccctgaagtccaagctggtgtccgattt<br>ccggaaggatttccagttttacaaagtgcgcgagatcaacaactaccaccacgcccacgacgcctacctgaacgccgtcgtgggaaccgccc<br>tgatcaaaaagtaccctaagctggaaagcgagttcgtgtacggcgactacaaggtgtacgacgtgcggaagatgatcgccaagagcgagca<br>ggaaatcggcaaggctaccgccaagtacttcttctacagcaacatcatgaactttttcaagaccgagattaccctggccaacggcgagatccgg<br>aagcggcctctgatcgagacaaacggcgaaaccggggagatcgtgtgggataagggccgggattttgccaccgtgcggaaagtgctgagc<br>atgccccaagtgaatatcgtgaaaaagaccgaggtgcagacaggcggcttcagcaaagagtctatcctgcccaagaggaacagcgataagc<br>tgatcgccagaaagaaggactgggaccctaagaagtacggcggcttcgacagccccaccgtggcctattctgtgctggtggtggccaaagtg<br>gaaaagggcaagtccaagaaactgaagagtgtgaaagagctgctggggatcaccatcatggaaagaagcagcttcgagaagaatcccatcg<br>actttctggaagccaagggctacaaagaagtgaaaaaggacctgatcatcaagctgcctaagtactccctgttcgagctggaaaacggccgga<br>agagaatgctggcctctgccggcgaactgcagaagggaaacgaactggccctgccctccaaatatgtgaacttcctgtacctggccagccact<br>atgagaagctgaagggctcccccgaggataatgagcagaaacagctgtttgtggaacagcacaagcactacctggacgagatcatcgagca<br>gatcagcgagttctccaagagagtgatcctggccgacgctaatctggacaaagtgctgtccgcctacaacaagcaccgggataagcccatca |

TABLE 1-continued

| SEQ ID NO | SEQUENCE |
|---|---|
| | gagagcaggccgagaatatcatccacctgtttaccctgaccaatctgggagcccctgccgccttcaagtactttgacaccaccatcgaccggaa<br>gaggtacaccagcaccaaagaggtgctggacgccaccctgatccaccagagcatcaccggcctgtacgagacacggatcgacctgtctcag<br>ctgggaggcgacaaaaggccggcggccacgaaaaaggccggccaggcaaaaaagaaaaagtaa |
| SEQ ID NO 33<br>3xFlag-NLS-SpCas9(G915F)-NLS<br>*Streptococcus pyogenes* | atggactataaggaccacgacggagactacaaggatcatgatattgattacaaagacgatgacgataagatggccccaaagaagaagcggaa<br>ggtcggtatccacggagtcccagcagccgacaagaagtacagcatcggcctggacatcggcaccaactctgtgggctgggccgtgatcacc<br>gacgagtacaaggtgcccagcaagaaattcaaggtgctgggcaacaccgaccggcacagcatcaagaagaacctgatcggagccctgctg<br>ttcgacagcggcgaaacagccgaggccacccggctgaagagaaccgccagaagaagatacaccagacggaagaaccggatctgctatct<br>gcaagagatcttcagcaacgagatggccaaggtggacgacagcttcttccacagactggaagagtccttcctggtggaagaggataagaagc<br>acgagcggcaccccatcttcggcaacatcgtggacgaggtggcctaccacgagaagtaccccaccatctaccacctgagaaagaaactggt<br>ggacagcaccgacaaggccgacctgcggctgatctatctggccctggcccacatgatcaagttccggggccacttcctgatcgagggcgacc<br>tgaaccccgacaacagcgacgttgacaagctgttcatccagctggtgcagacctacaaccagctgttcgaggaaaaccccatcaacgccagc<br>ggcgtggacgccaaggccatcctgtctgccagactgagcaagagcagacggctggaaaatctgatcgcccagctgcccggcgagaagaag<br>aatggcctgttcggaaacctgattgccctgagcctgggcctgacccccaacttcaagagcaacttcgacctggccgaggatgccaaactgcag<br>ctgagcaaggacacctacgacgacgacctggacaacctgctggcccagatcggcgaccagtacgccgacctgtttctggccgccaagaacc<br>tgtccgacgccatcctgctgagcgacatcctgagagtgaacaccgagatcaccaaggcccccctgagcgcctctatgatcaagagatacgac<br>gagcaccaccaggacctgaccctgctgaaagctctcgtgcggcagcagctgcctgagaagtacaaagagattttcttcgaccagagcaagaa<br>cggctacgccggctacattgacggcggagccagccaggaagagttctacaagttcatcaagcccatcctggaaaagatggacggcaccgag<br>gaactgctcgtgaagctgaacagagaggacctgctgcggaagcagcggaccttcgacaacggcagcatcccccaccagatccacctggga<br>gagctgcacgccattctgcggcggcaggaagatttttacccattcctgaaggacaaccgggaaaagatcgagaagatcctgaccttccgcatc<br>ccctactacgtgggccctctggccaggggaaacagcagattcgcctggatgaccagaaagagcgaggaaaccatcacccccctggaacttcg<br>aggaagtggtggacaagggcgcttccgcccagagcttcatcgagcggatgaccaacttcgataagaacctgcccaacgagaaggtgctgcc<br>caagcacagcctgctgtacgagtacttcaccgtgtataacgagctgaccaaagtgaaatacgtgaccgagggaatgagaaagcccgccttcct<br>gagcggcgagcagaaaaaggccatcgtggacctgctgttcaagaccaaccggaaagtgaccgtgaagcagctgaaagaggactacttcaa<br>gaaaatcgagtgcttcgactccgtggaaatctccggcgtggaagatcggttcaacgcctccctgggcacataccacgatctgctgaaaattatc<br>aaggacaaggacttcctggacaatgaggaaaacgaggacattctggaagatatcgtgctgaccctgacactgtttgaggacagagagatgatc<br>gaggaacggctgaaaacctatgcccacctgttcgacgacaaagtgatgaagcagctgaagcggcggagatacaccggctggggcaggctg<br>agccggaagctgatcaacggcatccgggacaagcagtccggcaagacaatcctggatttcctgaagtccgacggcttcgccaacagaaactt<br>catgcagctgatccacgacgacagcctgacctttaaagaggacatccagaaagcccaggtgtccggccagggcgatagcctgcacgagcac<br>attgccaatctggccggcagccccgccattaagaagggcatcctgcagacagtgaaggtggtggacgagctcgtgaaagtgatgggccggc<br>acaagcccgagaacatcgtgatcgaaatggccagagagaaccagaccacccagaagggacagaagaacagccgcgagagaatgaagcg<br>gatcgaagagggcatcaaagagctgggcagccagatcctgaaagaacaccccgtggaaaacacccagctgcagaacgagaagctgtacct<br>gtactacctgcagaatgggcgggatatgtacgtggaccaggaactggacatcaaccggctgtccgactacgatgtggaccatatcgtgcctca<br>gagctttctgaaggacgactccatcgacaacaaggtgctgaccagaagcgacaagaaccggggcaagagcgacaacgtgccctccgaaga<br>ggtcgtgaagaagatgaagaactactggcggcagctgctgaacgccaagctgattacccagagaaagttcgacaatctgaccaaggccgag<br>agaggcggcctgagcgaactggataaggcctttttcatcaagagacagctggtggaaacccggcagatcacaaagcacgtggcacagatcct<br>ggactcccggatgaacactaagtacgacgagaatgacaagctgatccgggaagtgaaagtgatcaccctgaagtccaagctggtgtccgattt<br>ccggaaggatttccagttttacaaagtgcgcgagatcaacaactaccaccacgcccacgacgcctacctgaacgccgtcgtgggaaccgccc<br>tgatcaaaaagtaccctaagctggaaagcgagttcgtgtacggcgactacaaggtgtacgacgtgcggaagatgatcgccaagagcgagca<br>ggaaatcggcaaggctaccgccaagtacttcttctacagcaacatcatgaactttttcaagaccgagattaccctggccaacggcgagatccgg<br>aagcggcctctgatcgagacaaacggcgaaaccggggagatcgtgtgggataagggccgggattttgccaccgtgcggaaagtgctgagc<br>atgccccaagtgaatatcgtgaaaaagaccgaggtgcagacaggcggcttcagcaaagagtctatcctgcccaagaggaacagcgataagc<br>tgatcgccagaaagaaggactgggaccctaagaagtacggcggcttcgacagccccaccgtggcctattctgtgctggtggtggccaaagtg<br>gaaaagggcaagtccaagaaactgaagagtgtgaaagagctgctggggatcaccatcatggaaagaagcagcttcgagaagaatcccatcg<br>actttctggaagccaagggctacaaagaagtgaaaaaggacctgatcatcaagctgcctaagtactccctgttcgagctggaaaacggccgga<br>agagaatgctggcctctgccggcgaactgcagaagggaaacgaactggccctgccctccaaatatgtgaacttcctgtacctggccagccact<br>atgagaagctgaagggctcccccgaggataatgagcagaaacagctgtttgtggaacagcacaagcactacctggacgagatcatcgagca<br>gatcagcgagttctccaagagagtgatcctggccgacgctaatctggacaaagtgctgtccgcctacaacaagcaccgggataagcccatca<br>gagagcaggccgagaatatcatccacctgtttaccctgaccaatctgggagcccctgccgccttcaagtactttgacaccaccatcgaccggaa<br>gaggtacaccagcaccaaagaggtgctggacgccaccctgatccaccagagcatcaccggcctgtacgagacacggatcgacctgtctcag<br>ctgggaggcgacaaaaggccggcggccacgaaaaaggccggccaggcaaaaaagaaaaagtaa |

TABLE 1-continued

| SEQ ID NO | SEQUENCE |
|---|---|
| SEQ ID NO 34 3xFlag-NLS-SpCas9(Q920P)-NLS *Streptococcus pyogenes* | atggactataaggaccacgacggagactacaaggatcatgatattgattacaaagacgatgacgataagatggccccaaagaagaagcggaa<br>ggtcggtatccacggagtcccagcagccgacaagaagtacagcatcggcctggacatcggcaccaactctgtgggctgggccgtgatcacc<br>gacgagtacaaggtgcccagcaagaaattcaaggtgctgggcaacaccgaccggcacagcatcaagaagaacctgatcggagccctgctg<br>ttcgacagcggcgaaacagccgaggccacccggctgaagagaaccgccagaagaagatacaccagacggaagaaccggatctgctatct<br>gcaagagatcttcagcaacgagatggccaaggtggacgacagcttcttccacagactggaagagtccttcctggtggaagaggataagaagc<br>acgagcggcaccccatcttcggcaacatcgtggacgaggtggcctaccacgagaagtaccccaccatctaccacctgagaaagaaactggt<br>ggacagcaccgacaaggccgacctgcggctgatctatctggccctggcccacatgatcaagttccggggccacttcctgatcgagggcgacc<br>tgaaccccgacaacagcgacgttgacaagctgttcatccagctggtgcagacctacaaccagctgttcgaggaaaaccccatcaacgccagc<br>ggcgtggacgccaaggccatcctgtctgccagactgagcaagagcagacggctggaaaatctgatcgcccagctgcccggcgagaagaag<br>aatggcctgttcggaaacctgattgccctgagcctgggcctgacccccaacttcaagagcaacttcgacctggccgaggatgccaaactgcag<br>ctgagcaaggacacctacgacgacgacctggacaacctgctggcccagatcggcgaccagtacgccgacctgtttctggccgccaagaacc<br>tgtccgacgccatcctgctgagcgacatcctgagagtgaacaccgagatcaccaaggcccccctgagcgcctctatgatcaagagatacgac<br>gagcaccaccaggacctgaccctgctgaaagctctcgtgcggcagcagctgcctgagaagtacaaagagattttcttcgaccagagcaagaa<br>cggctacgccggctacattgacggcggagccagccaggaagagttctacaagttcatcaagcccatcctggaaaagatggacggcaccgag<br>gaactgctcgtgaagctgaacagagaggacctgctgcggaagcagcggaccttcgacaacggcagcatcccccaccagatccacctggga<br>gagctgcacgccattctgcggcggcaggaagatttttacccattcctgaaggacaaccgggaaaagatcgagaagatcctgaccttccgcatc<br>ccctactacgtgggccctctggccaggggaaacagcagattcgcctggatgaccagaaagagcgaggaaaccatcaccccctggaacttcg<br>aggaagtggtggacaagggcgcttccgcccagagcttcatcgagcggatgaccaacttcgataagaacctgcccaacgagaaggtgctgcc<br>caagcacagcctgctgtacgagtacttcaccgtgtataacgagctgaccaaagtgaaatacgtgaccgagggaatgagaaagcccgccttcct<br>gagcggcgagcagaaaaaggccatcgtggacctgctgttcaagaccaaccggaaagtgaccgtgaagcagctgaaagaggactacttcaa<br>gaaaatcgagtgcttcgactccgtggaaatctccggcgtggaagatcggttcaacgcctccctgggcacataccacgatctgctgaaaattatc<br>aaggacaaggacttcctggacaatgaggaaaacgaggacattctggaagatatcgtgctgaccctgacactgtttgaggacagagagatgatc<br>gaggaacggctgaaaacctatgcccacctgttcgacgacaaagtgatgaagcagctgaagcggcggagatacaccggctggggcaggctg<br>agccggaagctgatcaacggcatccgggacaagcagtccggcaagacaatcctggatttcctgaagtccgacggcttcgccaacagaaactt<br>catgcagctgatccacgacgacagcctgacctttaaagaggacatccagaaagcccaggtgtccggccagggcgatagcctgcacgagcac<br>attgccaatctggccggcagccccgccattaagaagggcatcctgcagacagtgaaggtggtggacgagctcgtgaaagtgatgggccggc<br>acaagcccgagaacatcgtgatcgaaatggccagagagaaccagaccacccagaagggacagaagaacagccgcgagagaatgaagcg<br>gatcgaagagggcatcaaagagctgggcagccagatcctgaaagaacaccccgtggaaaacacccagctgcagaacgagaagctgtacct<br>gtactacctgcagaatgggcgggatatgtacgtggaccaggaactggacatcaaccggctgtccgactacgatgtggaccatatcgtgcctca<br>gagctttctgaaggacgactccatcgacaacaaggtgctgaccagaagcgacaagaaccggggcaagagcgacaacgtgccctccgaaga<br>ggtcgtgaagaagatgaagaactactggcggcagctgctgaacgccaagctgattacccagagaaagttcgacaatctgaccaaggccgag<br>agaggcggcctgagcgaactggataaggccggcttcatcaagagacccctggtggaaacccggcagatcacaaagcacgtggcacagatc<br>ctggactcccggatgaacactaagtacgacgagaatgacaagctgatccgggaagtgaaagtgatcaccctgaagtccaagctggtgtccga<br>tttccggaaggatttccagttttacaaagtgcgcgagatcaacaactaccaccacgcccacgacgcctacctgaacgccgtcgtgggaaccgc<br>cctgatcaaaaagtaccctaagctggaaagcgagttcgtgtacggcgactacaaggtgtacgacgtgcggaagatgatcgccaagagcgag<br>caggaaatcggcaaggctaccgccaagtacttcttctacagcaacatcatgaactttttcaagaccgagattaccctggccaacggcgagatcc<br>ggaagcggcctctgatcgagacaaacggcgaaaccggggagatcgtgtgggataagggccgggatttgccaccgtgcggaaagtgctga<br>gcatgccccaagtgaatatcgtgaaaaagaccgaggtgcagacaggcggcttcagcaaagagtctatcctgcccaagaggaacagcgataa<br>gctgatcgccagaaagaaggactgggaccctaagaagtacggcggcttcgacagccccaccgtggcctattctgtgctggtggtggccaaag<br>tggaaaagggcaagtccaagaaactgaagagtgtgaaagagctgctggggatcaccatcatggaaagaagcagcttcgagaagaatcccat<br>cgactttctggaagccaagggctacaaagaagtgaaaaaggacctgatcatcaagctgcctaagtactccctgttcgagctggaaaacggccg<br>gaagagaatgctggcctctgccggcgaactgcagaagggaaacgaactggccctgccctccaaatatgtgaacttcctgtacctggccagcc<br>actatgagaagctgaagggctcccccgaggataatgagcagaaacagctgtttgtggaacagcacaagcactacctggacgagatcatcgag<br>cagatcagcgagttctccaagagagtgatcctggccgacgctaatctggacaaagtgctgtccgcctacaacaagcaccgggataagcccat<br>cagagagcaggccgagaatatcatccacctgtttaccctgaccaatctgggagcccctgccgccttcaagtactttgacaccaccatcgaccgg<br>aagaggtacaccagcaccaaagaggtgctggacgccaccctgatccaccagagcatcaccggcctgtacgagacacggatcgacctgtctc<br>agctgggaggcgacaaaaggccggcggccacgaaaaaggccggccaggcaaaaaagaaaaagtaa |
| SEQ ID NO 35 | atggactataaggaccacgacggagactacaaggatcatgatattgattacaaagacgatgacgataagatggccccaaagaagaagcggaa<br>ggtcggtatccacggagtcccagcagccgacaagaagtacagcatcggcctggacatcggcaccaactctgtgggctgggccgtgatcacc |

TABLE 1-continued

| SEQ ID NO | SEQUENCE |
|---|---|
| 3xFlag-NLS-<br>SpCas9(F916P)-<br>NLS:<br>*Streptococcus*<br>*pyogenes* | gacgagtacaaggtgcccagcaagaaattcaaggtgctgggcaacaccgaccggcacagcatcaagaagaacctgatcggagccctgctg<br>ttcgacagcggcgaaacagccgaggccacccggctgaagagaaccgccagaagaagatacaccagacggaagaaccggatctgctatct<br>gcaagagatcttcagcaacgagatggccaaggtggacgacagcttcttccacagactggaagagtccttcctggtggaagaggataagaagc<br>acgagcggcaccccatcttcggcaacatcgtggacgaggtggcctaccacgagaagtaccccaccatctaccacctgagaaagaaactggt<br>ggacagcaccgacaaggccgacctgcggctgatctatctggccctggcccacatgatcaagttccggggccacttcctgatcgagggcgacc<br>tgaaccccgacaacagcgacgtggacaagctgttcatccagctggtgcagacctacaaccagctgttcgaggaaaaccccatcaacgccagc<br>ggcgtggacgccaaggccatcctgtctgccagactgagcaagagcagacggctggaaaatctgatcgcccagctgcccggcgagaagaag<br>aatggcctgttcggaaacctgattgccctgagcctgggcctgacccccaacttcaagagcaacttcgacctggccgaggatgccaaactgcag<br>ctgagcaaggacacctacgacgacgacctggacaacctgctggcccagatcggcgaccagtacgccgacctgtttctggccgccaagaacc<br>tgtccgacgccatcctgctgagcgacatcctgagagtgaacaccgagatcaccaaggcccccctgagcgcctctatgatcaagagatacgac<br>gagcaccaccaggacctgaccctgctgaaagctctcgtgcggcagcagctgcctgagaagtacaaagagattttcttcgaccagagcaagaa<br>cggctacgccggctacattgacggcggagccagccaggaagagttctacaagttcatcaagcccatcctggaaaagatggacggcaccgag<br>gaactgctcgtgaagctgaacagagaggacctgctgcggaagcagcggaccttcgacaacggcagcatcccccaccagatccacctggga<br>gagctgcacgccattctgcggcggcaggaagatttttacccattcctgaaggacaaccgggaaaagatcgagaagatcctgaccttccgcatc<br>ccctactacgtgggccctctggccaggggaaacagcagattcgcctggatgaccagaaagagcgaggaaaccatcaccccctggaacttcg<br>aggaagtggtggacaagggcgcttccgcccagagcttcatcgagcggatgaccaacttcgataagaacctgcccaacgagaaggtgctgcc<br>caagcacagcctgctgtacgagtacttcaccgtgtataacgagctgaccaaagtgaaatacgtgaccgagggaatgagaaagcccgccttcct<br>gagcggcgagcagaaaaaggccatcgtggacctgctgttcaagaccaaccggaaagtgaccgtgaagcagctgaaagaggactacttcaa<br>gaaaatcgagtgcttcgactccgtggaaatctccggcgtggaagatcggttcaacgcctccctgggcacataccacgatctgctgaaaattatc<br>aaggacaaggacttcctggacaatgaggaaaacgaggacattctggaagatatcgtgctgaccctgacactgtttgaggacagagagatgatc<br>gaggaacggctgaaaacctatgcccacctgttcgacgacaaagtgatgaagcagctgaagcggcggagatacaccggctggggcaggctg<br>agccggaagctgatcaacggcatccgggacaagcagtccggcaagacaatcctggatttcctgaagtccgacggcttcgccaacagaaactt<br>catgcagctgatccacgacgacagcctgacctttaaagaggacatccagaaagcccaggtgtccggccagggcgatagcctgcacgagcac<br>attgccaatctggccggcagccccgccattaagaagggcatcctgcagacagtgaaggtggtggacgagctcgtgaaagtgatgggccggc<br>acaagcccgagaacatcgtgatcgaaatggccagagagaaccagaccacccagaagggacagaagaacagccgcgagagaatgaagcg<br>gatcgaagagggcatcaaagagctgggcagccagatcctgaaagaacaccccgtggaaaacacccagctgcagaacgagaagctgtacct<br>gtactacctgcagaatgggcgggatatgtacgtggaccaggaactggacatcaaccggctgtccgactacgatgtggaccatatcgtgcctca<br>gagctttctgaaggacgactccatcgacaacaaggtgctgaccagaagcgacaagaaccggggcaagagcgacaacgtgccctccgaaga<br>ggtcgtgaagaagatgaagaactactggcggcagctgctgaacgccaagctgattacccagagaaagttcgacaatctgaccaaggccgag<br>agaggcggcctgagcgaactggataaggccggccccatcaagagacagctggtggaaacccggcagatcacaaagcacgtggcacagat<br>cctggactcccggatgaacactaagtacgacgagaatgacaagctgatccgggaagtgaaagtgatcaccctgaagtccaagctggtgtccg<br>atttccggaaggatttccagttttacaaagtgcgcgagatcaacaactaccaccacgcccacgacgcctacctgaacgccgtcgtgggaaccg<br>ccctgatcaaaaagtaccctaagctggaaagcgagttcgtgtacggcgactacaaggtgtacgacgtgcggaagatgatcgccaagagcga<br>gcaggaaatcggcaaggctaccgccaagtacttcttctacagcaacatcatgaactttttcaagaccgagattaccctggccaacggcgagatc<br>cggaagcggcctctgatcgagacaaacggcgaaaccggggagatcgtgtgggataagggccgggattttgccaccgtgcggaaagtgctg<br>agcatgccccaagtgaatatcgtgaaaaagaccgaggtgcagacaggcggcttcagcaaagagtctatcctgcccaagaggaacagcgata<br>agctgatcgccagaaagaaggactgggaccctaagaagtacggcggcttcgacagccccaccgtggcctattctgtgctggtggtggccaaa<br>gtggaaaagggcaagtccaagaaactgaagagtgtgaaagagctgctggggatcaccatcatggaaagaagcagcttcgagaagaatccca<br>tcgactttctggaagccaagggctacaaagaagtgaaaaaggacctgatcatcaagctgcctaagtactccctgttcgagctggaaaacggcc<br>ggaagagaatgctggcctctgccggcgaactgcagaagggaaacgaactggccctgccctccaaatatgtgaacttcctgtacctggccagc<br>cactatgagaagctgaagggctcccccgaggataatgagcagaaacagctgtttgtggaacagcacaagcactacctggacgagatcatcga<br>gcagatcagcgagttctccaagagagtgatcctggccgacgctaatctggacaaagtgctgtccgcctacaacaagcaccgggataagccca<br>tcagagagcaggccgagaatatcatccacctgtttaccctgaccaatctgggagcccctgccgccttcaagtactttgacaccaccatcgaccg<br>gaagaggtacaccagcaccaaagaggtgctggacgccaccctgatccaccagagcatcaccggcctgtacgagacacggatcgacctgtct<br>cagctgggaggcgacaaaaggccggcggccacgaaaaaggccggccaggcaaaaaagaaaaagtaa |
| SEQ ID NO<br>36<br>3xFlag-NLS-<br>SpCas9(R918A)-<br>NLS | atggactataaggaccacgacggagactacaaggatcatgatattgattacaaagacgatgacgataagatggccccaaagaagaagcggaa<br>ggtcggtatccacggagtcccagcagccgacaagaagtacagcatcggcctggacatcggcaccaactctgtgggctgggccgtgatcacc<br>gacgagtacaaggtgcccagcaagaaattcaaggtgctgggcaacaccgaccggcacagcatcaagaagaacctgatcggagccctgctg<br>ttcgacagcggcgaaacagccgaggccacccggctgaagagaaccgccagaagaagatacaccagacggaagaaccggatctgctatct<br>gcaagagatcttcagcaacgagatggccaaggtggacgacagcttcttccacagactggaagagtccttcctggtggaagaggataagaagc |

TABLE 1-continued

| SEQ ID NO | SEQUENCE |
|---|---|
| *Streptococcus* | acgagcggcaccccatcttcggcaacatcgtggacgaggtggcctaccacgagaagtaccccaccatctaccacctgagaaagaaactggt |
| *pyogenes* | ggacagcaccgacaaggccgacctgcggctgatctatctggccctggcccacatgatcaagttccggggccacttcctgatcgagggcgacc |
| | tgaaccccgacaacagcgacgttgacaagctgttcatccagctggtgcagacctacaaccagctgttcgaggaaaaccccatcaacgccagc |
| | ggcgtggacgccaaggccatcctgtctgccagactgagcaagagcagacggctggaaaatctgatcgcccagctgcccggcgagaagaag |
| | aatggcctgttcggaaacctgattgccctgagcctgggcctgacccccaacttcaagagcaacttcgacctggccgaggatgccaaactgcag |
| | ctgagcaaggacacctacgacgacgacctggacaacctgctggcccagatcggcgaccagtacgccgacctgtttctggccgccaagaacc |
| | tgtccgacgccatcctgctgagcgacatcctgagagtgaacaccgagatcaccaaggcccccctgagcgcctctatgatcaagagatacgac |
| | gagcaccaccaggacctgaccctgctgaaagctctcgtgcggcagcagctgcctgagaagtacaaagagattttcttcgaccagagcaagaa |
| | cggctacgccggctacattgacggcggagccagccaggaagagttctacaagttcatcaagcccatcctggaaaagatggacggcaccgag |
| | gaactgctcgtgaagctgaacagagaggacctgctgcggaagcagcggaccttcgacaacggcagcatcccccaccagatccacctggga |
| | gagctgcacgccattctgcggcggcaggaagatttttacccattcctgaaggacaaccgggaaaagatcgagaagatcctgaccttccgcatc |
| | ccctactacgtgggccctctggccaggggaaacagcagattcgcctggatgaccagaaagagcgaggaaaccatcacccccctggaacttcg |
| | aggaagtggtggacaagggcgcttccgcccagagcttcatcgagcggatgaccaacttcgataagaacctgcccaacgagaaggtgctgcc |
| | caagcacagcctgctgtacgagtacttcaccgtgtataacgagctgaccaaagtgaaatacgtgaccgagggaatgagaaagcccgccttcct |
| | gagcggcgagcagaaaaaggccatcgtggacctgctgttcaagaccaaccggaaagtgaccgtgaagcagctgaaagaggactacttcaa |
| | gaaaatcgagtgcttcgactccgtggaaatctccggcgtggaagatcggttcaacgcctccctgggcacataccacgatctgctgaaaattatc |
| | aaggacaaggacttcctggacaatgaggaaaacgaggacattctggaagatatcgtgctgaccctgacactgtttgaggacagagagatgatc |
| | gaggaacggctgaaaacctatgcccacctgttcgacgacaaagtgatgaagcagctgaagcggcggagatacaccggctggggcaggctg |
| | agccggaagctgatcaacggcatccgggacaagcagtccggcaagacaatcctggatttcctgaagtccgacggcttcgccaacagaaactt |
| | catgcagctgatccacgacgacagcctgacctttaaagaggacatccagaaagcccaggtgtccggccagggcgatagcctgcacgagcac |
| | attgccaatctggccggcagccccgccattaagaagggcatcctgcagacagtgaaggtggtggacgagctcgtgaaagtgatgggccggc |
| | acaagcccgagaacatcgtgatcgaaatggccagagagaaccagaccacccagaagggacagaagaacagccgcgagagaatgaagcg |
| | gatcgaagagggcatcaaagagctgggcagccagatcctgaaagaacaccccgtggaaaacacccagctgcagaacgagaagctgtacct |
| | gtactacctgcagaatgggcgggatatgtacgtggaccaggaactggacatcaaccggctgtccgactacgatgtggaccatatcgtgcctca |
| | gagctttctgaaggacgactccatcgacaacaaggtgctgaccagaagcgacaagaaccggggcaagagcgacaacgtgccctccgaaga |
| | ggtcgtgaagaagatgaagaactactggcggcagctgctgaacgccaagctgattacccagagaaagttcgacaatctgaccaaggccgag |
| | agaggcggcctgagcgaactggataaggccggcttcatcgccagacagctggtggaaacccggcagatcacaaagcacgtggcacagatc |
| | ctggactcccggatgaacactaagtacgacgagaatgacaagctgatccgggaagtgaaagtgatcaccctgaagtccaagctggtgtccga |
| | tttccggaaggatttccagttttacaaagtgcgcgagatcaacaactaccaccacgcccacgacgcctacctgaacgccgtcgtgggaaccgc |
| | cctgatcaaaaagtaccctaagctggaaagcgagttcgtgtacggcgactacaaggtgtacgacgtgcggaagatgatcgccaagagcgag |
| | caggaaatcggcaaggctaccgccaagtacttcttctacagcaacatcatgaactttttcaagaccgagattaccctggccaacggcgagatcc |
| | ggaagcggcctctgatcgagacaaacggcgaaaccggggagatcgtgtgggataagggccgggattttgccaccgtgcggaaagtgctga |
| | gcatgccccaagtgaatatcgtgaaaaagaccgaggtgcagacaggcggcttcagcaaagagtctatcctgcccaagaggaacagcgataa |
| | gctgatcgccagaaagaaggactgggaccctaagaagtacggcggcttcgacagccccaccgtggcctattctgtgctggtggtggccaaag |
| | tggaaaagggcaagtccaagaaactgaagagtgtgaaagagctgctggggatcaccatcatggaaagaagcagcttcgagaagaatcccat |
| | cgactttctggaagccaagggctacaaagaagtgaaaaaggacctgatcatcaagctgcctaagtactccctgttcgagctggaaaacggccg |
| | gaagagaatgctggcctctgccggcgaactgcagaagggaaacgaactggccctgccctccaaatatgtgaacttcctgtacctggccagcc |
| | actatgagaagctgaagggctcccccgaggataatgagcagaaacagctgtttgtggaacagcacaagcactacctggacgagatcatcgag |
| | cagatcagcgagttctccaagagagtgatcctggccgacgctaatctggacaaagtgctgtccgcctacaacaagcaccgggataagcccat |
| | cagagagcaggccgagaatatcatccacctgtttaccctgaccaatctgggagcccctgccgccttcaagtactttgacaccaccatcgaccgg |
| | aagaggtacaccagcaccaaagaggtgctggacgccaccctgatccaccagagcatcaccggcctgtacgagacacggatcgacctgtctc |
| | agctgggaggcgacaaaaggccggcggccacgaaaaaggccggccaggcaaaaaagaaaaagtaa |
| SEQ ID NO | atggactataaggaccacgacggagactacaaggatcatgatattgattacaaagacgatgacgataagatggccccaaagaagaagcggaa |
| 37 | ggtcggtatccacggagtcccagcagccgacaagaagtacagcatcggcctggacatcggcaccaactctgtgggctgggccgtgatcacc |
| 3xFlag-NLS- | gacgagtacaaggtgcccagcaagaaattcaaggtgctgggcaacaccgaccggcacagcatcaagaagaacctgatcggagccctgctg |
| SpCas9(R919P)- | ttcgacagcggcgaaacagccgaggccacccggctgaagagaaccgccagaagaagatacaccagacggaagaaccggatctgctatct |
| NLS | gcaagagatcttcagcaacgagatggccaaggtggacgacagcttcttccacagactggaagagtccttcctggtggaagaggataagaagc |
| *Streptococcus* | acgagcggcaccccatcttcggcaacatcgtggacgaggtggcctaccacgagaagtaccccaccatctaccacctgagaaagaaactggt |
| *pyogenes* | ggacagcaccgacaaggccgacctgcggctgatctatctggccctggcccacatgatcaagttccggggccacttcctgatcgagggcgacc |
| | tgaaccccgacaacagcgacgttgacaagctgttcatccagctggtgcagacctacaaccagctgttcgaggaaaaccccatcaacgccagc |

TABLE 1-continued

| SEQ ID NO | SEQUENCE |
|---|---|
| | ggcgtggacgccaaggccatcctgtctgccagactgagcaagagcagacggctggaaaatctgatcgcccagctgcccggcgagaagaag |
| | aatggcctgttcggaaacctgattgccctgagcctgggcctgacccccaacttcaagagcaacttcgacctggccgaggatgccaaactgcag |
| | ctgagcaaggacacctacgacgacgacctggacaacctgctggcccagatcggcgaccagtacgccgacctgtttctggccgccaagaacc |
| | tgtccgacgccatcctgctgagcgacatcctgagagtgaacaccgagatcaccaaggcccccctgagcgcctctatgatcaagagatacgac |
| | gagcaccaccaggacctgaccctgctgaaagctctcgtgcggcagcagctgcctgagaagtacaaagagattttcttcgaccagagcaagaa |
| | cggctacgccggctacattgacggcggagccagccaggaagagttctacaagttcatcaagcccatcctggaaaagatggacggcaccgag |
| | gaactgctcgtgaagctgaacagagaggacctgctgcggaagcagcggaccttcgacaacggcagcatcccccaccagatccacctggga |
| | gagctgcacgccattctgcggcggcaggaagatttttacccattcctgaaggacaaccgggaaaagatcgagaagatcctgaccttccgcatc |
| | ccctactacgtgggccctctggccaggggaaacagcagattcgcctggatgaccagaaagagcgaggaaaccatcacccccctggaacttcg |
| | aggaagtggtggacaagggcgcttccgcccagagcttcatcgagcggatgaccaacttcgataagaacctgcccaacgagaaggtgctgcc |
| | caagcacagcctgctgtacgagtacttcaccgtgtataacgagctgaccaaagtgaaatacgtgaccgagggaatgagaaagcccgccttcct |
| | gagcggcgagcagaaaaaggccatcgtggacctgctgttcaagaccaaccggaaagtgaccgtgaagcagctgaaagaggactacttcaa |
| | gaaaatcgagtgcttcgactccgtggaaatctccggcgtggaagatcggttcaacgcctccctgggcacataccacgatctgctgaaaattatc |
| | aaggacaaggacttcctggacaatgaggaaaacgaggacattctggaagatatcgtgctgaccctgacactgtttgaggacagagagatgatc |
| | gaggaacggctgaaaacctatgcccacctgttcgacgacaaagtgatgaagcagctgaagcggcggagatacaccggctggggcaggctg |
| | agccggaagctgatcaacggcatccgggacaagcagtccggcaagacaatcctggatttcctgaagtccgacggcttcgccaacagaaactt |
| | catgcagctgatccacgacgacagcctgacctttaaagaggacatccagaaagcccaggtgtccggccagggcgatagcctgcacgagcac |
| | attgccaatctggccggcagccccgccattaagaagggcatcctgcagacagtgaaggtggtggacgagctcgtgaaagtgatgggccggc |
| | acaagcccgagaacatcgtgatcgaaatggccagagagaaccagaccacccagaagggacagaagaacagccgcgagagaatgaagcg |
| | gatcgaagagggcatcaaagagctgggcagccagatcctgaaagaacaccccgtggaaaacacccagctgcagaacgagaagctgtacct |
| | gtactacctgcagaatgggcgggatatgtacgtggaccaggaactggacatcaaccggctgtccgactacgatgtggaccatatcgtgcctca |
| | gagctttctgaaggacgactccatcgacaacaaggtgctgaccagaagcgacaagaaccggggcaagagcgacaacgtgccctccgaaga |
| | ggtcgtgaagaagatgaagaactactggcggcagctgctgaacgccaagctgattacccagagaaagttcgacaatctgaccaaggccgag |
| | agaggcggcctgagcgaactggataaggccggcttcatcaagcccagctggtggaaacccggcagatcacaaagcacgtggcacagatc |
| | ctggactcccggatgaacactaagtacgacgagaatgacaagctgatccgggaagtgaaagtgatcaccctgaagtccaagctggtgtccga |
| | tttccggaaggatttccagttttacaaagtgcgcgagatcaacaactaccaccacgcccacgacgcctacctgaacgccgtcgtgggaaccgc |
| | cctgatcaaaaagtaccctaagctggaaagcgagttcgtgtacggcgactacaaggtgtacgacgtgcggaagatgatcgccaagagcgag |
| | caggaaatcggcaaggctaccgccaagtacttcttctacagcaacatcatgaactttttcaagaccgagattaccctggccaacggcgagatcc |
| | ggaagcggcctctgatcgagacaaacggcgaaaccggggagatcgtgtgggataagggccgggattttgccaccgtgcggaaagtgctga |
| | gcatgccccaagtgaatatcgtgaaaaagaccgaggtgcagacaggcggcttcagcaaagagtctatcctgcccaagaggaacagcgataa |
| | gctgatcgccagaaagaaggactgggaccctaagaagtacggcggcttcgacagccccaccgtggcctattctgtgctggtggtggccaaag |
| | tggaaaagggcaagtccaagaaactgaagagtgtgaaagagctgctggggatcaccatcatggaaagaagcagcttcgagaagaatcccat |
| | cgactttctggaagccaagggctacaaagaagtgaaaaaggacctgatcatcaagctgcctaagtactccctgttcgagctggaaaacggccg |
| | gaagagaatgctggcctctgccggcgaactgcagaagggaaacgaactggccctgccctccaaatatgtgaacttcctgtacctggccagcc |
| | actatgagaagctgaagggctcccccgaggataatgagcagaaacagctgtttgtggaacagcacaagcactacctggacgagatcatcgag |
| | cagatcagcgagttctccaagagagtgatcctggccgacgctaatctggacaaagtgctgtccgcctacaacaagcaccgggataagcccat |
| | cagagagcaggccgagaatatcatccacctgtttaccctgaccaatctgggagcccctgccgccttcaagtactttgacaccaccatcgaccgg |
| | aagaggtacaccagcaccaaagaggtgctggacgccaccctgatccaccagagcatcaccggcctgtacgagacacggatcgacctgtctc |
| | agctgggaggcgacaaaaggccggcggccacgaaaaaggccggccaggcaaaaaagaaaaagtaa |
| SEQ ID NO | atggactataaggaccacgacggagactacaaggatcatgatattgattacaaagacgatgacgataagatggccccaaagaagaagcggaa |
| 38 | ggtcggtatccacggagtcccagcagccgacaagaagtacagcatcggcctggacatcggcaccaactctgtgggctgggccgtgatcacc |
| 3xFlag-NLS- | gacgagtacaaggtgcccagcaagaaattcaaggtgctgggcaacaccgaccggcacagcatcaagaagaacctgatcggagccctgctg |
| SpCas9- | ttcgacagcggcgaaacagccgaggccacccggctgaagagaaccgccagaagaagatacaccagacggaagaaccggatctgctatct |
| NLS(N690C/ | gcaagagatcttcagcaacgagatggccaaggtggacgacagcttcttccacagactggaagagtccttcctggtggaagaggataagaagc |
| T769I/G915M/ | acgagcggcaccccatcttcggcaacatcgtggacgaggtggcctaccacgagaagtaccccaccatctaccacctgagaaagaaactggt |
| N980K): | ggacagcaccgacaaggccgacctgcggctgatctatctggccctggcccacatgatcaagttccggggccacttcctgatcgagggcgacc |
| LZ3Cas9Addgene | tgaaccccgacaacagcgacgtggacaagctgttcatccagctggtgcagacctacaaccagctgttcgaggaaaaccccatcaacgccagc |
| #140561 | ggcgtggacgccaaggccatcctgtctgccagactgagcaagagcagacggctggaaaatctgatcgcccagctgcccggcgagaagaag |
| *Streptococcus* | aatggcctgttcggaaacctgattgccctgagcctgggcctgacccccaacttcaagagcaacttcgacctggccgaggatgccaaactgcag |
| *pyogenes* | ctgagcaaggacacctacgacgacgacctggacaacctgctggcccagatcggcgaccagtacgccgacctgtttctggccgccaagaacc |

TABLE 1-continued

| SEQ ID NO | SEQUENCE |
| --- | --- |
| | tgtccgacgccatcctgctgagcgacatcctgagagtgaacaccgagatcaccaaggccccctgagcgcctctatgatcaagagatacgac<br>gagcaccaccaggacctgaccctgctgaaagctctcgtgcggcagcagctgcctgagaagtacaaagagattttcttcgaccagagcaagaa<br>cggctacgccggctacattgacggcggagccagccaggaagagttctacaagttcatcaagcccatcctggaaaagatggacggcaccgag<br>gaactgctcgtgaagctgaacagagaggacctgctgcggaagcagcggaccttcgacaacggcagcatcccccaccagatccacctggga<br>gagctgcacgccattctgcggcggcaggaagatttttacccattcctgaaggacaaccgggaaaagatcgagaagatcctgaccttccgcatc<br>ccctactacgtgggccctctggccaggggaaacagcagattcgcctggatgaccagaaagagcgaggaaaccatcacccccctggaacttcg<br>aggaagtggtggacaagggcgcttccgcccagagcttcatcgagcggatgaccaacttcgataagaacctgcccaacgagaaggtgctgcc<br>caagcacagcctgctgtacgagtacttcaccgtgtataacgagctgaccaaagtgaaatacgtgaccgagggaatgagaaagcccgccttcct<br>gagcggcgagcagaaaaaggccatcgtggacctgctgttcaagaccaaccggaaagtgaccgtgaagcagctgaaagaggactacttcaa<br>gaaaatcgagtgcttcgactccgtggaaatctccggcgtggaagatcggttcaacgcctccctgggcacataccacgatctgctgaaaattatc<br>aaggacaaggacttcctggacaatgaggaaaacgaggacattctggaagatatcgtgctgaccctgacactgtttgaggacagagagatgatc<br>gaggaacggctgaaaacctatgcccacctgttcgacgacaaagtgatgaagcagctgaagcggcggagatacaccggctggggcaggctg<br>agccggaagctgatcaacggcatccgggacaagcagtccggcaagacaatcctggatttcctgaagtccgacggcttcgcctgcagaaactt<br>catgcagctgatccacgacgacagcctgacctttaaagaggacatccagaaagcccaggtgtccggccagggcgatagcctgcacgagcac<br>attgccaatctggccggcagccccgccattaagaagggcatcctgcagacagtgaaggtggtggacgagctcgtgaaagtgatgggccggc<br>acaagcccgagaacatcgtgatcgaaatggccagagagaaccagatcacccagaagggacagaagaacagccgcgagagaatgaagcg<br>gatcgaagagggcatcaaagagctgggcagccagatcctgaaagaacaccccgtggaaaacacccagctgcagaacgagaagctgtacct<br>gtactacctgcagaatgggcgggatatgtacgtggaccaggaactggacatcaaccggctgtccgactacgatgtggaccatatcgtgcctca<br>gagctttctgaaggacgactccatcgacaacaaggtgctgaccagaagcgacaagaaccggggcaagagcgacaacgtgccctccgaaga<br>ggtcgtgaagaagatgaagaactactggcggcagctgctgaacgccaagctgattacccagagaaagttcgacaatctgaccaaggccgag<br>agaggcggcctgagcgaactggataaggccatgttcatcaagagacagctggtggaaacccggcagatcacaaagcacgtggcacagatc<br>ctggactcccggatgaacactaagtacgacgagaatgacaagctgatccgggaagtgaaagtgatcaccctgaagtccaagctggtgtccga<br>tttccggaaggatttccagttttacaaagtgcgcgagatcaacaaataccaccacgcccacgacgcctacctgaacgccgtcgtgggaaccgc<br>cctgatcaaaaagtaccctaagctggaaagcgagttcgtgtacggcgactacaaggtgtacgacgtgcggaagatgatcgccaagagcgag<br>caggaaatcggcaaggctaccgccaagtacttcttctacagcaacatcatgaactttttcaagaccgagattaccctggccaacggcgagatcc<br>ggaagcggcctctgatcgagacaaacggcgaaaccggggagatcgtgtgggataagggccgggattttgccaccgtgcggaaagtgctga<br>gcatgccccaagtgaatatcgtgaaaaagaccgaggtgcagacaggcggcttcagcaaagagtctatcctgcccaagaggaacagcgataa<br>gctgatcgccagaaagaaggactgggaccctaagaagtacggcggcttcgacagccccaccgtggcctattctgtgctggtggtggccaaag<br>tggaaaagggcaagtccaagaaactgaagagtgtgaaagagctgctggggatcaccatcatggaaagaagcagcttcgagaagaatcccat<br>cgactttctggaagccaagggctacaaagaagtgaaaaaggacctgatcatcaagctgcctaagtactccctgttcgagctggaaaacggccg<br>gaagagaatgctggcctctgccggcgaactgcagaagggaaacgaactggccctgccctccaaatatgtgaacttcctgtacctggccagcc<br>actatgagaagctgaagggctcccccgaggataatgagcagaaacagctgtttgtggaacagcacaagcactacctggacgagatcatcgag<br>cagatcagcgagttctccaagagagtgatcctggccgacgctaatctggacaaagtgctgtccgcctacaacaagcaccgggataagcccat<br>cagagagcaggccgagaatatcatccacctgtttaccctgaccaatctgggagcccctgccgccttcaagtactttgacaccaccatcgaccgg<br>aagaggtacaccagcaccaaagaggtgctggacgccaccctgatccaccagagcatcaccggcctgtacgagacacggatcgacctgtctc<br>agctgggaggcgacaaaaggccggcggccacgaaaaaggccggccaggcaaaaaagaaaaagtaa |
| SEQ ID NO<br>39<br>3xFlag-NLS-<br>SaCas9-P2A-<br>EGFP<br>*Staphylococcus*<br>*aureus* | atggactataaggaccacgacggagactacaaggatcatgatattgattacaaagacgatgacgataagatggccccgaagaaaaagcgcaa<br>ggtcgaagcgtccatgaaaaggaactacattctggggctggacatcgggattacaagcgtggggtatgggattattgactatgaaacaaggga<br>cgtgatcgacgcaggcgtcagactgttcaaggaggccaacgtggaaaacaatgagggacggagaagcaagaggggagccaggcgcctg<br>aaacgacggagaaggcacagaatccagagggtgaagaaactgctgttcgattacaacctgctgaccgaccattctgagctgagtggaattaat<br>ccttatgaagccagggtgaaaggcctgagtcagaagctgtcagaggaagagttttccgcagctctgctgcacctggctaagcgccgaggagt<br>gcataacgtcaatgaggtggaagaggacaccggcaacgagctgtctacaaaggaacagatctcacgcaatagcaaagctctggaagagaa<br>gtatgtcgcagagctacagctggaacggctgaagaaagatggcgaggtgagagggtcaattaataggttcaagacaagcgactacgtcaaag<br>aagccaagcagctgctgaaagtgcagaaggcttaccaccagctggatcagagcttcatcgatacttatatcgacctgctggagactcggagaa<br>cctactatgagggaccaggagaagggagccccttcggatggaaagacatcaaggaatggtacgagatgctgatgggacattgcacctattttc<br>cagaagagctgagaagcgtcaagtacgcttataacgcagatctgtacaacgccctgaatgacctgaacaacctggtcatcaccagggatgaaa<br>acgagaaactggaatactatgagaagttccagatcatcgaaaacgtgtttaagcagaagaaaaagcctacactgaaacagattgctaaggaga<br>tcctggtcaacgaagaggacatcaagggctaccgggtgacaagcactggaaaaccagagttcaccaatctgaaagtgtatcacgatattaagg<br>acatcacagcacggaaagaaatcattgagaacgccgaactgctggatcagattgctaagatcctgactatctaccagagttccgaggacatcca<br>ggaagagctgactaacctgaacagcgagctgacccaggaagagatcgaacagattagtaatctgaaggggtacaccggaacacacaacctg |

TABLE 1-continued

| SEQ ID NO | SEQUENCE |
|---|---|
| | tccctgaaagctatcaatctgattctggatgagctgtggcatacaaacgacaatcagattgcaatctttaaccggctgaagctggtaccaaaaaa<br>ggtggacctgagtcagcagaaagagatcccaaccacactggtggacgatttcattctgtcacccgtggtcaagcggagcttcatccagagcat<br>caaagtgatcaacgccatcatcaagaagtacggcctgcccaatgatatcattatcgagctggctagggagaagaacagcaaggacgcacaga<br>agatgatcaatgagatgcagaaacgaaaccggcagaccaatgaacgcattgaagagattatccgaactaccgggaaagagaacgcaaagta<br>cctgattgaaaaaatcaagctgcacgatatgcaggagggaaagtgtctgtattctctggaggccatcccccctggaggacctgctgaacaatcca<br>ttcaactacgaggtcgatcatattatccccagaagcgtgtccttcgacaattcctttaacaacaaggtgctggtcaagcaggaagagaactctaaa<br>aagggcaataggactcctttccagtacctgtctagttcagattccaagatctcttacgaaacctttaaaaagcacattctgaatctggccaaaggaa<br>agggccgcatcagcaagaccaaaaaggagtacctgctggaagagcgggacatcaacagattctccgtccagaaggattttattaaccggaat<br>ctggtggacacaagatacgctactcgcggcctgatgaatctgctgcgatcctatttccgggtgaacaatctggatgtgaaagtcaagtccatcaa<br>cggcgggttcacatcttttctgaggcgcaaatggaagtttaaaaaggagcgcaacaaagggtacaagcaccatgccgaagatgctctgattatc<br>gcaaatgccgacttcatctttaaggagtggaaaaagctggacaaagccaagaaagtgatggagaaccagatgttcgaagagaagcaggccg<br>aatctatgcccgaaatcgagacagaacaggagtacaaggagattttcatcactcctcaccagatcaagcatatcaaggatttcaaggactacaa<br>gtactctcaccgggtggataaaaagcccaacagagagctgatcaatgacaccctgtatagtacaagaaaagacgataaggggaataccctgat<br>tgtgaacaatctgaacggactgtacgacaaagataatgacaagctgaaaaagctgatcaacaaaagtcccgagaagctgctgatgtaccacca<br>tgatcctcagacatatcagaaactgaagctgattatggagcagtacggcgacgagaagaacccactgtataagtactatgaagagactgggaa<br>ctacctgaccaagtatagcaaaaaggataatggccccgtgatcaagaagatcaagtactatgggaacaagctgaatgcccatctggacatcac<br>agacgattaccctaacagtcgcaacaaggtggtcaagctgtcactgaagccatacagattcgatgtctatctggacaacggcgtgtataaatttgt<br>gactgtcaagaatctggatgtcatcaaaaaggagaactactatgaagtgaatagcaagtgctacgaagaggctaaaaagctgaaaaagattag<br>caaccaggcagagttcatcgcctccttttacaacaacgacctgattaagatcaatggcgaactgtatagggtcatcggggtgaacaatgatctgc<br>tgaaccgcattgaagtgaatatgattgacatcacttaccgagagtatctggaaaacatgaatgataagcgcccccctcgaattatcaaaacaatc<br>gcctctaagactcagagtatcaaaaagtactcaaccgacattctgggaaacctgtatgaggtgaagagcaaaaagcaccctcagattatcaaaa<br>agggcaggtccggcggcggagagggcagaggaagtcttctaacatgcggtgacgtggaggagaatcccggcccaatggtgagcaagggc<br>gaggagctgttcaccggggtggtgcccatcctggtcgagctggacggcgacgtaaacggccacaagttcagcgtgtccggcgagggcgag<br>ggcgatgccacctacggcaagctgaccctgaagttcatctgcaccaccggcaagctgcccgtgccctggcccaccctcgtgaccaccctgac<br>ctacggcgtgcagtgcttcagccgctaccccgaccacatgaagcagcacgacttcttcaagtccgccatgcccgaaggctacgtccaggagc<br>gcaccatcttcttcaaggacgacggcaactacaagacccgcgccgaggtgaagttcgagggcgacaccctggtgaaccgcatcgagctgaa<br>gggcatcgacttcaaggaggacggcaacatcctggggcacaagctggagtacaactacaacagccacaacgtctatatcatggccgacaag<br>cagaagaacggcatcaaggtgaacttcaagatccgccacaacatcgaggacggcagcgtgcagctcgccgaccactaccagcagaacacc<br>cccatcggcgacggccccgtgctgctgcccgacaaccactacctgagcacccagtccgccctgagcaaagaccccaacgagaagcgcgat<br>cacatggtcctgctggagttcgtgaccgccgccgggatcactctcggcatggacgagctgtacaagtaa |
| SEQ ID NO<br>40<br>FnCas12a-<br>NLS-<br>3xHA(addgene<br>#64709)<br>*Francisella*<br>*novicida* | atgagcatctaccaggagttcgtcaacaagtattcactgagtaagacactgcggttcgagctgatcccacagggcaagacactggagaacatc<br>aaggcccgaggcctgattctggacgatgagaagcgggcaaaagactataagaaagccaagcagatcattgataaataccaccagttctttatc<br>gaggaaattctgagctccgtgtgcatcagtgaggatctgctgcagaattactcagacgtgtacttcaagctgaagaagagcgacgatgacaacc<br>tgcagaaggacttcaagtccgccaaggacaccatcaagaaacagattagcgagtacatcaaggactccgaaaagtttaaaaatctgttcaacc<br>agaatctgatcgatgctaagaaaggccaggagtccgacctgatcctgtggctgaaacagtctaaggacaatgggattgaactgttcaaggctaa<br>ctccgatatcactgatattgacgaggcactggaaatcatcaagagcttcaagggatggaccacatactttaaaggcttccacgagaaccgcaag<br>aacgtgtactccagcaacgacattcctacctccatcatctaccgaatcgtcgatgacaatctgccaaagttcctggagaacaaggccaaatatga<br>atctctgaaggacaaagctcccgaggcaattaattacgaacagatcaagaaagatctggctgaggaactgacattcgatatcgactataagact<br>agcgaggtgaaccagagggtcttttccctggacgaggtgtttgaaatcgccaatttcaacaattacctgaaccagtccggcattactaaattcaat<br>accatcattggcgggaagtttgtgaacggggagaataccaagcgcaagggaattaacgaatacatcaatctgtatagccagcagatcaacgac<br>aaaactctgaagaaatacaagatgtctgtgctgttcaaacagatcctgagtgataccgagtccaagtcttttgtcattgataaactggaagatgact<br>cagacgtggtcactaccatgcagagcttttatgagcagatcgccgctttcaagacagtggaggaaaaatctattaaggaaactctgagtctgctg<br>ttcgatgacctgaaagcccagaagctggacctgagtaagatctacttcaaaaacgataagagtctgacagacctgtcacagcaggtgtttgatg<br>actattccgtgattgggaccgccgtcctggagtacattacacagcagatcgctccaaagaacctggataatccctctaagaaagagcaggaact<br>gatcgctaagaaaaccgagaaggcaaaatatctgagtctggaaacaattaagctggcactggaggagttcaacaagcacagggatattgaca<br>aacagtgccgctttgaggaaatcctggccaacttcgcagccatccccatgatttttgatgagatcgcccagaacaaagacaatctggctcagatc<br>agtattaagtaccagaaccagggcaagaaagacctgctgcaggcttcagcagaagatgacgtgaaagccatcaaggatctgctggaccaga<br>ccaacaatctgctgcacaagctgaaaatcttccatattagtcagtcagaggataaggctaatatcctggataaagacgaacacttctacctggtgtt<br>cgaggaatgttacttcgagctggcaaacattgtcccccctgtataacaagattaggaactacatcacacagaagccttactctgacgagaagtttaa<br>actgaacttcgaaaatagtaccctggccaacgggtgggataagaacaaggagcctgacaacacagctatcctgttcatcaaggatgacaagta |

TABLE 1-continued

| SEQ ID NO | SEQUENCE |
|---|---|
| | ctatctgggagtgatgaataagaaaaacaataagatcttcgatgacaaagccattaaggagaacaaaggggaaggatacaagaaaatcgtgta<br>taagctgctgcccggcgcaaataagatgctgcctaaggtgttcttcagcgccaagagtatcaaattctacaacccatccgaggacatcctgcgg<br>attagaaatcactcaacacatactaagaacgggagcccccagaagggatatgagaaatttgagttcaacatcgaggattgcaggaagtttattg<br>acttctacaagcagagcatctccaaacaccctgaatggaaggattttggcttccggttttccgacacacagagatataactctatcgacgagttcta<br>ccgcgaggtggaaaatcaggggtataagctgacttttgagaacatttctgaaagttacatcgacagcgtggtcaatcagggaaagctgtacctgt<br>tccagatctataacaaagatttttcagcatacagcaagggcagaccaaacctgcatacactgtactggaaggccctgttcgatgagaggaatctg<br>caggacgtggtctataaactgaacggagaggccgaactgttttaccggaagcagtctattcctaagaaaatcactcacccagctaaggaggcc<br>atcgctaacaagaacaaggacaatcctaagaaagagagcgtgttcgaatacgatctgattaaggacaagcggttcaccgaagataagttcttttt<br>ccattgtccaatcaccattaacttcaagtcaagcggcgctaacaagttcaacgacgagatcaatctgctgctgaaggaaaaagcaaacgatgtg<br>cacatcctgagcattgaccgaggagagcggcatctggcctactataccctggtggatggcaaagggaatatcattaagcaggatacattcaac<br>atcattggcaatgaccggatgaaaaccaactaccacgataaactggctgcaatcgagaaggatagagactcagctaggaaggactggaagaa<br>aatcaacaacattaaggagatgaaggaaggctatctgagccaggtggtccatgagattgcaaagctggtcatcgaatacaatgccattgtggtg<br>ttcgaggatctgaacttcggctttaagagggggcgctttaaggtggaaaaacaggtctatcagaagctggagaaaatgctgatcgaaaagctga<br>attacctggtgtttaaagataacgagttcgacaagaccggaggcgtcctgagagcctaccagctgacagctccctttgaaactttcaagaaaatg<br>ggaaaacagacaggcatcatctactatgtgccagccggattcacttccaagatctgccccgtgaccggctttgtcaaccagctgtaccctaaata<br>tgagtcagtgagcaagtcccaggaatttttcagcaagttcgataagatctgttataatctggacaaggggtacttcgagttttccttcgattacaaga<br>acttcggcgacaaggccgctaaggggaaatggaccattgcctccttcggatctcgcctgatcaactttcgaaattccgataaaaaccacaattgg<br>gacactagggaggtgtacccaaccaaggagctggaaaagctgctgaaagactactctatcgagtatggacatggcgaatgcatcaaggcagc<br>catctgtggcgagagtgataagaaatttttcgccaagctgacctcagtgctgaatacaatcctgcagatgcggaactcaaagaccgggacaga<br>actggactatctgattagccccgtggctgatgtcaacggaaacttcttcgacagcagacaggcacccaaaaatatgcctcaggatgcagacgc<br>caacggggcctaccacatcgggctgaagggactgatgctgctgggccggatcaagaacaatcaggaggggaagaagctgaacctggtcatt<br>aagaacgaggaatacttcgagtttgtccagaatagaaataacaaaaggccggcggccacgaaaaaggccggccaggcaaaaaagaaaaag<br>ggatcctacccatacgatgttccagattacgcttatccctacgacgtgcctgattatgcatacccatatgatgtccccgactatgcctaa |
| SEQ ID NO 41 AsCas12a-NLS-3xHA(addgene #69982) *Acidaminococcus* spec | atgacacagttcgagggctttaccaacctgtatcaggtgagcaagacactgcggtttgagctgatcccacagggcaagaccctgaagcacatc<br>caggagcagggcttcatcgaggaggacaaggcccgcaatgatcactacaaggagctgaagcccatcatcgatcggatctacaagacctatg<br>ccgaccagtgcctgcagctggtgcagctggattgggagaacctgagcgccgccatcgactcctatagaaaggagaaaaccgaggagacaa<br>ggaacgccctgatcgaggagcaggccacatatcgcaatgccatccacgactacttcatcggccggacagacaacctgaccgatgccatcaat<br>aagagacacgccgagatctacaagggcctgttcaaggccgagctgtttaatggcaaggtgctgaagcagctgggcaccgtgaccacaaccg<br>agcacgagaacgccctgctgcggagcttcgacaagtttacaacctacttctccggcttttatgagaacaggaagaacgtgttcagcgccgagg<br>atatcagcacagccatcccacaccgcatcgtgcaggacaacttccccaagtttaaggagaattgtcacatcttcacacgcctgatcaccgccgt<br>gcccagcctgcgggagcactttgagaacgtgaagaaggccatcggcatcttcgtgagcacctccatcgaggaggtgttttccttccctttttataa<br>ccagctgctgacacagacccagatcgacctgtataaccagctgctgggaggaatctctcgggaggcaggcaccgagaagatcaagggcctg<br>aacgaggtgctgaatctggccatccagaagaatgatgagacagcccacatcatcgcctccctgccacacagattcatcccccctgtttaagcaga<br>tcctgtccgataggaacaccctgtctttcatcctggaggagtttaagagcgacgaggaagtgatccagtccttctgcaagtacaagacactgctg<br>agaaacgagaacgtgctggagacagccgaggccctgtttaacgagctgaacagcatcgacctgacacacatcttcatcagccacaagaagct<br>ggagacaatcagcagcgccctgtgcgaccactgggatacactgaggaatgccctgtatgagcggagaatctccgagctgacaggcaagatc<br>accaagtctgccaaggagaaggtgcagcgcagcctgaagcacgaggatatcaacctgcaggagatcatctctgccgcaggcaaggagctg<br>agcgaggccttcaagcagaaaaccagcgagatcctgtcccacgcacacgccgccctggatcagccactgcctacaaccctgaagaagcag<br>gaggagaaggagatcctgaagtctcagctggacagcctgctgggcctgtaccacctgctggactggtttgccgtggatgagtccaacgaggt<br>ggaccccgagttctctgcccggctgaccggcatcaagctggagatggagccttctctgagcttctacaacaaggccagaaattatgccaccaa<br>gaagccctactccgtggagaagttcaagctgaactttcagatgcctacactggcctctggctgggacgtgaataaggagaagaacaatggcgc<br>catcctgtttgtgaagaacggcctgtactatctgggcatcatgccaaagcagaagggcaggtataaggccctgagcttcgagcccacagagaa<br>aaccagcgagggctttgataagatgtactatgactacttccctgatgccgccaagatgatcccaaagtgcagcacccagctgaaggccgtgac<br>agcccactttcagacccacacaacccccatcctgctgtccaacaatttcatcgagcctctggagatcacaaaggagatctacgacctgaacaat<br>cctgagaaggagccaaagaagtttcagacagcctacgccaagaaaaccggcgaccagaagggctacagagaggccctgtgcaagtggatc<br>gacttcacaagggatttctgtccaagtataccaagacaacctctatcgatctgtctagcctgcggccatcctctcagtataaggacctgggcgag<br>tactatgccgagctgaatcccctgctgtaccacatcagcttccagagaatcgccgagaaggagatcatggatgccgtggagacaggcaagct<br>gtacctgttccagatctataacaaggactttgccaagggccaccacggcaagcctaatctgcacacactgtattggaccggcctgttttctccag<br>agaacctggccaagacaagcatcaagctgaatggccaggccgagctgttctaccgccctaagtccaggatgaagaggatggcacaccggct<br>gggagagaagatgctgaacaagaagctgaaggatcagaaaaccccaatccccgacaccctgtaccaggagctgtacgactatgtgaatcac |

TABLE 1-continued

| SEQ ID NO | SEQUENCE |
|---|---|
| | agactgtcccacgacctgtctgatgaggccagggccctgctgcccaacgtgatcaccaaggaggtgtctcacgagatcatcaaggataggcg<br>ctttaccagcgacaagttctttttccacgtgcctatcacactgaactatcaggccgccaattccccatctaagttcaaccagagggtgaatgcctac<br>ctgaaggagcaccccgagacacctatcatcggcatcgatcggggcgagagaaacctgatctatatcacagtgatcgactccaccggcaagat<br>cctggagcagcggagcctgaacaccatccagcagtttgattaccagaagaagctggacaacagggagaaggagagggtggcagcaaggc<br>aggcctggtctgtggtgggcacaatcaaggatctgaagcagggctatctgagccaggtcatccacgagatcgtggacctgatgatccactacc<br>aggccgtggtggtgctggagaacctgaatttcggctttaagagcaagaggaccggcatcgccgagaaggccgtgtaccagcagttcgagaa<br>gatgctgatcgataagctgaattgcctggtgctgaaggactatccagcagagaaagtgggaggcgtgctgaacccataccagctgacagacc<br>agttcacctcctttgccaagatgggcacccagtctggcttcctgttttacgtgcctgccccatatacatctaagatcgatcccctgaccggcttcgt<br>ggaccccttcgtgtggaaaaccatcaagaatcacgagagccgcaagcacttcctggagggcttcgactttctgcactacgacgtgaaaaccgg<br>cgacttcatcctgcactttaagatgaacagaaatctgtccttccagaggggcctgcccggctttatgcctgcatgggatatcgtgttcgagaagaa<br>cgagacacagtttgacgccaagggcacccctttcatcgccggcaagagaatcgtgccagtgatcgagaatcacagattcaccggcagatacc<br>gggacctgtatcctgccaacgagctgatcgccctgctggaggagaagggcatcgtgttcagggatggctccaacatcctgccaaagctgctg<br>gagaatgacgattctcacgccatcgacaccatggtggccctgatccgcagcgtgctgcagatgcggaactccaatgccgccacaggcgagg<br>actatatcaacagccccgtgcgcgatctgaatggcgtgtgcttcgactcccggtttcagaacccagagtggcccatggacgccgatgccaatg<br>gcgcctaccacatcgccctgaagggccagctgctgctgaatcacctgaaggagagcaaggatctgaagctgcagaacggcatctccaatca<br>ggactggctggcctacatccaggagctgcgcaacaaaaggccggcggccacgaaaaaggccggccaggcaaaaaagaaaaagggatcc<br>tacccatacgatgttccagattacgcttatccctacgacgtgcctgattatgcatacccatatgatgtccccgactatgcctaa |
| SEQ ID NO<br>42<br>HLbCas12a-<br>NLS-<br>3xHA(addgene<br>#69988)<br>*Lachnospiraceae*<br>*bacterium* | atgagcaagctggagaagtttacaaactgctactccctgtctaagaccctgaggttcaaggccatccctgtgggcaagacccaggagaacatc<br>gacaataagcggctgctggtggaggacgagaagagagccgaggattataagggcgtgaagaagctgctggatcgctactatctgtcttttatc<br>aacgacgtgctgcacagcatcaagctgaagaatctgaacaattacatcagcctgttccggaagaaaaccagaaccgagaaggagaataagg<br>agctggagaacctggagatcaatctgcggaaggagatcgccaaggccttcaagggcaacgagggctacaagtccctgtttaagaaggatatc<br>atcgagacaatcctgccagagttcctggacgataaggacgagatcgccctggtgaacagcttcaatggctttaccacagccttcaccggcttctt<br>tgataacagagagaatatgttttccgaggaggccaagagcacatccatcgccttcaggtgtatcaacgagaatctgacccgctacatctctaata<br>tggacatcttcgagaaggtggacgccatctttgataagcacgaggtgcaggagatcaaggagaagatcctgaacagcgactatgatgtggag<br>gatttctttgagggcgagttctttaactttgtgctgacacaggagggcatcgacgtgtataacgccatcatcggcggcttcgtgaccgagagcgg<br>cgagaagatcaagggcctgaacgagtacatcaacctgtataatcagaaaaccaagcagaagctgcctaagtttaagccactgtataagcaggt<br>gctgagcgatcgggagtctctgagcttctacggcgagggctatacatccgatgaggaggtgctggaggtgtttagaaacaccctgaacaagaa<br>cagcgagatcttcagctccatcaagaagctggagaagctgttcaagaattttgacgagtactctagcgccggcatctttgtgaagaacggcccc<br>gccatcagcacaatctccaaggatatcttcggcgagtggaacgtgatccgggacaagtggaatgccgagtatgacgatatccacctgaagaa<br>gaaggccgtggtgaccgagaagtacgaggacgatcggagaaagtccttcaagaagatcggctccttttctctggagcagctgcaggagtacg<br>ccgacgccgatctgtctgtggtggagaagctgaaggagatcatcatccagaaggtggatgagatctacaaggtgtatggctcctctgagaagc<br>tgttcgacgccgattttgtgctggagaagagcctgaagaagaacgacgccgtggtggccatcatgaaggacctgctggattctgtgaagagctt<br>cgagaattacatcaaggccttctttggcgagggcaaggagacaaacagggacgagtccttctatggcgattttgtgctggcctacgacatcctg<br>ctgaaggtggaccacatctacgatgccatccgcaattatgtgacccagaagccctactctaaggataagttcaagctgtattttcagaaccctcag<br>ttcatgggcggctgggacaaggataaggagacagactatcgggccaccatcctgagatacggctccaagtactatctggccatcatggataag<br>aagtacgccaagtgcctgcagaagatcgacaaggacgatgtgaacggcaattacgagaagatcaactataagctgctgcccggccctaataa<br>gatgctgccaaaggtgttcttttctaagaagtggatggcctactataaccccagcgaggacatccagaagatctacaagaatggcacattcaag<br>aagggcgatatgtttaacctgaatgactgtcacaagctgatcgacttctttaaggatagcatctcccggtatccaaagtggtccaatgcctacgatt<br>tcaacttttctgagacagagaagtataaggacatcgccggcttttacagagaggtggaggagcagggctataaggtgagcttcgagtctgcca<br>gcaagaaggaggtggataagctggtggaggagggcaagctgtatatgttccagatctataacaaggacttttccgataagtctcacggcacac<br>ccaatctgcacaccatgtacttcaagctgctgtttgacgagaacaatcacggacagatcaggctgagcggaggagcagagctgttcatgaggc<br>gcgcctccctgaagaaggaggagctggtggtgcacccagccaactcccctatcgccaacaagaatccagataatcccaagaaaaccacaac<br>cctgtcctacgacgtgtataaggataagaggttttctgaggaccagtacgagctgcacatcccaatcgccatcaataagtgccccaagaacatct<br>tcaagatcaatacagaggtgcgcgtgctgctgaagcacgacgataacccctatgtgatcggcatcgataggggcgagcgcaatctgctgtata<br>tcgtggtggtggacggcaagggcaacatcgtggagcagtattccctgaacgagatcatcaacaacttcaacggcatcaggatcaagacagatt<br>accactctctgctggacaagaaggagaaggagaggttcgaggcccgccagaactggacctccatcgagaatatcaaggagctgaaggccg<br>gctatatctctcaggtggtgcacaagatctgcgagctggtggagaagtacgatgccgtgatcgccctggaggacctgaactctggctttaagaa<br>tagccgcgtgaaggtggagaagcaggtgtatcagaagttcgagaagatgctgatcgataagctgaactacatggtggacaagaagtctaatcc<br>ttgtgcaacaggcggcgccctgaagggctatcagatcaccaataagttcgagagctttaagtccatgtctacccagaacggcttcatcttttacat<br>ccctgcctggctgacatccaagatcgatccatctaccggctttgtgaacctgctgaaaaccaagtataccagcatcgccgattccaagaagttca |

TABLE 1-continued

| SEQ ID NO | SEQUENCE |
|---|---|
| | tcagctcctttgacaggatcatgtacgtgcccgaggaggatctgttcgagtttgccctggactataagaacttctctcgcacagacgccgattaca<br>tcaagaagtggaagctgtactcctacggcaaccggatcagaatcttccggaatcctaagaagaacaacgtgttcgactgggaggaggtgtgcc<br>tgaccagcgcctataaggagctgttcaacaagtacggcatcaattatcagcagggcgatatcagagccctgctgtgcgagcagtccgacaag<br>gccttctactctagctttatggccctgatgagcctgatgctgcagatgcggaacagcatcacaggccgcaccgacgtggattttctgatcagccc<br>tgtgaagaactccgacggcatcttctacgatagccggaactatgaggcccaggagaatgccatcctgccaaagaacgccgacgccaatggc<br>gcctataacatcgccagaaaggtgctgtgggccatcggccagttcaagaaggccgaggacgagaagctggataaggtgaagatcgccatct<br>ctaacaaggagtggctggagtacgcccagaccagcgtgaagcacaaaaggccggcggccacgaaaaaggccggccaggcaaaaaagaa<br>aaagggatcctacccatacgatgttccagattacgcttatccctacgacgtgcctgattatgcatacccatatgatgtccccgactatgcctaa |
| SEQ ID NO 43 3xGS | ggcggcgggagcgggggtggcagcggcggcgggtcg |
| SEQ ID NO 44 (SGGS)2-XTEN-(SGGS)2 | tctggaggatctagcggaggatcctctggcagcgagacaccaggaacaagcgagtcagcaacaccagagagcagtggcggcagcagcgg<br>cggctcg |
| SEQ ID NO 45 A(EAAAK)4 A | gctgaggcggcggcaaaagaagcagcggcaaaagaagctgccgcaaaggaagcagcagcaaaagcccttgaagccgaagctgctgcta<br>aggaggctgccgcaaaagaggctgccgccaaagaagcagccgctaaagcg |
| SEQ ID NO 46 3xFlag-NLS | ggatccgactataaggaccacgacggagactacaaggatcatgatattgattacaaagacgatgacgataagatggccccaaagaagaagcg<br>gaaggtcggtatccacggagtcccagcagcg |
| SEQ ID NO 47 3xFlag | ggatccgactataaggaccacgacggagactacaaggatcatgatattgattacaaagacgatgacgataagggtatccacggagtcccagc<br>agcg |
| SEQ ID NO 48 (H4)3: | GGTTCTGGAAGTGAGGCAGCTGCGAAGGAGGCTGCGGCGAAAGAAGCTGCAGCAAA<br>GGAAGCAGCAGCAAAGGCACTGGAGGCCGCTGCTGCTAAAGAGGCTGCCGCCAAAG<br>AAGCTGCGGCAAAGGAAGCTGCGGCTAAGGGAAGTGGGAGCGCAGCGGCCAAAGAG<br>GCAGCGGCCAAGGAAGCTGCTGCAAAAGAAGCAGCAGCTAAAGGGAGCGGATCG |
| SEQ ID NO 49 GPcPcPc | GCCGGAAGCGGTGGTTCAGGGGGATCCGGAGGAAGTCCTGTTCCCTCTACCCCACCA<br>ACTAATAGCAGCTCAACCCCTCCGACCCCCTCTCCGTCACCGGTGCCGAGTACCCCGC<br>CAACCAATAGCTCATCAACTCCGCCTACGCCGTCCCCTAGTCCAGTACCTAGCACCCC<br>TCCAACAAATTCTAGCAGTACACCACCCACACCAAGCCCTAGCGCGTCG |
| SEQ ID NO 50 GPGcP | GCTGGTTCTGGTGGCTCAGGGGGTTCCGGTGGTTCCCCAGTACCAAGTACTCCTCCCA<br>CTCCCTCTCCAAGTACGCCGCCTACACCCTCACCCAGCGGCGGCTCTGGCAATTCCAG<br>TGGTTCAGGCGGTAGTCCCGTGCCAAGTACGCCACCAACTCCAAGTCCATCAACACC<br>ACCGACCCCTTCTCCGTCTGCATCG |
| SEQ ID NO 51 GPbGbP | GCGGGTTCTGGAGGTTCAGGCGGGAGCGGTGGCAGTCCAGTGCCGAGCACACCGCCA<br>ACACCGAGCCCAAGTACGCCACCGACTCCAAGTCCCAGCATACAGCGAACACCGAAG<br>ATTCAGGTCTACTCACGACACCCAGCGGAAAACGGCAAATCTAATTTTCTGAATTGCT<br>ATGTTTCCGGTTTTCACCCCTCAGACATCGAGGTCGACCTGCTGAAGAACGGTGAAAG |

TABLE 1-continued

| SEQ ID NO | SEQUENCE |
|---|---|
| | GATTGAAAAGGTTGAACACTCCGACTTGAGCTTTAGTAAGGACTGGTCATTCTATTTG<br>CTGTATTACACCGAGTTCACTCCGACCGAAAAGGATGAATACGCATGTCGAGTGAAT<br>CATGTCACGCTGAGCCAACCCAAGATCGTGAAATGGGACAGGGACGGGGGGTCTGG<br>GGGTAGCGGAGGAAGCGGCGGGTCTATCCAACGCACTCCAAAAATTCAAGTCTACTC<br>AAGACACCCTGCCGAGAATGGAAAATCAAACTTTTTGAATTGCTACGTCTCTGGATTC<br>CATCCGTCAGACATCGAAGTTGATCTGTTGAAAAACGGTGAGCGAATTGAGAAAGTG<br>GAGCATTCAGATCTTAGCTTCAGTAAAGACTGGTCCTTTTATCTCTTGTATTACACGG<br>AGTTCACTCCCACAGAAAAAGATGAATACGCCTGTCGAGTTAACCACGTCACGCTGT<br>CACAGCCAAAGATAGTGAAATGGGATCGCGACCCAGTGCCCTCAACACCCCCTACTC<br>CTAGTCCGAGCACTCCTCCAACGCCTTCACCATCTGCCTCG |
| SEQ ID NO<br>52<br>GPZP | GCTGGTTCCGGCGGATCTGGTGGATCTGGTGGCAGCCCCGTCCCTTCTACTCCACCCA<br>CACCGTCCCCGTCAACTCCTCCCACCCCGTCTCCGTCCGATGGAAGGTACTCTCTCAC<br>GTACATCTACACTGGGTTGTCAAAGCATGTGGAAGACGTGCCAGCCTTCCAGGCGCTT<br>GGAAGCCTCAATGACCTTCAGTTTTTCGCTACAATAGCAAGGATCGAAAGTCACAA<br>CCTATGGGTCTCTGGAGACAGGTCGAAGGGATGGAGGACTGGAAACAGGATAGCCA<br>ATTGCAAAAAGCGAGAGAGGATATCTTTATGGAGACGCTTAAAGACATTGTTGAGTA<br>TTACAACGACTCTAACGGTAGTCACGTATTGCAGGGCCGATTTGGGTGTGAGATAGA<br>GAATAACCGGAGTTCCGGCGCTTTTTGGAAATATTATTACGATGGCAAGGACTACATC<br>GAGTTTAACAAAGAAATTCCAGCCTGGGTGCCTTTTGACCCAGCTGCACAAATTACA<br>AAACAGAAGTGGGAGGCGGAGCCAGTGTACGTTCAAAGGGCAAAAGCATACTTGGA<br>GGAAGAGTGTCCCGCAACTCTCCGAAAGTACTTGAAGTATTCTAAAAACATACTGGA<br>TCGACAGGATCCCCCTTCAGTAGTCGTAACCTCCCACCAGGCCCCAGGTGAGAAGAA<br>GAAGTTGAAATGCCTTGCTTACGACTTCTACCCAGGCAAGATTGATGTTCACTGGACA<br>AGGGCTGGTGAGGTCCAAGAGCCCGAACTTAGAGGGGATGTGTTGCATAACGGTAAT<br>GGGACGTATCAGTCATGGGTCGTGGTGGCAGTCCCTCCTCAAGATACGGCACCATAC<br>TCTTGCCATGTGCAACACAGCTCACTGGCGCAGCCACTCGTAGTGCCTTGGGAGGCCA<br>GCCCCGTGCCATCAACTCCCCCAACTCCATCACCTAGTACCCCCCCTACTCCGTCAGC<br>CTCG |
| SEQ ID NO<br>53<br>GGZGZP | GCTGGTTCTGGGGGGTCAGGAGGGAGTGGAGGGTCTGGAGGTTCTGGAGGCTCAGGA<br>GGTAGCGGTGGTAGTGACGGCAGGTACAGTCTCACCTATATCTATACAGGATTGTCTA<br>AGCATGTTGAAGACGTGCCCGCCTTTCAGGCACTGGGTTCTTTGAACGACCTCCAGTT<br>TTTCCGCTACAACAGTAAAGACCGAAAATCTCAGCCCATGGGGCTCTGGAGACAAGT<br>TGAAGGTATGGAGGACTGGAAACAGGACAGTCAATTGCAAAAGGCCAGAGAAGATA<br>TTTTTATGGAAACCTTGAAGGATATTGTCGAGTACTACAACGATTCAAACGGGTCCCA<br>CGTGCTGCAGGGCCGATTCGGTTGCGAGATAGAAAATAATCGATCTAGTGGTGCCTTT<br>TGGAAGTATTACTACGACGGAAAAGATTATATCGAATTTAATAAAGAGATTCCTGCG<br>TGGGTGCCGTTTGACCCGGCGGCACAAATTACTAAACAAAAGTGGGAAGCGGAACCG<br>GTGTATGTTCAGAGGGCTAAGGCGTACCTTGAAGAAGAGTGCCCCGCTACGTTGAGG<br>AAATACCTCAAATATTCCAAAAATATCTTGGATCGACAAGATCCACCTAGCGTGGTTG<br>TTACTTCACACCAAGCACCAGGTGAAAAAAAAAAATTGAAGTGTCTTGCATATGACT<br>TCTATCCTGGGAAGATCGACGTACACTGGACACGAGCCGGAGAGGTACAAGAACCTG<br>AACTGCGAGGGGACGTCCTCCATAACGGGAACGGTACCTATCAAAGTTGGGTGGTGG<br>TTGCGGTTCCACCTCAGGACACTGCGCCTTACTCCTGTCACGTGCAGCATTCCTCTCTC<br>GCTCAACCCCTTGTCGTGCCGTGGGAGGCCTCCGGAGGGTCTGGCGGAAGCGGAGGA<br>TCTGGTGGGTCCGATGGTAGGTACTCACTTACTTACATATACACGGGTCTTAGTAAAC<br>ACGTCGAGGATGTCCCGGCGTTCCAAGCTCTGGGTAGTTTGAATGATCTCCAATTTTT<br>TAGATACAATAGCAAAGATCGAAAAAGCCAACCAATGGGACTCTGGAGACAGGTGG<br>AGGGAATGGAAGATTGGAAACAAGATTCTCAACTCCAGAAGGCTAGGGAAGACATTT<br>TCATGGAAACGCTCAAAGATATTGTAGAGTATTATAATGATTCTAACGGCAGCCACG |

TABLE 1-continued

| SEQ ID NO | SEQUENCE |
|---|---|
| | TCCTTCAGGGGCGATTTGGGTGTGAGATTGAAAACAATCGATCTAGCGGTGCATTTTG<br>GAAATATTACTATGATGGCAAAGACTATATCGAATTCAACAAGGAAATTCCAGCATG<br>GGTCCCATTCGACCCCGCGGCTCAAATTACCAAGCAAAAATGGGAAGCCGAACCTGT<br>CTACGTACAACGGGCGAAGGCATATCTTGAGGAGGAATGCCCCGCGACCCTCCGAAA<br>GTACCTTAAGTACTCCAAGAACATTCTCGATCGGCAGGACCCCCCTTCTGTGGTAGTC<br>ACCAGCCATCAGGCACCTGGGGAGAAGAAGAAACTCAAGTGCCTGGCCTACGATTTC<br>TACCCTGGGAAAATCGATGTCCACTGGACGAGAGCGGGTGAGGTGCAAGAGCCAGA<br>ATTGAGAGGTGATGTCCTTCATAACGGCAATGGCACCTATCAGTCATGGGTGGTCGTG<br>GCTGTTCCCCCTCAAGACACGGCACCGTATAGCTGTCATGTCCAACACTCCTCCCTCG<br>CTCAACCACTCGTGGTCCCATGGGAGGCTAGCCCAGTGCCCAGCACACCCCCTACTCC<br>CTCTCCTTCTACTCCACCGACCCCTTCACCGTCCGCTTCG |
| SEQ ID NO<br>54<br>GGGCTGAG<br>AGAGGGAC<br>AAGT | GGGCTGAGAGAGGGACAAGTgttttagagctagaaatagcaagttaaaataaggctagtccgttatcaacttgaaaaagtgg<br>caccgagtcggtgc |
| SEQ ID NO<br>55<br>AGTGTGCA<br>TTGCCACC<br>TCAG | AGTGTGCATTGCCACCTCAGgttttagagctagaaatagcaagttaaaataaggctagtccgttatcaacttgaaaaagtggc<br>accgagtcggtgc |
| SEQ ID NO<br>56<br>GCAGGACT<br>CCTTTCCT<br>CCAT | GCAGGACTCCTTTCCTCCATgttttagagctagaaatagcaagttaaaataaggctagtccgttatcaacttgaaaaagtggca<br>ccgagtcggtgc |
| SEQ ID NO<br>57<br>ATAGGAGA<br>AGATGATG<br>TATA | ATAGGAGAAGATGATGTATAgttttagagctagaaatagcaagttaaaataaggctagtccgttatcaacttgaaaaagtgg<br>caccgagtcggtgc |
| SEQ ID NO<br>58<br>AAAACGTT<br>TCCAAGAC<br>ATGA | AAAACGTTTCCAAGACATGAgttttagagctagaaatagcaagttaaaataaggctagtccgttatcaacttgaaaaagtggc<br>accgagtcggtgc |
| SEQ ID NO<br>59<br>CCGCCGTC<br>CAAGACCT<br>ACCG | CCGCCGTCCAAGACCTACCGgttttagagctagaaatagcaagttaaaataaggctagtccgttatcaacttgaaaaagtggc<br>accgagtcggtgc |
| SEQ ID NO<br>60<br>CCAAGAAG | CCAAGAAGCGCACCACCTCCgttttagagctagaaatagcaagttaaaataaggctagtccgttatcaacttgaaaaagtggc<br>accgagtcggtgc |

TABLE 1-continued

| SEQ ID NO | SEQUENCE |
|---|---|
| CGCACCAC CTCC | |
| SEQ ID NO 61 AGCCTGGA AGCACGA ATGGT | AGCCTGGAAGCACGAATGGTgttttagagctagaaatagcaagttaaaataaggctagtccgttatcaacttgaaaaagtg gcaccgagtcggtgc |
| SEQ ID NO 62 ACATACCA AGAGAATC ACCC: | ACATACCAAGAGAATCACCCgttttagagctagaaatagcaagttaaaataaggctagtccgttatcaacttgaaaaagtg gcaccgagtcggtgc |
| SEQ ID NO 63 GAAGGAG GAGGCCTA AGGA: | GAAGGAGGAGGCCTAAGGAgttttagagctagaaatagcaagttaaaataaggctagtccgttatcaacttgaaaaagtg gcaccgagtcggtgc |
| SEQ ID NO 64 AAGAAGA CTAGCTGA GCTCT: | AAGAAGACTAGCTGAGCTCTgttttagagctagaaatagcaagttaaaataaggctagtccgttatcaacttgaaaaagtg gcaccgagtcggtgc |
| SEQ ID NO 65 POLL: | MDPRGILKAFPKRQKIHADASSKVLAKIPRREEGEEAEEWLSSLRAHVVRTGIGRARAE LFEKQIVQHGGQLCPAQGPGVTHIVVDEGMDYERALRLLRLPQLPPGAQLVKSAWLSL CLQERRLVDVAGFSIFIPSRYLDHPQPSKAEQDASIPPGTHEALLQTALSPPPPPTRPVSPP QKAKEAPNTQAQPISDDEASDGEETQVSAADLEALISGHYPTSLEGDCEPSPAPAVLDK WVCAQPSSQKATNHNLHITEKLEVLAKAYSVQGDKWRALGYAKAINALKSFHKPVTS YQEACSIPGIGKRMAEKIIEILESGHLRKLDHISESVPVLELFSNIWGAGTKTAQMWYQQ GFRSLEDIRSQASLTTQQAIGLKHYSDFLERMPREEATEIEQTVQKAAQAFNSGLLCVAC GSYRRGKATCGDVDVLITHPDGRSHRGIFSRLLDSLRQEGFLTDDLVSQEENGQQQKYL GVCRLPGPGRRHRRLDIIVVPYSEFACALLYFTGSAHFNRSMRALAKTKGMSLSEHALS TAVVRNTHGCKVGPGRVLPTPTEKDVFRLLGLPYREPAERDW |
| SEQ ID NO 66 POLM: | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPVP VECRHRLEVAGPRKGPLSPAWMPAYACQRPTPLTHHNTGLSEALEILAEAAGFEGSEGR LLTFCRAASVLKALPSPVTTLSQLQGLPHFGEHSSRVVQELLEHGVCEEVERVRRSERY QTMKLFTQIFGVGVKTADRWYREGLRTLDDLREQPQKLTQQQKAGLQHHQDLSTPVL RSDVDALQQVVEEAVGQALPGATVTLTGGFRRGKLQGHDVDFLITHPKEGQEAGLLPR VMCRLQDQGLILYHQHQHSCCESPTRLAQQSHMDAFERSFCIFRLPQPPGAAVGGSTRP CPSWKAVRVDLVVAPVSQFPFALLGWTGSKLFQRELRRFSRKEKGLWLNSHGLFDPEQ KTFFQAASEEDIFRHLGLEYLPPEQRNA |
| SEQ ID NO 67 POLM(H329G): | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPVP VECRHRLEVAGPRKGPLSPAWMPAYACQRPTPLTHHNTGLSEALEILAEAAGFEGSEGR |

TABLE 1-continued

| SEQ ID NO | SEQUENCE |
|---|---|
| | LLTFCRAASVLKALPSPVTTLSQLQGLPHFGEHSSRVVQELLEHGVCEEVERVRRSERY<br>QTMKLFTQIFGVGVKTADRWYREGLRTLDDLREQPQKLTQQQKAGLQHHQDLSTPVL<br>RSDVDALQQVVEEAVGQALPGATVTLTGGFRRGKLQGGDVDFLITHPKEGQEAGLLPR<br>VMCRLQDQGLILYHQHQHSCCESPTRLAQQSHMDAFERSKCIFRLPQPPGAAVGGSTRP<br>CPSWKAVRVDLVVAPVSQFPFALLGWTGSKLFQRELRRFSRKEKGLWLNSHGLFDPEQ<br>KTFFQAASEEDIFRHLGLEYLPPEQRNA |
| SEQ ID NO<br>68<br>POLM(H329G,<br>R389K): | MALPKRRRARVGSPSGDAASSTPPSTRFPGVAIYLVEPRMGRSRRAFLTGLARSKGFRV<br>LDACSSEATHVVMEETSAEEAVSWQERRMAAAPPGCTPPALLDISWLTESLGAGQPVP<br>VECRHRLEVAGPRKGPLSPAWMPAYACQRPTPLTHHNTGLSEALEILAEAAGFEGSEGR<br>LLTFCRAASVLKALPSPVTTLSQLQGLPHFGEHSSRVVQELLEHGVCEEVERVRRSERY<br>QTMKLFTQIFGVGVKTADRWYREGLRTLDDLREQPQKLTQQQKAGLQHHQDLSTPVL<br>RSDVDALQQVVEEAVGQALPGATVTLTGGFRRGKLQGGDVDFLITHPKEGQEAGLLPR<br>VMCRLQDQGLILYHQHQHSCCESPTRLAQQSHMDAFERSFCIFRLPQPPGAAVGGSTRP<br>CPSWKAVRVDLVVAPVSQFPFALLGWTGSKLFQRELRRFSRKEKGLWLNSHGLFDPEQ<br>KTFFQAASEEDIFRHLGLEYLPPEQRNA |
| SEQ ID NO<br>69<br>BRCT(POLM)<br>POLL1: | MALPKRRRARVGSPSGDAASSTPPSTRFPGVAIYLVEPRMGRSRRAFLTGLARSKGFRV<br>LDACSSEATHVVMEETSAEEAVSWQERRMAAAPPGCTPPALLDISWLTESLGAGQPIPS<br>RYLDHPQPSKAEQDASIPPGTHEALLQTALSPPPPPTRPVSPPQKAKEAPNTQAQPISDDE<br>ASDGEETQVSAADLEALISGHYPTSLEGDCEPSPAPAVLDKWVCAQPSSQKATNHNLHI<br>TEKLEVLAKAYSVQGDKWRALGYAKAINALKSFHKPVTSYQEACSIPGIGKRMAEKIIEI<br>LESGHLRKLDHISESVPVLELFSNIWGAGTKTAQMWYQQGFRSLEDIRSQASLTTQQAIG<br>LKHYSDFLERMPREEATEIEQTVQKAAQAFNSGLLCVACGSYRRGKATCGDVDVLITHP<br>DGRSHRGIFSRLLDSLRQEGFLTDDLVSQEENGQQQKYLGVCRLPGPGRRHRRLDIIVVP<br>YSEFACALLYFTGSAHFNRSMRALAKTKGMSLSEHALSTAVVRNTHGCKVGPGRVLPT<br>PTEKDVFRLLGLPYREPAERDW |
| SEQ ID NO<br>70<br>BRCT(POLM)<br>POLL2: | MALPKRRRARVGSPSGDAASSTPPSTRFPGVAIYLVEPRMGRSRRAFLTGLARSKGFRV<br>LDACSSEATHVVMEETSAEEAVSWQERRMAAAPPGCTPPALLDISWLTESLGAGQPVP<br>VECRHRLEVAGPRKGPLSSSQKATNHNLHITEKLEVLAKAYSVQGDKWRALGYAKAIN<br>ALKSFHKPVTSYQEACSIPGIGKRMAEKIIEILESGHLRKLDHISESVPVLELFSNIWGAGT<br>KTAQMWYQQGFRSLEDIRSQASLTTQQAIGLKHYSDFLERMPREEATEIEQTVQKAAQA<br>FNSGLLCVACGSYRRGKATCGDVDVLITHPDGRSHRGIFSRLLDSLRQEGFLTDDLVSQ<br>EENGQQQKYLGVCRLPGPGRRHRRLDIIVVPYSEFACALLYFTGSAHFNRSMRALAKTK<br>GMSLSEHALSTAVVRNTHGCKVGPGRVLPTPTEKDVFRLLGLPYREPAERDW |
| SEQ ID NO<br>71<br>3xFlag-NLS-<br>EXOG: | MDYKDHDGDYKDHDIDYKDDDDKMAPKKKRKVGIHGVPAAAIKSIASRLRGSRRFLS<br>GFVAGAVVGAAGAGLAALQFFRSQGAEGALTGKQPDGSAEKAVLEQFGFPLTGTEARC<br>YTNHALSYDQAKRVPRWVLEHISKSKIMGDADRKHCKFKPDPNIPPTFSAFNEDYVGSG<br>WSRGHMAPAGNNKFSSKAMAETFYLSNIVPQDFDNNSGYWNRIEMYCRELTERFEDV<br>WVVSGPLTLPQTRGDGKKIVSYQVIGEDNVAVPSHLYKVILARRSSVSTEPLALGAFVV<br>PNEAIGFQPQLTEFQVSLQDLEKLSGLVFFPHLDRTSDIRNICSVDTCKLLDFQEFTLYLS<br>TRKIEGARSVLRLEKIMENLKNAEIEPDDYFMSRYEKKLEELKAKEQSGTQIRKPS |
| SEQ ID NO<br>72<br>3xFlag-NLS-<br>nucS: | MDYKDHDGDYKDHDIDYKDDDDKMAPKKKRKVGIHGVPAAPRLLPISAATLALAQLT<br>YGWGNLGHETVAYIAQSFVASSTESFCQNILGDDSTSYLANVATWADTYKYTDAGEFS<br>KPYHFIDAQDNPPQSCGVDYDRDCGSAGCSISAIQNYTNILLESPNGSEALNALKFVVHII<br>GDIHQPLHDENLEAGGNGIDVTYDGETTNLHHIWDTNMPEEAAGGYSLSVAKTYADLL<br>TERIKTGTYSSKKDSWTDGIDIKDPVSTSMIWAADANTYVCSTVLDDGLAYINSTDLSGE<br>YYDKSQPVFEELIAKAGYRLAAWLDLIASQPS |

TABLE 1-continued

| SEQ ID NO | SEQUENCE |
| --- | --- |
| SEQ ID NO 73 3xFlag-NLS-NucP1: | MDYKDHDGDYKDHDIDYKDDDDKMAPKKKRKVGIHGVPAAWGALGHATVAYVAQH<br>YVSPEAASWAQGILGSSSSSYLASIASWADEYRLTSAGKWSASLHFIDAEDNPPTNCNV<br>DYERDCGSSGCSISAIANYTQRVSDSSLSSENHAEALRFLVHFIGDMTQPLHDEAYAVG<br>GNKINVTFDGYHDNLHSDWDTYMPQKLIGGHALSDAESWAKTLVQNIESGNYTAQAIG<br>WIKGDNISEPITTATRWASDANALVCTVVMPHGAAALQTGDLYPTYYDSVIDTIELQIA<br>KGGYRLANWINEI |
| SEQ ID NO 74 3xFlag-NLS-MGME1: | MDYKDHDGDYKDHDIDYKDDDDKMAPKKKRKVGIHGVPAAKMKLFQTICRQLRSSK<br>FSVESAALVAFSTSSYSCGRKKKVNPYEEVDQEKYSNLVQSVLSSRGVAQTPGSVEEDA<br>LLCGPVSKHKLPNQGEDRRVPQNWFPIFNPERSDKPNASDPSVPLKIPLQRNVIPSVTRV<br>LQQTMTKQQVFLLERWKQRMILELGEDGFKEYTSSFHVCDHVYMKNLARDVFLQGKR<br>FHEALESILSPQETLKERDENLLKSGYIESVQHILKDVSGVRALESAVQHETLNYIGLLDC<br>VAEYQGKLCVIDWKTSEKPKPFIQSTFDNPLQVVAYMGAMNHDTNYSFQVQCGLIVVA<br>YKDGSPAHPHFMDAELCSQYWIKWLLRLEEYTEKKKNQNIQKPEYSE |
| SEQ ID NO 75 3xFlag-NLS-recj: | MDYKDHDGDYKDHDIDYKDDDDKMAPKKKRKVGIHGVPAAVKQQIQLRRREVDETA<br>DLPAELPPLLRRLYASRGVRSAQELERSVKGMLPWQQLSGVEKAVEILYNAFREGTRIIV<br>VGDFDADGATSTALSVLAMRSLGCSNIDYLVPNRFEDGYGLSPEVVDQAHARGAQLIV<br>TVDNGISSHAGVEHARSLGIPVIVTDHHLPGDTLPAAEAIINPNLRDCNFPSKSLAGVGV<br>AFYLMLALRTFLRDQGWFDERNIAIPNLAELLDLVALGTVADVVPLDANNRILTWQGM<br>SRIRAGKCRPGIKALLEVANRDAQKLAASDLGFALGPRLNAAGRLDDMSVGVALLLCD<br>NIGEARVLANELDALNQTRKEIEQGMQIEALTLCEKLERSRDTLPGGLAMYHPEWHQG<br>VVGILASRIKERFHRPVIAFAPAGDGTLKGSGRSIQGLHMRDALERLDTLYPGMMLKFG<br>GHAMAAGLSLEEDKFKLFQQRFGELVTEWLDPSLLQGEVVSDGPLSPAEMTMEVAQLL<br>RDAGPWGQMFPEPLFDGHFRLLQQRLVGERHLKVMVEPVGGGPLLDGIAFNVDTALW<br>PDNGVREVQLAYKLDINEFRGNRSLQIIIDNIWPI |
| SEQ ID NO 76 3xFlag-NLS-T4 DNA polymerase: | MDYKDHDGDYKDHDIDYKDDDDKMAPKKKRKVGIHGVPAAKEFYISIETVGNNIVER<br>YIDENGKERTREVEYLPTMFRHCKEESKYKDIYGKNCAPQKFPSMKDARDWMKRMED<br>IGLEALGMNDFKLAYISDTYGSEIVYDRKFVRVANCDIEVTGDKFPDPMKAEYEIDAITH<br>YDSIDDRFYVFDLLNSMYGSVSKWDAKLAAKLDCEGGDEVPQEILDRVIYMPFDNERD<br>MLMEYINLWEQKRPAIFTGWNIEGFDVPYIMNRVKMILGERSMKRFSPIGRVKSKLIQN<br>MYGSKEIYSIDGVSILDYLDLYKKFAFTNLPSFSLESVAQHETKKGKLPYDGPINKLRET<br>NHQRYISYNIIDVESVQAIDKIRGFIDLVLSMSYYAKMPFSGVMSPIKTWDAIIFNSLKGE<br>HKVIPQQGSHVKQSFPGAFVFEPKPIARRYIMSFDLTSLYPSIIRQVNISPETIRGQFKVHPI<br>HEYIAGTAPKPSDEYSCSPNGWMYDKHQEGIIPKEIAKVFFQRKDWKKKMFAEEMNAE<br>AIKKIIMKGAGSCSTKPEVERYVKFSDDFLNELSNYTESVLNSLIEECEKAATLANTNQL<br>NRKILINSLYGALGNIHFRYYDLRNATAITIFGQVGIQWIARKINEYLNKVCGTNDEDFIA<br>AGDTDSVYVCVDKVIEKVGLDRFKEQNDLVEFMNQFGKKKMEPMIDVAYRELCDYM<br>NNREHLMHMDREAISCPPLGSKGVGGFWKAKKRYALNVYDMEDKRFAEPHLKIMGM<br>ETQQSSTPKAVQEALEESIRRILQEGEESVQEYYKNFEKEYRQLDYKVIAEVKTANDIAK<br>YDDKGWPGFKCPFHIRGVLTYRRAVSGLGVAPILDGNKVMVLPLREGNPFGDKCIAWP<br>SGTELPKEIRSDVLSWIDHSTLFQKSFVKPLAGMCESAGMDYEEKASLDFLFG |
| SEQ ID NO 77 3xFlag-NLS-T4 DNA polymerase (Y320A): | MDYKDHDGDYKDHDIDYKDDDDKMAPKKKRKVGIHGVPAAKEFYISIETVGNNIVER<br>YIDENGKERTREVEYLPTMFRHCKEESKYKDIYGKNCAPQKFPSMKDARDWMKRMED<br>IGLEALGMNDFKLAYISDTYGSEIVYDRKFVRVANCDIEVTGDKFPDPMKAEYEIDAITH<br>YDSIDDRFYVFDLLNSMYGSVSKWDAKLAAKLDCEGGDEVPQEILDRVIYMPFDNERD<br>MLMEYINLWEQKRPAIFTGWNIEGFDVPYIMNRVKMILGERSMKRFSPIGRVKSKLIQN<br>MYGSKEIYSIDGVSILDYLDLYKKFAFTNLPSFSLESVAQHETKKGKLPYDGPINKLRET |

TABLE 1-continued

| SEQ ID NO | SEQUENCE |
|---|---|
| | NHQRYISANIIDVESVQAIDKIRGFIDLVLSMSYYAKMPFSGVMSPIKTWDAIIFNSLKGE<br>HKVIPQQGSHVKQSFPGAFVFEPKPIARRYIMSFDLTSLYPSIIRQVNISPETIRGQFKVHPI<br>HEYIAGTAPKPSDEYSCSPNGWMYDKHQEGIIPKEIAKVFFQRKDWKKKMFAEEMNAE<br>AIKKIIMKGAGSCSTKPEVERYVKFSDDFLNELSNYTESVLNSLIEECEKAATLANTNQL<br>NRKILINSLYGALGNIHFRYYDLRNATAITIFGQVGIQWIARKINEYLNKVCGTNDEDFIA<br>AGDTDSVYVCVDKVIEKVGLDRFKEQNDLVEFMNQFGKKKMEPMIDVAYRELCDYM<br>NNREHLMHMDREAISCPPLGSKGVGGFWKAKKRYALNVYDMEDKRFAEPHLKIMGM<br>ETQQSSTPKAVQEALEESIRRILQEGEESVQEYYKNFEKEYRQLDYKVIAEVKTANDIAK<br>YDDKGWPGFKCPFHIRGVLTYRRAVSGLGVAPILDGNKVMVLPLREGNPFGDKCIAWP<br>SGTELPKEIRSDVLSWIDHSTLFQKSFVKPLAGMCESAGMDYEEKASLDFLFG |
| SEQ ID NO 78 3xFlag-NLS-T4 DNA polymerase (A737V): | MDYKDHDGDYKDHDIDYKDDDDKMAPKKKRKVGIHGVPAAKEFYISIETVGNNIVER<br>YIDENGKERTREVEYLPTMFRHCKEESKYKDIYGKNCAPQKFPSMKDARDWMKRMED<br>IGLEALGMNDFKLAYISDTYGSEIVYDRKFVRVANCDIEVTGDKFPDPMKAEYEIDAITH<br>YDSIDDRFYVFDLLNSMYGSVSKWDAKLAAKLDCEGGDEVPQEILDRVIYMPFDNERD<br>MLMEYINLWEQKRPAIFTGWNIEGFDVPYIMNRVKMILGERSMKRFSPIGRVKSKLIQN<br>MYGSKEIYSIDGVSILDYLDLYKKFAFTNLPSFSLESVAQHETKKGKLPYDGPINKLRET<br>NHQRYISYNIIDVESVQAIDKIRGFIDLVLSMSYYAKMPFSGVMSPIKTWDAIIFNSLKGE<br>HKVIPQQGSHVKQSFPGAFVFEPKPIARRYIMSFDLTSLYPSIIRQVNISPETIRGQFKVHPI<br>HEYIAGTAPKPSDEYSCSPNGWMYDKHQEGIIPKEIAKVFFQRKDWKKKMFAEEMNAE<br>AIKKIIMKGAGSCSTKPEVERYVKFSDDFLNELSNYTESVLNSLIEECEKAATLANTNQL<br>NRKILINSLYGALGNIHFRYYDLRNATAITIFGQVGIQWIARKINEYLNKVCGTNDEDFIA<br>AGDTDSVYVCVDKVIEKVGLDRFKEQNDLVEFMNQFGKKKMEPMIDVAYRELCDYM<br>NNREHLMHMDREAISCPPLGSKGVGGFWKAKKRYALNVYDMEDKRFAEPHLKIMGM<br>ETQQSSTPKVVQEALEESIRRILQEGEESVQEYYKNFEKEYRQLDYKVIAEVKTANDIAK<br>YDDKGWPGFKCPFHIRGVLTYRRAVSGLGVAPILDGNKVMVLPLREGNPFGDKCIAWP<br>SGTELPKEIRSDVLSWIDHSTLFQKSFVKPLAGMCESAGMDYEEKASLDFLFG |
| SEQ ID NO 79 APEX1: | MAPKRGKKGAVAEDGDELRTEPEAKKSKTAAKKNDKEAAGEGPALYEDPPDQKTSPS<br>GKPATLKICSWNVDGLRAWIKKKGLDWVKEEAPDILCLQETKCSENKLPAELQELPGLS<br>HQYWSAPSDKEGYSGVGLLSRQCPLKVSYGIGDEEHDQEGRVIVAEFDSFVLVTAYVP<br>NAGRGLVRLEYRQRWDEAFRKFLKGLASRKPLVLCGDLNVAHEEIDLRNPKGNKKNA<br>GFTPQERQGFGELLQAVPLADSFRHLYPNTPYAYTFWTYMIVINARSKNVGWRLDYFLL<br>SHSLLPALCDSKIRSKALGSDHCPITLYLAL |
| SEQ ID NO 80 VStag-APEX2-NLS-NLS (Addgene #124617): | MVRGSGKPIPNPLLGLDSTGKSYPTVSADYQDAVEKAKKKLRGFIAEKRCAPLMLRLAF<br>HSAGTFDKGTKTGGPFGTIKHPAELAHSANNGLDIAVRLLEPLKAEFPILSYADFYQLAG<br>VVAVEVTGGPKVPFHPGREDKPEPPPEGRLPDPIKGSDHLRDVFGKAMGLTDQDIVALS<br>GGHTIGAAHKERSGFEGPWTSNPLIFDNSYFTELLSGEKEGLLQLPSDKALLSDPVFRPL<br>VDKYAADEDAFFADYAEAHQKLSELGFADAEFSRADPKKKRKVDPKKKRKVDPKKKR<br>KV |
| SEQ ID NO 81 XRCC4: | MERKISRIHLVSEPSITHFLQVSWEKTLESGFVITLTDGHSAWTGTVSESEISQEADDMA<br>MEKGKYVGELRKALLSGAGPADVYTFNFSKESCYFFEEKNLKDVSFRLGSFNLEKVENP<br>AEVIRELICYCLDTIAENQAKNEHLQKENERLLRDWNDVQGRFEKCVSAKEALETDLYK<br>RFILVLNEKKTKIRSLHNKLLNAAQEREKDIKQEGETAICSEMTADRDPVYDESTDEESE<br>NQTDLSGLASAAVSKDDSIISSLDVTDIAPSRKRRQRMQRNLGTEPKMAPQENQLQEKE<br>KPDSSLPETSKKEHISAENMSLETLRNSSPEDLFDEI |

TABLE 1-continued

| SEQ ID NO | SEQUENCE |
|---|---|
| SEQ ID NO 82 V5tag-XRN1(Addgene #66596): | MDAQTRRRERRAEKQAQWKAANGGSPPHMAYPYDVPDYAPPSRAQASNSAVDGTAG MGVPKFYRWISERYPCLSEVVKEHQIPEFDNLYLDMNGIIHQCSHPNDDDVHFRISDDKI FTDIFHYLEVLFRIIKPRKVFFMAVDGVAPRAKMNQQRGRRFRSAKEAEDKIKKAIEKG ETLPTEARFDSNCITPGTEFMARLHEHLKYFVNMKISTDKSWQGVTIYFSGHETPGEGEH KIMEFIRSEKAKPDHDPNTRHCLYGLDADLIMLGLTSHEAHFSLLREEVRFGGKKTQRV CAPEETTFHLLHLSLMREYIDYEFSVLKEKITFKYDIERIIDDWILMGFLVGNDFIPHLPHL HINHDALPLLYGTYVTILPELGGYINESGHLNLPRFEKYLVKLSDFDREHFSEVFVDLKW FESKVGNKYLNEAAGVAAEEARNYKEKKKLKGQENSLCWTALDKNEGEMITSKDNLE DETEDDDLFETEFRQYKRTYYMTKMGVDVVSDDFLADQAACYVQAIQWILHYYYHGV QSWSWYYPYHYAPFLSDIHNISTLKIHEELGKPFKPFEQLLAVLPAASKNLLPACYQHLM TNEDSPIIEYYPPDFKTDLNGKQQEWEAVVLIPFIDEKRLLEAMETCNHSLKKEERKRNQ HSECLMCWYDRDTEFIYPSPWPEKFPAIERCCTRYKIISLDAWRVDINKNKITRIDQKAL YFCGFPTLKHIRHKFFLKKSGVQVFQQSSRGENMMLEILVDAESDELTVENVASSVLGK SVFVNWPHLEEARVVAVSDGETKFYLEEPPGTQKLYSGRTAPPSKVVHLGDKEQSNWA KEVQGISEHYLRRKGIINETSAVVYAQLLTGRKYQINQNGEVRLEKQWSKQVVPFVYQ TIVKDIRAFDSRFSNIKTLDDLFPLRSMVFMLGTPYYGCTGEVQDSGDVITEGRIRVIFSIP CEPNLDALIQNQHKYSIKYNPGYVLASRLGVSGYLVSRFTGSIFIGRGSRRNPHGDHKAN VGLNLKFNKKNEEVPGYTKKVGSEWMYSSAAEQLLAEYLERAPELFSYIAKNSQEDVF YEDDIWPGENENGAEKVQEIITWLKGHPVSTLSRSSCDLQILDAAIVEKIEEEVEKCKQR KNNKKVRVTVKPHLLYRPLEQQHGVIPDRDAEFCLFDRVVNVRENFSVPVGLRGTIIGI KGANREADVLEEVLFDEEFPGGLTIRCSPGRGYRLPTSALVNLSHGSRSETGNQKLTAIV KPQPAVHQHSSSSSVSSGHLGALNHSPQSLFVPTQVPTKDDDEFCNIWQSLQGSGKMQY FQPTIQEKGAVLPQEISQVNQHHKSGFNDNSVKYQQRKHDPHRKFKEECKSPKAECWS QKMSNKQPNSGIENFLASLNISKENEVQSSHHGEPPSEEHLSPQSFAMGTRMLKEILKID GSNTVDHKNEIKQIANEIPVSSNRRDEYGLPSQPKQNKKLASYMNKPHSANEYHNVQS MDNMCWPAPSQIPPVSTPVTELSRICSLVGMPQPDFSFLRMPQTMTVCQVKLSNGLLVH GPQCHSENEAKEKAALFALQQLGSLGMNFPLPSQVFANYPSAVPPGTIPPAFPPPTGWD HYGSNYALGAANIMPSSSHLFGSMPWGPSVPVPGKPFHHTLYSGTMPMAGGIPGGVHN QFIPLQVIKKRVANKKNEENKEAQSSQATPVQTSQPDSSNIVKVSPRESSSASLKSSPIAQ PASSFQVETASQGHSISHHKSTPISSSRRKSRKLAVNFGVSKPSE |
| SEQ ID NO 83 DNA2: | MEQLNELELLMEKSFWEEAELPAELFQKKVVASFPRTVLSTGMDNRYLVLAVNTVQNK EGNCEKRLVITASQSLENKELCILRNDWCSVPVEPGDIIHLEGDCTSDTWIIDKDFGYLIL YPDMLISGTSIASSIRCMRRAVLSETFRSSDPATRQMLIGTVLHEVFQKAINNSFAPEKLQ ELAFQTIQEIRHLKEMYRLNLSQDEIKQEVEDYLPSFCKWAGDFMHKNTSTDFPQMQLS LPSDNSKDNSTCNIEVVKPMDIEESIWSPRFGLKGKIDVTVGVKIHRGYKTKYKIMPLEL KTGKESNSIEHRSQVVLYTLLSQERRADPEAGLLLYLKTGQMYPVPANHLDKRELLKLR NQMAFSLFHRISKSATRQKTQLASLPQIIEEEKTCKYCSQIGNCALYSRAVEQQMDCSSV PIVMLPKIEEETQHLKQTHLEYFSLWCLMLTLESQSKDNKKNHQNIWLMPASEMEKSGS CIGNLIRMEHVKIVCDGQYLHNFQCKHGAIPVTNLMAGDRVIVSGEERSLFALSRGYVK EINMTTVTCLLDRNLSVLPESTLFRLDQEEKNCDIDTPLGNLSKLMENTFVSKKLRDLIID FREPQFISYLSSVLPHDAKDTVACILKGLNKPQRQAMKKVLLSKDYTLIVGMPGTGKTT TICTLVRILYACGFSVLLTSYTHSAVDNILLKLAKFKIGFLRLGQIQKVHPAIQQFTEQEIC RSKSIKSLALLEELYNSQLIVATTCMGINHPIFSRKIFDFCIVDEASQISQPICLGPLFFSRRF VLVGDHQQLPPLVLNREARALGMSESLFKRLEQNKSAVVQLTVQYRMNSKIMSLSNKL TYEGKLECGSDKVANAVINLRHFKDVKLELEFYADYSDNPWLMGVFEPNNPVCFLNTD KVPAPEQVEKGGVSNVTEAKLIVFLTSIFVKAGCSPSDIGIIAPYRQQLKIINDLLARSIGM VEVNTVDKYQGRDKSIVLVSFVRSNKDGTVGELLKDWRRLNVAITRAKHKLILLGCVP SLNCYPPLEKLLNHLNSEKLIIDLPSREHESLCHILGDFQRE |

TABLE 1-continued

| SEQ ID NO | SEQUENCE |
|---|---|
| SEQ ID NO 84 Myc-POLQ-Flag(Addgene #73132): | MEQKLISEEDLLRKRGILNLLRRSGKRRRSESGSDSFSGSGGDSSASPQFLSGSVLSPPPG<br>LGRCLKAAAAGECKPTVPDYEIDKLLLANWGLPKAVLEKYHSFGVKKMFEWQAECLL<br>LGQVLEGKNLVYSAPTSAGKTLVAELLILKRVLEMRKKALFILPFVSVAKEKKYYLQSL<br>FQEVGIKVDGYMGSTSPSRHFSSLDIAVCTIERANGLINRLIEENKMDLLGMVVVDELH<br>MLGDSHRGYLLELLLTKICYITRKSASCQADLASSLSNAVQIVGMSATLPNLELVASWL<br>NAELYHTDFRPVPLLESVKVGNSIYDSSMKLVREFEPMLQVKGDEDHVVSLCYETICDN<br>HSVLLFCPSKKWCEKLADIIAREFYNLHHQAEGLVKPSECPPVILEQKELLEVMDQLRRL<br>PSGLDSVLQKTVPWGVAFHHAGLTFEERDIIEGAFRQGLIRVLAATSTLSSGVNLPARRV<br>IIRTPIFGGRPLDILTYKQMVGRAGRKGVDTVGESILICKNSEKSKGIALLQGSLKPVRSC<br>LQRREGEEVTGSMIRAILEIIVGGVASTSQDMHTYAACTFLAASMKEGKQGIQRNQESV<br>QLGAIEACVMWLLENEFIQSTEASDGTEGKVYHPTHLGSATLSSSLSPADTLDIFADLQR<br>AMKGFVLENDLHILYLVTPMFEDWTTIDWYRFFCLWEKLPTSMKRVAELVGVEEGFLA<br>RCVKGKVVARTERQHRQMAIHKRFFTSLVLLDLISEVPLREINQKYGCNRGQIQSLQQS<br>AAVYAGMITVFSNRLGWHNMELLLSQFQKRLTFGIQRELCDLVRVSLLNAQRARVLYA<br>SGFHTVADLARANIVEVEVILKNAVPFKSARKAVDEEEEAVEERRNMRTIWVTGRKGL<br>TEREAAALIVEEARMILQQDLVEMGVQWNPCALLHSSTCSLTHSESEVKEHTFISQTKSS<br>YKKLTSKNKSNTIFSDSYIKHSPNIVQDLNKSREHTSSFNCNFQNGNQEHQRCSIFRARK<br>RASLDINKEKPGASQNEGKTSDKKVVQTFSQKTKKAPLNFNSEKMSRSFRSWKRRKHL<br>KRSRDSSPLKDSGACRIHLQGQTLSNPSLCEDPFTLDEKKTEFRNSGPFAKNVSLSGKEK<br>DNKTSFPLQIKQNCSWNITLTNDNFVEHIVTGSQSKNVTCQATSVVSEKGRGVAVEAEK<br>INEVLIQNGSKNQNVYMKHHDIHPINQYLRKQSHEQTSTITKQKNIIERQMPCEAVSSYIN<br>RDSNVTINCERIKLNTEENKPSHFQALGDDISRTVIPSEVLPSAGAFSKSEGQHENFLNISR<br>LQEKTGTYTTNKTKNNHVSDLGLVLCDFEDSFYLDTQSEKIIQQMATENAKLGAKDTN<br>LAAGIMQKSLVQQNSMNSFQKECHIPFPAEQHPLGATKIDHLDLKTVGTMKQSSDSHG<br>VDILTPESPIFHSPILLEENGLFLKKNEVSVTDSQLNSFLQGYQTQETVKPVILLIPQKRTPT<br>GVEGECLPVPETSLNMSDSLLFDSFSDDYLVKEQLPDMQMKEPLPSEVTSNHFSDSLCL<br>QEDLIKKSNVNENQDTHQQLTCSNDESIIFSEMDSVQMVEALDNVDIFPVQEKNHTVVS<br>PRALELSDPVLDEHHQGDQDGGDQDERAEKSKLTGTRQNHSFIWSGASFDLSPGLQRIL<br>DKVSSPLENEKLKSMTINFSSLNRKNTELNEEQEVISNLETKQVQGISFSSNNEVKSKIEM<br>LENNANHDETSSLLPRKESNIVDDNGLIPPTPIPTSASKLTFPGILETPVNPWKTNNVLQP<br>GESYLFGSPSDIKNHDLSPGSRNGFKDNSPISDTSFSLQLSQDGLQLTPASSSSESLSIIDVA<br>SDQNLFQTFIKEWRCKKRFSISLACEKIRSLTSSKTATIGSRFKQASSPQEIPIRDDGFPIKG<br>CDDTLVVGLAVCWGGRDAYYFSLQKEQKHSEISASLVPPSLDPSLTLKDRMWYLQSCL<br>RKESDKECSVVIYDFIQSYKILLLSCGISLEQSYEDPKVACWLLDPDSQEPTLHSIVTSFLP<br>HELPLLEGMETSQGIQSLGLNAGSEHSGRYRASVESILIFNSMNQLNSLLQKENLQDVFR<br>KVEMPSQYCLALLELNGIGFSTAECESQKHIMQAKLDAIETQAYQLAGHSFSFTSSDDIA<br>EVLFLELKLPPNREMKNQGSKKTLGSTRRGIDNGRKLRLGRQFSTSKDVLNKLKALHPL<br>PGLILEWRRITNAITKVVFPLQREKCLNPFLGMERIYPVSQSHTATGRITFTEPNIQNVPR<br>DFEIKMPTLVGESPPSQAVGKGLLPMGRGKYKKGFSVNPRCQAQMEERAADRGMPFSI<br>SMRHAFVPFPGGSILAADYSQLELRILAHLSHDRRLIQVLNTGADVFRSIAAEWKMIEPE<br>SVGDDLRQQAKQICYGIIYGMGAKSLGEQMGIKENDAACYIDSFKSRYTGINQFMTETV<br>KNCKRDGFVQTILGRRRYLPGIKDNNPYRKAHAERQAINTIVQGSAADIVKIATVNIQKQ<br>LETFHSTFKSHGHREGMLQSDRTGLSRKRKLQGMFCPIRGGFFILQLHDELLYEVAEED<br>VVQVAQIVKNEMESAVKLSVKLKVKVKIGASWGELKDFDVPGMDYKDDDDK |
| SEQ ID NO 85 POLB: | MDYKDHDGDYKDHDIDYKDDDDKMAPKKKRKVGIHGVPAAASKRKAPQETLNGGIT<br>DMLTELANFEKNVSQAIHKYNAYRKAASVIAKYPHKIKSGAEAKKLPGVGTKIAEKIDE<br>FLATGKLRKLEKIRQDDTSSSINFLTRVSGIGPSAARKFVDEGIKTLEDLRKNEDKLNHH<br>QRIGLKYFGDFEKRIPREEMLQMQDIVLNEVKKVDSEYIATVCGSFRRGAESSGDMDVL<br>LTHPSFTSESTKQPKLLHQVVEQLQKVHFITDTLSKGETKFMGVCQLPSKNDEKEYPHR |

TABLE 1-continued

| SEQ ID NO | SEQUENCE |
|---|---|
| | RIDIRLIPKDQYYCGVLYFTGSDIFNKNMRAHALEKGFTINEYTIRPLGVTGVAGEPLPVD<br>SEKDIFDYIQWKYREPKDRSE |
| SEQ ID NO 86 POLH: | MATGQDRVVALVDMDCFFVQVEQRQNPHLRNKPCAVVQYKSWKGGGIIAVSYEARAF<br>GVTRSMWADDAKKLCPDLLLAQVRESRGKANLTKYREASVEVMEIMSRFAVIERASID<br>EAYVDLTSAVQERLQKLQGQPISADLLPSTYIEGLPQGPTTAEETVQKEGMRKQGLFQW<br>LDSLQIDNLTSPDLQLTVGAVIVEEMRAAIERETGFQCSAGISHNKVLAKLACGLNKPNR<br>QTLVSHGSVPQLFSQMPIRKIRSLGGKLGASVIEILGIEYMGELTQFTESQLQSHFGEKNG<br>SWLYAMCRGIEHDPVKPRQLPKTIGCSKNFPGKTALATREQVQWWLLQLAQELEERLT<br>KDRNDNDRVATQLVVSIRVQGDKRLSSLRRCCALTRYDAHKMSHDAFTVIKNCNTSGI<br>QTEWSPPLTMLFLCATKFSASAPSSSTDITSFLSSDPSSLPKVPVTSSEAKTQGSGPAVTA<br>TKKATTSLESFFQKAAERQKVKEASLSSLTAPTQAPMSNSPSKPSLPFQTSQSTGTEPFFK<br>QKSLLLKQKQLNNSSVSSPQQNPWSNCKALPNSLPTEYPGCVPVCEGVSKLEESSKATP<br>AEMDLAHNSQSMHASSASKSVLEVTQKATPNPSLLAAEDQVPCEKCGSLVPVWDMPE<br>HMDYHFALELQKSFLQPHSSNPQVVSAVSHQGKRNPKSPLACTNKRPRPEGMQTLESFF<br>KPLTH |
| SEQ ID NO 87 POLG: | MASRLLWRKVAGATVGPGPVPAPGRWVSSSVPASDPSDGQRRRQQQQQQQQQQQQQ<br>PQQPQVLSSEGGQLRHNPLDIQMLSRGLHEQIFGQGGEMPGEAAVRRSVEHLQKHGLW<br>GQPAVPLPDVELRLPPLYGDNLDQHFRLLAQKQSLPYLEAANLLLQAQLPPKPPAWAW<br>AEGWTRYGPEGEAVPVAIPEERALVFDVEVCLAEGTCPTLAVAISPSAWYSWCSQRLVE<br>ERYSWTSQLSPADLIPLEVPTGASSPTQRDWQEQLVVGHNVSFDRAHIREQYLIQGSRM<br>RFLDTMSMHMAISGLSSFQRSLWIAAKQGKHKVQPPTKQGQKSQRKARRGPAISSWDW<br>LDISSVNSLAEVHRLYVGGPPLEKEPRELFVKGTMKDIRENFQDLMQYCAQDVWATHE<br>VFQQQLPLFLERCPHPVTLAGMLEMGVSYLPVNQNWERYLAEAQGTYEELQREMKKS<br>LMDLANDACQLLSGERYKEDPWLWDLEWDLQEFKQKKAKKVKKEPATASKLPIEGAG<br>APGDPMDQEDLGPCSEEEEFQQDVMARACLQKLKGTTELLPKRPQHLPGHPGWYRKL<br>CPRLDDPAWTPGPSLLSLQMRVTPKLMALTWDGFPLHYSERHGWGYLVPGRRDNLAK<br>LPTGTTLESAGVVCPYRAIESLYRKHCLEQGKQQLMPQEAGLAEEFLLTDNSAIWQTVE<br>ELDYLEVEAEAKMENLRAAVPGQPLALTARGGPKDTQPSYHHGNGPYNDVDIPGCWFF<br>KLPHKDGNSCNVGSPFAKDFLPKMEDGTLQAGPGGASGPRALEINKMISFWRNAHKRIS<br>SQMVVWLPRSALPRAVIRHPDYDEEGLYGAILPQVVTAGTITRRAVEPTWLTASNARPD<br>RVGSELKAMVQAPPGYTLVGADVDSQELWIAAVLGDAHFAGMHGCTAFGWMTLQGR<br>KSRGTDLHSKTATTVGISREHAKIFNYGRIYGAGQPFAERLLMQFNHRLTQQEAAEKAQ<br>QMYAATKGLRWYRLSDEGEWLVRELNLPVDRTEGGWISLQDLRKVQRETARKSQWK<br>KWEVVAERAWKGGTESEMFNKLESIATSDIPRTPVLGCCISRALEPSAVQEEFMTSRVN<br>WVVQSSAVDYLHLMLVAMKWLFEEFAIDGRFCISIHDEVRYLVREEDRYRAALALQIT<br>NLLTRCMFAYKLGLNDLPQSVAFFSAVDIDRCLRKEVTMDCKTPSNPTGMERRYGIPQG<br>EALDIYQIIELTKGSLEKRSQPGP |
| SEQ ID NO 88 POLN: | MENYEALVGFDLCNTPLSSVAQKIMSAMHSGDLVDSKTWGKSTETMEVINKSSVKYSV<br>QLEDRKTQSPEKKDLKSLRSQTSRGSAKLSPQSFSVRLTDQLSADQKQKSISSLTLSSCLI<br>PQYNQEASVLQKKGHKRKHFLMENINNENKGSINLKRKHITYNNLSEKTSKQMALEED<br>TDDAEGYLNSGNSGALKKHFCDIRHLDDWAKSQLIEMLKQAAALVITVMYTDGSTQLG<br>ADQTPVSSVRGIVVLVKRQAEGGHGCPDAPACGPVLEGFVSDDPCIYIQIEHSAIWDQEQ<br>EAHQQFARNVLFQTMKCKCPVICFNAKDFVRIVLQFFGNDGSWKHVADFIGLDPRIAA<br>WLIDPSDATPSFEDLVEKYCEKSITVKVNSTYGNSSRNIVNQNVRENLKTLYRLTMDLC<br>SKLKDYGLWQLFRTLELPLIPILAVMESHAIQVNKEEMEKTSALLGARLKELEQEAHFV<br>AGERFLITSNNQLREILFGKLKLHLLSQRNSLPRTGLQKYPSTSEAVLNALRDLHPLPKIIL<br>EYRQVHKIKSTFVDGLLACMKKGSISSTWNQTGTVTGRLSAKHPNIQGISKHPIQITTPK<br>NFKGKEDKILTISPRAMFVSSKGHTFLAADFSQIELRILTHLSGDPELLKLFQESERDDVF |

TABLE 1-continued

| SEQ ID NO | SEQUENCE |
|---|---|
| | STLTSQWKDVPVEQVTHADREQTKKVVYAVVYGAGKERLAACLGVPIQEAAQFLESFL<br>QKYKKIKDFARAAIAQCHQTGCVVSIMGRRRPLPRIHAHDQQLRAQAERQAVNFVVQG<br>SAADLCKLAMIHVFTAVAASHTLTARLVAQIHDELLFEVEDPQIPECAALVRRTMESLE<br>QVQALELQLQVPLKVSLSAGRSWGHLVPLQEAWGPPPGPCRTESPSNSLAAPGSPASTQ<br>PPPLHFSPSFCL |
| SEQ ID NO 89 TENT4A: | MASPCPEEAAMRREVVKRIETVVKDLWPTADVQIFGSFSTGLYLPTSDIDLVVFGKWER<br>PPLQLLEQALRKHNVAEPCSIKVLDKATVPIIKLTDQETEVKVDISFNMETGVRAAEFIK<br>NYMKKYSLLPYLILVLKQFLLQRDLNEVFTGGISSYSLILMAISFLQLHPRIDARRADENL<br>GMLLVEFFELYGRNFNYLKTGIRIKEGGAYIAKEEIMKAMTSGYRPSMLCIEDPLLPGND<br>VGRSSYGAMQVKQVFDYAYIVLSHAVSPLARSYPNRDAESTLGRIIKVTQEVIDYRRWI<br>KEKWGSKAHPSPGMDSRIKIKERIATCNGEQTQNREPESPYGQRLTLSLSSPQLLSSGSSA<br>SSVSSLSGSDVDSDTPPCTTPSVYQFSLQAPAPLMAGLPTALPMPSGKPQPTTSRTLIMTT<br>NNQTRFTIPPPTLGVAPVPCRQAGVEGTASLKAVHHMSSPAIPSASPNPLSSPHLYHKHN<br>GMKLSMKGSHGHTQGGGYSSVGSGGVRPPVGNRGHHQYNRTGWRRKKHTHTRDSLP<br>VSLSR |
| SEQ ID NO 90 DNA Ligase 4: | MAASQTSQTVASHVPFADLCSTLERIQKSKGRAEKIRHFREFLDSWRKFHDALHKNHK<br>DVTDSFYPAMRLILPQLERERMAYGIKETMLAKLYIELLNLPRDGKDALKLLNYRTPTG<br>THGDAGDFAMIAYFVLKPRCLQKGSLTIQQVNDLLDSIASNNSAKRKDLIKKSLLQLITQ<br>SSALEQKWLIRMIIKDLKLGVSQQTIFSVFHNDAAELHNVTTDLEKVCRQLHDPSVGLSD<br>ISITLFSAFKPMLAAIADIEHIEKDMKHQSFYIETKLDGERMQMHKDGDVYKYFSRNGY<br>NYTDQFGASPTEGSLTPFIHNAFKADIQICILDGEMMAYNPNTQTFMQKGTKFDIKRMV<br>EDSDLQTCYCVFDVLMVNNKKLGHETLRKRYEILSSIFTPIPGRIEIVQKTQAHTKNEVID<br>ALNEAIDKREEGIMVKQPLSIYKPDKRGEGWLKIKPEYVSGLMDELDILIVGGYWGKGS<br>RGGMMSHFLCAVAEKPPPGEKPSVFHTLSRVGSGCTMKELYDLGLKLAKYWKPFHRK<br>APPSSILCGTEKPEVYIEPCNSVIVQIKAAEIVPSDMYKTGCTLRFPRIEKIRDDKEWHEC<br>MTLDDLEQLRGKASGKLASKHLYIGGDDEPQEKKRKAAPKMKKVIGIIEHLKAPNLTN<br>VNKISNIFEDVEFCVMSGTDSQPKPDLENRIAEFGGYIVQNPGPDTYCVIAGSENIRVKNII<br>LSNKHDVVKPAWLLECFKTKSFVPWQPRFMIHMCPSTKEHFAREYDCYGDSYFIDTDL<br>NQLKEVFSGIKNSNEQTPEEMASLIADLEYRYSWDCSPLSMFRRHTVYLDSYAVINDLS<br>TKNEGTRLAIKALELRFHGAKVVSCLAEGVSHVIIGEDHSRVADFKAFRRTFKRKFKILK<br>ESWVTDSIDKCELQEENQYLI |
| SEQ ID NO 91 XRN: | MGSAACPRGALPELAPCCQPREQSQPHTRWDAGCGIQHPGGEEFRTLGGARAYRVPNS<br>QEGRSSPTRFFPAPEGPAHCFVSSPDRAFWVSEEVQRLLLSNACQPKECNGVKIPVDASK<br>PNPNDVEFDNLYLDMNGIIHPCTHPEDKPAPKNEDEMMVAIFEYIDRLFSIVRPRRLLYM<br>AIDGVAPRAKMNQQRSRRFRASKEGMEAAVEKQRVREEILAKGGFLPPEEIKERFDSNC<br>ITPGTEFMDNLAKCLRYYIADRLNNDPGWKNLTVILSDASAPGEGEHKIMDYIRRQRAQ<br>PNHDPNTHHCLCGADADLIMLGLATHEPNFTIIREEFKPNKPKPCGLCNQFGHEVKDCE<br>GLPREKKGKHDELADSLPCAEGEFIFLRLNVLREYLERELTMASLPFTFDVERSIDDWVF<br>MCFFVGNDFLPHLPSLEIRENAIDRLVNIYKNVVHKTGGYLTESGYVNLQRVQMIMLAV<br>GEVEDSIFKKRKDDEDSFRRRQKEKRKRMKRDQPAFTPSGILTPHALGSRNSPGSQVAS<br>NPRQAAYEMRMQNNSSPSISPNTSFTSDGSPSPLGGIKRKAEDSDSEPEPEDNVRLWEAG<br>WKQRYYKNKFDVDAADEKFRRKVVQSYVEGLCWVLRYYYQGCASWKWYYPFHYAP<br>FASDFEGIADMPSDFEKGTKPFKPLEQLMGVFPAASGNFLPPSWRKLMSDPDSSIIDFYPE<br>DFAIDLNGKKYAWQGVALLPFVDERRLRAALEEVYPDLTPEETRRNSLGGDVLFVGKH<br>HPLHDFILELYQTGSTEPVEVPPELCHGIQGKFSLDEEAILPDQIVCSPVPMLRDLTQNTV<br>VSINFKDPQFAEDYIFKAVMLPGARKPAAVLKPSDWEKSSNGRQWKPQLGFNRDRRPV<br>HLDQAAFRTLGHVMPRGSGTGIYSNAAPPPVTYQGNLYRPLLRGQAQIPKLMSNMRPQ |

TABLE 1-continued

| SEQ ID NO | SEQUENCE |
|---|---|
| | DSWRGPPPLFQQQRFDRGVGAEPLLPWNRMLQTQNAAFQPNQYQMLAGPGGYPPRRD<br>DRGGRQGYPREGRKYPLPPPSGRYNWN |
| SEQ ID NO 92 3xFlag_NLS_ PolIV: | MDYKDHDGDYKDHDIDYKDDDDKMAPKKKRKVGIHGVPAASLKGKFFAFLPNPNTSS<br>NKFFKSILEKKGATIVSSIQNCLQSSRKEVIILIEDSFVDSDMHLTQKDIFQREAGLNDVDE<br>FLGKIEQSGIQCVKTSCITKWVQNDKFAFQKDDLIKFQPSIIVISDNADDGQSSTDKESEIS<br>TDVESERNDDSNNKDMIQASKPLKRLLQEDKGRASLVTDKTKYKNNELIIGALKRLTKK<br>YEIEGEKFRARSYRLAKQSMENCDFNVRSGEEAHTKLRNIGPSIAKKIQVILDTGVLPGL<br>NDSVGLEDKLKYFKNCYGIGSEIAKRWNLLNFESFCVAAKKDPEEFVSDWTILFGWSYY<br>DDWLCKMSRNECFAHLKKVQKALRGIDPECQVELQGSYNRGYSKCGDIDLLFFKPFCN<br>DTTELAKIMETLCIKLYKDGYIHCFLQLTPNLEKLFLKRIVERFRTAKIVGYGERKRWYS<br>SEIIKKFFMGVKLSPRELEELKEMKNDEGTLLIEEEEEETKLKPIDQYMSLNAKDGNYCR<br>RLDFFCCKWDELGAGRIHYTGSKEYNRWIRILAAQKGFKLTQHGLFRNNILLESFNERRI<br>FELLNLKYAEPEHRNIEWEKKTG |
| SEQ ID NO 93 3xFlag_NLS_ XseA: | MDYKDHDGDYKDHDIDYKDDDDKMAPKKKRKVGIHGVPAALPSQSPAIFTVSRLNQT<br>VRLLLEHEMGQVWISGEISNFTQPASGHWYFTLKDDTAQVRCAMFRNSNRRVTFRPQH<br>GQQVLVRANITLYEPRGDYQIIVESMQPAGEGLLQQKYEQLKAKLQAEGLFDQQYKKP<br>LPSPAHCVGVITSKTGAALHDILHVLKRRDPSLPVIIYPAAVQGDDAPGQIVRAIELANQ<br>RNECDVLIVGRGGGSLEDLWSFNDERVARAIFTSRIPVVSAVGHETDVTIADFVADLRAP<br>TPSAAAEVVSRNQQELLRQVQSTRQRLEMAMDYYLANRTRRFTQIHHRLQQQHPQLRL<br>ARQQTMLERLQKRMSFALENQLKRTGQQQQRLTQRLNQQNPQPKIHRAQTRIQQLEYR<br>LAETLRAQLSATRERFGNAVTHLEAVSPLSTLARGYSVTTATDGNVLKKVKQVKAGEM<br>LTTRLEDGWIESEVKNIQPVKKSRKKVH |
| SEQ ID NO 94 3xFlag_NLS_ XseB: | MDYKDHDGDYKDHDIDYKDDDDKMAPKKKRKVGIHGVPAAPKKNEAPASFEKALSE<br>LEQIVTRLESGDLPLEEALNEFERGVQLARQGQAKLQQAEQRVQILLSDNEDASLTPFTP<br>DNE |
| SEQ ID NO 95 3xFlag-NLS- SpCas9-NLS (Addgene #1000000055) | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIKRQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF |

TABLE 1-continued

| SEQ ID NO | SEQUENCE |
|---|---|
| | ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO 96 3xFlag-NLS-SpCas9(delta F916)-NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGIKRQLVETRQITKHVAQILDSRMNTKYDENDKLIREVKVITLKSKLVSDFR<br>KDFQFYKVREINNYHHAHDAYLNAVVGTALIKKYPKLESEFVYGDYKVYDVRKMIAK<br>SEQEIGKATAKYFFYSNIMNFFKTEITLANGEIRKRPLIETNGETGEIVWDKGRDFATVRK<br>VLSMPQVNIVKKTEVQTGGFSKESILPKRNSDKLIARKKDWDPKKYGGFDSPTVAYSVL<br>VVAKVEKGKSKKLKSVKELLGITIMERSSFEKNPIDFLEAKGYKEVKKDLIIKLPKYSLFE<br>LENGRKRMLASAGELQKGNELALPSKYVNFLYLASHYEKLKGSPEDNEQKQLFVEQHK<br>HYLDEIIEQISEFSKRVILADANLDKVLSAYNKHRDKPIREQAENIIHLFTLTNLGAPAAF<br>KYFDTTIDRKRYTSTKEVLDATLIHQSITGLYETRIDLSQLGGDKRPAATKKAGQAKKK<br>K |
| SEQ ID NO 97 3xFlag-NLS-SpCas9(G915F)-NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAFFIKRQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV |

TABLE 1-continued

| SEQ ID NO | SEQUENCE |
|---|---|
| | LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>98<br>3xFlag-NLS-<br>SpCas9(Q920P)-<br>NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIKRPLVETRQVIKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>99<br>3xFlag-NLS-<br>SpCas9(F916P)-<br>NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGPIKRQLVETRQVIKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR |

TABLE 1-continued

| SEQ ID NO | SEQUENCE |
|---|---|
| | KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>100<br>3xFlag-NLS-<br>SpCas9(R918A)-<br>NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIARQLVETRQVIKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>101<br>3xFlag-NLS-<br>SpCas9(R919P)-<br>NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIKPQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA |

TABLE 1-continued

| SEQ ID NO | SEQUENCE |
|---|---|
| | KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>102<br>3xFlag-NLS-<br>SpCas9-<br>NLS(N690C<br>T769I<br>G915M<br>N980K):<br>LZ3Cas9Addgene<br>#140561: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRRYTGWGRLSRKLINGIRDK<br>QSGKTILDFLKSDGFACRNFMQLIHDDSLTFKEDIQKAQVSGQGDSLHEHIANLAGSPAI<br>KKGILQTVKVVDELVKVMGRHKPENIVIEMARENQITQKGQKNSRERMKRIEEGIKELG<br>SQILKEHPVENTQLQNEKLYLYYLQNGRDMYVDQELDINRLSDYDVDHIVPQSFLKDDS<br>IDNKVLTRSDKNRGKSDNVPSEEVVKKMKNYWRQLLNAKLITQRKFDNLTKAERGGLS<br>ELDKAMFIKRQLVETRQITKHVAQILDSRMNTKYDENDKLIREVKVITLKSKLVSDFRK<br>DFQFYKVREINKYHHAHDAYLNAVVGTALIKKYPKLESEFVYGDYKVYDVRKMIAKSE<br>QEIGKATAKYFFYSNIMNFFKTEITLANGEIRKRPLIETNGETGEIVWDKGRDFATVRKV<br>LSMPQVNIVKKTEVQTGGFSKESILPKRNSDKLIARKKDWDPKKYGGFDSPTVAYSVLV<br>VAKVEKGKSKKLKSVKELLGITIMERSSFEKNPIDFLEAKGYKEVKKDLIIKLPKYSLFEL<br>ENGRKRMLASAGELQKGNELALPSKYVNFLYLASHYEKLKGSPEDNEQKQLFVEQHKH<br>YLDEIIEQISEFSKRVILADANLDKVLSAYNKHRDKPIREQAENIIHLFTLTNLGAPAAFK<br>YFDTTIDRKRYTSTKEVLDATLIHQSITGLYETRIDLSQLGGDKRPAATKKAGQAKKKK |
| SEQ ID NO<br>103<br>3xFlag-NLS-<br>SaCas9-P2A-<br>EGFP: | MDYKDHDGDYKDHDIDYKDDDDKMAPKKKRKVEASMKRNYILGLDIGITSVGYGIID<br>YETRDVIDAGVRLFKEANVENNEGRRSKRGARRLKRRRRHRIQRVKKLLFDYNLLTDH<br>SELSGINPYEARVKGLSQKLSEEEFSAALLHLAKRRGVHNVNEVEEDTGNELSTKEQISR<br>NSKALEEKYVAELQLERLKKDGEVRGSINRFKTSDYVKEAKQLLKVQKAYHQLDQSFI<br>DTYIDLLETRRTYYEGPGEGSPFGWKDIKEWYEMLMGHCTYFPEELRSVKYAYNADLY<br>NALNDLNNLVITRDENEKLEYYEKFQIIENVFKQKKKPTLKQIAKEILVNEEDIKGYRVT<br>STGKPEFTNLKVYHDIKDITARKEIIENAELLDQIAKILTIYQSSEDIQEELTNLNSELTQEE<br>IEQISNLKGYTGTHNLSLKAINLILDELWHTNDNQIAIFNRLKLVPKKVDLSQQKEIPTTL<br>VDDFILSPVVKRSFIQSIKVINAIIKKYGLPNDIIIELAREKNSKDAQKMINEMQKRNRQTN<br>ERIEEIIRTTGKENAKYLIEKIKLHDMQEGKCLYSLEAIPLEDLLNNPFNYEVDHIIPRSVS<br>FDNSFNNKVLVKQEENSKKGNRTPFQYLSSSDSKISYETFKKHILNLAKGKGRISKTKKE<br>YLLEERDINRFSVQKDFINRNLVDTRYATRGLMNLLRSYFRVNNLDVKVKSINGGFTSF<br>LRRKWKFKKERNKGYKHHAEDALIIANADFIFKEWKKLDKAKKVMENQMFEEKQAES<br>MPEIETEQEYKEIFITPHQIKHIKDFKDYKYSHRVDKKPNRELINDTLYSTRKDDKGNTLI<br>VNNLNGLYDKDNDKLKKLINKSPEKLLMYHHDPQTYQKLKLIMEQYGDEKNPLYKYY<br>EETGNYLTKYSKKDNGPVIKKIKYYGNKLNAHLDITDDYPNSRNKVVKLSLKPYRFDV<br>YLDNGVYKFVTVKNLDVIKKENYYEVNSKCYEEAKKLKKISNQAEFIASFYNNDLIKIN<br>GELYRVIGVNNDLLNRIEVNMIDITYREYLENMNDKRPPRIIKTIASKTQSIKKYSTDILG |

TABLE 1-continued

| SEQ ID NO | SEQUENCE |
|---|---|
| | NLYEVKSKKHPQIIKKGRSGGGEGRGSLLTCGDVEENPGPMVSKGEELFTGVVPILVEL<br>DGDVNGHKFSVSGEGEGDATYGKLTLKFICTTGKLPVPWPTLVTTLTYGVQCFSRYPDH<br>MKQHDFFKSAMPEGYVQERTIFFKDDGNYKTRAEVKFEGDTLVNRIELKGIDFKEDGNI<br>LGHKLEYNYNSHNVYIMADKQKNGIKVNFKIRHNIEDGSVQLADHYQQNTPIGDGPVL<br>LPDNHYLSTQSALSKDPNEKRDHMVLLEFVTAAGITLGMDELYK |
| SEQ ID NO<br>104<br>FnCas12a-<br>NLS-<br>3xHA(addgene<br>#64709): | MSIYQEFVNKYSLSKTLREELIPQGKTLENIKARGLILDDEKRAKDYKKAKQIIDKYHQF<br>FIEEILSSVCISEDLLQNYSDVYFKLKKSDDDNLQKDFKSAKDTIKKQISEYIKDSEKFKN<br>LFNQNLIDAKKGQESDLILWLKQSKDNGIELFKANSDITDIDEALEIIKSFKGWTTYFKGF<br>HENRKNVYSSNDIPTSIIYRIVDDNLPKFLENKAKYESLKDKAPEAINYEQIKKDLAEELT<br>FDIDYKTSEVNQRVFSLDEVFEIANFNNYLNQSGITKFNTIIGGKFVNGENTKRKGINEYI<br>NLYSQQINDKTLKKYKMSVLFKQILSDTESKSFVIDKLEDDSDVVTTMQSFYEQIAAFKT<br>VEEKSIKETLSLLFDDLKAQKLDLSKIYFKNDKSLTDLSQQVFDDYSVIGTAVLEYITQQI<br>APKNLDNPSKKEQELIAKKTEKAKYLSLETIKLALEEFNKHRDIDKQCRFEEILANFAAIP<br>MIFDEIAQNKDNLAQISIKYQNQGKKDLLQASAEDDVKAIKDLLDQTNNLLHKLKIFHIS<br>QSEDKANILDKDEHFYLVFEECYFELANIVPLYNKIRNYITQKPYSDEKFKLNFENSTLA<br>NGWDKNKEPDNTAILFIKDDKYYLGVMNKKNNKIFDDKAIKENKGEGYKKIVYKLLPG<br>ANKMLPKVFFSAKSIKFYNPSEDILRIRNHSTHTKNGSPQKGYEKFEFNIEDCRKFIDFYK<br>QSISKHPEWKDFGFRFSDTQRYNSIDEFYREVENQGYKLIFENISESYIDSVVNQGKLYL<br>FQIYNKDFSAYSKGRPNLHTLYWKALFDERNLQDVVYKLNGEAELFYRKQSIPKKITHP<br>AKEAIANKNKDNPKKESVFEYDLIKDKRFTEDKFFFHCPITINFKSSGANKFNDEINLLLK<br>EKANDVHILSIDRGERHLAYYTLVDGKGNIIKQDTFNIIGNDRMKTNYHDKLAAIEKDR<br>DSARKDWKKINNIKEMKEGYLSQVVHEIAKLVIEYNAIVVFEDLNFGFKRGRFKVEKQV<br>YQKLEKMLIEKLNYLVFKDNEFDKTGGVLRAYQLTAPEETFKKMGKQTGITYYVPAGFT<br>SKICPVTGFVNQLYPKYESVSKSQEFFSKFDKICYNLDKGYFEFSFDYKNFGDKAAKGK<br>WTIASFGSRLINFRNSDKNHNWDTREVYPTKELEKLLKDYSIEYGHGECIKAAICGESDK<br>KFFAKLTSVLNTILQMRNSKTGTELDYLISPVADVNGNFFDSRQAPKNMPQDADANGA<br>YHIGLKGLMLLGRIKNNQEGKKLNLVIKNEEYFEFVQNRNNKRPAATKKAGQAKKKK<br>GSYPYDVPDYAYPYDVPDYAYPYDVPDYA |
| SEQ ID NO<br>105<br>AsCas12a-<br>NLS-<br>3xHA(addgene<br>#69982): | MTQFEGFTNLYQVSKTLRFELIPQGKTLKHIQEQGFIEEDKARNDHYKELKPIIDRIYKTY<br>ADQCLQLVQLDWENLSAAIDSYRKEKTEETRNALIEEQATYRNAIHDYFIGRTDNLTDAI<br>NKRHAEIYKGLFKAELFNGKVLKQLGTVTTTEHENALLRSFDKFTTYFSGFYENRKNVF<br>SAEDISTAIPHRIVQDNFPKFKENCHIFTRLITAVPSLREHFENVKKAIGIFVSTSIEEVFSFP<br>FYNQLLTQTQIDLYNQLLGGISREAGTEKIKGLNEVLNLAIQKNDETAHIIASLPHRFIPLF<br>KQILSDRNTLSFILEEFKSDEEVIQSFCKYKTLLRNENVLETAEALFNELNSIDLTHIFISHK<br>KLETTSSALCDHWDTLRNALYERRISELTGKITKSAKEKVQRSLKHEDINLQEIISAAGKE<br>LSEAFKQKTSEILSHAHAALDQPLPTTLKKQEEKEILKSQLDSLLGLYHLLDWFAVDESN<br>EVDPEFSARLTGIKLEMEPSLSFYNKARNYATKKPYSVEKFKLNFQMPTLASGWDVNK<br>EKNNGAILFVKNGLYYLGIMPKQKGRYKALSFEPTEKTSEGFDKMYYDYFPDAAKMIP<br>KCSTQLKAVTAHFQTHTTPILLSNNFIEPLEITKEIYDLNNPEKEPKKFQTAYAKKTGDQK<br>GYREALCKWIDFTRDFLSKYTKTTSIDLSSLRPSSQYKDLGEYYAELNPLLYHISFQRIAE<br>KEIMDAVETGKLYLFQIYNKDFAKGHHGKPNLHTLYWTGLFSPENLAKTSIKLNGQAEL<br>FYRPKSRMKRMAHRLGEKMLNKKLKDQKTPIPDTLYQELYDYVNHRLSHDLSDEARA<br>LLPNVITKEVSHEIIKDRRFTSDKFFFHVPITLNYQAANSPSKFNQRVNAYLKEHPETPIIG<br>IDRGERNLIYITVIDSTGKILEQRSLNTIQQFDYQKKLDNREKERVAARQAWSVVGTIKD<br>LKQGYLSQVIHEIVDLMIHYQAVVVLENLNFGFKSKRTGIAEKAVYQQFEKMLIDKLNC<br>LVLKDYPAEKVGGVLNPYQLTDQFTSFAKMGTQSGFLFYVPAPYTSKIDPLTGFVDPFV<br>WKTIKNHESRKHFLEGFDFLHYDVKTGDFILHFKMNRNLSFQRGLPGFMPAWDIVFEK<br>NETQFDAKGTPFIAGKRIVPVIENHRFTGRYRDLYPANELIALLEEKGIVFRDGSNILPKL<br>LENDDSHAIDTMVALIRSVLQMRNSNAATGEDYINSPVRDLNGVCFDSRFQNPEWPMD |

TABLE 1-continued

| SEQ ID NO | SEQUENCE |
|---|---|
| | ADANGAYHIALKGQLLLNHLKESKDLKLQNGISNQDWLAYIQELRNKRPAATKKAGQ<br>AKKKKGSYPYDVPDYAYPYDVPDYAYPYDVPDYA |
| SEQ ID NO 106 HLbCas12a-NLS-3xHA(addgene #69988): | MSKLEKFTNCYSLSKTLRFKAIPVGKTQENIDNKRLLVEDEKRAEDYKGVKKLLDRYYL<br>SFINDVLHSIKLKNLNNYISLFRKKTRTEKENKELENLEINLRKEIAKAFKGNEGYKSLFK<br>KDIIETILPEFLDDKDEIALVNSFNGFTTAFTGFFDNRENMFSEEAKSTSIAFRCINENLTR<br>YISNMDIFEKVDAIFDKHEVQEIKEKILNSDYDVEDFFEGEFFNFVLTQEGIDVYNAIIGGF<br>VTESGEKIKGLNEYINLYNQKTKQKLPKFKPLYKQVLSDRESLSFYGEGYTSDEEVLEVF<br>RNTLNKNSEIFSSIKKLEKLFKNFDEYSSAGIFVKNGPAISTISKDIFGEWNVIRDKWNAE<br>YDDIHLKKKAVVTEKYEDDRRKSFKKIGSFSLEQLQEYADADLSVVEKLKEIIIQKVDEI<br>YKVYGSSEKLFDADFVLEKSLKKNDAVVAIMKDLLDSVKSFENYIKAFFGEGKETNRD<br>ESFYGDFVLAYDILLKVDHIYDAIRNYVTQKPYSKDKFKLYFQNPQFMGGWDKDKETD<br>YRATILRYGSKYYLAIMDKKYAKCLQKIDKDDVNGNYEKINYKLLPGPNKMLPKVFFS<br>KKWMAYYNPSEDIQKIYKNGTFKKGDMFNLNDCHKLIDFFKDSISRYPKWSNAYDFNF<br>SETEKYKDIAGFYREVEEQGYKVSFESASKKEVDKLVEEGKLYMFQIYNKDFSDKSHGT<br>PNLHTMYFKLLFDENNHGQIRLSGGAELFMRRASLKKEELVVHPANSPIANKNPDNPKK<br>TTTLSYDVYKDKRFSEDQYELHIPIAINKCPKNIFKINTEVRVLLKHDDNPYVIGIDRGER<br>NLLYIVVVDGKGNIVEQYSLNEIINNFNGIRIKTDYHSLLDKKEKERFEARQNWTSIENIK<br>ELKAGYISQVVHKICELVEKYDAVIALEDLNSGFKNSRVKVEKQVYQKFEKMLIDKLNY<br>MVDKKSNPCATGGALKGYQITNKFESFKSMSTQNGFIFYIPAWLTSKIDPSTGFVNLLKT<br>KYTSIADSKKFISSFDRIMYVPEEDLEEFALDYKNFSRTDADYIKKWKLYSYGNRIRIFRN<br>PKKNNVFDWEEVCLTSAYKELFNKYGINYQQGDIRALLCEQSDKAFYSSFMALMSLML<br>QMRNSITGRTDVDFLISPVKNSDGIFYDSRNYEAQENAILPKNADANGAYNIARKVLWA<br>IGQFKKAEDEKLDKVKIAISNKEWLEYAQTSVKHKRPAATKKAGQAKKKKGSYPYDVP<br>DYAYPYDVPDYAYPYDVPDYA |
| SEQ ID NO 107 3xGS: | GGGSGGGSGGGS |
| SEQ ID NO 108 (SGGS)2-XTEN-(SGGS)2 | SGGSSGGSSGSETPGTSESATPESSGGSSGGS |
| SEQ ID NO 109 (H4)2: | AEAAAKEAAAKEAAAKEAAAKALEAEAAAKEAAAKEAAAKEAAAKA |
| SEQ ID NO 110 3xFlag-NLS: | GSDYKDHDGDYKDHDIDYKDDDDKMAPKKKRKVGIHGVPAA |
| SEQ ID NO 111 3xFlag: | GSDYKDHDGDYKDHDIDYKDDDDKGIHGVPAA |
| SEQ ID NO 112 (H4)3: | GSGSEAAAKEAAAKEAAAKEAAAKALEAAAAKEAAAKEAAAKEAAAKGSGSAAAKE<br>AAAKEAAAKEAAAKGSGS |

TABLE 1-continued

| SEQ ID NO | SEQUENCE |
|---|---|
| SEQ ID NO 113 GPcPcPc: | AGSGGSGGSGGSPVPSTPPTNSSSTPPTPSPSPVPSTPPTNSSSTPPTPSPSPVPSTPPTNSSS TPPTPSPSAS |
| SEQ ID NO 114 GPGcP: | AGSGGSGGSGGSPVPSTPPTPSPSTPPTPSPSGGSGNSSGSGGSPVPSTPPTPSPSTPPTPSPS AS |
| SEQ ID NO 115 GPbGbP: | AGSGGSGGSGGSPVPSTPPTPSPSTPPTPSPSIQRTPKIQVYSRHPAENGKSNFLNCYVSGF HPSDIEVDLLKNGERIEKVEHSDLSFSKDWSFYLLYYTEFTPTEKDEYACRVNHVTLSQP KIVKWDRDGGSGGSGGSGGSIQRTPKIQVYSRHPAENGKSNFLNCYVSGFHPSDIEVDL LKNGERIEKVEHSDLSFSKDWSFYLLYYTEFTPTEKDEYACRVNHVTLSQPKIVKWDRD PVPSTPPTPSPSTPPTPSPSAS |
| SEQ ID NO 116 GPZP: | AGSGGSGGSGGSPVPSTPPTPSPSTPPTPSPSDGRYSLTYIYTGLSKHVEDVPAFQALGSL NDLQFFRYNSKDRKSQPMGLWRQVEGMEDWKQDSQLQKAREDIFMETLKDIVEYYND SNGSHVLQGRFGCEIENNRSSGAFWKYYYDGKDYIEFNKEIPAWVPFDPAAQITKQKW EAEPVYVQRAKAYLEEECPATLRKYLKYSKNILDRQDPPSVVVTSHQAPGEKKKLKCL AYDFYPGKIDVHWTRAGEVQEPELRGDVLHNGNGTYQSWVVVAVPPQDTAPYSCHVQ HSSLAQPLVVPWEASPVPSTPPTPSPSTPPTPSAS |
| SEQ ID NO 117 GGZGZP: | AGSGGSGGSGGSGGSGGSGGSGGSDGRYSLTYIYTGLSKHVEDVPAFQALGSLNDLQFF RYNSKDRKSQPMGLWRQVEGMEDWKQDSQLQKAREDIFMETLKDIVEYYNDSNGSHV LQGRFGCEIENNRSSGAFWKYYYDGKDYIEFNKEIPAWVPFDPAAQITKQKWEAEPVY VQRAKAYLEEECPATLRKYLKYSKNILDRQDPPSVVVTSHQAPGEKKKLKCLAYDFYP GKIDVHWTRAGEVQEPELRGDVLHNGNGTYQSWVVVAVPPQDTAPYSCHVQHSSLAQ PLVVPWEASGGSGGSGGSGGSDGRYSLTYIYTGLSKHVEDVPAFQALGSLNDLQFFRYN SKDRKSQPMGLWRQVEGMEDWKQDSQLQKAREDIFMETLKDIVEYYNDSNGSHVLQG RFGCEIENNRSSGAFWKYYYDGKDYIEFNKEIPAWVPFDPAAQITKQKWEAEPVYVQR AKAYLEEECPATLRKYLKYSKNILDRQDPPSVVVTSHQAPGEKKKLKCLAYDFYPGKID VHWTRAGEVQEPELRGDVLHNGNGTYQSWVVVAVPPQDTAPYSCHVQHSSLAQPLVV PWEASPVPSTPPTPSPSTPPTPSPSAS |

The skilled person in the art would appreciate that the amino acid sequences, peptides, polypeptides, nucleases, polymerases, blunting enzymes, guide RNAs, and single guide RNAs disclosed herein can be encoded by nucleic acid molecules. The skilled person in the art would also appreciate that vectors comprising these nucleic acid molecules could be used as vehicles to carry the genetic materials into cells. The vector can be a plasmid and is generally made of a DNA sequence that consists of an insert and a larger sequence that serves as the "backbone" of the vector.

EXAMPLES

While several experimental Examples are contemplated, these Examples are intended non-limiting.

Example 1

Indels Editing in PCSK9 Gene Using Cas9 and Blunting Enzymes

To test for the efficiency of inducing indels in a target gene using Cas9 and blunting enzymes, Cas9 and PCSK9 exon 12 targeting sgRNA were co-transferred into cultured mammalian cells in combination with DNA polymerase μ (POLM), EXOG, T4 DNA polymerase (T4pol), DNA polymerase λ (POLL), MGME1, RecJ exonuclease (RecJ) or Nuclease S1 (nucS). Cas9 and sgRNA alone served as the negative control. The occurrence of indels for the control and each of the combinations was measured. HEK293T cells were used.

Figure 12A:
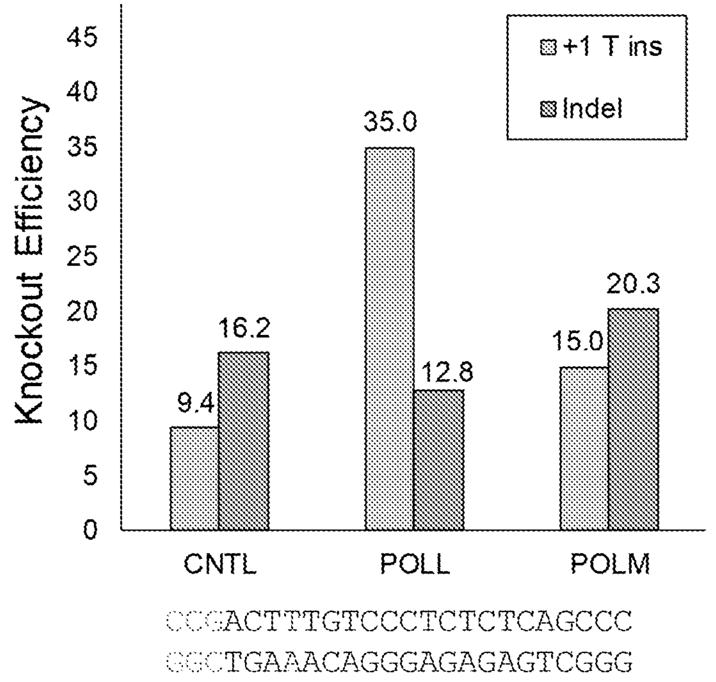
FIG. 12A is a diagram showing probability distribution of +1 T insertion and indel mutations in PCSK9 exon 12 when induced by Cas9 and POLL, and Cas9 and POLM for a target sequence of the sequences of SEQ ID NO: 146 (ccgactttgtccctctctcagccc) and SEQ ID NO: 147 (gggctgagagagggacaaagtcgg) according to embodiments of the present teachings.
Figure 12B:
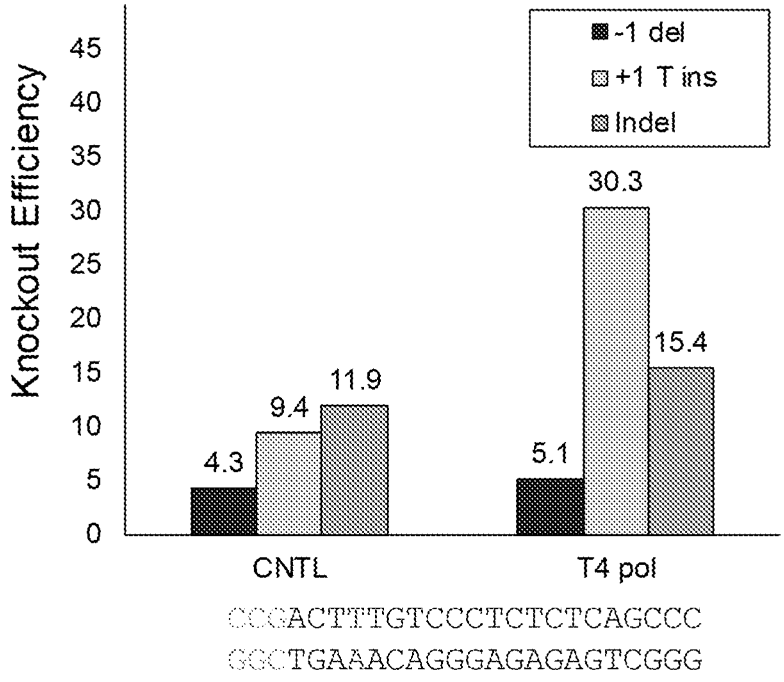
FIG. 12B is a diagram showing probability distribution of −1 deletion, +1T insertion and indel mutations in PCSK9 exon 12 when induced by Cas9 and T4 polymerase for a target sequence of the sequences of SEQ ID NO: 148 (ccgactttgtccctctctcagccc) and SEQ ID NO: 149 (gggctgagagagggacaaagtcgg) according to embodiments of the present teachings.
Figure 13A:
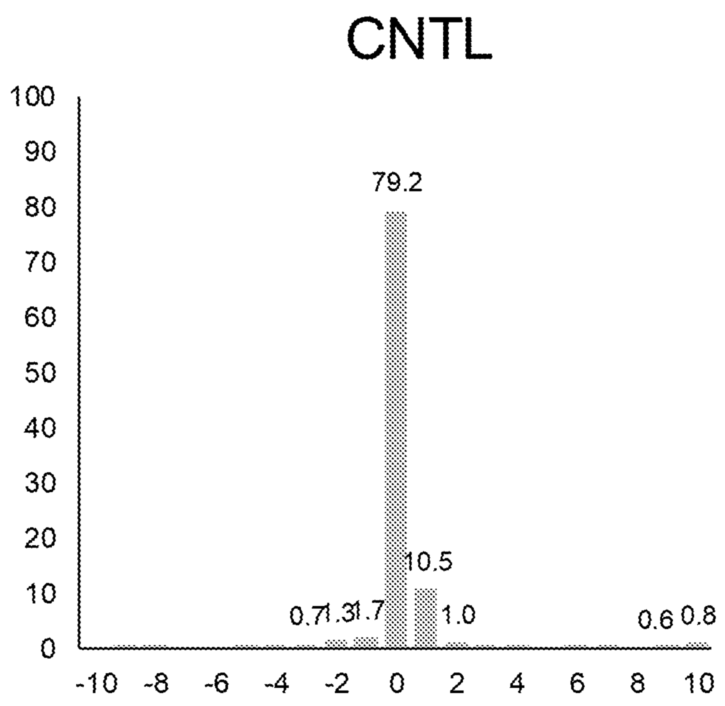
FIG. 13A is a diagram showing probability distribution of indel mutations in GYPB gene when induced by Cas9 only according to embodiments of the present teachings.
Figure 13B:
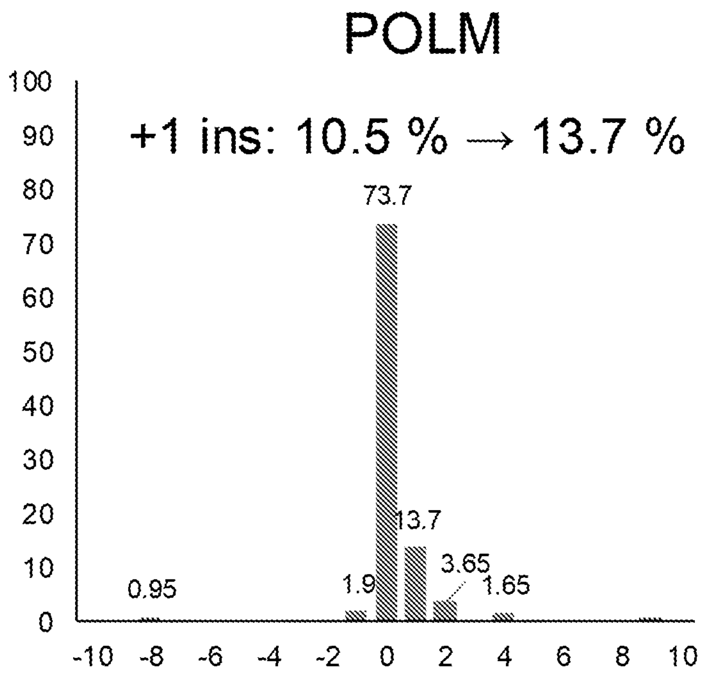
FIG. 13B is a diagram showing the probability distribution of indel mutations in GYPB when induced by Cas9 and POLM according to embodiments of the present teachings.
Figure 13C:
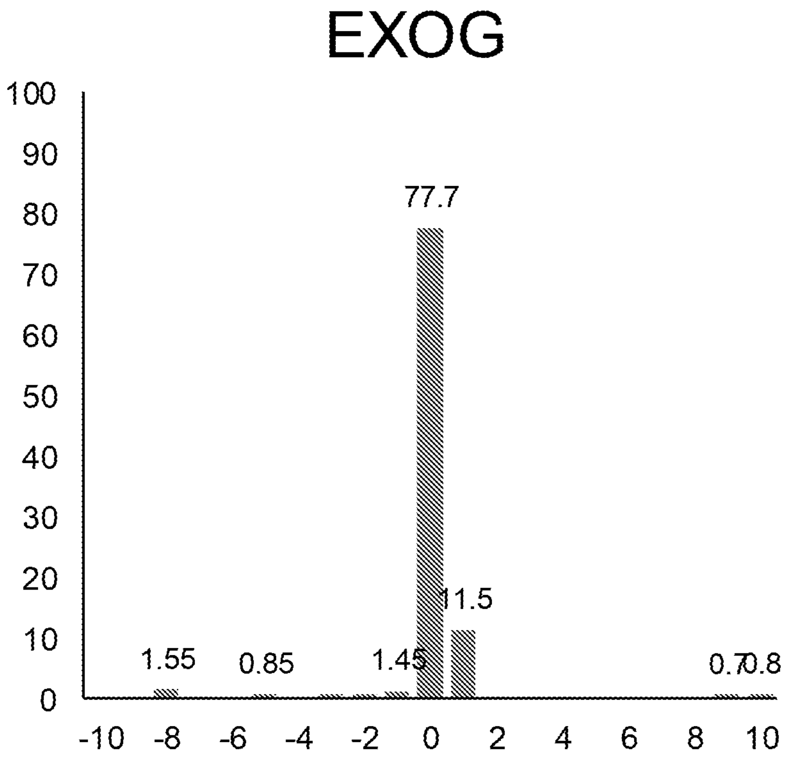
FIG. 13C is a diagram showing the probability distribution of indel mutations in GYPB when induced by Cas9 and EXOG according to embodiments of the present teachings.
Figure 13D:
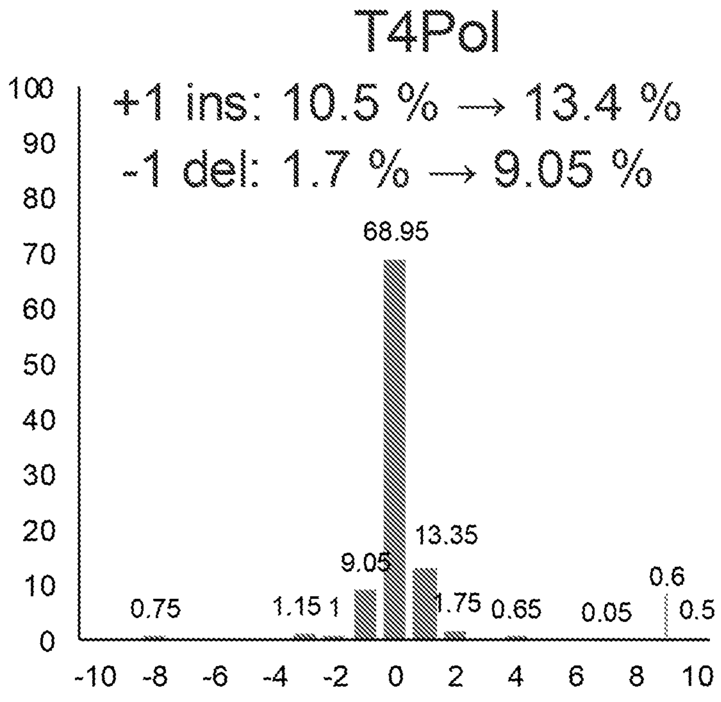
FIG. 13D is a diagram showing the probability distribution of indel mutations in GYPB when induced by Cas9 and T4pol according to embodiments of the present teachings.
Figure 13E:
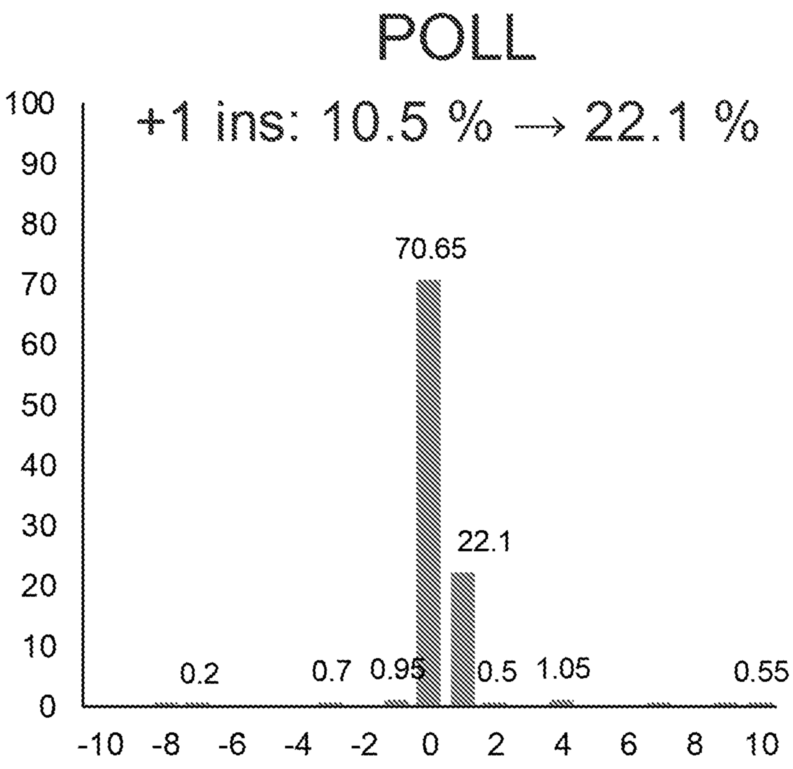
FIG. 13E is a diagram showing the probability distribution of indel mutations in GYPB when induced by Cas9 and POLL according to embodiments of the present teachings.
Figure 13F:
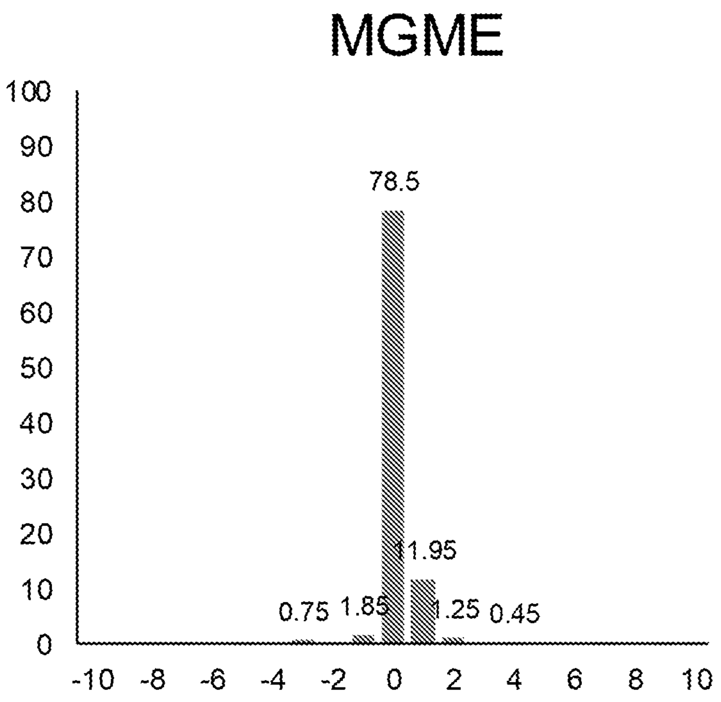
FIG. 13F is a diagram showing the probability distribution of indel mutations in GYPB when induced by Cas9 and MGME according to embodiments of the present teachings.
Figure 13G:
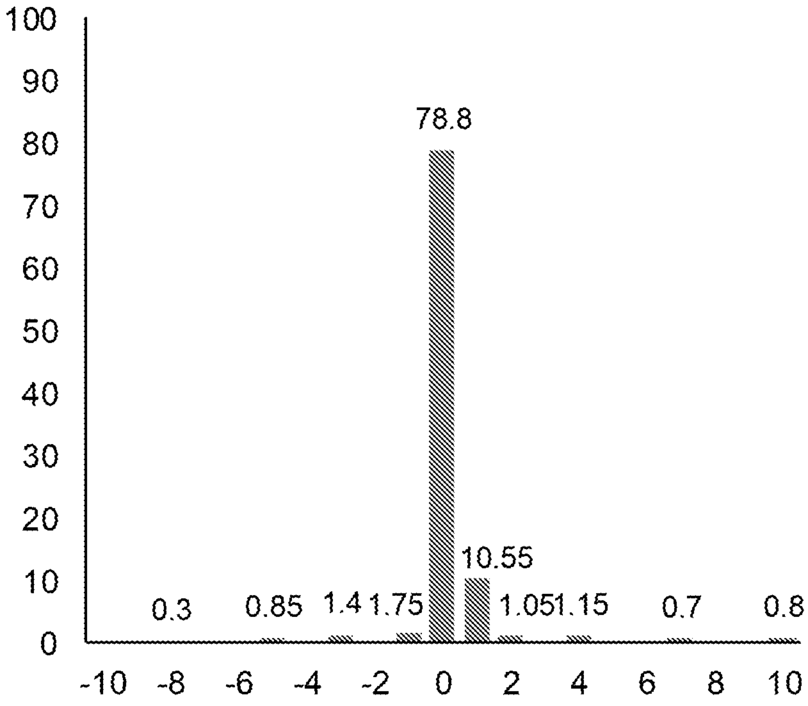
FIG. 13G is a diagram showing the probability distribution of indel mutations in GYPB when induced by Cas9 and RecJ according to embodiments of the present teachings.
Figure 13H:
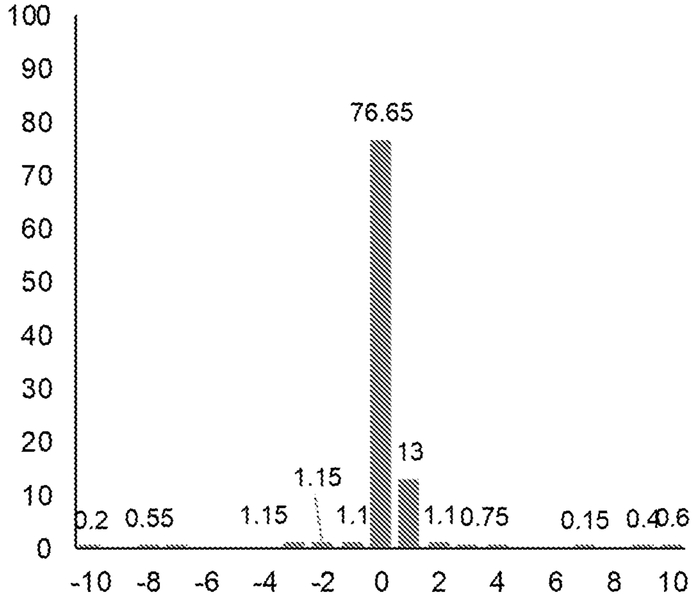
FIG. 13H is a diagram showing the probability distribution of indel mutations in GYPB when induced by Cas9 and nucS according to embodiments of the present teachings.
Figure 14A:
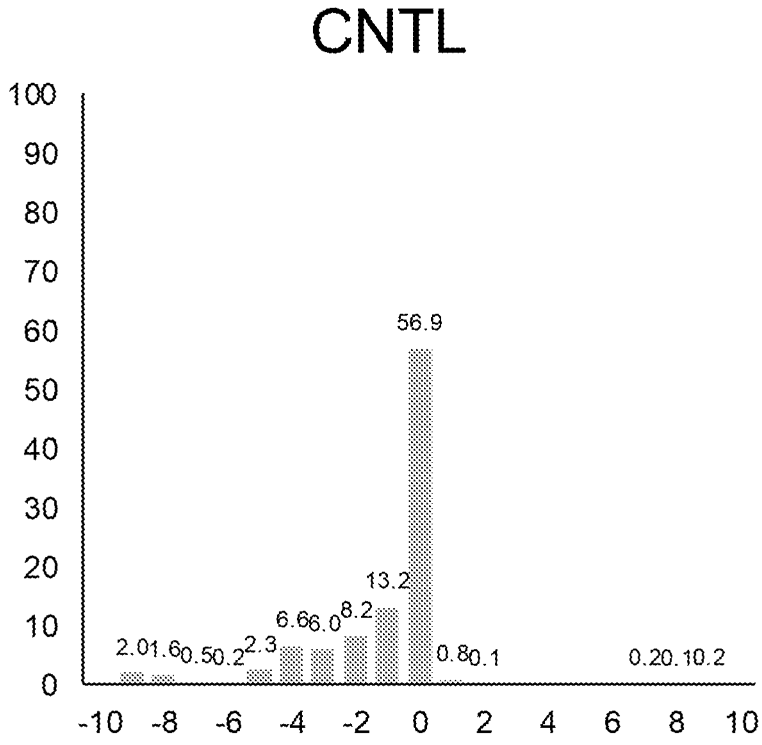
FIG. 14A is a diagram showing the probability distribution of indel mutations in TPH2 exon 9 when induced by Cas9 alone according to embodiments of the present teachings.
Figure 14B:
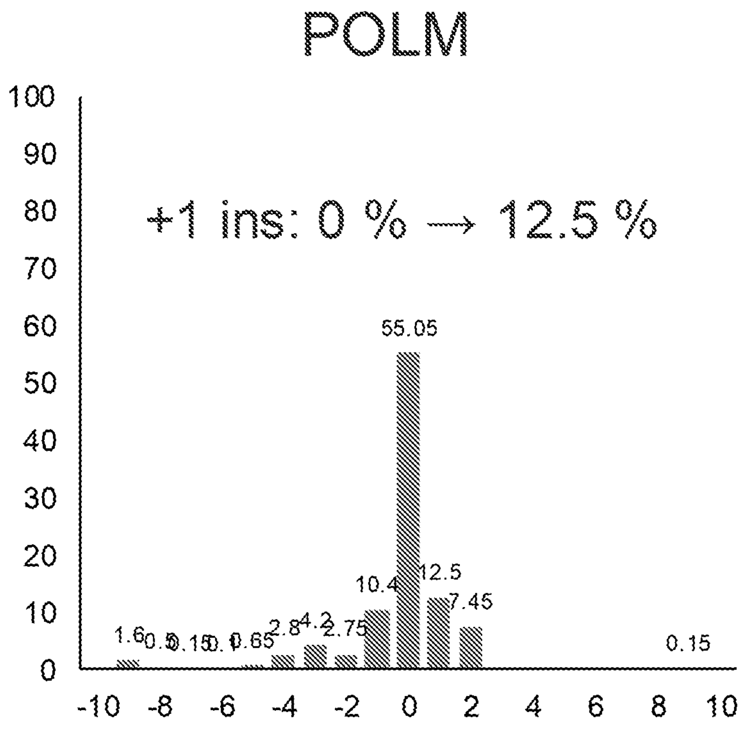
FIG. 14B is a diagram showing the probability distribution of indel mutations in TPH2 exon 9 when induced by Cas9 and POLM according to embodiments of the present teachings.
Figure 14C:
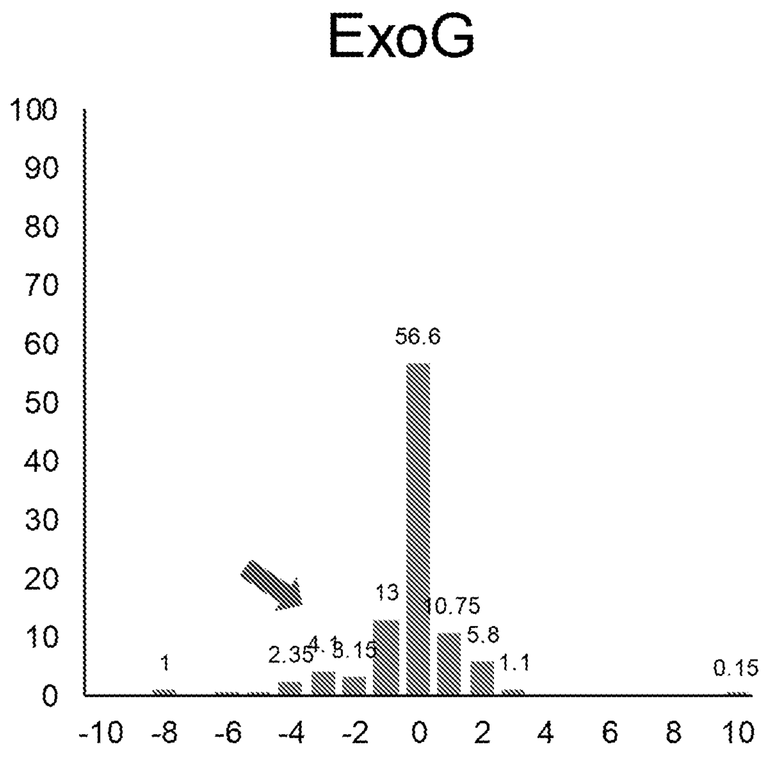
FIG. 14C is a diagram showing the probability distribution of indel mutations in TPH2 exon 9 when induced by Cas9 and EXOG according to embodiments of the present teachings.
Figure 14D:
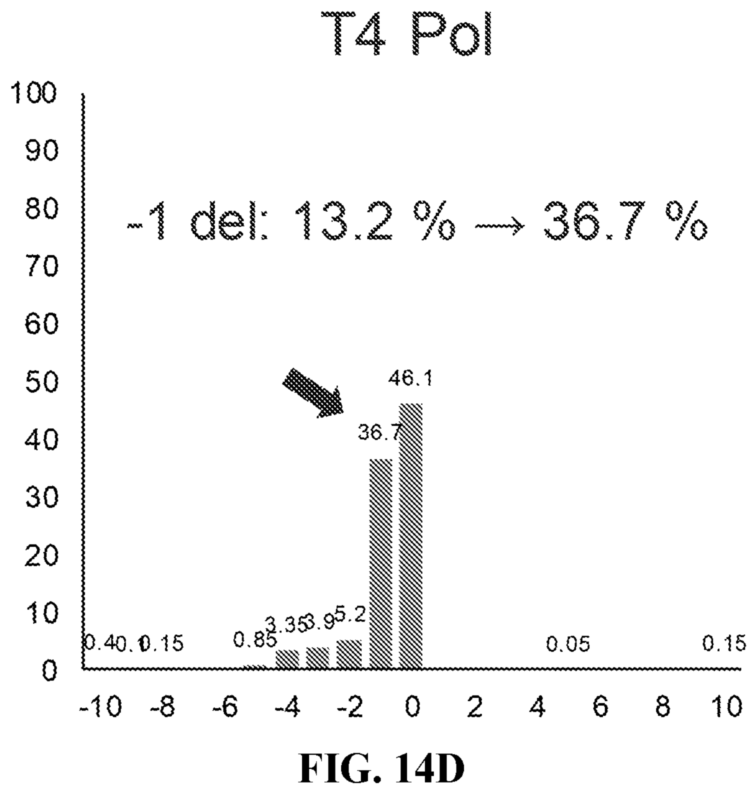
FIG. 14D is a diagram showing the probability distribution of indel mutations in TPH2 exon 9 when induced by Cas9 and T4pol according to embodiments of the present teachings.
Figure 14E:
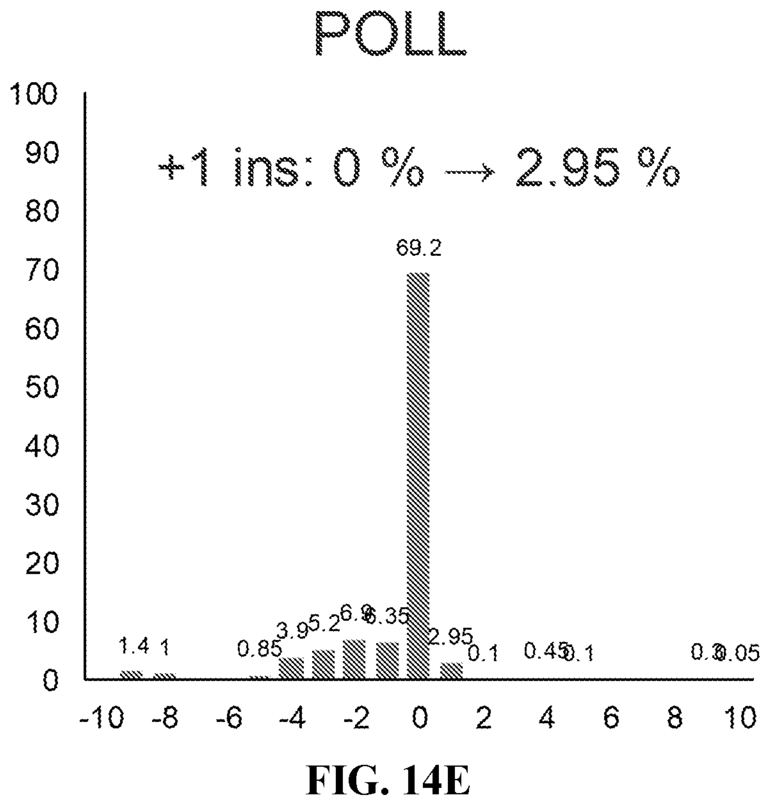
FIG. 14E is a diagram showing the probability distribution of indel mutations in TPH2 exon 9 when induced by Cas9 and POLL according to embodiments of the present teachings.
Figure 14F:
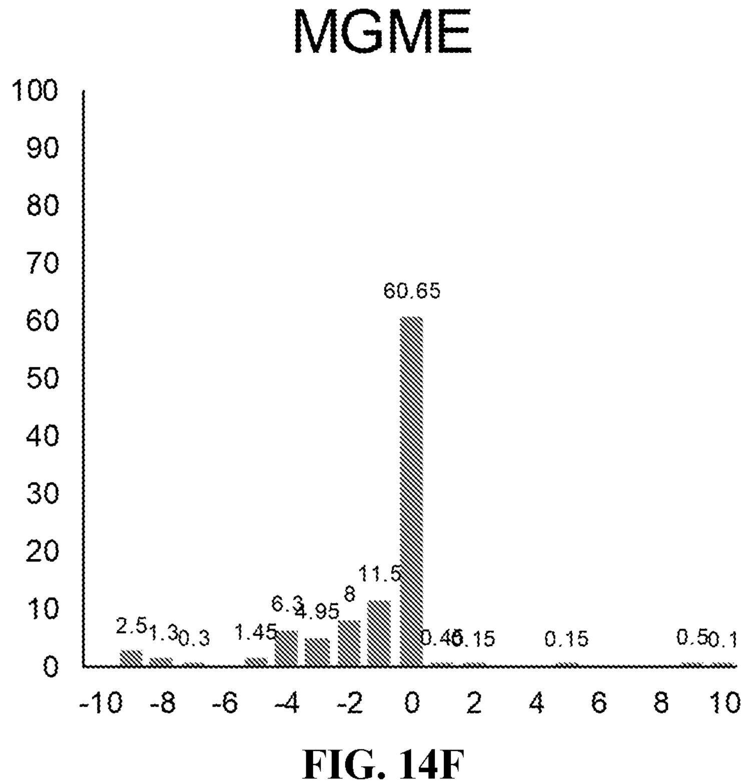
FIG. 14F is a diagram showing the probability distribution of indel mutations in TPH2 exon 9 when induced by Cas9 and MGME according to embodiments of the present teachings.
Figure 14G:
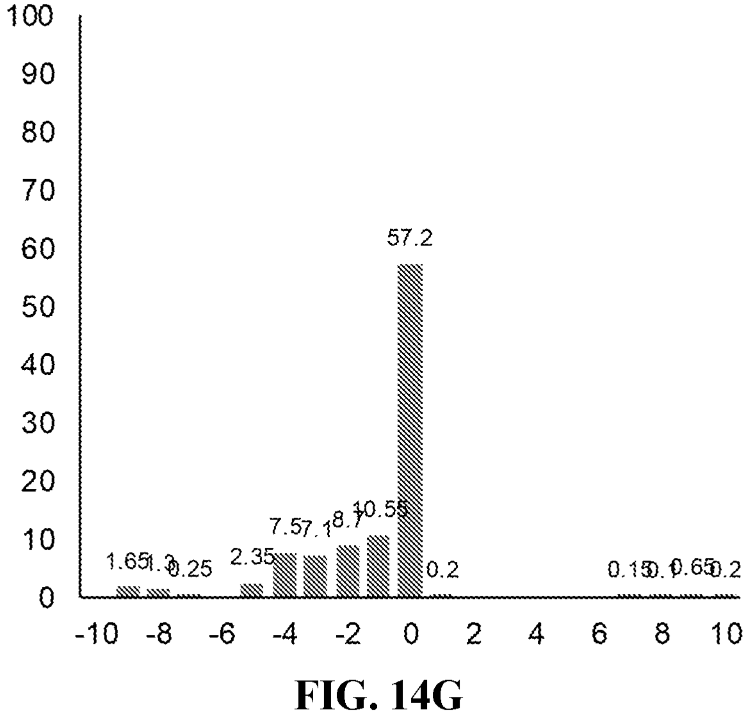
FIG. 14G is a diagram showing the probability distribution of indel mutations in TPH2 exon 9 when induced by Cas9 and RecJ according to embodiments of the present teachings.
Figure 14H:
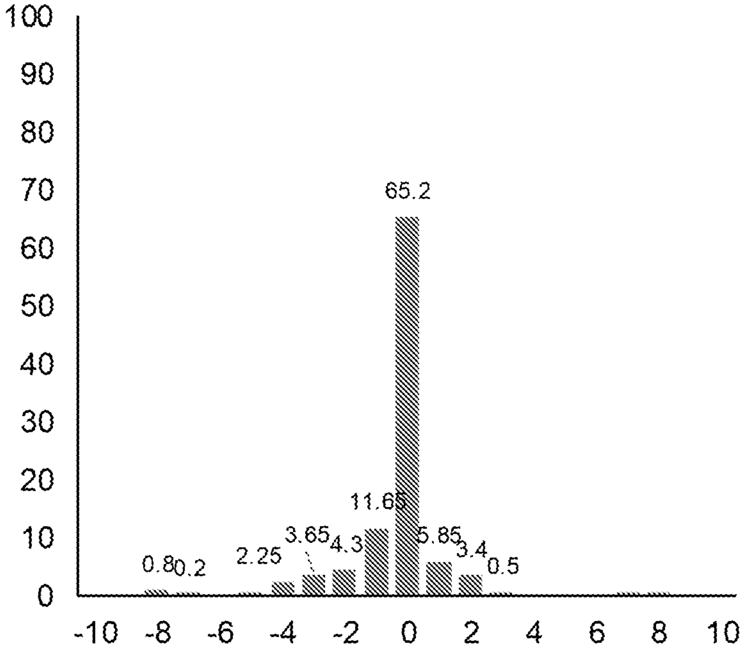
FIG. 14H is a diagram showing the probability distribution of indel mutations in TPH2 exon 9 when induced by Cas9 and nucS according to embodiments of the present teachings.

Results for each of the combinations are presented in FIGS. 11A-11H and comparisons between the control and blunting enzymes are presented in FIGS. 12A-12B.

POLM (FIG. 11B), T4pol (FIG. 11D) and POLL (FIG. 11E) were found to increase the percentage of +1 insertion from 14.4% to 19.6%, 14.4% to 36.75%, and 14.4% to 39.55%, respectively. EXOG (FIG. 11C), MGME1 (FIG. 11F) and RecJ (FIG. 11G) were found to increase the percentage of −1 deletion from 4.3% to 5.05%, 4.3% to 6.35%, and 4.3% to 5.5% respectively.

POLL (FIG. 12A) and T4pol (FIG. 12B) were found to increase the +1 insertion frequency from 9.4% to 35.0% and 9.4% to 30.3% respectively.

Example 2

Indels Editing in GYPB Gene Using Cas9 and Blunting Enzymes

To test for the efficiency of inducing indels in a target gene using Cas9 and blunting enzymes, Cas9 and GYPB targeting sgRNA were co-transferred into cultured mammalian cells in combination with DNA polymerase μ (POLM), EXOG, T4 DNA polymerase (T4pol), DNA polymerase λ (POLL), MGME1, RecJ exonuclease (RecJ) or Nuclease S1 (nucS). Cas9 and sgRNA alone served as the negative control. The occurrence of indels for the control and each of the combinations was measured. Results for each of the combinations are presented in FIGS. 13A-13H.

POLM (FIG. 13B), T4pol (FIG. 13D) and POLL (FIG. 13E) were found to increase the percentage of +1 insertion mutations from 10.5% to 13.7%, 10.5% to 13.4%, and 10.5% to 22.1% respectively. T4 polymerase (FIG. 13D) was found to increase the percentage of −1 deletion mutations from 1.7% to 9.05%

Example 3

Indels Editing in TPH2 Gene Using Cas9 and Blunting Enzymes

To test for the efficiency of inducing indels in a target gene using Cas9 and blunting enzymes, Cas9 and TPH2 targeting sgRNA were co-transferred into cultured mammalian cells in combination with POLM, EXOG, T4 polymerase, DNA polymerase λ (POLL), MGME1, RecJ exonuclease (RecJ) or Nuclease S1 (nucS). Cas9 and sgRNA alone served as the negative control. The occurrence of indels for the control and each of the combinations was measured. Results for each of the combinations are presented in FIGS. 14A-14H.

DNA polymerase μ (POLM) (FIG. 14B) and DNA polymerase λ (POLL) (FIG. 14E) were found to increase the percentage of +1 insertion mutations from 0% to 12.5% and 0% to 2.95 respectively. T4 DNA polymerase (T4pol) (FIG. 14D) were found to increase the percentage of −1 deletion mutations from 13.2% to 36.7%.

One skilled in the art will appreciate further features and advantages of the invention based on the above-described embodiments. Accordingly, the invention is not to be limited by what has been particularly shown and described, except as indicated by the appended claims.

What is claimed is:

1. A composition comprising: (a) a target specific nuclease, wherein a target comprises a double stranded DNA (dsDNA); (b) a double strand break (DSB)-end blunting enzyme; and (c) a single guide RNA (sgRNA) comprising a variable sequence of nucleic acids for target recognition and one or more stem loops, wherein the nucleic acid sequence of the stem loop is at least 90% identical to a nucleic acid transcribed from a nucleic acid sequence selected from the group consisting of SEQ ID NOs: 54-64.

2. The composition of claim 1, wherein the nucleic acid sequence of the stem loop is at least 95% identical to a nucleic acid transcribed from nucleotides 21-96 of SEQ ID NOs: 54-64.

3. The composition of claim 1, wherein the sgRNA comprises a variable sequence of nucleic acid for target recognition of about 17 to about 23 nucleotides in length.

4. The composition of claim 1, further comprising a MS2-binding protein linked to the sgRNA.

5. The composition of claim 1, wherein the target specific nuclease induces staggered ends upon target specific nuclease cleaving the dsDNA, optionally wherein the target specific nuclease is an altered scissile variant.

6. The composition of claim 1, wherein the target specific nuclease is selected from the group consisting of Cas12a, LbCas12a, FnCas12a, AsCas12a, Cas9, SpCas9, SaCas9, LZ3Cas9 (SpCas9 N690C, T769I, G915M, and N980K mutant), SpCas9 G915F mutant, SpCas9 ΔF916 mutant, SpCas9 F916P mutant, SpCas9 R918A mutant, SpCas9 R919P mutant, SpCas9 Q920P mutant, Cascφ, and the double combinations of Cas9 nickase, zinc finger nuclease (ZFN), and TAL Effector Nuclease (TALEN).

7. The composition of claim 1, wherein the target specific nuclease comprises an amino acid sequence at least 85% identical to an amino acid sequence selected from the group consisting of SEQ ID NOs: 95-106.

8. The composition of claim 1, wherein the target specific nuclease specifically binds to a protospacer-adjacent motif (PAM), optionally wherein the PAM is selected from the group consisting of NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

9. The composition of claim 1, wherein the DSB-end blunting enzyme is a polymerase.

10. The composition of claim 9, wherein the polymerase is selected from the group consisting of DNA polymerase λ (lambda) (POLL), DNA polymerase μ (mu) (POLM), DNA polymerase β (beta) (POLB), DNA polymerase γ (gamma) (POLG), DNA polymerase ι (iota) (POLI), DNA polymerase κ (eta) (POLH), TENT4A, DNA polymerase ν (nu) (POLN), DNA Ligase 4, DNTT, XRCC4, DNA Polymerase IV, fungi pol IV-like DNA polymerase, DNA polymerase/3'-5' exonuclease Pol X, and T4 DNA polymerase (T4pol).

11. The composition of claim 1, wherein the DSB-end blunting enzyme is a single-strand DNA specific nuclease.

12. The composition of claim 11, wherein the single-strand DNA specific nuclease is selected from the group consisting of MGME1, FEN1, DNA2, XRN2, EXOG, EXO1, AP endonuclease, RecJ exonuclease (RecJ), XseA, XseB, nuclease S1 (nucS), P1 nuclease, Artemis, T4 DNA polymerase (T4pol), and Csm1, optionally wherein the DSB-end blunting enzyme is modified with a protein tag comprising Myc, Flag or VStag.

13. The composition of claim 1, wherein the DSB-end blunting enzyme comprises an amino acid sequence that is at least 85% identical to an amino acid sequence selected from the group consisting of SEQ ID NOs: 65-94.

14. The composition of claim 1, wherein the DSB-end blunting enzyme is covalently bound to the nuclease by a linker.

15. The composition of claim 14, wherein the linker is a peptide.

16. The composition of claim 1, wherein the composition further comprises an inhibitor of the microhomology-mediated end joining (MMEJ) pathway.

17. The composition of claim 16, wherein the MMEJ pathway inhibitor is a CtIP or MRN inhibitor, optionally wherein the CtIP inhibitor is selected from KLHL15 and PIN1, and optionally wherein the MRN inhibitor is selected from E1b55K and E40rf6.

18. A composition comprising: (a) a first nucleic acid molecule encoding a target specific nuclease, wherein a target comprises a double stranded DNA (dsDNA); (b) a second nucleic acid molecule encoding a DSB-end blunting enzyme; and (c) a third nucleic acid molecule encoding a sgRNA comprising a variable sequence of nucleic acid for target recognition and one or more stem loops, wherein the nucleic acid sequence of the stem loop is at least 90% identical to a nucleic acid transcribed from a nucleic acid sequence selected from the group consisting of SEQ ID NOs: 54-64.

19. A method of treating a disease caused by a frameshift mutation in a dsDNA in a subject, the method comprising: administering to the subject a therapeutically effective amount of a composition comprising: (a) a target specific nuclease, wherein a target comprises a double stranded DNA (dsDNA); (b) a double strand break (DSB)-end blunting enzyme; and (c) a single guide RNA (sgRNA) comprising a variable sequence of nucleic acid for target recognition and one or more stem loops, wherein the nucleic acid sequence of the stem loop is at least 90% identical to a nucleic acid transcribed from a nucleic acid sequence selected from the group consisting of SEQ ID NOs: 54-64, and wherein at least one base pair in the dsDNA is inserted or deleted within the frameshift mutation.

* * * * *